US 11,339,172 B2

United States Patent
Tran et al.

(10) Patent No.: US 11,339,172 B2
(45) Date of Patent: May 24, 2022

(54) MODULATORS OF THE BETA-3 ADRENERGIC RECEPTOR USEFUL FOR THE TREATMENT OR PREVENTION OF HEART FAILURE AND DISORDERS RELATED THERETO

(71) Applicant: Arena Pharmaceuticals, Inc., San Diego, CA (US)

(72) Inventors: Thuy-Anh Tran, San Diego, CA (US); Brett Ullman, San Diego, CA (US); Bryan Aubrey Kramer, San Diego, CA (US); Quyen-Quyen Thuy Do, San Diego, CA (US); Young-Jun Shin, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 16/769,507

(22) PCT Filed: Dec. 6, 2018

(86) PCT No.: PCT/US2018/064316
§ 371 (c)(1),
(2) Date: Jun. 3, 2020

(87) PCT Pub. No.: WO2019/113359
PCT Pub. Date: Jun. 13, 2019

(65) Prior Publication Data
US 2020/0385395 A1 Dec. 10, 2020

Related U.S. Application Data

(60) Provisional application No. 62/595,133, filed on Dec. 6, 2017.

(51) Int. Cl.
*C07D 491/08* (2006.01)
*C07D 491/048* (2006.01)
*A61P 9/00* (2006.01)

(52) U.S. Cl.
CPC .......... *C07D 491/048* (2013.01); *A61P 9/00* (2018.01)

(58) Field of Classification Search
CPC ................................................. C07D 491/08
See application file for complete search history.

(56) References Cited

U.S. PATENT DOCUMENTS 6,867,220 B2 * 3/2005 Cecchi .................. A61P 15/06
514/318

FOREIGN PATENT DOCUMENTS

| WO | WO 2001/043744 | 6/2001 |
| WO | WO 2006/060122 | 6/2006 |
| WO | WO 2017/214002 | 12/2017 |

OTHER PUBLICATIONS

Berge, et al., "Pharmaceutical salts," Journal of Pharmaceutical Sciences, 1977, 66:1-19.
Collier et al., "Radiosynthesis and in-vivo evaluation of the pseudopeptide S-opioid antagonist," J. Labelled Compd. Radiopharm., 1999, 42, S264-S266.
Francis et al., "Intropes," J Am College of Cardiology, 63(20): 2069-2078, 2014.
Higuchi and Stella, "Pro-drugs as novel delivery systems," ACS Symposium Series, 1975, 129 pages.
International Search Report and Written Opinion in International Appln. No. PCT/US2018/064316, dated Feb. 13, 2019, 10 pages.
Kulandavelu et al., "Alterations in Beta3-adrenergic cardiac innercation and nitric oxide signaling in heart failure," J Am College Cardiology, 2012, 59(22): 1988-90.
Le Bas et al., "Radioiodinated analogs of EP 00652218 for the exploration of the tachykinin NK1 receptor by spect," J. Labelled Compd. Radiopharm, 2001, 44, S280-S282.
Morimoto et al., "Endogenous β3-adrenoreceptor activation contributes to left ventricular and cardiomyocyte dysfunction in heart failure," Am J Physiol Heart Circ Physiol, 2004, 286:H2425-H2433.
Stahly, "Diversity in single- and multiple-component crystals. The search for the prevalence of polymorphs and cocrystals," Crystal Growth & Design 2007, 7(6):1007-1026.
Zhu et al., "Synthesis and Mode of Action of 125I- and 3H-Labeled Thieno[2,3-c]pyridine Antagonists of Cell Adhesion Molecule Expression," J. Org. Chem., 2002, 67:943-948.

* cited by examiner

*Primary Examiner* — David K O'Dell
(74) *Attorney, Agent, or Firm* — Fish & Richardson P.C.

(57) ABSTRACT

The present invention relates to compounds of Formula (Ia) and pharmaceutical compositions thereof that modulate the activity of the beta-3 adrenergic receptor. Compounds of the present invention and pharmaceutical compositions thereof are directed to methods useful in the treatment of a beta-3 adrenergic receptor-mediated disorder, such as, heart failure and related disorders thereto.

26 Claims, 21 Drawing Sheets

General Synthetic Scheme for the Preparation of Certain Compounds of Formula (Ia)

MODULATORS OF THE BETA-3 ADRENERGIC RECEPTOR USEFUL FOR THE TREATMENT OR PREVENTION OF HEART FAILURE AND DISORDERS RELATED THERETO

FIELD OF THE INVENTION

The present invention relates to compounds of Formula (Ia) and pharmaceutical compositions thereof that modulate the activity of the beta-3 adrenergic receptor. Compounds of the present invention and pharmaceutical compositions thereof are directed to methods useful in the treatment of a beta-3 adrenergic receptor-mediated disorder, such as, heart failure; cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; left ventricular ejection fraction (LVEF)<40% by radionuclide ventriculography; LVEF≤35% by echocardiography or ventricular contrast angiography; and conditions related thereto.

BACKGROUND OF THE INVENTION

Acute heart failure is a rapid decline in heart function that can cause anoxia of tissues (particularly the brain), leading to death. Acute heart failure can occur in previously asymptomatic individuals (e.g., individuals with pulmonary edema or cardiogenic shock), or in individuals with an acute exacerbation of chronic heart failure.

In the healthy heart, the actions of beta-1 and beta-2 adrenergic receptors are dominant and act through a Gs-coupled pathway to increase the force and frequency of myocardial contraction, while beta-3 adrengergic receptors act through a Gi-coupled eNOS pathway to exert weak negative inotropic effects. In the failing heart, beta-1 and beta-2 adrenergic receptors are downregulated or desensitized, while beta-3 adrenergic receptors are upregulated, thereby emphasizing the negative effects of beta-3 agonism on cardiac contractility. Morimoto, *Am J Physiol Heart Circ Physiol*, 286: H2425-H2433, 2004; Kulandavelu, *J Am College Cardiology*, 59(22): 1988-90, 2012.

In individuals experiencing acute heart failure, the short-term goal is to increase contractility and improve hemodynamic status. The current standard of care for acute heart failure includes the administration of inotropes—agents that alter the force or energy of cardiac contractions. These agents are typically administered in an intensive care setting by continuous injection. Examples of such agents include adrenaline, dobutamine, dopamine, levosimendan, and noradrenaline. However, the initial improvement in contractility afforded by these agents can be followed by accelerated mortality. Katz A M and Konstam M A, *Heart Failure: Pathophysiology, Molecular Biology and Clinical Management*, Lippincott, Williams & Wilkins, 2nd edition, 1999. The excessive mortality following administration of these agents has been linked to increased tachycardia and myocardial oxygen consumption that leads to arrhythmia and myocardial ischemia. Francis et al., *J Am College of Cardiology*, 63(20): 2069-2078, 2014.

SUMMARY OF THE INVENTION

One aspect of the present invention encompasses certain 1-oxa-8-azaspiro[4.5]decan-3-yl-aminopropanyl-ether derivatives selected from compounds of Formula (Ia) and pharmaceutically acceptable salts, solvates, hydrates, and N-oxides thereof:

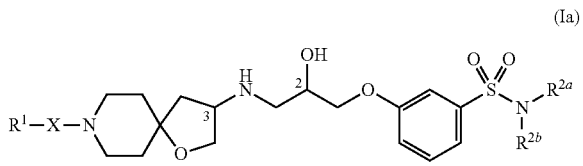

(Ia)

wherein:

X is —SO$_2$— or absent;

R$^1$ is selected from: aryl, C$_1$-C$_6$-alkylene-aryl, C$_1$-C$_6$-alkylene-heteroaryl, C$_3$-C$_7$ cycloalkyl, heteroaryl, and heterocyclyl; each optionally substituted with one or more substituents selected from: C$_1$-C$_6$ alkoxy, C$_1$-C$_6$ alkoxycarbonyl, C$_1$-C$_7$ alkyl, C$_1$-C$_6$ alkylamino, C$_1$-C$_6$ alkylcarboxamide, C$_1$-C$_6$ alkylsulfonamido, C$_1$-C$_6$ alkylsulfonyl, amino, aryloxy, arylsulfonyl, carboxamide, carbamimidoyl, carboxy, cyano, C$_3$-C$_7$ cycloalkyl, C$_2$-C$_8$ dialkylamino, C$_2$-C$_8$ dialkylsulfamoyl, C$_1$-C$_6$ haloalkoxy, C$_1$-C$_6$ haloalkyl, halogen, heterocyclyl, hydroxycarbamimidoyl, hydroxyl, oxo, and sulfamoyl; and wherein said C$_1$-C$_6$ alkoxy, C$_1$-C$_7$ alkyl, C$_1$-C$_6$ alkylamino, aryloxy, C$_3$-C$_7$ cycloalkyl, and C$_2$-C$_5$ dialkylamino are each optionally substituted with one or more substituents selected from: amino, C$_1$-C$_6$ alkoxy, C$_1$-C$_6$ alkylamino, C$_1$-C$_6$ alkylcarboxamide, carboxy, —Y—C$_1$-C$_6$-alkylene-Z optionally substituted with oxo, C$_3$-C$_7$ cycloalkyl, cyano, C$_2$-C$_6$ dialkylamino, C$_1$-C$_6$ haloalkyl, C$_1$-C$_6$ haloalkylamino, heterocyclyl, hydroxyl, oxo, and phenyl;

Y is selected from: —O— and —NH—;

Z is selected from: C$_1$-C$_6$ alkoxy, amino, C$_1$-C$_6$ alkylamino, cyano, C$_2$-C$_6$ dialkylamino, hydroxyl, and phenyl;

R$^{2a}$ is H or selected from: C$_1$-C$_6$ alkoxy, C$_1$-C$_6$ alkyl, C$_3$-C$_7$ cycloalkyl, and heterocyclyl; each optionally substituted with one or more substituents selected from: C$_1$-C$_6$ alkoxy, C$_1$-C$_6$ alkylamino, C$_1$-C$_6$ alkyl, C$_1$-C$_6$ alkylenehydroxyl, amino, C$_3$-C$_7$ cycloalkyl, cyano, C$_2$-C$_8$ dialkylamino, heterocyclyl optionally substituted with one oxo group, halogen, hydroxyl, and oxo; and R$^{2b}$ is H or C$_1$-C$_6$ alkyl.

One aspect of the present invention relates to pharmaceutical products selected from: a pharmaceutical composition, a formulation, a unit dosage form, and a kit; each comprising a compound of the present invention.

One aspect of the present invention relates to pharmaceutical compositions comprising a compound of the present invention, and a pharmaceutically acceptable carrier.

One aspect of the present invention relates to methods for preparing pharmaceutical compositions comprising the step of admixing a compound of the present invention and a pharmaceutically acceptable carrier.

One aspect of the present invention relates to methods for treating or preventing a beta-3 adrenergic receptor-mediated disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing heart failure in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating a hypotensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a borderline hypotensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a normotensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a hypertensive patient, comprising administering to the patient in need thereof, a therapeutically effective amount of a compound of the present invention; a pharmaceutical product of the present invention; or a pharmaceutical composition of the present invention.

One aspect of the present invention relates to methods for treating a patient following myocardial infarction, comprising administering to the patient in need thereof, a therapeutically effective amount of a compound of the present invention; a pharmaceutical product of the present invention; or a pharmaceutical composition of the present invention.

One aspect of the present invention relates to uses of a compound of the present invention in the manufacture of a medicament for treating or preventing a beta-3 adrenergic receptor-mediated disorder in an individual.

One aspect of the present invention relates to uses of a compound of the present invention in the manufacture of a medicament for treating or preventing heart failure in an individual.

One aspect of the present invention relates to uses of a compound of the present invention in the manufacture of a medicament for treating a hypotensive patient.

One aspect of the present invention relates to uses of a compound of the present invention in the manufacture of a medicament for treating a borderline hypotensive patient.

One aspect of the present invention relates to uses of a compound of the present invention in the manufacture of a medicament for treating a normotensive patient.

One aspect of the present invention relates to uses of a compound of the present invention in the manufacture of a medicament for treating a hypertensive patient.

One aspect of the present invention relates to uses of a compound of the present invention in the manufacture of a medicament for treating a patient following myocardial infarction.

One aspect of the present invention relates to compounds of the present invention; a pharmaceutical product of the present invention; or a pharmaceutical composition of the present invention; for use in a method of treatment of the human or animal body by therapy.

One aspect of the present invention relates to compounds of the present invention; pharmaceutical products of the present invention; or pharmaceutical compositions of the present invention; for use in a method for treating or preventing a beta-3 adrenergic receptor-mediated disorder in an individual.

One aspect of the present invention relates to compounds of the present invention; pharmaceutical products of the present invention; or pharmaceutical compositions of the present invention; for use in a method for treating or preventing heart failure in an individual.

One aspect of the present invention relates to compounds of the present invention; pharmaceutical products of the present invention; or pharmaceutical compositions of the present invention; for use in a method for treating a hypotensive patient.

One aspect of the present invention relates to compounds of the present invention; pharmaceutical products of the present invention; or pharmaceutical compositions of the present invention; for use in a method for treating a borderline hypotensive patient.

One aspect of the present invention relates to compounds of the present invention; pharmaceutical products of the present invention; or pharmaceutical compositions of the present invention; for use in a method for treating a normotensive patient.

One aspect of the present invention relates to compounds of the present invention; pharmaceutical products of the present invention; or pharmaceutical compositions of the present invention; for use in a method for treating a hypertensive patient.

One aspect of the present invention relates to compounds of the present invention; pharmaceutical products of the present invention; or pharmaceutical compositions of the present invention; for use in a method for treating a patient following myocardial infarction.

In some embodiments, the beta-3 adrenergic receptor-mediated disorder is selected from the list consisting of: heart failure; cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; LVEF<40% by radionuclide ventriculography; and LVEF≤35% by echocardiography or ventricular contrast angiography.

In some embodiments, the beta-3 adrenergic receptor-mediated disorder is heart failure.

In some embodiments, the beta-3 adrenergic receptor-mediated disorder is reduced cardiac performance in heart failure.

In some embodiments, the beta-3 adrenergic receptor-mediated disorder is mortality, reinfarction, and/or hospitalization in connection with heart failure.

In some embodiments, the beta-3 adrenergic receptor-mediated disorder is acute heart failure.

In some embodiments, the beta-3 adrenergic receptor-mediated disorder is acute decompensated heart failure.

In some embodiments, the beta-3 adrenergic receptor-mediated disorder is congestive heart failure.

In some embodiments, the beta-3 adrenergic receptor-mediated disorder is severe congestive heart failure.

In some embodiments, the beta-3 adrenergic receptor-mediated disorder is organ damage associated with heart failure (e.g., kidney damage or failure, heart valve problems, heart rhythm problems, and/or liver damage).

In some embodiments, the beta-3 adrenergic receptor-mediated disorder is heart failure due to left ventricular dysfunction. In some embodiments, the beta-3 adrenergic receptor-mediated disorder is heart failure with normal ejection fraction. In some embodiments, the beta-3 adrenergic receptor-mediated disorder is cardiovascular mortality following myocardial infarction. In some embodiments, the beta-3 adrenergic receptor-mediated disorder is cardiovascular mortality in patients with left ventricular failure or left ventricular dysfunction. In some embodiments, the beta-3 adrenergic receptor-mediated disorder is left ventricular failure. In some embodiments, the beta-3 adrenergic receptor-mediated disorder is left ventricular dysfunction.

In some embodiments, the beta-3 adrenergic receptor-mediated disorder is class II heart failure using the New York Heart Association (NYHA) classification system.

In some embodiments, the beta-3 adrenergic receptor-mediated disorder is class III heart failure using the New York Heart Association (NYHA) classification system.

In some embodiments, the beta-3 adrenergic receptor-mediated disorder is class IV heart failure using the New York Heart Association (NYHA) classification system.

In some embodiments, the beta-3 adrenergic receptor-mediated disorder is left ventricular ejection fraction (LVEF)<40% by radionuclide ventriculography.

In some embodiments, the beta-3 adrenergic receptor-mediated disorder is left ventricular ejection fraction (LVEF)≤35% by echocardiography or ventricular contrast angiography.

Described herein are beta-3 adrenergic receptor antagonists that are useful for boosting contractility of the heart. These compounds are selective for the beta-3 adrenergic receptor and have a distinct mechanism of action that differs from currently prescribed inotropes with known cardiotoxic effects.

Because increased beta-3 adrenergic receptor activity is known to inhibit contractility in the failing heart, studies were conducted to evaluate the effect of beta-3 adrenergic receptor antagonists on contractile function. As described herein, these studies demonstrate that the inhibition of the beta-3 adrenergic receptor by beta-3 adrenergic receptor antagonists improves contractile function and hemodynamic status in the failing heart. There is a need for new agents that increase cardiac contractility while avoiding cardiotoxic effects.

These and other aspects of the invention disclosed herein will be set forth in greater detail as the patent disclosure proceeds.

BRIEF DESCRIPTION OF THE DRAWINGS

FIG. 4 shows a general synthetic scheme for the preparation of Compounds of Formula (Ia). It is understood that one or more chiral intermediates can be used in the scheme to provide chiral compounds of Formula (Ia). For example, the stereochemistry at C(2) for Intermediate 3-2 can be either (R) or (S), and the stereochemistry for C(3) for Intermediate 1-1 can be either (R) or (S). $PG^1$ and $PG^2$ are protecting groups such as, BOC (tert-butyloxycarbonyl), Cbz (carboxybenzyl or alternatively named benzyloxy carbamate) and the like.

DETAILED DESCRIPTION OF THE INVENTION

Definitions

Figure 1:
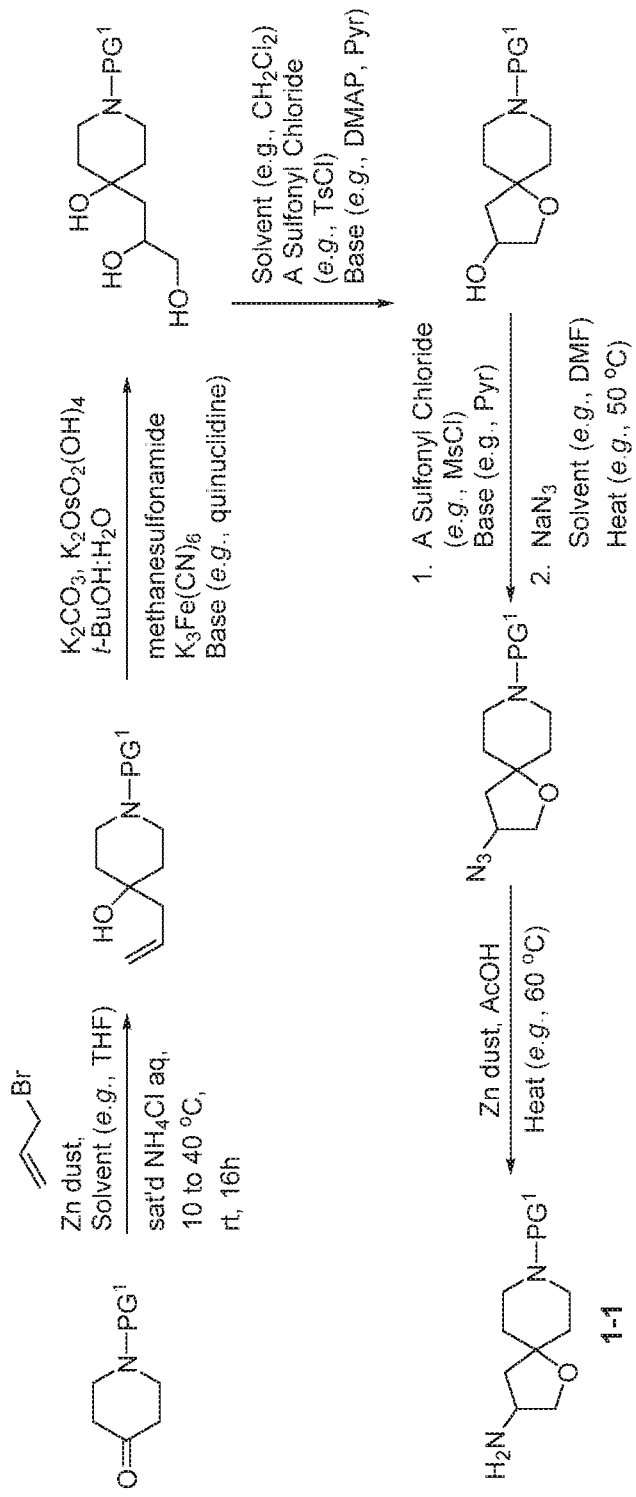
FIG. 1 shows a general synthetic scheme for the preparation of intermediates useful in preparing Compounds of Formula (Ia), wherein $PG^1$ (i.e., Protecting Group 1) can be a variety of protecting groups known to one skilled in the art, such as, a benzyloxy carbamate (i.e., CBz) group.
Figure 2:
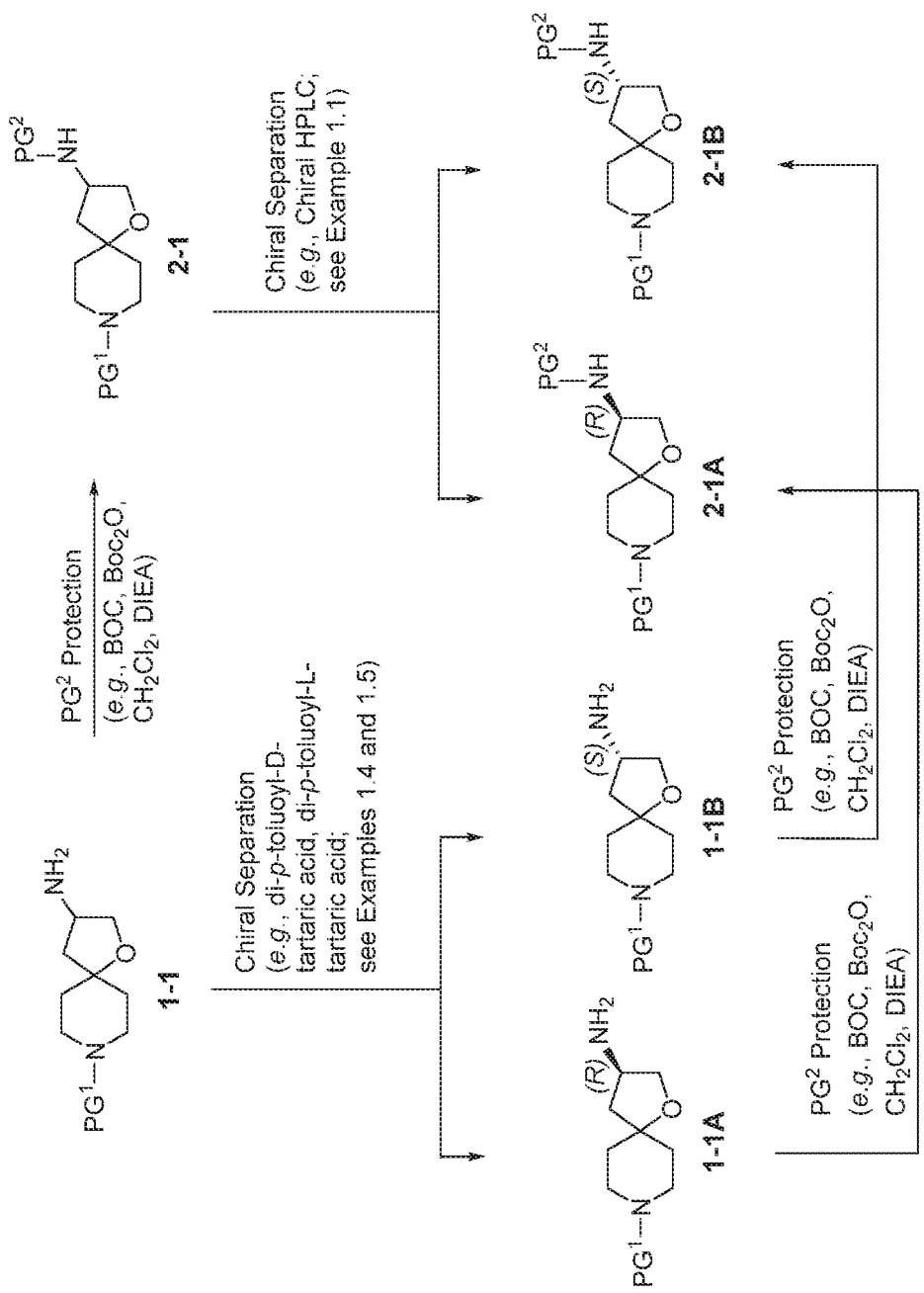
FIG. 2 shows a general synthetic scheme for the preparation of intermediates useful in preparing Compounds of Formula (Ia), wherein $PG^1$ (Protecting Group 1) and $PG^2$ (Protecting Group 2) can be a variety of protecting groups known to one skilled in the art, such as, a benzyloxy carbamate (Cbz) group and a tert-butoxycarbonyl (BOC) group. In certain instances, $PG^1$ and $PG^2$ are different and are orthogonal protecting groups, such as, $PG^1$ is Cbz and $PG^2$ is BOC.
Figure 3:
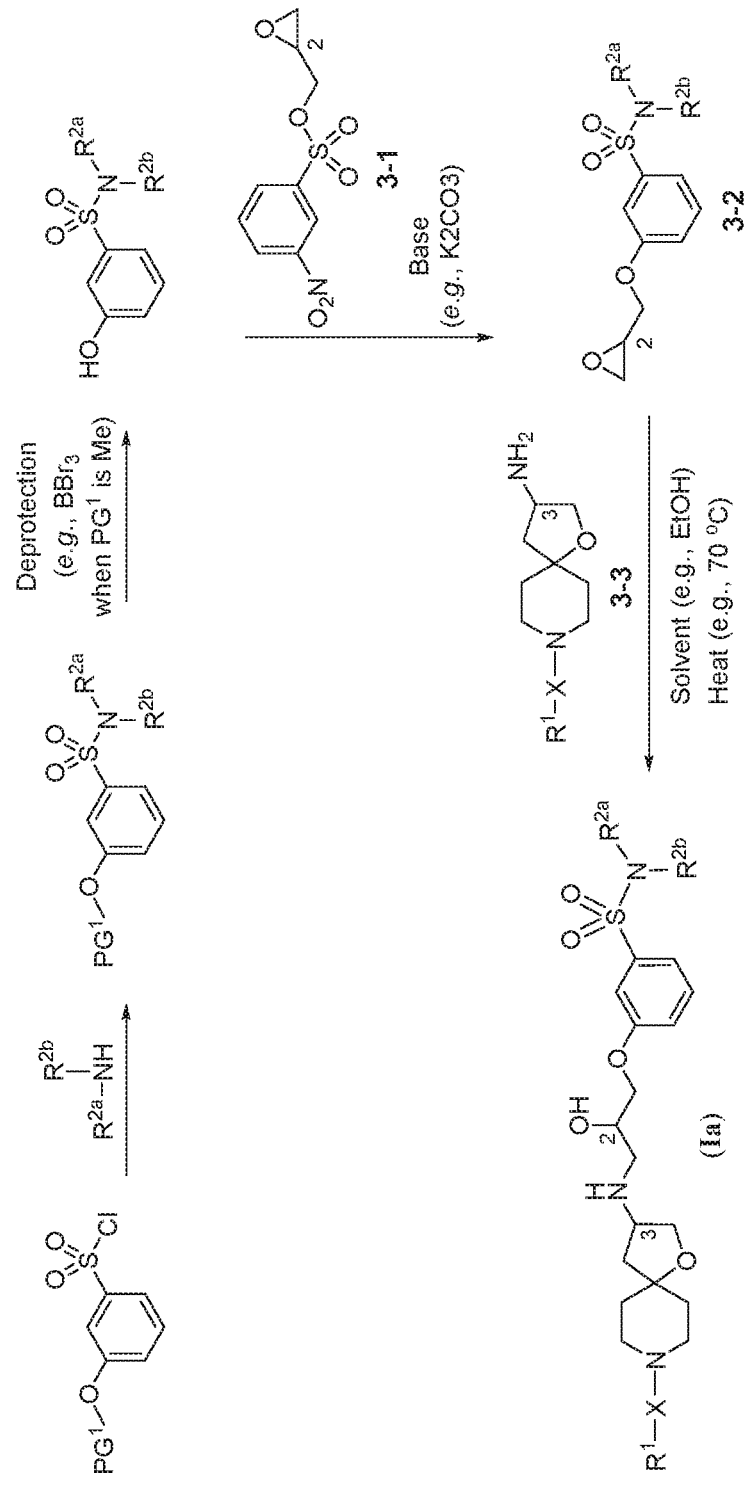
FIG. 3 shows a general synthetic scheme for the preparation of Compounds of Formula (Ia). It is understood that one or more chiral intermediates can be used in the scheme to provide chiral compounds of Formula (Ia). For example, the stereochemistry at C(2) for Intermediates 3-1 and 3-2 can be either (R) or (S), and the stereochemistry for C(3) for Intermediate 3-3 can be either (R) or (S).
Figure 4:
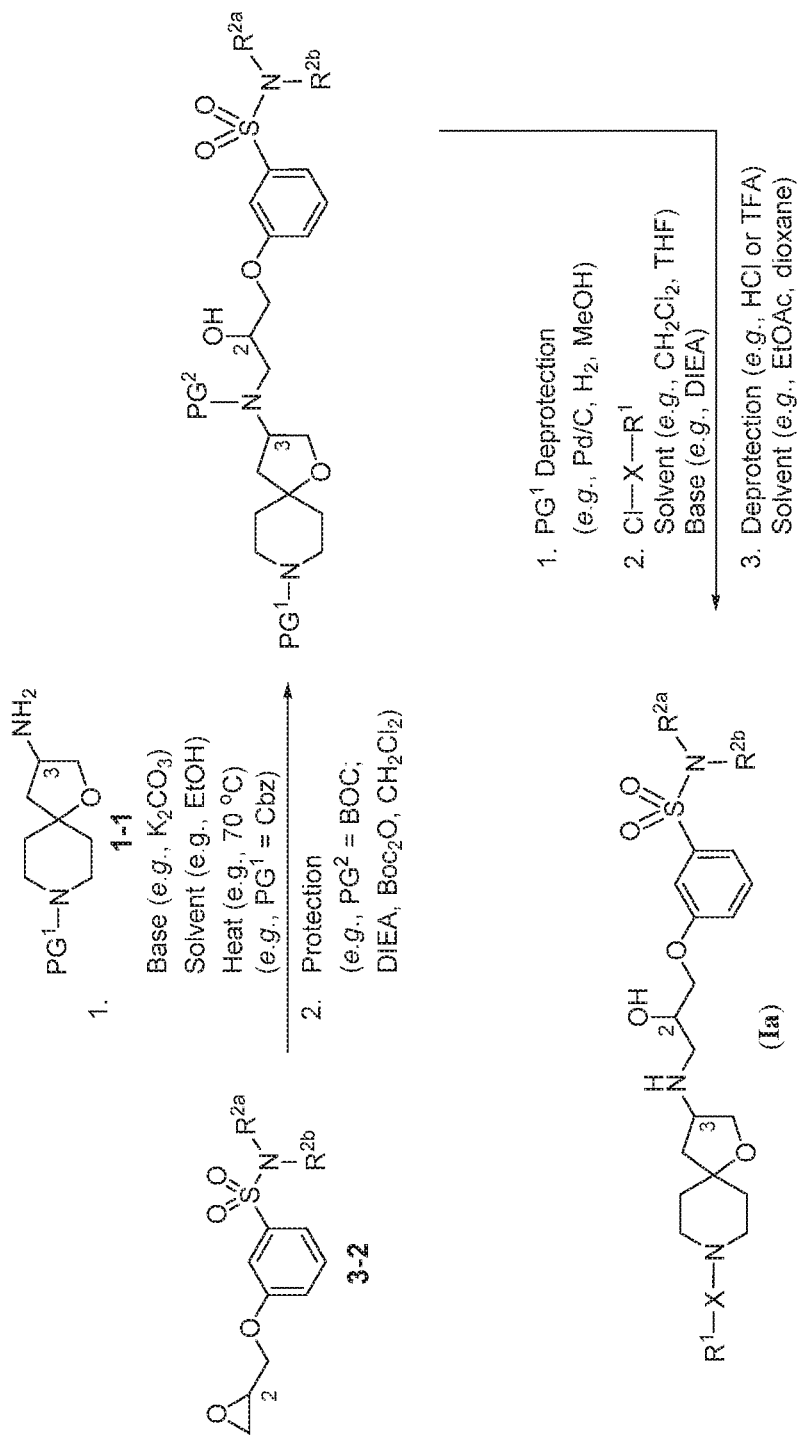
Figure 5:
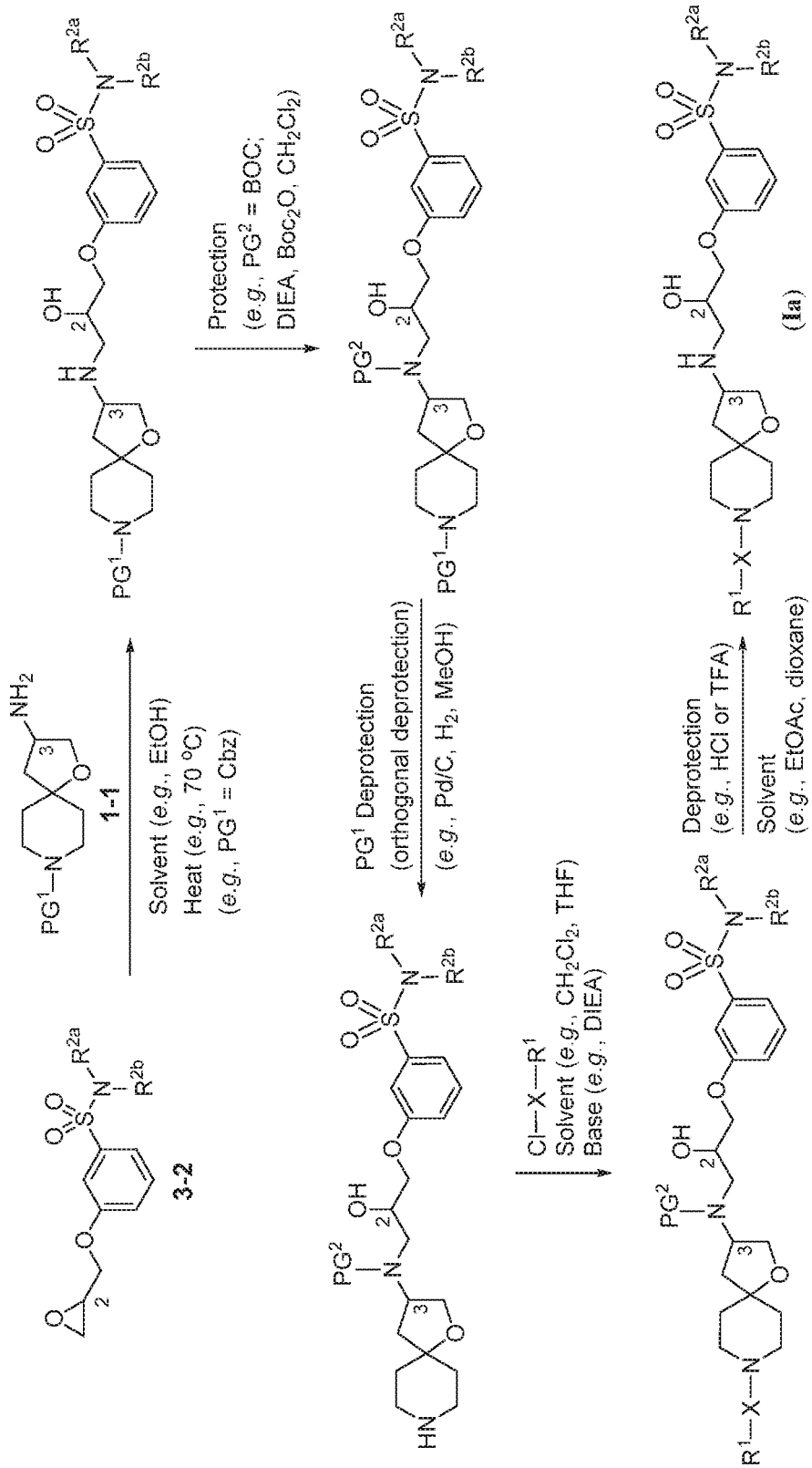
FIG. 5 shows a general synthetic scheme for the preparation of Compounds of Formula (Ia). It is understood that one or more chiral intermediates can be used in the scheme to provide chiral compounds of Formula (Ia). For example, the stereochemistry at C(2) for Intermediate 3-2 can be either (R) or (S), and the stereochemistry for C(3) for Intermediate 1-1 can be either (R) or (S).
Figure 6:
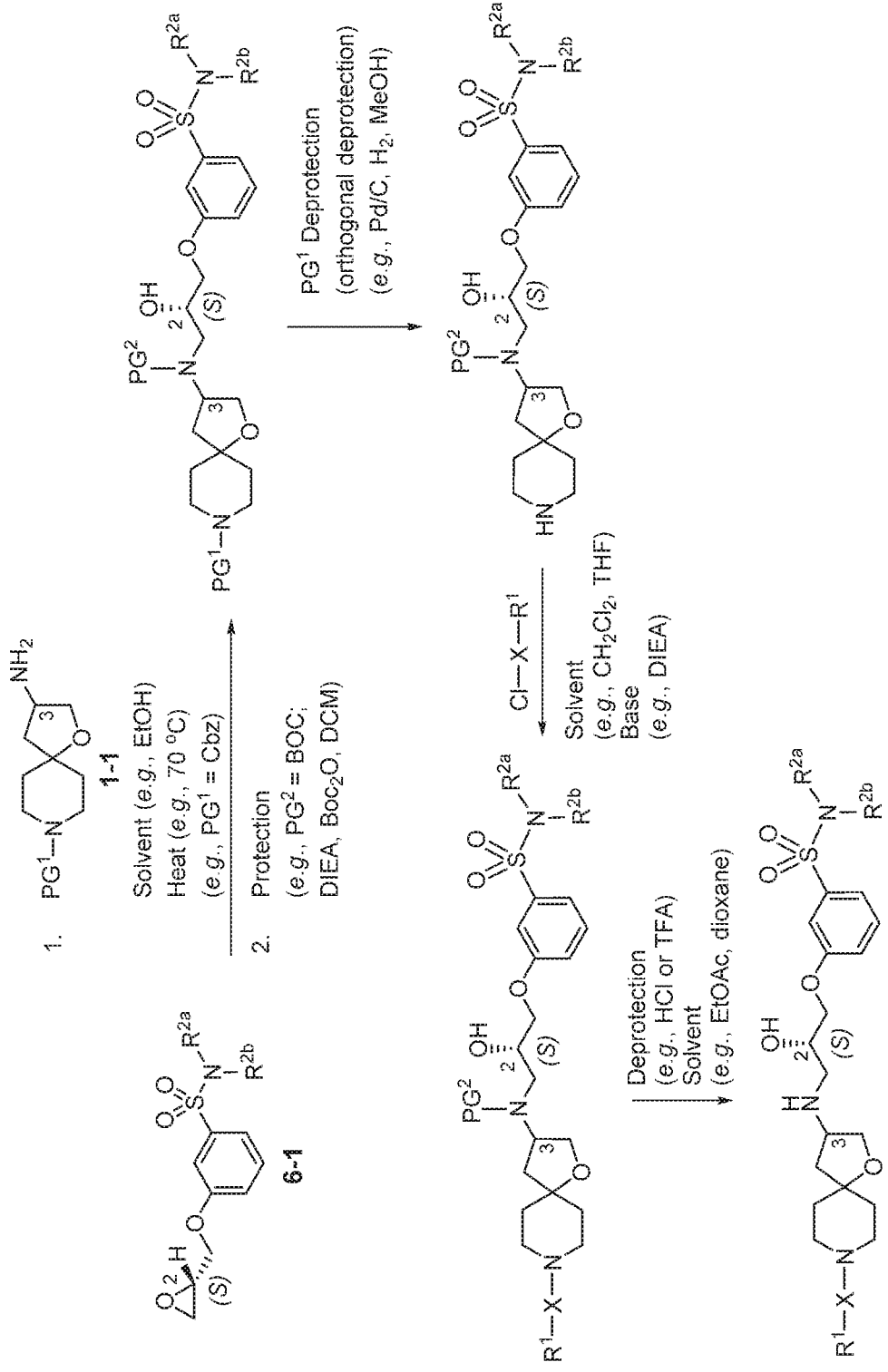
FIG. 6 shows a general synthetic scheme utilizing the chiral oxirane Intermediate 6-1 for the preparation of Compounds of Formula (Ia) where C(2) has the (S) stereochemistry. It is understood that Intermediate 1-1 can be utilized where C(3) is either (R) or (S).
Figure 7:
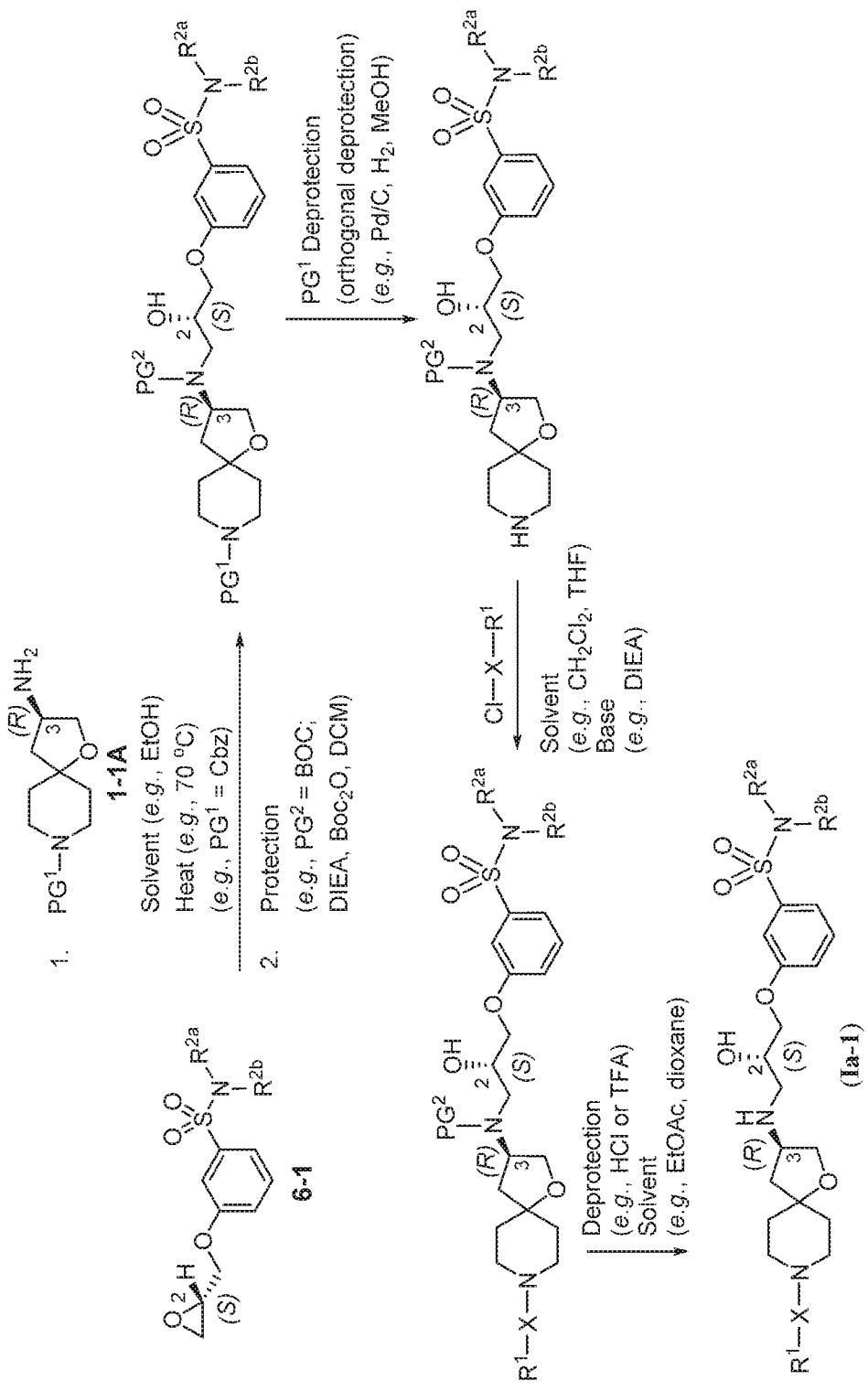
FIG. 7 shows a general synthetic scheme for the preparation of Compounds of Formula (Ia-1) utilizing the chiral oxirane Intermediate 6-1 and the chiral amine Intermediate 1-1A (see FIG. 2) where the Compounds of Formula (Ia-1) have the (S) stereochemistry for C(2) and the (R) stereochemistry for C(3).
Figure 8:
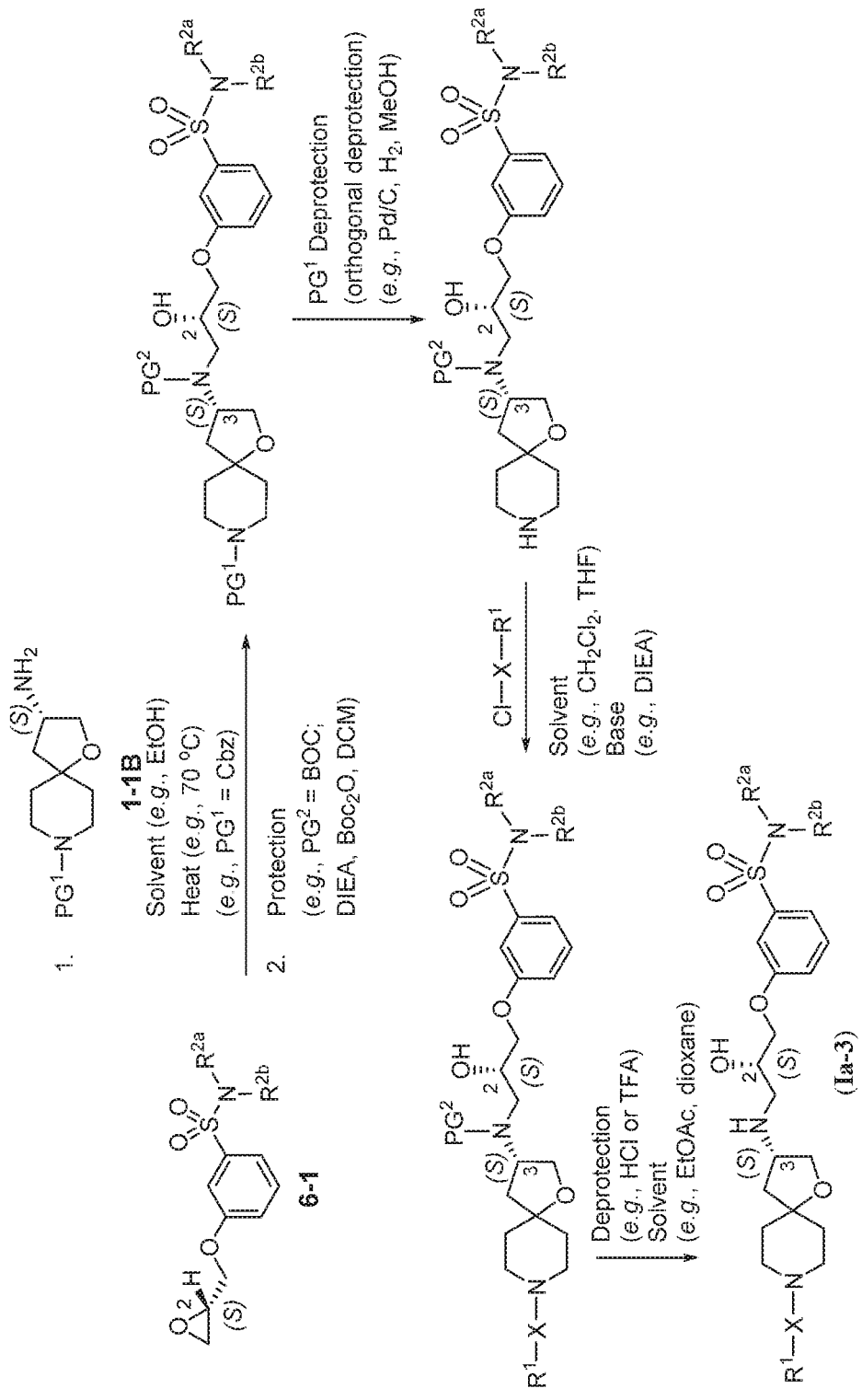
FIG. 8 shows a general synthetic scheme for the preparation of Compounds of Formula (Ia-3) utilizing the chiral oxirane Intermediate 6-1 and the chiral amine Intermediate 1-1B (see FIG. 2) where the Compounds of Formula (Ia-3) have the (S) stereochemistry for C(2) and the (S) stereochemistry for C(3).
Figure 9:
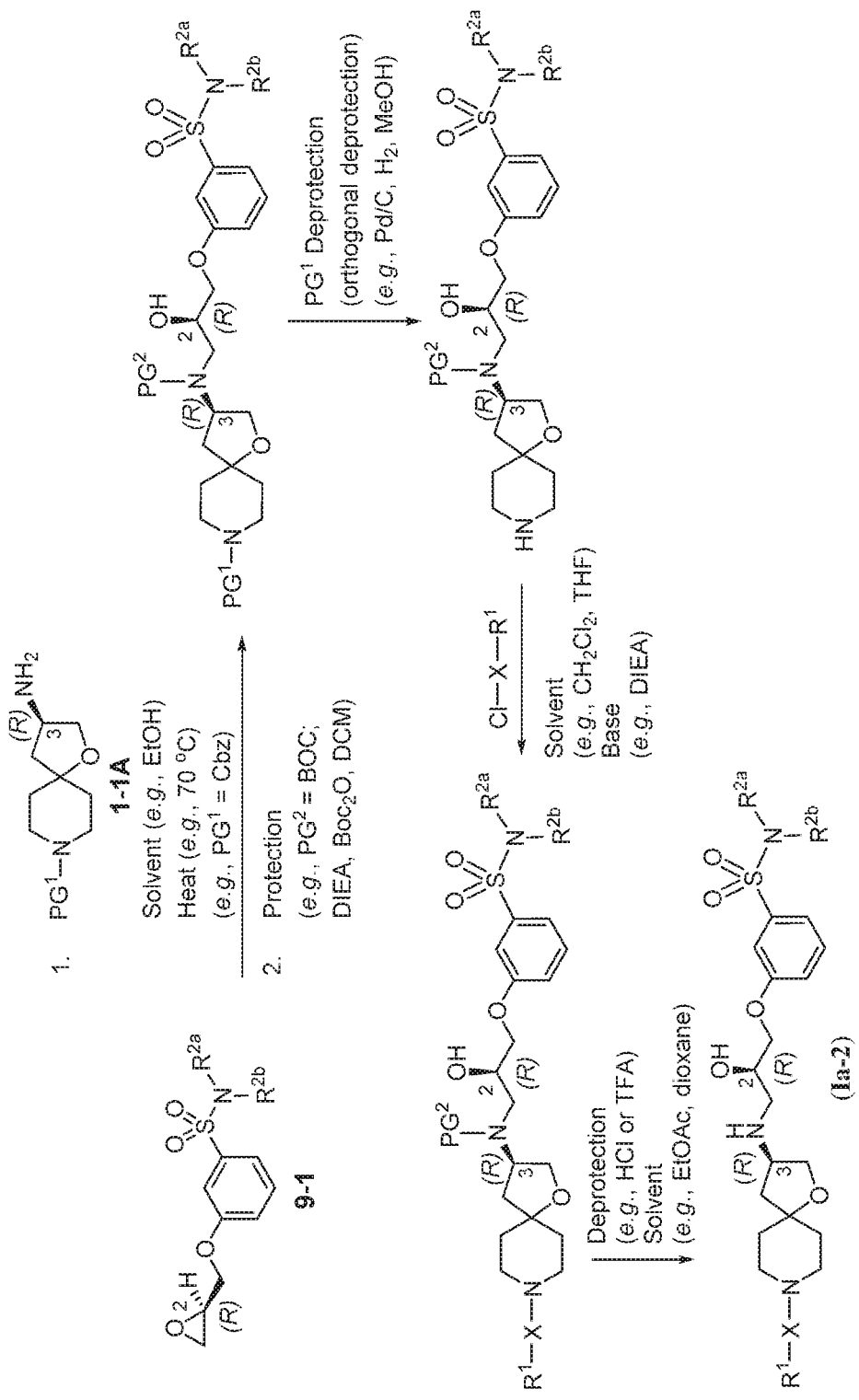
FIG. 9 shows a general synthetic scheme for the preparation of Compounds of Formula (Ia-2) utilizing the chiral oxirane Intermediate 9-1 and the chiral amine Intermediate 1-1A (see FIG. 2) where the Compounds of Formula (Ia-2) have the (R) stereochemistry for C(2) and the (R) stereochemistry for C(3).
Figure 10:
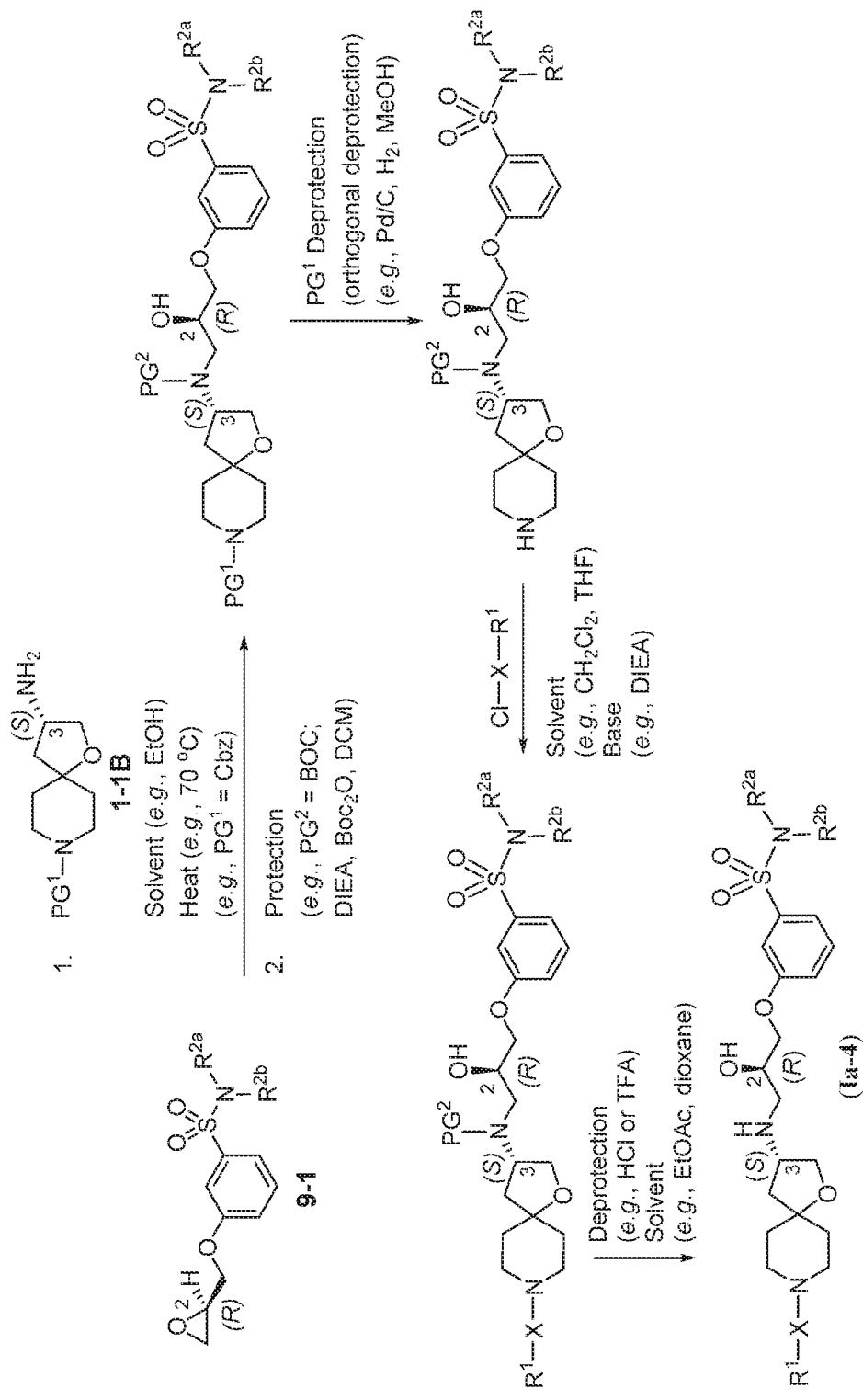
FIG. 10 shows a general synthetic scheme for the preparation of Compounds of Formula (Ia-4) utilizing the chiral oxirane Intermediate 9-1 and the chiral amine Intermediate 1-1B (see FIG. 2) where the Compounds of Formula (Ia-4) have the (R) stereochemistry for C(2) and the (S) stereochemistry for C(3).
Figure 11:
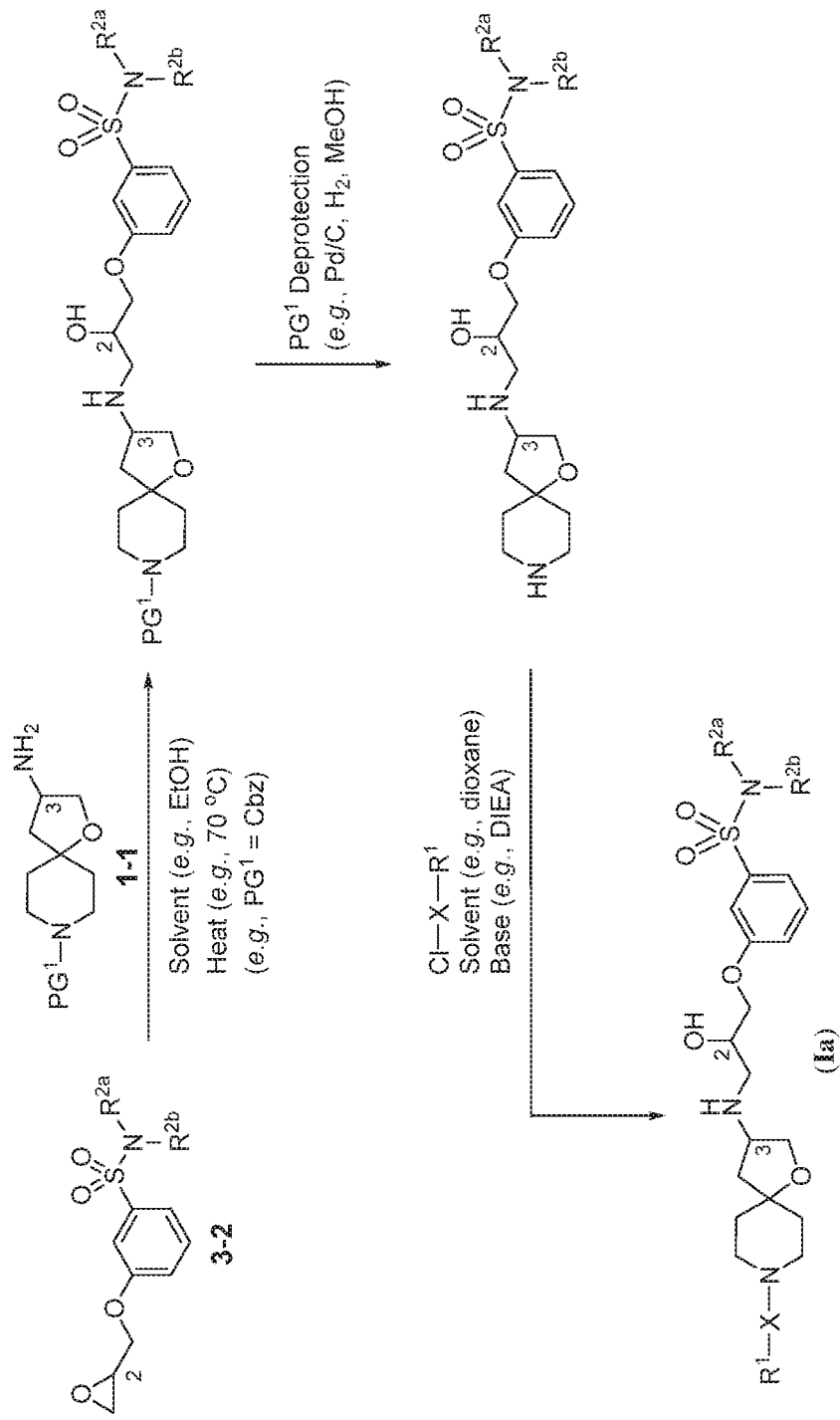
FIG. 11 shows a general synthetic scheme for the preparation of Compounds of Formula (Ia). It is understood that one or more chiral intermediates can be used in the scheme to provide chiral compounds of Formula (Ia). For example, chiral oxirane Intermediates 6-1 or 9-1 could replace Intermediate 3-2 and/or chiral amine Intermediates 1-1A or 1-1B could replace Intermediate 1-1 in the synthetic scheme shown in FIG. 11.
Figure 12:
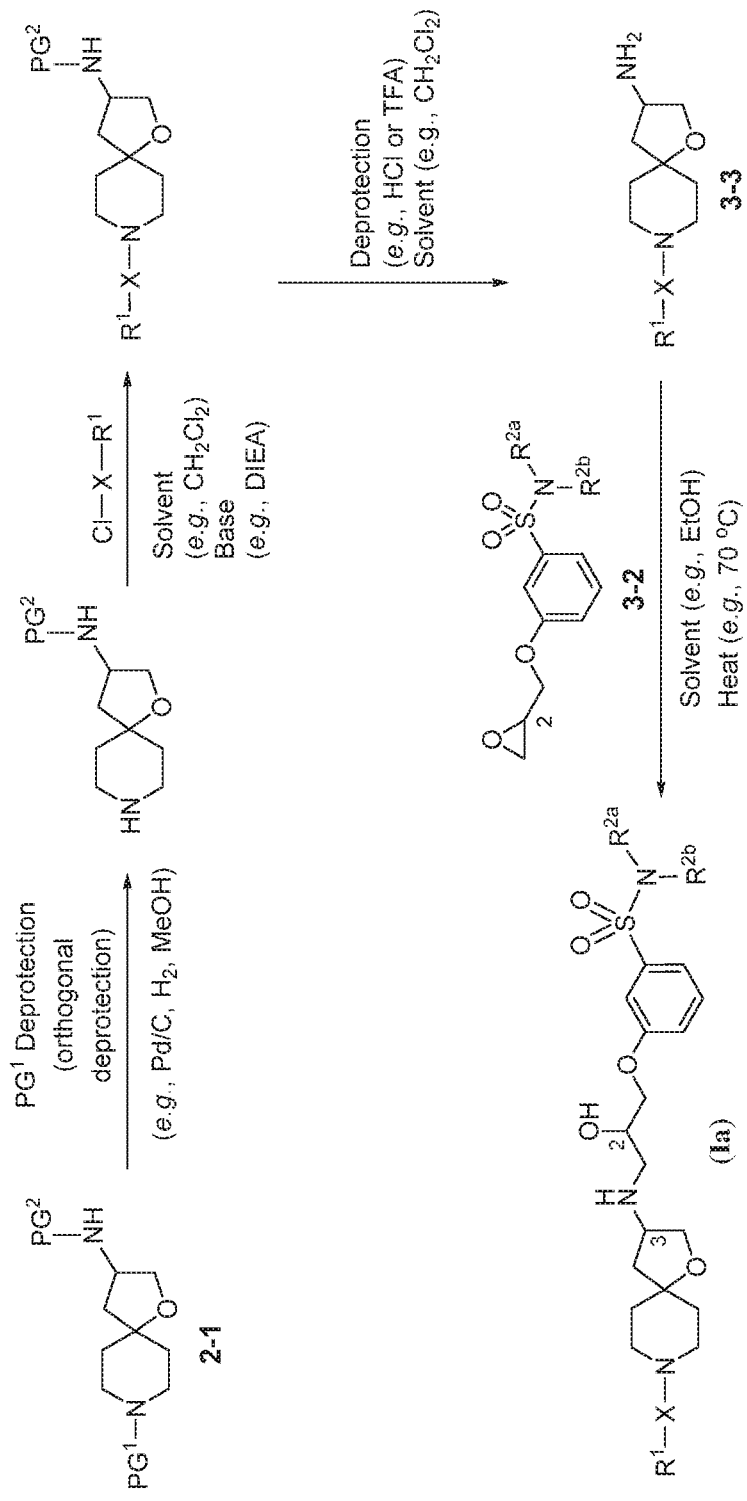
FIG. 12 shows a general synthetic scheme for the preparation of Compounds of Formula (Ia). It is understood that one or more chiral intermediates can be used in the scheme to provide chiral compounds of Formula (Ia). For example, chiral oxirane Intermediates 6-1 or 9-1 could replace Intermediate 3-2 and/or chiral amine Intermediates 2-1A or 2-1B could replace Intermediate 2-1 in the synthetic scheme shown in FIG. 12.
Figure 13:
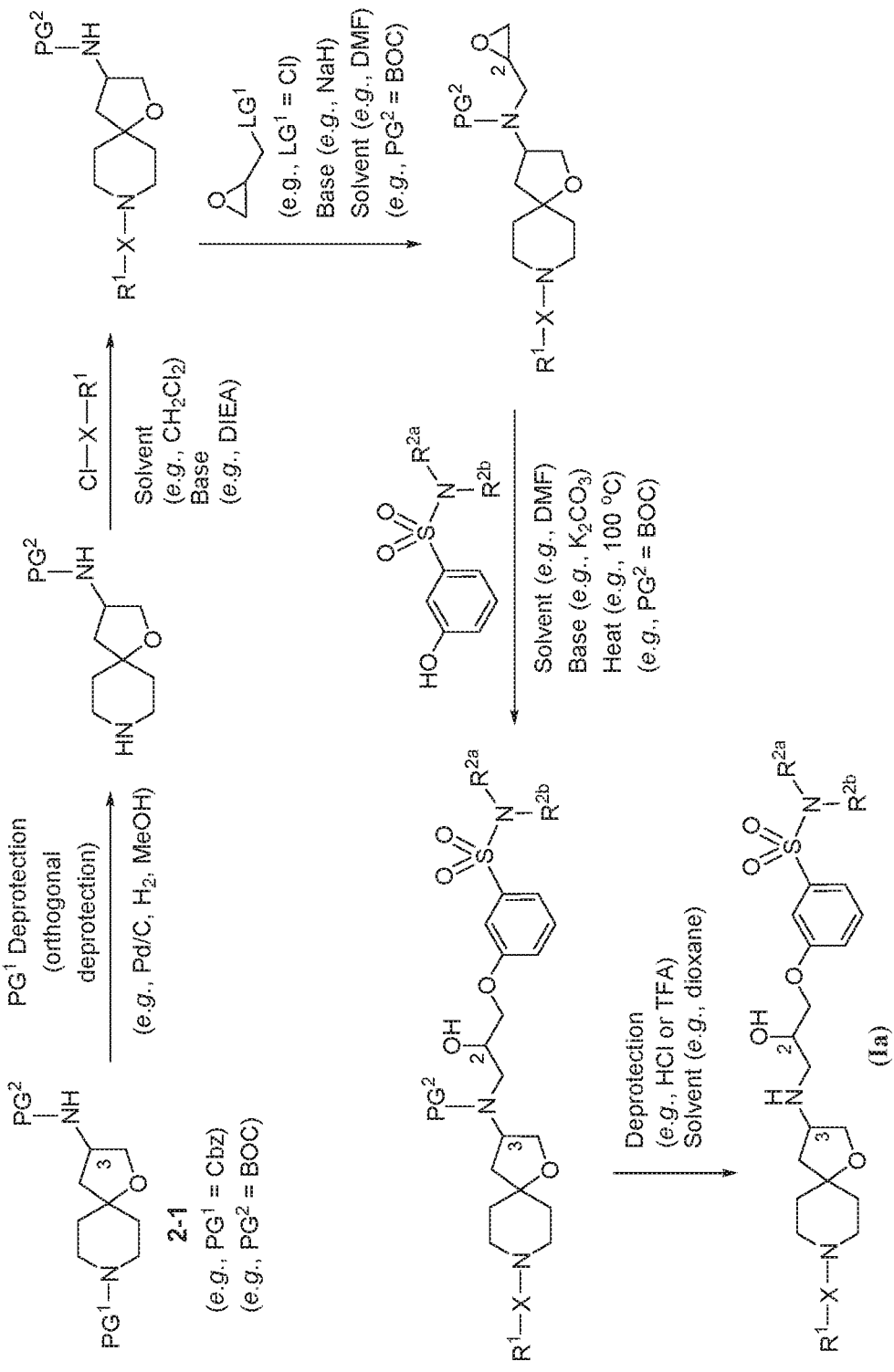
FIG. 13 shows a general synthetic scheme for the preparation of Compounds of Formula (Ia). It is understood that one or more chiral intermediates can be used in the scheme to provide chiral compounds of Formula (Ia). For example, chiral amine Intermediates 2-1A or 2-1B could replace Intermediate 2-1 in the synthetic scheme shown in FIG. 13.
Figure 14:
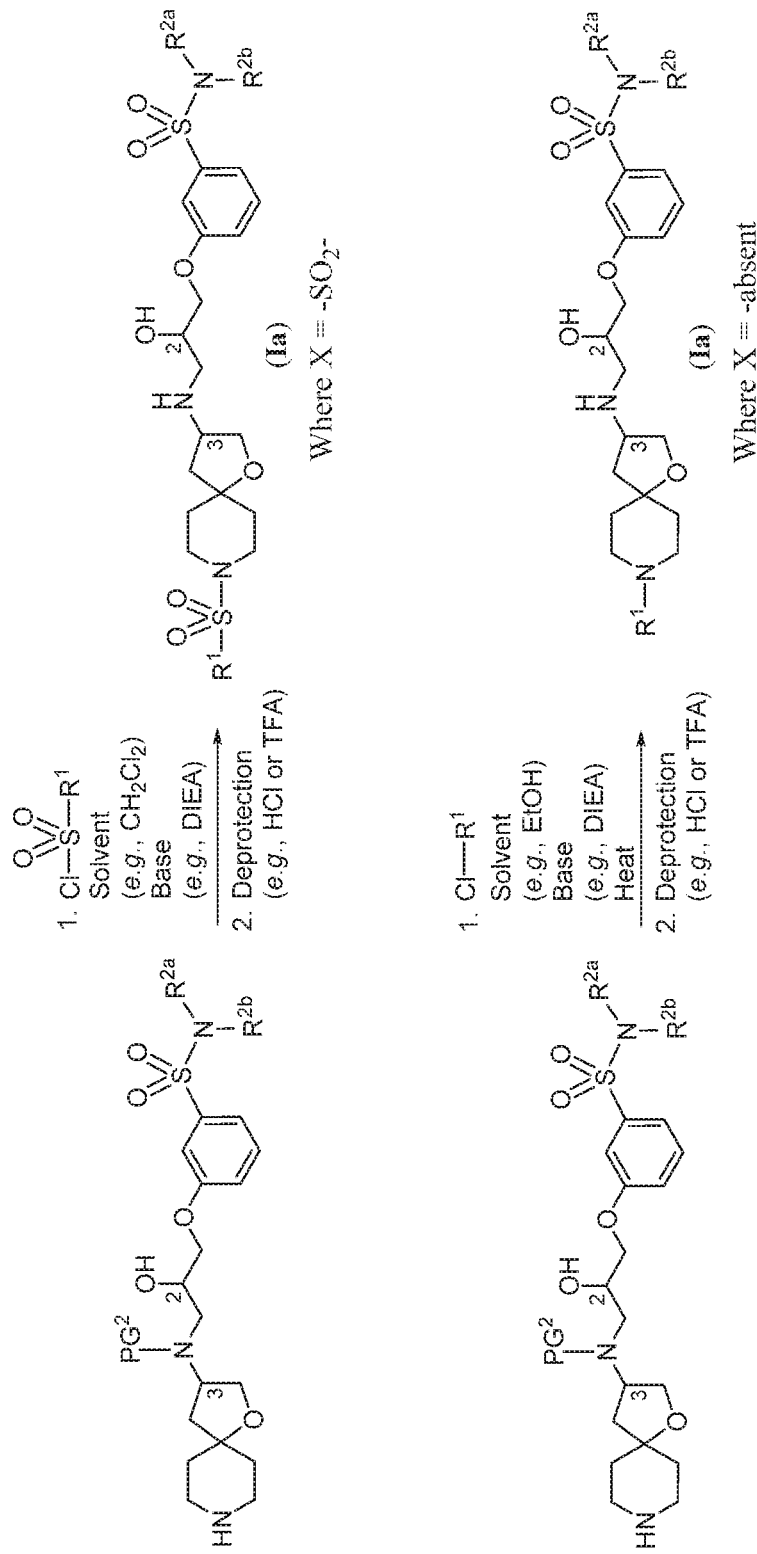
FIG. 14 shows general synthetic schemes for the preparation of Compounds of Formula (Ia) wherein X is —$SO_2$— and absent. It is understood that the intermediates can be chiral providing chiral compounds of Formula (Ia).
Figure 15:
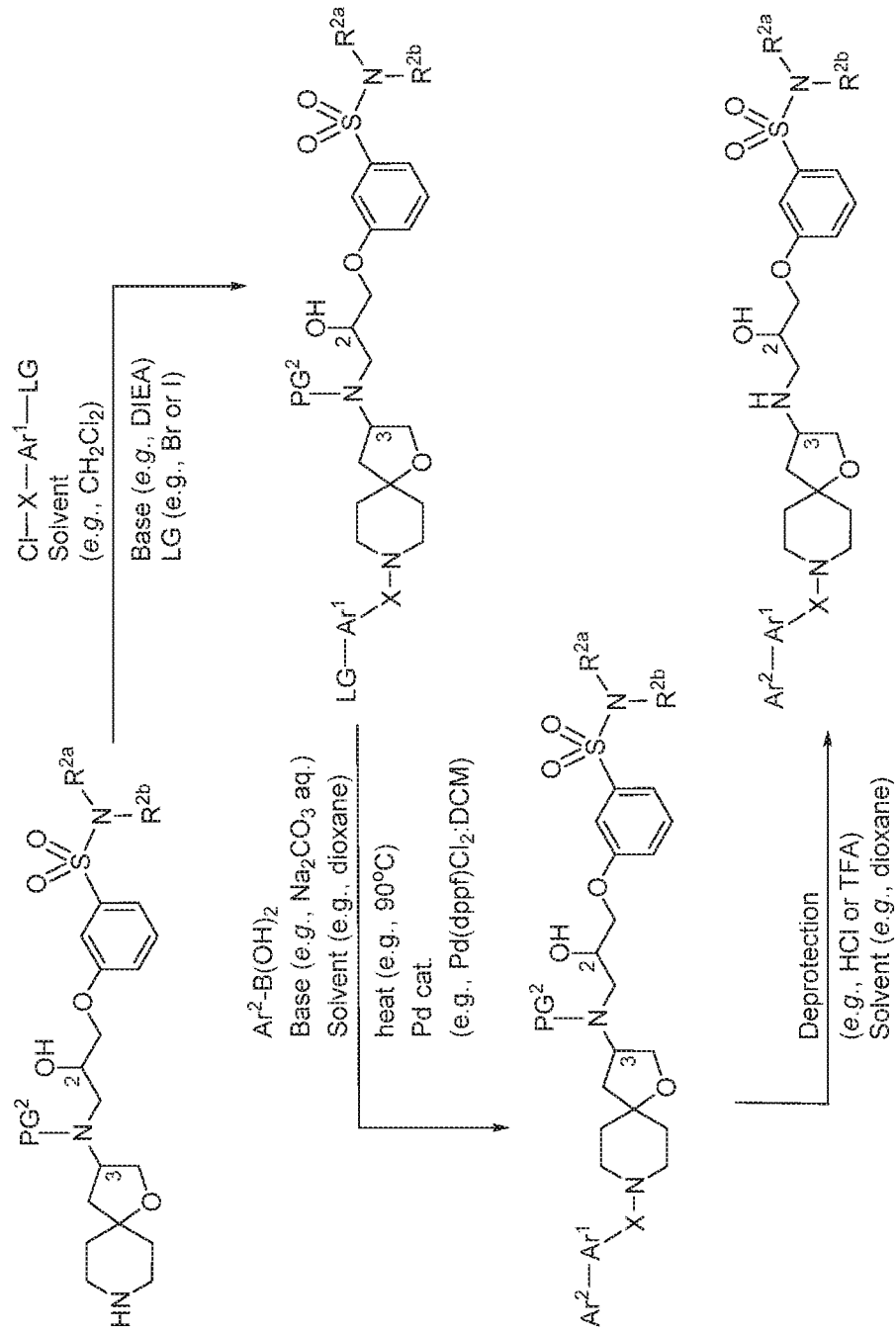
FIG. 15 shows a general synthetic scheme for the preparation of certain Compounds of Formula (Ia) wherein $R^1$ is —$Ar^1$—$Ar^2$. It is understood that $Ar^1$ and $Ar^2$ can be optionally substituted with one or more groups as described herein.
Figure 16:
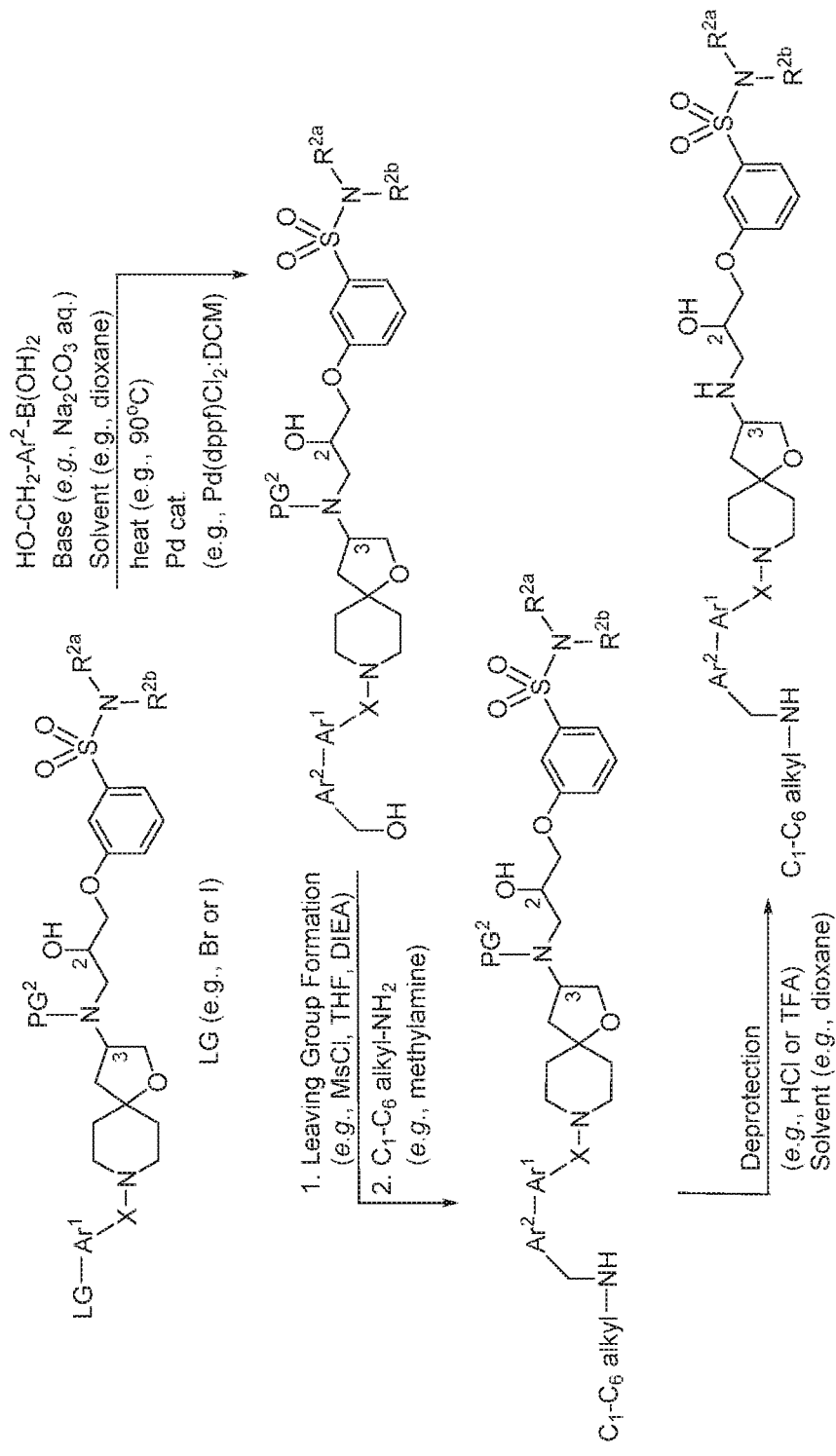
FIG. 16 shows a general synthetic scheme for the preparation of certain Compounds of Formula (Ia) wherein $R^1$ is —$Ar^1$—$Ar^2$, wherein $Ar^1$ and $Ar^2$ are independently aryl or heteroaryl as described herein provided that $Ar^1$ and $Ar^2$ are monocyclic. The scheme specifically shows $Ar^2$ substituted with at least —$CH_2OH$ or —$CH_2NH$—$C_1$-$C_6$ alkyl. It is understood that $Ar^1$ and $Ar^2$ (excluding the ring atom for $Ar^2$ that is bonded to either —$CH_2OH$ or —$CH_2NH$—$C_1$-$C_6$ alkyl) can be optionally substituted with one or more groups as described herein.
Figure 17A:
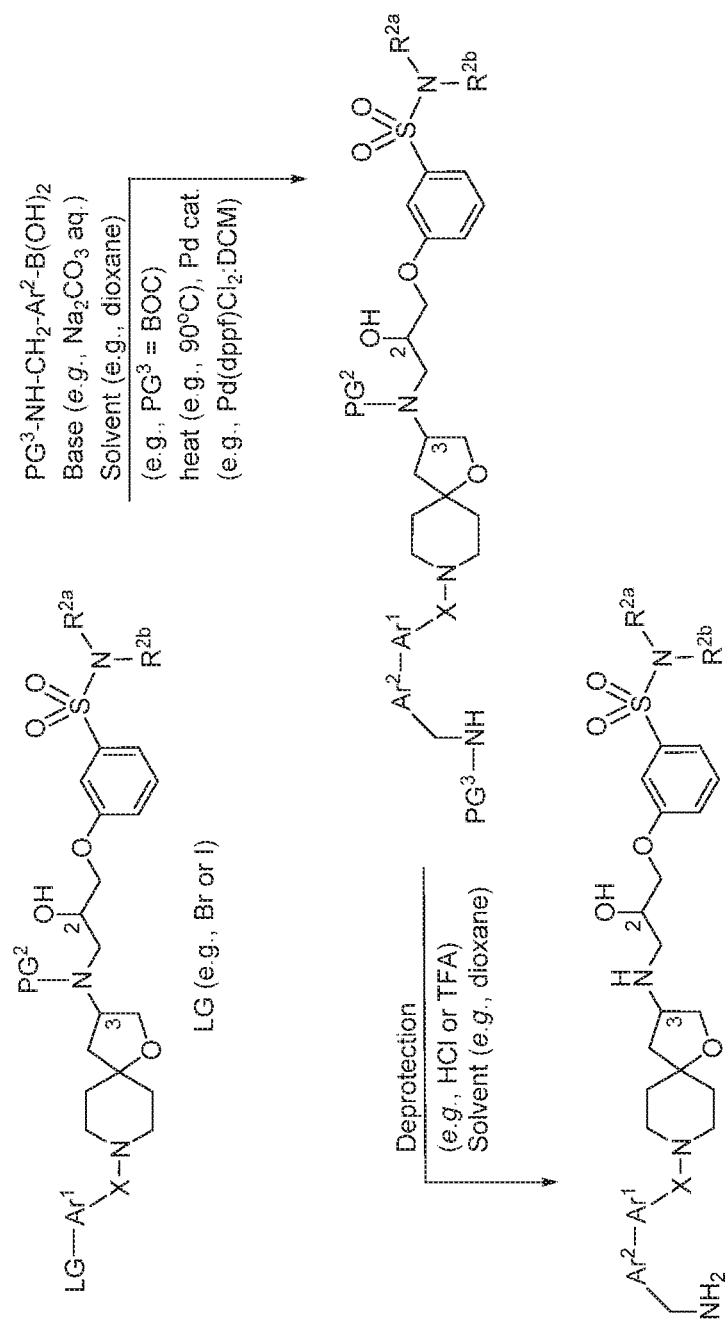
FIG. 17A shows a general synthetic scheme for the preparation of certain Compounds of Formula (Ia) wherein $R^1$ is —$Ar^1$—$Ar^2$, wherein $Ar^1$ and $Ar^2$ are independently aryl or heteroaryl as described herein provided that $Ar^1$ and $Ar^2$ are monocyclic. The scheme specifically shows $Ar^2$ substituted with at least —$CH_2NH_2$. It is understood that $Ar^1$ and $Ar^2$ (excluding the ring atom for $Ar^2$ that is bonded to —$CH_2NH_2$) can be optionally substituted with one or more groups as described herein.
Figure 17B:
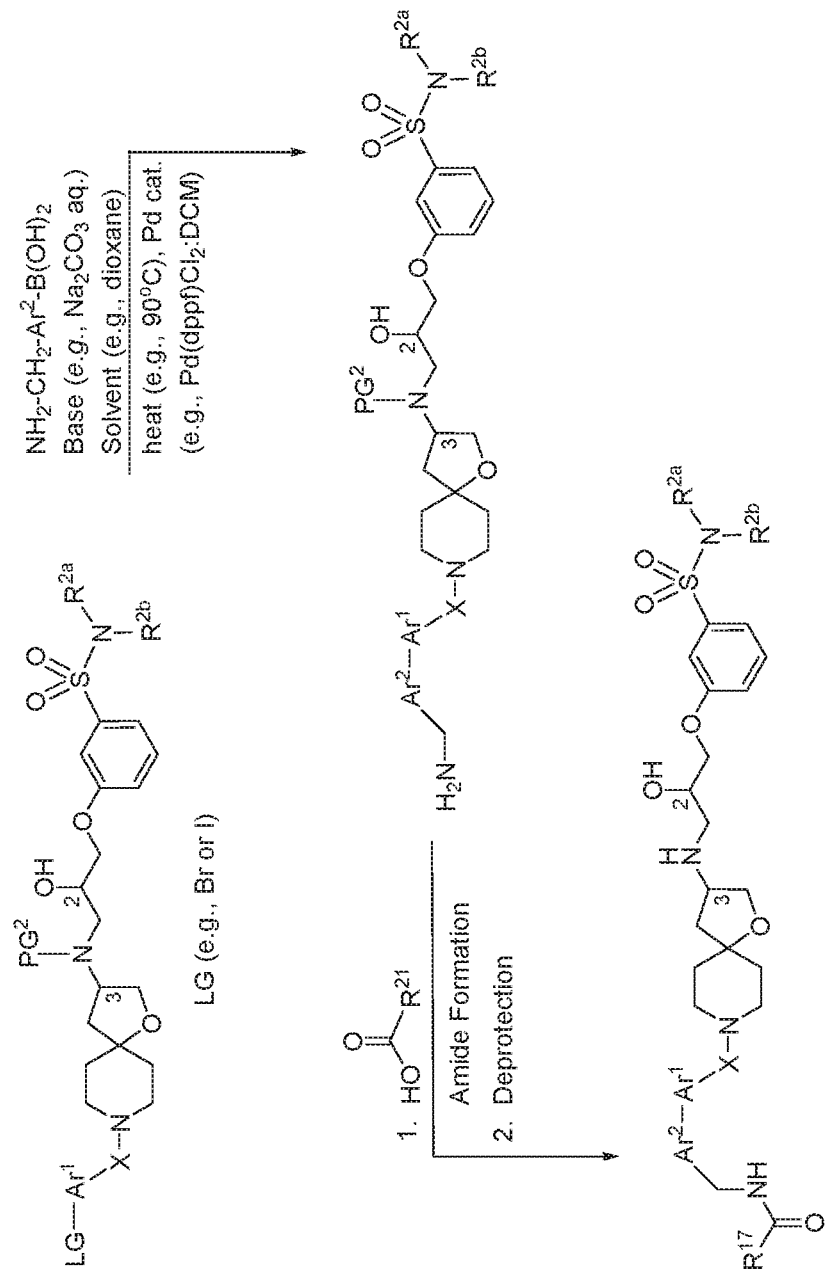
FIG. 17B shows a general synthetic scheme for the preparation of certain Compounds of Formula (Ia) wherein $R^1$ is —$Ar^1$—$Ar^2$. The scheme specifically shows $Ar^2$ substituted with at least —$CH_2NH_2$. The amine can optionally be coupled with a carboxylic acid to form an amide (i.e., —$CH_2NHC(=O)R^{17}$, wherein $R^{17}$ is $C_1$-$C_6$-alkyl). It is understood that $Ar^1$ and $Ar^2$ (excluding the ring atom for $Ar^2$ that is bonded to —$CH_2NH_2$ or —$CH_2NHC(=O)R^{17}$) can be optionally substituted with one or more groups as described herein.
Figure 18:
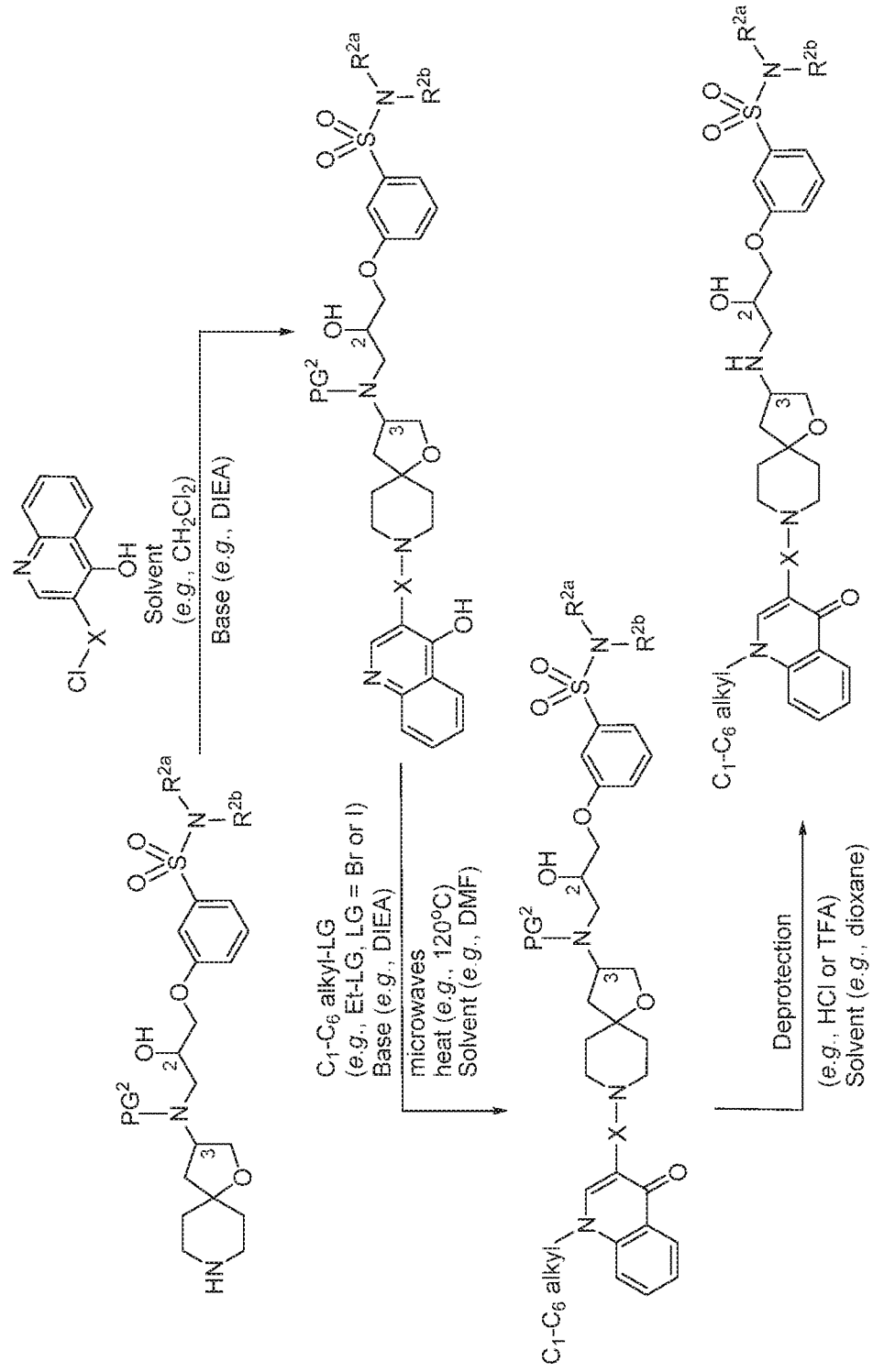
FIG. 18 shows a general synthetic scheme for the preparation of certain Compounds of Formula (Ia) wherein $R^1$ is 4-hydroxy-quinolin-3-yl (or a tautomer related thereto, such as, 4-oxo-1,4-dihydroquinolin-3-yl) or 1-($C_1$-$C_6$-alkyl)-4-oxo-1,4-dihydroquinolin-3-yl, such as, 1-ethyl-4-oxo-1,4-dihydroquinolin-3-yl. It is understood that the quinoline-3-yl ring (or the tautomer related thereto, such as, 4-oxo-1,4-dihydroquinolin-3-yl) can be optionally substituted with one or more substituents as described herein.
Figure 19:
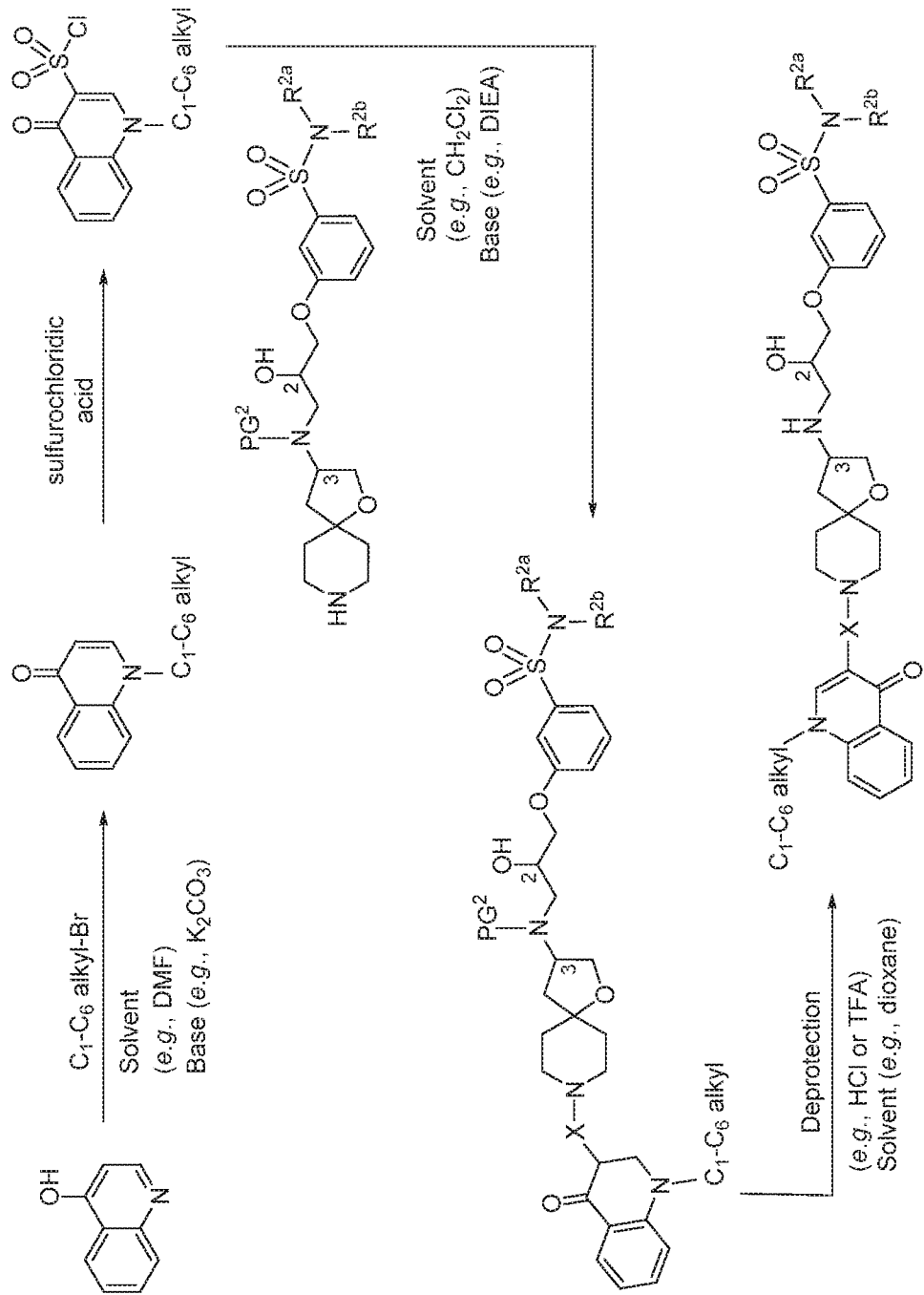
FIG. 19 shows a general synthetic scheme for the preparation of certain Compounds of Formula (Ia) wherein $R^1$ is 1-($C_1$-$C_6$-alkyl)-4-oxo-1,4-dihydroquinolin-3-yl, such as, 1-ethyl-4-oxo-1,4-dihydroquinolin-3-yl. It is understood that the 1,4-dihydroquinolin-3-yl can be optionally substituted with one or more substituents as described herein.

For clarity and consistency, the following definitions will be used throughout this patent document.

As used herein, "administering" refers to providing a compound of the invention or other therapy, remedy or treatment to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories. A health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. When the compound is administered to the individual, the body is transformed by the compound in some way. When a compound of the invention is provided in combination with one or more other agents, "administration" is understood to include the compound and other agents are administered at the same time or at different times. When the agents of a combination are administered at the same time, they can be administered together in a single composition or they can be administered separately.

The term "antagonist" as used herein" refers to a moiety that can competitively bind to the $β_3$-adrenergic receptor as an agonist (for example, the endogenous ligand) but does not activate or substantially reduces the intracellular response compared to an agonist, and can thereby inhibit the intracellular responses by an agonist or partial agonist. An "antagonist" does not diminish the baseline intracellular response, or does so to a negligible extent, in the absence of an agonist or partial agonist.

The term "composition" refers to a compound or crystalline form thereof, including but not limited to, salts, solvates, and hydrates of a compound of the present invention, in combination with at least one additional component, such as, a composition obtained/prepared during synthesis, pre-formulation, in-process testing (i.e., TLC, HPLC, NMR samples), and the like.

The term "hydrate" as used herein means a compound of the invention or a salt thereof that further includes a stoichiometric or non-stoichiometric amount of water bound by non-covalent intermolecular forces.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit, or ameliorate the disease, condition, or disorder.

The term "individual" refers to any animal, including mammals, such as, mice, rats, other rodents, rabbits, dogs, cats, swine, cattle, sheep, horses, primates, and humans. In some embodiment "individual" refers to humans.

The term "pharmaceutical composition" refers to a specific composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The phrase "pharmaceutically acceptable salts, solvates, and hydrates" when referring to a compound/compounds as described herein embraces pharmaceutically acceptable solvates and/or hydrates of the compound/compounds, pharmaceutically acceptable salts of the compound/compounds, as well as pharmaceutically acceptable solvates and/or hydrates of pharmaceutically acceptable salts of the compound/compounds. It is also understood that when the phrase "pharmaceutically acceptable solvates and hydrates" or the phrase "pharmaceutically acceptable solvate or hydrate" is used when referring to a compound/compounds as described herein that are salts, it embraces pharmaceutically acceptable solvates and/or hydrates of such salts. It is also understood by a person of ordinary skill in the art that hydrates are a subgenus of solvates.

The term "prescribing" refers to order, authorize, or recommend the use of a drug or other therapy, remedy, or treatment. In some embodiments, a health care provider orally advises, recommends, or authorizes the use of a compound, dosage regimen, or other treatment to an individual. The health care provider may or may not provide a written prescription for the compound, dosage regimen, or treatment. Further, the health care provider may or may not provide the compound or treatment to the individual. For example, the health care provider can advise the individual where to obtain the compound without providing the compound. In some embodiments, a health care provider can provide a written prescription for the compound, dosage regimen, or treatment to the individual. A prescription can be written on paper or recorded on electronic media. In addition, a prescription can be called in (oral) or faxed in (written) to a pharmacy or a dispensary. In some embodiments, a sample of the compound or treatment is given to the individual. As used herein, giving a sample of a compound constitutes an implicit prescription for the compound. Different health care systems around the world use different methods for prescribing and administering compounds or treatments, and these methods are encompassed by the disclosure herein.

A health care provider can include, for example, a physician, nurse, nurse practitioner, or other health care professional who can prescribe or administer compounds (drugs) for the disorders disclosed herein. In addition, a health care provider can include anyone who can recommend, prescribe, administer, or prevent an individual from receiving a compound or drug, including, for example, an insurance provider.

The terms "prevent," "preventing," and "prevention" refer to the elimination or reduction of the occurrence or onset of one or more symptoms associated with a particular disorder. For example, the terms "prevent," "preventing," and "prevention" can refer to the administration of therapy on a prophylactic or preventative basis to an individual who may ultimately manifest at least one symptom of a disorder but who has not yet done so. Such individuals can be identified on the basis of risk factors that are known to correlate with the subsequent occurrence of the disease, such as the presence of a biomarker. Alternatively, prevention therapy can be administered as a prophylactic measure without prior identification of a risk factor. Delaying the onset of the at least one episode and/or symptom of a disorder can also be considered prevention or prophylaxis.

The term "solvate" as used herein means a compound of the invention or a salt thereof that further includes a stoichiometric or non-stoichiometric amount of a solvent bound by non-covalent intermolecular forces. Preferred solvents are volatile, non-toxic, and/or acceptable for administration to humans in trace amounts.

The terms "treat," "treating," and "treatment" refer to the administration of therapy to an individual who already manifests, or who has previously manifested, at least one symptom of a disease, disorder, condition, dependence, or behavior. For example, "treating" can include any of the following with respect to a disease, disorder, condition, dependence, or behavior: alleviating, abating, ameliorating, improving, inhibiting (e.g., arresting the development), relieving, or causing regression. "Treating" can also include treating the symptoms, preventing additional symptoms, preventing the underlying physiological causes of the symptoms, or stopping the symptoms (either prophylactically and/or therapeutically) of a disease, disorder, condition, dependence, or behavior. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder.

The term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which can include one or more of the following:

(1) preventing the disorder, for example, preventing a disease, condition, or disorder in an individual who may be predisposed to the disease, condition, or disorder but does not yet experience or display the relevant pathology or symptomatology;

(2) inhibiting the disorder, for example, inhibiting a disease, condition, or disorder in an individual who is experiencing or displaying the relevant pathology or symptomatology (i.e., arresting further development of the pathology and/or symptomatology); and (3) ameliorating the disorder, for example, ameliorating a disease, condition, or disorder in an individual who is experiencing or displaying the relevant pathology or symptomatology (i.e., reversing the pathology and/or symptomatology).

Chemical Group, Moiety or Radical

The term "$C_1$-$C_6$ alkylene" refers to a radical consisting of a straight or branched, saturated aliphatic, divalent radical having 1 to 6 carbon atoms. Some embodiments contain 1 to 5 carbons (i.e., "$C_1$-$C_5$ alkylene"). Some embodiments contain 1 to 4 carbons (i.e., "$C_1$-$C_6$ alkylene"). Some embodiments contain 1 to 3 carbons (i.e., "$C_1$-$C_3$ alkylene"). Some embodiments contain 1 or 2 carbons (i.e., "$C_1$-$C_2$ alkylene"). Some embodiments contain 1 carbon atom (i.e., —$CH_2$—). Examples include, methylene (i.e., —$CH_2$—), ethylene (i.e., —$CH_2CH_2$—), n-propylene (i.e., —$CH_2CH_2CH_2$—), propane-1,1-diyl [i.e., —$CH(CH_2CH_3)$—], propane-1,2-diyl [i.e., —$CH_2CH(CH_3)$—], n-butylene (i.e., —$CH_2CH_2CH_2CH_2$—), n-pentylene (i.e., —$CH_2CH_2CH_2CH_2CH_2$—), n-hexylene, and the like.

The term "$C_1$-$C_6$ alkoxy" refers to a radical consisting of a $C_1$-$C_6$ alkyl group bonded directly to an oxygen atom, wherein $C_1$-$C_6$ alkyl has the same definition as found herein. Some embodiments contain 1 to 5 carbons (i.e., $C_1$-$C_5$ alkoxy). Some embodiments contain 1 to 4 carbons (i.e., $C_1$-$C_4$ alkoxy). Some embodiments contain 1 to 3 carbons (i.e., $C_1$-$C_3$ alkoxy). Some embodiments contain 1 or 2 carbons. Examples include methoxy, ethoxy, n-propoxy, isopropoxy, n-butoxy, t-butoxy, isobutoxy, s-butoxy, and the like.

The term "$C_1$-$C_6$ alkoxycarbonyl" refers to a radical consisting of a single $C_1$-$C_6$ alkoxy group bonded to the carbon of a carbonyl group, wherein $C_1$-$C_6$ alkoxy has the same definition as found herein. The alkoxycarbonyl group may be represented by the following:

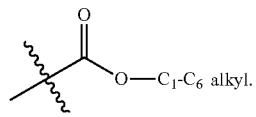

The term "$C_1$-$C_7$ alkyl" refers to a straight or branched carbon radical containing 1 to 7 carbons. Some embodiments are 1 to 6 carbons (i.e., $C_1$-$C_6$ alkyl), some embodiments are 1 to 5 carbons (i.e., $C_1$-$C_5$ alkyl), some embodiments are 1 to 4 carbons (i.e., $C_1$-$C_4$ alkyl), some embodiments are 1 to 3 carbons (i.e., $C_1$-$C_3$ alkyl), and some embodiments are 1 or 2 carbons. Examples of include methyl, ethyl, n-propyl, isopropyl, n-butyl, sec-butyl, isobutyl, tert-butyl, pentyl, isopentyl, tert-pentyl, neo-pentyl, 1-methylbutyl [i.e., —$CH(CH_3)CH_2CH_2CH_3$], 2-methylbutyl [i.e., —$CH_2CH(CH_3)CH_2CH_3$], n-hexyl, n-heptyl, and the like.

The term "$C_1$-$C_6$ alkylamino" refers to a radical consisting of one $C_1$-$C_6$ alkyl group bonded to an NH group, wherein $C_1$-$C_6$ alkyl has the same meaning as described herein. Some embodiments are "$C_1$-$C_2$ alkylamino." Some examples include methylamino, ethylamino, n-propylamino, isopropylamino, n-butylamino, s-butylamino, isobutylamino, t-butylamino, and the like.

The term "$C_1$-$C_6$ alkylcarboxamide" refers to a radical consisting of a single $C_1$-$C_6$ alkyl group bonded to either the carbon or the nitrogen of an amide group, wherein $C_1$-$C_6$ alkyl has the same definition as found herein. The $C_1$-$C_6$ alkylcarboxamido group may be represented by the following:

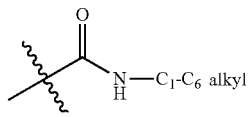

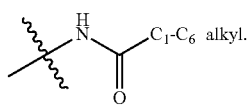

Examples include, N-methylcarboxamide, N-ethylcarboxamide, N-n-propylcarboxamide, N-isopropylcarboxamide, N-n-butylcarboxamide, N-s-butylcarboxamide, N-isobutylcarboxamide, N-t-butylcarboxamide, and the like.

The term "$C_1$-$C_6$-alkylene-aryl" refers to a radical consisting of an aryl group bonded to a $C_1$-$C_6$ alkylene radical, wherein aryl and $C_1$-$C_6$ alkylene have the same definitions as described herein. Examples include benzyl (i.e., —$CH_2$-phenyl), phenethyl (i.e., —$CH_2CH_2$-phenyl), and the like.

The term "$C_1$-$C_6$-alkylene-heteroaryl" refers to a radical consisting of a heteroaryl group bonded to a $C_1$-$C_6$ alkylene radical, wherein heteroaryl and $C_1$-$C_6$ alkylene have the same definitions as described herein. Examples include pyridin-4-ylmethyl [i.e., —$CH_2$-(pyridin-4-yl)], pyridin-3-ylmethyl [i.e., —$CH_2$-(pyridin-3-yl)], 2-(pyridin-4-yl)ethyl [i.e., —$CH_2CH_2$-(pyridin-4-yl)], 2-(pyridin-2-yl)ethyl [i.e., —$CH_2CH_2$-(pyridin-2-yl)], and the like;

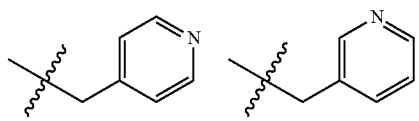

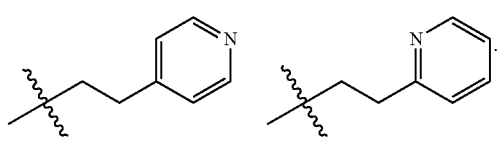

The term "$C_1$-$C_6$ alkylenehydroxyl" refers to a radical consisting of a hydroxyl group bonded to a $C_1$-$C_6$ alkylene radical, wherein hydroxyl and $C_1$-$C_6$ alkylene have the same definitions as described herein. Examples include hydroxymethyl, 2-hydroxyethyl, 1-hydroxyethyl, and the like.

The term "$C_1$-$C_6$ alkylsulfonamido" refers to a radical consisting of a single $C_1$-$C_6$ alkyl group bonded to either the sulfur or the nitrogen of an —$SO_2$—NH— group, wherein $C_1$-$C_6$ alkyl has the same definition as found herein and the $C_1$-$C_6$ alkylsulfonamido group may be represented by the following:

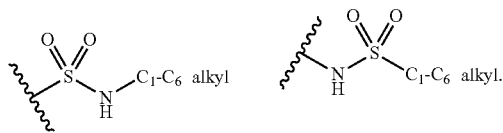

Examples include, —$NHSO_2CH_3$, —$NHSO_2CH_2CH_3$, —$NHSO_2CH_2CH_2CH_3$, —$SO_2NHCH_3$, —$SO_2NHCH_2CH_3$, —$SO_2NHCH_2CH_2CH_3$, and the like.

The term "$C_1$-$C_6$ alkylsulfonyl" refers to a radical consisting a $C_1$-$C_6$ alkyl radical bonded to the sulfur of a sulfone radical of the formula: —S(=O)$_2$— wherein $C_1$-$C_6$ alkyl has the same definition as described herein. Examples include methylsulfonyl, ethylsulfonyl, n-propylsulfonyl, isopropylsulfonyl, n-butylsulfonyl, sec-butylsulfonyl, isobutylsulfonyl, t-butylsulfonyl, and the like.

The term "amino" refers to the group —$NH_2$.

The term "aryl" refers to a ring system containing 6 to 12 carbon atoms that may contain a single ring, two fused rings, or two rings bonded by a single bond (i.e., biphenyl) and wherein at least one ring is aromatic. Examples include phenyl, biphenyl, indanyl, tetrahydronaphthalenyl, naphthalenyl, and the like. Examples of biphenyl groups include: [1,1'-biphenyl]-2-yl (i.e., biphenyl-2-yl), [1,1'-biphenyl]-3-yl (i.e., biphenyl-3-yl), or [1,1'-biphenyl]-4-yl (i.e., biphenyl-4-yl) with the following structures respectively:

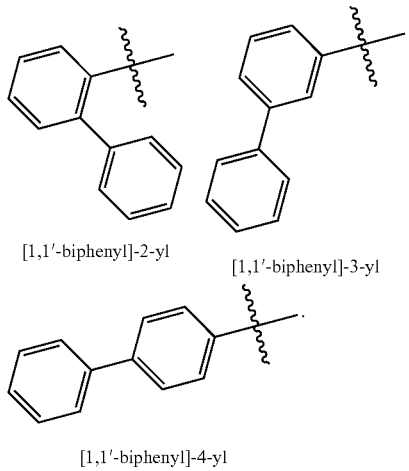

[1,1'-biphenyl]-2-yl
[1,1'-biphenyl]-3-yl
[1,1'-biphenyl]-4-yl

When a substituent is present on the aryl ring, the substituent can be bonded at any available ring carbon.

The term "aryloxy" refers to a radical consisting an aryl radical bonded directly to an oxygen atom, wherein aryl has the same definition as found herein. Examples include phenoxy, naphthalen-2-yloxy, [1,1'-biphenyl]-4-yloxy, and the like.

The term "arylsulfonyl" refers to a radical consisting an aryl radical bonded to the sulfur of a sulfone radical of the formula: —S(=O)$_2$— wherein aryl has the same definition as described herein. Examples include phenylsulfonyl, naphthalen-2-ylsulfonyl, and the like.

The term "carbamimidoyl" refers to the following group:

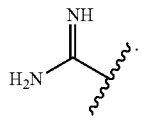

The term "carboxamide" refers to the group —$CONH_2$.

The term "carboxy" or "carboxyl" refers to the group —$CO_2H$; also referred to as a carboxylic acid group.

The term "cyano" refers to the group —CN.

The term "$C_3$-$C_7$ cycloalkyl" refers to a radical consisting of a saturated ring radical containing 3 to 7 carbons. Some embodiments contain 3 to 6 carbons (i.e., $C_3$-$C_6$ cycloalkyl). Some embodiments contain 3 to 5 carbons (i.e., $C_3$-$C_5$ cycloalkyl). Some embodiments contain 5 to 7 carbons (i.e., $C_5$-$C_7$ cycloalkyl). Some embodiments contain 3 to 4 carbons (i.e., $C_3$-$C_4$ cycloalkyl). Examples include cyclopropyl, cyclobutyl, cyclopentyl, cyclohexyl, and cycloheptyl.

The term "$C_2$-$C_8$ dialkylamino" refers to a radical consisting an amino group substituted with two alkyl groups, the alkyl groups can be the same or different provided that two alkyl groups do not exceed a total of 8 carbon atoms between the two alkyl groups. Some embodiments are $C_2$-$C_6$ dialkylamino. Some embodiments are $C_2$-$C_4$ dialkylamino. Some examples include dimethylamino, methylethylamino, diethylamino, methylpropylamino, methylbutylamino, methylpentylamino, methylisopropylamino, ethylpropylamino, ethylisopropylamino, dipropylamino, propylisopropylamino, and the like.

The term "$C_2$-$C_8$ dialkylsulfamoyl" refers to a sulfonamide group where the nitrogen is substituted with two alkyl groups, the alkyl groups can be the same or different provided that two alkyl groups do not exceed a total of 8 carbon atoms between the two alkyl groups. The $C_1$-$C_6$ alkyl has the same definition as described herein. Examples include, —$SO_2N(CH_3)_2$, —$SO_2N(CH_3)(CH_2CH_3)$, —$SO_2N(CH_3)(CH_2CH_2CH_3)$, —$SO_2N(CH_2CH_3)_2$, —$SO_2N(CH_2CH_3)(CH_2CH_2CH_3)$, and the like.

The term "$C_1$-$C_6$ haloalkoxy" refers to a radical consisting a $C_1$-$C_6$ haloalkyl group bonded directly to an oxygen atom, wherein $C_1$-$C_6$ haloalkyl has the same definition as found herein. Some embodiments contain 1 to 5 carbons (i.e., $C_1$-$C_5$ haloalkoxy). Some embodiments contain 1 to 4 carbons (i.e., $C_1$-$C_4$ haloalkoxy). Some embodiments contain 1 to 3 carbons (i.e., $C_1$-$C_3$ haloalkoxy). Some embodiments contain 1 or 2 carbons. Examples include fluoromethoxy, difluoromethoxy, trifluoromethoxy, chlorodifluoromethoxy, 1-fluoroethoxy, 2,2,2-trifluoroethoxy, pentafluoroethoxy, 4,4,4-trifluorobutoxy, and the like.

The term "$C_1$-$C_6$ haloalkyl" refers to a radical consisting a $C_1$-$C_6$ alkyl group substituted with one or more halogens, wherein $C_1$-$C_6$ alkyl and halogen has the same definitions as described herein. The $C_1$-$C_6$ haloalkyl may be fully substituted in which case it can be represented by the formula $C_nL_{2n+1}$, wherein L is a halogen and "n" is 1, 2, 3, 4, 5, or 6. When more than one halogen is present then they may be the same or different and selected from: fluorine, chlorine, bromine, and iodine. In some embodiments, haloalkyl contains 1 to 5 carbons (i.e., $C_1$-$C_5$ haloalkyl). In some embodiments, haloalkyl contains 1 to 4 carbons (i.e., $C_1$-$C_4$ haloalkyl). In some embodiments, haloalkyl contains 1 to 3 carbons (i.e., $C_1$-$C_3$ haloalkyl). In some embodiments, haloalkyl contains 1 or 2 carbons. Examples of haloalkyl groups include fluoromethyl, difluoromethyl, trifluoromethyl, chlorodifluoromethyl, 1-fluoroethyl, 2,2,2-trifluoroethyl, pentafluoroethyl, 4,4,4-trifluorobutyl, and the like.

The term "$C_1$-$C_6$ haloalkylamino" refers to a radical consisting of one $C_1$-$C_6$ haloalkyl group bonded to an NH group, wherein $C_1$-$C_6$ haloalkyl has the same meaning as described herein. Some embodiments are "$C_1$-$C_2$ haloalkylamino." Some examples include 2-fluoroethylamino, 2,2,2-trifluoroethylamino, (1,1,1-trifluoropropan-2-yl)amino, 3,3,3-trifluoropropylamino, 2,2,2-trifluoropropylamino, and the like.

The term "halogen" refers to fluoro, chloro, bromo, or iodo group. In some embodiments, halogen is fluoro, chloro, or bromo. In some embodiments, halogen is fluoro or chloro. In some embodiments, halogen is fluoro.

The term "heteroaryl" refers to a ring system containing 5 to 18 ring atoms, that may contain a single ring, two fused rings, two rings bonded by a single bond, three rings each bonded by a single bond, three fused rings, two fused rings and a single ring bonded by a single bond, wherein at least one ring atom is a heteroatom, selected from, O, S, N, and NH, and at least one ring is aromatic. It is understood that in the context of this definition fused rings include two rings that share either one common ring atom (i.e., spiro) or two common ring atoms. Example of two rings that share one common ring atom and two common ring atoms including the following respectively:

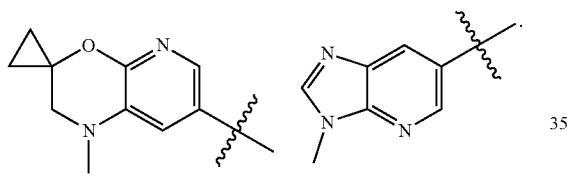

When a heteroaryl group is substituted with an oxo group, the oxo group can be on any available ring atom, for example, a ring carbon to form a carbonyl group, a ring nitrogen to form an N-oxide, and a ring sulfur to form either a sulfoxide (i.e., —S(=O)—) or a sulfone (i.e., —S(=O)$_2$—). Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, triazinyl, and the like. Some embodiments contain 8 to 14 ring atoms for example quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran, 2,3-dihydrobenzofuranyl, 4H-benzo[1,3]dioxinyl, 3,4-dihydro-1H-isoquinolinyl, 1,4,6,7-tetrahydroimidazo[4,5-c]pyridinyl, 7,8-dihydro-5H-[1,6]naphthyridinyl, 5,6-dihydro-8H-[1,2,4]triazolo[4,3-a]pyrazinyl, benzo[1,3]dioxolyl, pyrazolo[1,5-a]pyrimidinyl, 1,2,3,4-tetrahydroquinolinyl, and the like. When the "heteroaryl" is a ring system containing two rings bonded by a single bond it is understood that the two rings can be bonded at any available ring carbon or available nitrogen atom. Some embodiments include 3-(1H-pyrazol-4-yl)phenyl, 3-(pyridin-4-yl)phenyl, 3-(pyridin-2-yl)phenyl, 5-phenylthiophen-2-yl, 3-(pyridin-3-yl)phenyl, 3-(pyrimidin-5-yl)phenyl, 5-(phenyl)pyridin-3-yl, 5-(1H-pyrazol-4-yl)pyridin-3-yl, 4-(pyridin-3-yl)phenyl, 4-(pyridin-4-yl)phenyl, 4-(pyridin-2-yl)phenyl, (corresponding to the following chemical structures) and the like.

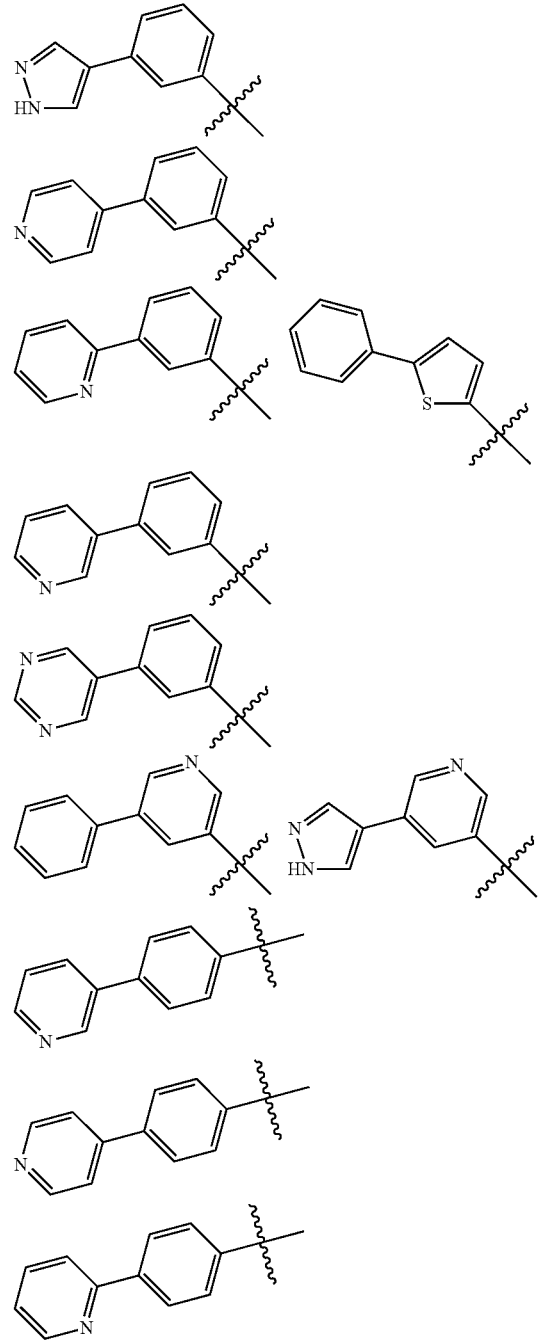

In some embodiments, "heteroaryl" is selected from the group: (1H-pyrazolyl)phenyl, (1H-pyrazolyl)pyridinyl, (pyridinyl)phenyl, (pyrimidinyl)phenyl, 1,2,3,4-tetrahydropyrido[3,2-b]pyrazinyl, 1,2-dihydroquinolinyl, 1,4-dihydroquinolinyl, 1H-benzo[d]imidazolyl, 1H-indazolyl, 1H-indolyl, 1H-pyrazolo[4,3-b]pyridinyl, 1H-pyrazolyl, 1H-pyrrolo[2,3-b]pyridinyl, 1H-pyrrolo[3,2-b]pyridinyl, 2,3-dihydro-[1,4]dioxino[2,3-b]pyridinyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzofuranyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, (phenyl)pyridinyl, 5,6,7,8-tetrahydroquinolinyl, 6,7-dihydro-5H-pyrrolo[3,4-b]pyridin-3-yl, benzo[c][1,2,5]oxadiazolyl, benzofuranyl, chromanyl, isoquinolinyl, isoxazolyl, phenylthiophenyl, pyridinyl, pyrrolo[1,2-a]pyrimidinyl, quinolinyl, and thiazolyl. In some embodiments, "heteroaryl" is selected from the group: 1,2,3,4-tetrahydropyrido[3,2-b]pyrazin-7-yl, 1,2-dihydroquinolin-6-yl, 1,4-dihydroquinolin-3-yl, 1H-benzo[d]imidazol-5-yl, 1H-indazol-5-yl, 1H-indol-2-yl, 1H-indol-3-yl, 1H-indol-5-yl, 1H-indol-6-yl, 1H-pyrazol-4-yl, 1H-pyrazolo[4,3-b]pyridin-6-yl, 1H-pyrrolo[2,3-b]pyridin-3-yl, 1H-pyrrolo[3,2-b]pyridin-6-yl, 2,3-dihydro-[1,4]dioxino[2,3-b]pyridin-7-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 1,4-dihydroquinolin-3-yl, 2,3-dihydro-1H-pyrrolo[2,3-b]pyridin-5-yl, 2,3-dihydrobenzofuran-5-yl, 3-(1H-pyrazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3,4-dihydro-2H-benzo[b][1,4]oxazin-6-yl, 3,4-dihydro-2H-benzo[b][1,4]oxazin-7-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-5-yl, 3H-imidazo[4,5-b]pyridin-6-yl, 4-(pyridin-2-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5,6,7,8-tetrahydroquinolin-3-yl, 5-phenylthiophen-2-yl, 6,7-dihydro-5H-pyrrolo[3,4-b]pyridin-3-yl, benzo[c][1,2,5]oxadiazol-4-yl, benzofuran-2-yl, benzofuran-5-yl, chroman-6-yl, chroman-7-yl, isoquinolin-5-yl, isoxazol-4-yl, pyridin-2-yl, pyridin-3-yl, pyrrolo[1,2-a]pyrimidin-3-yl, quinolin-3-yl, quinolin-6-yl, quinolin-7-yl, and thiazol-4-yl. When referring to a heteroaryl group, it is understood that the terms thiophenyl, thiophen-2-yl, thiophen-3-yl, and the like, refer to the following heteroaryl groups respectively:

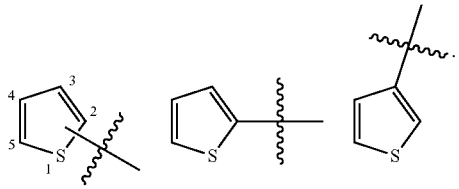

The term "heterocyclyl" refers to a non-aromatic ring radical containing 3 to 8 ring atoms, wherein one, two, or three of the ring atoms are heteroatoms selected from, for example: O, S, and N, wherein N is optionally substituted with H, $C_1$-$C_4$ acyl, or $C_1$-$C_4$ alkyl. In some embodiments, "heterocyclyl" refers to a non-aromatic ring radical containing 3 to 8 ring atoms, wherein one or two of the ring atoms are heteroatoms selected from, for example: O, S, and NH. Examples of a heterocyclyl group include aziridinyl, azetidinyl, piperidinyl, morpholinyl, oxetanyl, imidazolidinyl, piperazinyl, pyrrolidinyl, thiomorpholinyl, [1,4]oxazepanyl, azepanyl, tetrahydrofuranyl, tetrahydropyranyl, tetrahydrothiopyranyl, and the like.

The term "hydroxycarbamimidoyl" refers to a radical consisting a hydroxyl group bonded at one nitrogen of a carbamimidoyl. The hydroxycarbamimidoyl group can be represented by the following:

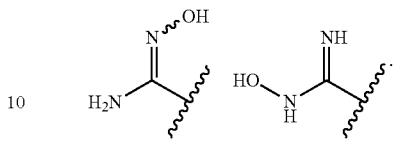

The term "hydroxyl" refers to the group —OH.
The term "phenyl" refers to the aromatic ring radical $C_6H_5$—.
The term "oxo" refers to the diradical =O.
The term "sulfamoyl" refers to the group —S(=O)$_2$NH$_2$.

Compounds of the Invention

One aspect of the present invention encompasses, inter alia, certain 1-oxa-8-azaspiro[4.5]decan-3-yl-aminopropanyl-ether derivatives selected from compounds of Formula (Ia) and pharmaceutically acceptable salts, solvates, hydrates, and N-oxides thereof:

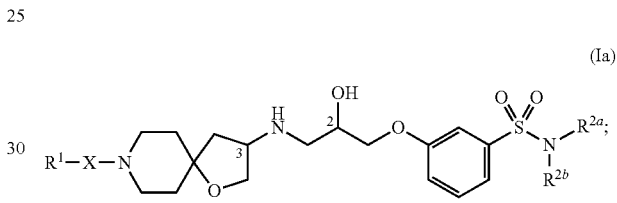

wherein: $R^1$ (as well as Y and Z that are both related to $R^1$), X, $R^{2a}$, and $R^{2b}$ all have the same definitions as described herein, supra and infra. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, Y, Z, X, $R^{2a}$, and $R^{2b}$) contained within the generic chemical formulae described herein, for example, Formulae (Ia), (Ia-1), (Ia-2), (Ia-3), (Ia-4), (Ib-1), (Ib-2), (Ic), and the formulae disclosed in the figures, are specifically embraced by the present invention just as if each and every combination was individually and explicitly recited, to the extent that such combinations embrace compounds that result in stable compounds (i.e., compounds that can be isolated, characterized, and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group substituted with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention. One example relates to compounds containing the group described herein as 4-hydroxyquinolin-3-yl, such as Compound 548. Even thou one tautomer is shown for a compound, such as a compound shown in Table A, it is understood that the compound embraces all such tautomers; below are representative tautomers of 4-hydroxyquinolin-3-yl:

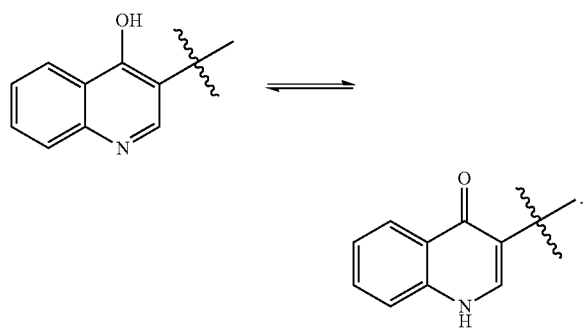

It is understood and appreciated that compounds of Formula (Ia) and formulae related thereto may have one or more chiral centers and therefore can exist as enantiomers and/or diastereoisomers. The invention is understood to extend to and embrace all such enantiomers, diastereoisomers, and mixtures thereof, including but not limited to racemates.

In some embodiments, compounds of the present can have the following defined stereochemistry as shown in Formula (Ia-1):

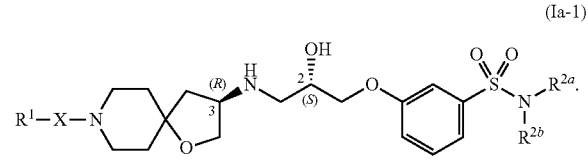

wherein: $R^1$, X, $R^{2a}$, and $R^{2b}$, have the same definitions as described herein, supra and infra, and wherein the carbon designated as C(3) of the oxa-azaspiro[4.5]decanyl group bonded to the nitrogen has the (R) stereochemistry and the carbon designated as C(2) of the propyl group bonded to the hydroxyl group has the (S) stereochemistry.

In some embodiments, compounds of the present can have the following defined stereochemistry as shown in Formula (Ia-2):

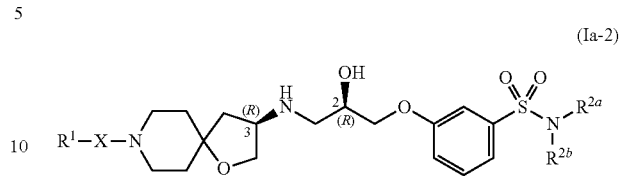

wherein: $R^1$, X, $R^{2a}$, and $R^{2b}$, have the same definitions as described herein, supra and infra, and wherein the carbon designated as C(3) of the oxa-azaspiro[4.5]decanyl group bonded to the nitrogen has the (R) stereochemistry and the carbon designated as C(2) of the propyl group bonded to the hydroxyl group has the (R) stereochemistry.

In some embodiments, compounds of the present can have the following defined stereochemistry as shown in Formula (Ia-3):

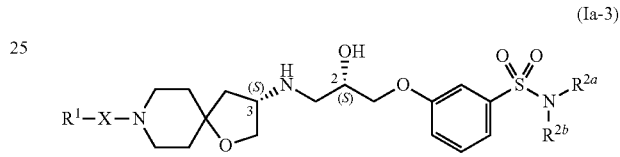

wherein: $R^1$, X, $R^{2a}$, and $R^{2b}$, have the same definitions as described herein, supra and infra, and wherein the carbon designated as C(3) of the oxa-azaspiro[4.5]decanyl group bonded to the nitrogen has the (S) stereochemistry and the carbon designated as C(2) of the propyl group bonded to the hydroxyl group has the (S) stereochemistry.

In some embodiments, compounds of the present can have the following defined stereochemistry as shown in Formula (Ia-4):

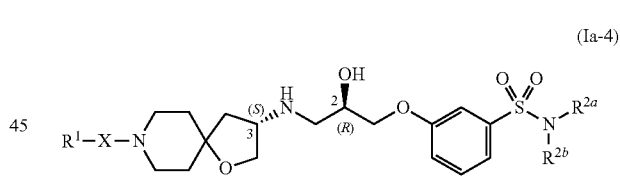

wherein: $R^1$, X, $R^{2a}$, and $R^{2b}$, have the same definitions as described herein, supra and infra, and wherein the carbon designated as C(3) of the oxa-azaspiro[4.5]decanyl group bonded to the nitrogen has the (S) stereochemistry and the carbon designated as C(2) of the propyl group bonded to the hydroxyl group has the (R) stereochemistry.

It is understood that any formulae described herein for which the stereochemistry is not specifically shown can be written to specifically show the stereochemistry as (R) and (S), (R) and (R), (S) and (S), or (S) and (R) for C(3) and C(2) respectively in a similar manner as Formulae (Ia-1), (Ia-2), (Ia-3), and Ia-4) shows the respective stereochemistry for Formula (Ia), supra. Similarly, any chemical name described herein for which the stereochemistry is not specifically shown can alternatively be defined using the language as described for Formulae (Ia-1), (Ia-2), (Ia-3), and (Ia-4), supra, to define the stereochemistry for the chemical name as (R) and (S), (R) and (R), (S) and (S), and/or (S) and (R) respectively.

Accordingly, in some embodiments, the stereochemistry for the C(3) carbon of the oxa-azaspiro[4.5]decanyl group bonded to the nitrogen is (R). In some embodiments, the stereochemistry for the C(3) carbon of the oxa-azaspiro[4.5]decanyl group bonded to the nitrogen is (S). In some embodiments, the stereochemistry for the C(2) carbon of the propyl group bonded to the hydroxyl group is (S). In some embodiments, the stereochemistry for the C(2) carbon of the propyl group bonded to the hydroxyl group is (R). In some embodiments, the stereochemistry for the C(3) carbon of the oxa-azaspiro[4.5]decanyl group bonded to the nitrogen is (R) and the stereochemistry for the C(2) carbon of the propyl group bonded to the hydroxyl group is (S). In some embodiments, the stereochemistry for the C(3) carbon of the oxa-azaspiro[4.5]decanyl group bonded to the nitrogen is (R) and the stereochemistry for the C(2) carbon of the propyl group bonded to the hydroxyl group is (R). In some embodiments, the stereochemistry for the C(3) carbon of the oxa-azaspiro[4.5]decanyl group bonded to the nitrogen is (S) and the stereochemistry for the C(2) carbon of the propyl group bonded to the hydroxyl group is (S). In some embodiments, the stereochemistry for the C(3) carbon of the oxa-azaspiro[4.5]decanyl group bonded to the nitrogen is (S) and the stereochemistry for the C(2) carbon of the propyl group bonded to the hydroxyl group is (R).

It is understood that compounds of Formula (Ia) and the formulae used throughout this disclosure represent all individual enantiomers and mixtures thereof, unless specifically stated or shown otherwise.

The X Group

In some embodiments, X is —$SO_2$— or absent.

In some embodiments, X is —$SO_2$—.

In some embodiments, the present invention relates to compounds of Formula (Ib-1) and pharmaceutically acceptable salts, solvates, hydrates, and N-oxides thereof:

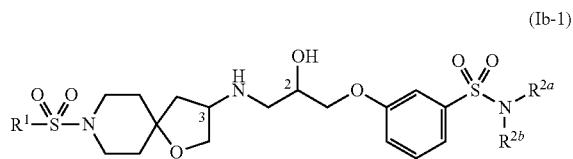

(Ib-1)

wherein: $R^1$, $R^{2a}$, and $R^{2b}$ have the same definitions as described herein, supra and infra, and each can be selected independently from any of the embodiments as described herein, supra and infra.

In some embodiments, X is absent.

In some embodiments, the present invention relates to compounds of Formula (Ib-2) and pharmaceutically acceptable salts, solvates, hydrates, and N-oxides thereof:

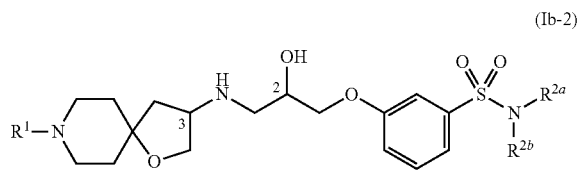

(Ib-2)

wherein: $R^1$, $R^{2a}$, and $R^{2b}$ have the same definitions as described herein, supra and infra, and each can be selected independently from any of the embodiments as described herein, supra and infra.

The Y and Z Groups

The Y and Z groups are related to —Y—$C_1$-$C_6$-alkylene-Z optionally substituted with oxo.

In some embodiments, Y is selected from: —O— and —NH—; and Z is selected from: $C_1$-$C_6$ alkoxy, amino, $C_1$-$C_6$ alkylamino, cyano, $C_2$-$C_6$ dialkylamino, hydroxyl, and phenyl.

In some embodiments, Y is —NH—; and Z is selected from: $C_1$-$C_6$ alkoxy, amino, cyano, $C_2$-$C_6$ dialkylamino, and hydroxyl.

In some embodiments, Y is selected from: —O— and —NH—; and Z is selected from: $C_1$-$C_6$ alkoxy, amino, cyano, $C_2$-$C_6$ dialkylamino, hydroxyl, and phenyl.

In some embodiments, Y is —O—; and Z is phenyl.

Y is selected from: —O— and —NH—.

In some embodiments, Y is —O—.

In some embodiments, Y is —NH—.

In some embodiments, Z is selected from: $C_1$-$C_6$ alkoxy, amino, $C_1$-$C_6$ alkylamino, cyano, $C_2$-$C_6$ dialkylamino, hydroxyl, and phenyl. In some embodiments, Z is $C_1$-$C_6$ alkoxy. In some embodiments, Z is amino. In some embodiments, Z is $C_1$-$C_6$ alkylamino. In some embodiments, Z is cyano. In some embodiments, Z is $C_2$-$C_6$ dialkylamino. In some embodiments, Z is hydroxyl. In some embodiments, Z is phenyl.

The $R^1$ Group

In some embodiments, $R^1$ is selected from: $C_1$-$C_6$-alkylene-aryl, $C_1$-$C_6$-alkylene-heteroaryl, $C_3$-$C_7$ cycloalkyl, heterocyclyl, aryl, and heteroaryl; each optionally substituted with one or more substituents as described herein.

In some embodiments, $R^1$ is selected from: aryl, $C_1$-$C_6$-alkylene-aryl, $C_1$-$C_6$-alkylene-heteroaryl, $C_3$-$C_7$ cycloalkyl, heteroaryl, and heterocyclyl; each optionally substituted with one or more substituents selected from: $C_1$-$C_6$ alkoxy, $C_1$-$C_6$ alkoxycarbonyl, $C_1$-$C_7$ alkyl, $C_1$-$C_6$ alkylamino, $C_1$-$C_6$ alkylcarboxamide, $C_1$-$C_6$ alkylsulfonamido, $C_1$-$C_6$ alkylsulfonyl, amino, aryloxy, arylsulfonyl, carboxamide, carbamimidoyl, carboxy, cyano, $C_3$-$C_7$ cycloalkyl, $C_2$-$C_8$ dialkylamino, $C_2$-$C_8$ dialkylsulfamoyl, $C_1$-$C_6$ haloalkoxy, $C_1$-$C_6$ haloalkyl, halogen, heterocyclyl, hydroxycarbamimidoyl, hydroxyl, oxo, and sulfamoyl; and wherein said $C_1$-$C_6$ alkoxy, $C_1$-$C_7$ alkyl, $C_1$-$C_6$ alkylamino, aryloxy, $C_3$-$C_7$ cycloalkyl, and $C_2$-$C_8$ dialkylamino are each optionally substituted with one or more substituents selected from: amino, $C_1$-$C_6$ alkoxy, $C_1$-$C_6$ alkylamino, $C_1$-$C_6$ alkylcarboxamide, carboxy, —Y—$C_1$-$C_6$-alkylene-Z optionally substituted with oxo, $C_3$-$C_7$ cycloalkyl, cyano, $C_2$-$C_6$ dialkylamino, $C_1$-$C_6$ haloalkyl, $C_1$-$C_6$ haloalkylamino, heterocyclyl, hydroxyl, oxo, and phenyl;

Y is selected from: —O— and —NH—; and

Z is selected from: $C_1$-$C_6$ alkoxy, amino, $C_1$-$C_6$ alkylamino, cyano, $C_2$-$C_6$ dialkylamino, hydroxyl, and phenyl.

In some embodiments, $R^1$ is selected from: aryl, $C_1$-$C_6$-alkylene-aryl, $C_1$-$C_6$-alkylene-heteroaryl, $C_3$-$C_7$ cycloalkyl, heteroaryl, and heterocyclyl; each optionally substituted with one or more substituents selected from: $C_1$-$C_6$ alkoxy, $C_1$-$C_6$ alkoxycarbonyl, $C_1$-$C_7$ alkyl, $C_1$-$C_6$ alkylamino, $C_1$-$C_6$ alkylcarboxamide, $C_1$-$C_6$ alkylsulfonamido, $C_1$-$C_6$ alkylsulfonyl, amino, aryloxy, arylsulfonyl, carboxamide, carbamimidoyl, cyano, $C_3$-$C_7$ cycloalkyl, $C_2$-$C_8$ dialkylamino, $C_2$-$C_8$ dialkylsulfamoyl, $C_1$-$C_6$ haloalkoxy, $C_1$-$C_6$ haloalkyl, halogen, heterocyclyl, hydroxycarbamimidoyl, hydroxyl, oxo, and sulfamoyl; and wherein said $C_1$-$C_6$ alkoxy, $C_1$-$C_7$ alkyl, $C_1$-$C_6$ alkylamino, aryloxy, $C_3$-$C_7$ cycloalkyl, and $C_2$-$C_5$ dialkylamino are each optionally substituted with one or more substituents selected from: amino, $C_1$-$C_6$ alkoxy, $C_1$-$C_6$ alkylamino, $C_1$-$C_6$ alkylcarboxamide, carboxy, —Y—C$_1$-C$_6$-alkylene-Z optionally substituted with oxo, C$_3$-C$_7$ cycloalkyl, cyano, C$_2$-C$_6$ dialkylamino, C$_1$-C$_6$ haloalkyl, C$_1$-C$_6$ haloalkylamino, heterocyclyl, hydroxyl, oxo, and phenyl;

Y is selected from: —O— and —NH—; and

Z is selected from: C$_1$-C$_6$ alkoxy, amino, C$_1$-C$_6$ alkylamino, cyano, C$_2$-C$_6$ dialkylamino, hydroxyl, and phenyl.

In some embodiments, R$^1$ is selected from: C$_1$-C$_6$-alkylene-aryl, C$_1$-C$_6$-alkylene-heteroaryl, C$_3$-C$_7$ cycloalkyl, heterocyclyl, aryl, and heteroaryl; each optionally substituted with one or more substituents selected from: (2-ethyl)(methyl)amino, 4-(trifluoromethyl)phenoxy, acetamido, amino, bromo, carbamimidoyl, carboxamide, carboxy, chloro, cyano, cyclopropyl, dimethylamino, dimethylcarbamoyl, ethoxy, ethyl, ethylamino, fluoro, heptyl, hydroxycarbamimidoyl, hydroxyl, isobutyl, isopropoxy, isopropyl, isopropyl(methyl)amino, methoxy, methoxycarbonyl, methyl, methyl(propyl)amino, methylamino, methylsulfonamido, methylsulfonyl, morpholino, N,N-dimethylsulfamoyl, oxo, phenoxy, phenylsulfonyl, piperazinyl, piperidinyl, propoxy, propyl, sec-butyl, sulfamoyl, tert-butyl, tert-pentyl, trifluoromethoxy, and trifluoromethyl; and wherein (2-ethyl)(methyl)amino, cyclopropyl, ethoxy, ethyl, ethylamino, isopropyl(methyl)amino, methoxy, methyl, methyl(propyl)amino, phenoxy, and propoxy are each optionally substituted with one or more substituents selected from: 2-(dimethylamino)ethylamino, 2,2,2-trifluoroethylamino, 2,2-difluoroethylamino, 2-amino-2-oxoacetamido, 2-aminoacetamido, 2-fluoroethylamino, 2-hydroxyethylamino, 2-methoxyethylamino, acetamido, amino, amino, oxo, amino, benzyloxy, carboxy, cyano, cyanomethylamino, cyclopropyl, dimethylamino, ethylamino, hydroxyl, hydroxyl, oxo, isobutylamino, isopentylamino, isopropylamino, methoxy, methylamino, morpholino, oxo, phenyl, pyrrolidinyl, thiazolidinyl, and trifluoromethyl.

In some embodiments, R$^1$ is selected from: C$_1$-C$_6$-alkylene-aryl, C$_1$-C$_6$-alkylene-heteroaryl, C$_3$-C$_7$ cycloalkyl, heterocyclyl, aryl, and heteroaryl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, heptyl, hydroxycarbamimidoyl, hydroxyl, hydroxymethyl, isobutyl, isopropoxy, isopropyl, methoxy, methoxycarbonyl, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl.

In some embodiments, R$^1$ is selected from: (1,2,3,4-tetrahydropyrimidin-5-yl)phenyl, (5-isoxazol-3-yl)thiophen-3-yl, (5-isoxazol-3-yl)thiophen-2-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydropyridinyl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-3-yl, (1H-pyrazol-5-yl)thiophen-2-yl, 1H-pyrazolo[3,4-b]pyridinyl, 1H-pyrazolo[4,3-b]pyridinyl, 1H-pyrazolyl, 1H-pyrrolo[2,3-b]pyridinyl, 1H-pyrrolo[3,2-b]pyridinyl, 1-phenyl-1H-pyrazolyl, 2-(pyridin-4-yl)ethyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(phenyl)pyrimidinyl, 4-(pyridin-3-yl)phenyl, 4-(pyridin-4-yl)phenyl, 4-phenylpyrimidinyl, 5-(1H-pyrazol-4-yl)pyridinyl, 5-(phenyl)pyridinyl, 5,6,7,8-tetrahydro-1,6-naphthyridinyl, 5,6,7,8-tetrahydronaphthalenyl, 5,6,7,8-tetrahydroquinolinyl, 5-phenyl-2,3-dihydrobenzofuranyl, 5-phenylpyrimidinyl, 5-phenylthiophen-3-yl, 5-phenylthiophen-2-yl, 6,7-dihydro-5H-cyclopenta[b]pyridinyl, 6,7-dihydro-5H-pyrrolo[3,4-b]pyridinyl, 6-phenylpyrimidinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, benzyl, biphenylyl, chromanyl, cyclohexyl, furanyl, imidazo[1,2-a]pyridinyl, imidazo[2,1-b]thiazolyl, indolinyl, isoxazolyl, naphthalenyl, phenyl, pyrazinyl, pyridinyl, pyrimidinyl, quinolinyl, thiophen-3-yl, and thiophen-2-yl; each optionally substituted with one or more substituents selected from: C$_1$-C$_6$ alkoxy, C$_1$-C$_6$ alkoxycarbonyl, C$_1$-C$_7$ alkyl, C$_1$-C$_6$ alkylamino, C$_1$-C$_6$ alkylcarboxamide, C$_1$-C$_6$ alkylsulfonamido, C$_1$-C$_6$ alkylsulfonyl, amino, aryloxy, arylsulfonyl, carboxamide, carbamimidoyl, carboxy, cyano, C$_3$-C$_7$ cycloalkyl, C$_2$-C$_8$ dialkylamino, C$_2$-C$_8$ dialkylsulfamoyl, C$_1$-C$_6$ haloalkoxy, C$_1$-C$_6$ haloalkyl, halogen, heterocyclyl, hydroxycarbamimidoyl, hydroxyl, oxo, and sulfamoyl; and wherein said C$_1$-C$_6$ alkoxy, C$_1$-C$_7$ alkyl, C$_1$-C$_6$ alkylamino, aryloxy, C$_3$-C$_7$ cycloalkyl, and C$_2$-C$_8$ dialkylamino are each optionally substituted with one or more substituents selected from: amino, C$_1$-C$_6$ alkoxy, C$_1$-C$_6$ alkylamino, C$_1$-C$_6$ alkylcarboxamide, carboxy, —Y—C$_1$-C$_6$-alkylene-Z optionally substituted with oxo, C$_3$-C$_7$ cycloalkyl, cyano, C$_2$-C$_6$ dialkylamino, C$_1$-C$_6$ haloalkyl, C$_1$-C$_6$ haloalkylamino, heterocyclyl, hydroxyl, oxo, and phenyl;

Y is selected from: —O— and —NH—; and

Z is selected from: C$_1$-C$_6$ alkoxy, amino, C$_1$-C$_6$ alkylamino, cyano, C$_2$-C$_6$ dialkylamino, hydroxyl, and phenyl.

In some embodiments, R$^1$ is selected from: (1,2,3,4-tetrahydropyrimidin-5-yl)phenyl, (5-isoxazol-3-yl)thiophen-3-yl, (5-isoxazol-3-yl)thiophen-2-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydropyridinyl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-3-yl, (1H-pyrazol-5-yl)thiophen-2-yl, 1H-pyrazolo[3,4-b]pyridinyl, 1H-pyrazolo[4,3-b]pyridinyl, 1H-pyrazolyl, 1H-pyrrolo[2,3-b]pyridinyl, 1H-pyrrolo[3,2-b]pyridinyl, 1-phenyl-1H-pyrazolyl, 2-(pyridin-4-yl)ethyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(phenyl)pyrimidinyl, 4-(pyridin-3-yl)phenyl, 4-(pyridin-4-yl)phenyl, 4-phenylpyrimidinyl, 5-(1H-pyrazol-4-yl)pyridinyl, 5-(phenyl)pyridinyl, 5,6,7,8-tetrahydro-1,6-naphthyridinyl, 5,6,7,8-tetrahydronaphthalenyl, 5,6,7,8-tetrahydroquinolinyl, 5-phenyl-2,3-dihydrobenzofuranyl, 5-phenylpyrimidinyl, 5-phenylthiophen-3-yl, 5-phenylthiophen-2-yl, 6,7-dihydro-5H-cyclopenta[b]pyridinyl, 6,7-dihydro-5H-pyrrolo[3,4-b]pyridinyl, 6-phenylpyrimidinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, benzyl, biphenylyl, chromanyl, cyclohexyl, furanyl, imidazo[1,2-a]pyridinyl, imidazo[2,1-b]thiazolyl, indolinyl, isoxazolyl, naphthalenyl, phenyl, pyrazinyl, pyridinyl, pyrimidinyl, quinolinyl, thiophen-3-yl, and thiophen-2-yl; each optionally substituted with one or more substituents selected from: (2-ethyl)(methyl)amino, 4-(trifluoromethyl)phenoxy, acetamido, amino, bromo, carbamimidoyl, carboxamide, carboxy, chloro, cyano, cyclopropyl, dimethylamino, dimethylcarbamoyl, ethoxy, ethyl, ethylamino, fluoro, heptyl, hydroxycarbamimidoyl, hydroxyl, isobutyl, isopropoxy, isopropyl, isopropyl(methyl)amino, methoxy, methoxycarbonyl, methyl, methyl(propyl)amino, methylamino, methylsulfonamido, methylsulfonyl, morpholino, N,N-dimethylsulfamoyl, oxo, phenoxy, phenylsulfonyl, piperazinyl, piperidinyl, propoxy, propyl, sec-butyl, sulfamoyl, tert-butyl, tert-pentyl, trifluoromethoxy, and trifluoromethyl; and wherein (2-ethyl)(methyl)amino, cyclopropyl, ethoxy, ethyl, ethylamino, isopropyl(methyl)amino, methoxy, methyl, methyl(propyl)amino, phenoxy, and propoxy are each optionally substituted with one or more substituents selected from: 2-(dimethylamino)ethylamino, 2,2,2-trifluoroethylamino, 2,2-difluoroethylamino, 2-amino-2-oxoacetamido, 2-aminoacetamido, 2-fluoroethylamino, 2-hydroxyethylamino, 2-methoxyethylamino, acetamido, amino, amino, oxo, amino, benzyloxy, carboxy, cyano, cyanomethylamino, cyclopropyl, dimethylamino, ethylamino, hydroxyl, hydroxyl, oxo, isobutylamino, isopentylamino, isopropylamino, methoxy, methylamino, morpholino, oxo, phenyl, pyrrolidinyl, thiazolidinyl, and trifluoromethyl.

In some embodiments, $R^1$ is selected from: (1,2,3,4-tetrahydropyrimidin-5-yl)phenyl, (5-isoxazol-3-yl)thiophen-3-yl, (5-isoxazol-3-yl)thiophen-2-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydropyridinyl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-3-yl, (1H-pyrazol-5-yl)thiophen-2-yl, 1H-pyrazolo[3,4-b]pyridinyl, 1H-pyrazolo[4,3-b]pyridinyl, 1H-pyrazolyl, 1H-pyrrolo[2,3-b]pyridinyl, 1H-pyrrolo[3,2-b]pyridinyl, 1-phenyl-1H-pyrazolyl, 2-(pyridin-4-yl)ethyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(phenyl)pyrimidinyl, 4-(pyridin-3-yl)phenyl, 4-(pyridin-4-yl)phenyl, 4-phenylpyrimidinyl, 5-(1H-pyrazol-4-yl)pyridinyl, 5-(phenyl)pyridinyl, 5,6,7,8-tetrahydro-1,6-naphthyridinyl, 5,6,7,8-tetrahydronaphthalenyl, 5,6,7,8-tetrahydroquinolinyl, 5-phenyl-2,3-dihydrobenzofuranyl, 5-phenylpyrimidinyl, 5-phenylthiophen-3-yl, 5-phenylthiophen-2-yl, 6,7-dihydro-5H-cyclopenta[b]pyridinyl, 6,7-dihydro-5H-pyrrolo[3,4-b]pyridinyl, 6-phenylpyrimidinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, benzyl, biphenylyl, chromanyl, cyclohexyl, furanyl, imidazo[1,2-a]pyridinyl, imidazo[2,1-b]thiazolyl, indolinyl, isoxazolyl, naphthalenyl, phenyl, pyrazinyl, pyridinyl, pyrimidinyl, quinolinyl, thiophen-3-yl, and thiophen-2-yl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, heptyl, hydroxycarbamimidoyl, hydroxyl, hydroxymethyl, isobutyl, isopropoxy, isopropyl, methoxy, methoxycarbonyl, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl.

In some embodiments, $R^1$ is selected from: (1,2,3,4-tetrahydropyrimidin-5-yl)phenyl, (5-isoxazol-3-yl)thiophen-2-yl, (pyridin-2-yl)phenyl, [3,3'-bipyridin]-5-yl, 1,2,3, 4-tetrahydropyrido[2,3-b][1,4]oxazepin-8-yl, 1',2'-dihydrospiro[cyclopropane-1,3'-pyrido[2,3-b][1,4]oxazine]-7'-yl, 1,4-dihydropyridin-3-yl, 1,4-dihydroquinolin-3-yl, 1,5-naphthyridin-3-yl, 1,8-naphthyridin-3-yl, 1H-benzo[d]imidazol-5-yl, 1H-benzo[d]imidazol-6-yl, 1H-imidazo[4,5-b]pyridin-6-yl, 1H-imidazol-4-yl, 1H-indazol-5-yl, 1H-indazol-6-yl, 1H-indol-5-yl, 1H-pyrazol-3-yl, 1H-pyrazol-4-yl, (1H-pyrazol-5-yl)thiophen-2-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-phenyl-1H-pyrazol-4-yl, 2-(pyridin-4-yl)ethyl, 2,3-dihydro-[1,4]dioxino[2,3-b]pyridin-7-yl, 2,3-dihydro-1H-benzo[d]imidazol-5-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzo[b][1,4]dioxin-6-yl, 2,3-dihydrobenzo[d]thiazol-6-yl, 2,3-dihydrobenzofuran-5-yl, 2,3-dihydrobenzofuran-7-yl, 2,3-dihydrofuro[2,3-b]pyridin-5-yl, 2-phenylthiazol-5-yl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-6-yl, 4'-(1,2,4-oxadiazol-3-yl)biphenyl-3-yl, 4-(2H-tetrazol-5-yl)phenyl, 4-(phenyl)pyrimidin-2-yl, 4-(pyridin-3-yl)phenyl, 4-(pyridin-4-yl)phenyl, 4-phenylpyrimidin-2-yl, 5-(1H-pyrazol-4-yl)pyridin-3-yl, 5-(phenyl)pyridin-3-yl, 5,6,7,8-tetrahydro-1,6-naphthyridin-3-yl, 5,6,7,8-tetrahydronaphthalen-1-yl, 5,6,7,8-tetrahydronaphthalen-2-yl, 5,6,7,8-tetrahydronaphthalenyl, 5,6,7,8-tetrahydroquinolin-3-yl, 5-phenyl-2,3-dihydrobenzofuran-7-yl, 5-phenylpyrimidin-2-yl, 5-phenylthiophen-2-yl, 6,7-dihydro-5H-cyclopenta[b]pyridin-3-yl, 6,7-dihydro-5H-pyrrolo[3,4-b]pyridin-3-yl, 6-phenylpyrimidin-2-yl, 7,8-dihydro-5H-pyrano[4,3-b]pyridin-3-yl, benzo[c][1,2,5]oxadiazol-4-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, benzyl, biphenyl-2-yl, biphenyl-3-yl, biphenyl-4-yl, chroman-6-yl, cyclohexyl, furan-3-yl, imidazo[1,2-a]pyridin-6-yl, imidazo[2,1-b]thiazol-5-yl, indolin-5-yl, isoxazol-4-yl, naphthalen-1-yl, naphthalen-2-yl, phenyl, pyrazin-2-yl, pyridin-2-yl, pyridin-3-yl, pyrimidin-2-yl, pyrimidin-4-yl, pyrimidin-5-yl, quinolin-3-yl, quinolin-6-yl, quinolin-8-yl, thiophen-2-yl, and thiophen-3-yl; each optionally substituted with one or more substituents selected from: $C_1$-$C_6$ alkoxy, $C_1$-$C_6$ alkoxycarbonyl, $C_1$-$C_7$ alkyl, $C_1$-$C_6$ alkylamino, $C_1$-$C_6$ alkylcarboxamide, $C_1$-$C_6$ alkylsulfonamido, $C_1$-$C_6$ alkylsulfonyl, amino, aryloxy, arylsulfonyl, carbamimidoyl, carbamimidoyl, carboxy, cyano, $C_3$-$C_7$ cycloalkyl, $C_2$-$C_8$ dialkylamino, $C_2$-$C_8$ dialkylsulfamoyl, $C_1$-$C_6$ haloalkoxy, $C_1$-$C_6$ haloalkyl, halogen, heterocyclyl, hydroxycarbamimidoyl, hydroxyl, oxo, and sulfamoyl; and wherein said $C_1$-$C_6$ alkoxy, $C_1$-$C_7$ alkyl, $C_1$-$C_6$ alkylamino, aryloxy, $C_3$-$C_7$ cycloalkyl, and $C_2$-$C_8$ dialkylamino are each optionally substituted with one or more substituents selected from: amino, $C_1$-$C_6$ alkoxy, $C_1$-$C_6$ alkylamino, $C_1$-$C_6$ alkylcarboxamide, carboxy, —Y—$C_1$-$C_6$-alkylene-Z optionally substituted with oxo, $C_3$-$C_7$ cycloalkyl, cyano, $C_2$-$C_6$ dialkylamino, $C_1$-$C_6$ haloalkyl, $C_1$-$C_6$ haloalkylamino, heterocyclyl, hydroxyl, oxo, and phenyl;

Y is selected from: —O— and —NH—; and

Z is selected from: $C_1$-$C_6$ alkoxy, amino, $C_1$-$C_6$ alkylamino, cyano, $C_2$-$C_6$ dialkylamino, hydroxyl, and phenyl.

In some embodiments, $R^1$ is selected from: (1,2,3,4-tetrahydropyrimidin-5-yl)phenyl, (5-isoxazol-3-yl)thiophen-2-yl, (pyridin-2-yl)phenyl, [3,3'-bipyridin]-5-yl, 1,2,3,4-tetrahydropyrido[2,3-b][1,4]oxazepin-8-yl, 1',2'-dihydrospiro[cyclopropane-1,3'-pyrido[2,3-b][1,4]oxazine]-7'-yl, 1,4-dihydropyridin-3-yl, 1,4-dihydroquinolin-3-yl, 1,5-naphthyridin-3-yl, 1,8-naphthyridin-3-yl, 1H-benzo[d]imidazol-5-yl, 1H-benzo[d]imidazol-6-yl, 1H-imidazo[4,5-b]pyridin-6-yl, 1H-imidazol-4-yl, 1H-indazol-5-yl, 1H-indazol-6-yl, 1H-indol-5-yl, 1H-pyrazol-3-yl, 1H-pyrazol-4-yl, (1H-pyrazol-5-yl)thiophen-2-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-phenyl-1H-pyrazol-4-yl, 2-(pyridin-4-yl)ethyl, 2,3-dihydro-[1,4]dioxino[2,3-b]pyridin-7-yl, 2,3-dihydro-1H-benzo[d]imidazol-5-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzo[b][1,4]dioxin-6-yl, 2,3-dihydrobenzo[d]thiazol-6-yl, 2,3-dihydrobenzofuran-5-yl, 2,3-dihydrobenzofuran-7-yl, 2,3-dihydrofuro[2,3-b]pyridin-5-yl, 2-phenylthiazol-5-yl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-6-yl, 4'-(1,2,4-oxadiazol-3-yl)biphenyl-3-yl, 4-(2H-tetrazol-5-yl)phenyl, 4-(phenyl)pyrimidin-2-yl, 4-(pyridin-3-yl)phenyl, 4-(pyridin-4-yl)phenyl, 4-phenylpyrimidin-2-yl, 5-(1H-pyrazol-4-yl)pyridin-3-yl, 5-(phenyl)pyridin-3-yl, 5,6,7,8-tetrahydro-1,6-naphthyridin-3-yl, 5,6,7,8-tetrahydronaphthalen-1-yl, 5,6,7,8-tetrahydronaphthalen-2-yl, 5,6,7,8-tetrahydronaphthalenyl, 5,6,7,8-tetrahydroquinolin-3-yl, 5-phenyl-2,3-dihydrobenzofuran-7-yl, 5-phenylpyrimidin-2-yl, 5-phenylthiophen-2-yl, 6,7-dihydro-5H-cyclopenta[b]pyridin-3-yl, 6,7-dihydro-5H-pyrrolo[3,4-b]pyridin-3-yl, 6-phenylpyrimidin-2-yl, 7,8-dihydro-5H-pyrano[4,3-b]pyridin-3-yl, benzo[c][1,2,5]oxadiazol-4-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, benzyl, biphenyl-2-yl, biphenyl-3-yl, biphenyl-4-yl, chroman-6-yl, cyclohexyl, furan-3-yl, imidazo[1,2-a]pyridin-6-yl, imidazo[2,1-b]thiazol-5-yl, indolin-5-yl, isoxazol-4-yl, naphthalen-1-yl, naphthalen-2-yl, phenyl, pyrazin-2-yl, pyridin-2-yl, pyridin-3-yl, pyrimidin-2-yl, pyrimidin-4-yl, pyrimidin-5-yl, quinolin-3-yl, quinolin-6-yl, quinolin-8-yl, thiophen-2-yl, and thiophen-3-yl; each optionally substituted with one or more substituents selected from: (2-ethyl)(methyl)amino, 4-(trifluoromethyl)phenoxy, acetamido, amino, bromo, carbamimidoyl, carboxamide, carboxy, chloro, cyano, cyclopropyl, dimethylamino, dimethylcarbamoyl, ethoxy, ethyl, ethylamino, fluoro, heptyl, hydroxycarbamimidoyl, hydroxyl, isobutyl, isopropoxy, isopropyl, isopropyl(methyl)amino, methoxy, methoxycarbonyl, methyl, methyl(propyl)amino, methylamino, methylsulfonamido, methylsulfonyl, morpholino, N,N-dimethylsulfamoyl, oxo, phenoxy, phenylsulfonyl, piperazinyl, piperidinyl, propoxy, propyl, sec-butyl, sulfamoyl, tert-butyl, tert-pentyl, trifluoromethoxy, and trifluoromethyl; and wherein (2-ethyl)(methyl)amino, cyclopropyl, ethoxy, ethyl, ethylamino, isopropyl(methyl)amino, methoxy, methyl, methyl(propyl)amino, phenoxy, and propoxy are each optionally substituted with one or more substituents selected from: 2-(dimethylamino)ethylamino, 2,2,2-trifluoroethylamino, 2,2-difluoroethylamino, 2-amino-2-oxoacetamido, 2-aminoacetamido, 2-fluoroethylamino, 2-hydroxyethylamino, 2-methoxyethylamino, acetamido, amino, amino, oxo, amino, benzyloxy, carboxy, cyano, cyanomethylamino, cyclopropyl, dimethylamino, ethylamino, hydroxyl, hydroxyl, oxo, isobutylamino, isopentylamino, isopropylamino, methoxy, methylamino, morpholino, oxo, phenyl, pyrrolidinyl, thiazolidinyl, and trifluoromethyl.

In some embodiments, $R^1$ is selected from: (1,2,3,4-tetrahydropyrimidin-5-yl)phenyl, (5-isoxazol-3-yl)thiophen-2-yl, (pyridin-2-yl)phenyl, [3,3'-bipyridin]-5-yl, 1,2,3,4-tetrahydropyrido[2,3-b][1,4]oxazepin-8-yl, 1',2'-dihydrospiro[cyclopropane-1,3'-pyrido[2,3-b][1,4]oxazine]-7'-yl, 1,4-dihydropyridin-3-yl, 1,4-dihydroquinolin-3-yl, 1,5-naphthyridin-3-yl, 1,8-naphthyridin-3-yl, 1H-benzo[d]imidazol-5-yl, 1H-benzo[d]imidazol-6-yl, 1H-imidazo[4,5-b]pyridin-6-yl, 1H-imidazol-4-yl, 1H-indazol-5-yl, 1H-indazol-6-yl, 1H-indol-5-yl, 1H-pyrazol-3-yl, 1H-pyrazol-4-yl, (1H-pyrazol-5-yl)thiophen-2-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-phenyl-1H-pyrazol-4-yl, 2-(pyridin-4-yl)ethyl, 2,3-dihydro-[1,4]dioxino[2,3-b]pyridin-7-yl, 2,3-dihydro-1H-benzo[d]imidazol-5-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzo[b][1,4]dioxin-6-yl, 2,3-dihydrobenzo[d]thiazol-6-yl, 2,3-dihydrobenzofuran-5-yl, 2,3-dihydrobenzofuran-7-yl, 2,3-dihydrofuro[2,3-b]pyridin-5-yl, 2-phenylthiazol-5-yl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-6-yl, 4'-(1,2,4-oxadiazol-3-yl)biphenyl-3-yl, 4-(2H-tetrazol-5-yl)phenyl, 4-(phenyl)pyrimidin-2-yl, 4-(pyridin-3-yl)phenyl, 4-(pyridin-4-yl)phenyl, 4-phenylpyrimidin-2-yl, 5-(1H-pyrazol-4-yl)pyridin-3-yl, 5-(phenyl)pyridin-3-yl, 5,6,7,8-tetrahydro-1,6-naphthyridin-3-yl, 5,6,7,8-tetrahydronaphthalen-1-yl, 5,6,7,8-tetrahydronaphthalen-2-yl, 5,6,7,8-tetrahydronaphthalenyl, 5,6,7,8-tetrahydroquinolin-3-yl, 5-phenyl-2,3-dihydrobenzofuran-7-yl, 5-phenylpyrimidin-2-yl, 5-phenylthiophen-2-yl, 6,7-dihydro-5H-cyclopenta[b]pyridin-3-yl, 6,7-dihydro-5H-pyrrolo[3,4-b]pyridin-3-yl, 6-phenylpyrimidin-2-yl, 7,8-dihydro-5H-pyrano[4,3-b]pyridin-3-yl, benzo[c][1,2,5]oxadiazol-4-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, benzyl, biphenyl-2-yl, biphenyl-3-yl, biphenyl-4-yl, chroman-6-yl, cyclohexyl, furan-3-yl, imidazo[1,2-a]pyridin-6-yl, imidazo[2,1-b]thiazol-5-yl, indolin-5-yl, isoxazol-4-yl, naphthalen-1-yl, naphthalen-2-yl, phenyl, pyrazin-2-yl, pyridin-2-yl, pyridin-3-yl, pyrimidin-2-yl, pyrimidin-4-yl, pyrimidin-5-yl, quinolin-3-yl, quinolin-6-yl, quinolin-8-yl, thiophen-2-yl, and thiophen-3-yl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, heptyl, hydroxycarbamimidoyl, hydroxyl, hydroxymethyl, isobutyl, isopropoxy, isopropyl, methoxy, methoxycarbonyl, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl.

In some embodiments, $R^1$ is selected from: (1,2,3,4-tetrahydropyrimidin-5-yl)phenyl, (5-isoxazol-3-yl)thiophen-2-yl, (5-isoxazol-3-yl)thiophen-3-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydropyridinyl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-2-yl, (1H-pyrazol-5-yl)thiophen-3-yl, 1H-pyrazolo[3,4-b]pyridinyl, 1H-pyrazolo[4,3-b]pyridinyl, 1H-pyrazolyl, 1H-pyrrolo[2,3-b]pyridinyl, 1H-pyrrolo[3,2-b]pyridinyl, 1-phenyl-1H-pyrazolyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(pyridin-3-yl)phenyl, 4-(pyridin-4-yl)phenyl, 5-(1H-pyrazol-4-yl)pyridinyl, 5-(phenyl)pyridinyl, 5,6,7,8-tetrahydro-1,6-naphthyridinyl, 5,6,7,8-tetrahydronaphthalenyl, 5,6,7,8-tetrahydroquinolinyl, 5-phenyl-2,3-dihydrobenzofuranyl, 5-phenylthiophen-2-yl, 5-phenylthiophen-3-yl, 6,7-dihydro-5H-cyclopenta[b]pyridinyl, 6,7-dihydro-5H-pyrrolo[3,4-b]pyridinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, biphenylyl, chromanyl, furanyl, imidazo[1,2-a]pyridinyl, imidazo[2,1-b]thiazolyl, indolinyl, isoxazolyl, naphthalenyl, phenyl, pyridinyl, pyrimidinyl, quinolinyl, thiophen-2-yl, and thiophen-3-yl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino) methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, hydroxycarbamimidoyl, hydroxyl, hydroxymethyl, isobutyl, isopropoxy, isopropyl, methoxy, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl.

In some embodiments, $R^1$ is selected from: (1,2,3,4-tetrahydropyrimidin-5-yl)phenyl, (5-isoxazol-3-yl)thiophen-2-yl, (pyridin-2-yl)phenyl, [3,3'-bipyridin]-5-yl, 1,2,3,4-tetrahydropyrido[2,3-b][1,4]oxazepin-8-yl, 1',2'-dihydrospiro[cyclopropane-1,3'-pyrido[2,3-b][1,4]oxazine]-7'-yl, 1,4-dihydropyridin-3-yl, 1,4-dihydroquinolin-3-yl, 1,5-naphthyridin-3-yl, 1,8-naphthyridin-3-yl, 1H-benzo[d]imidazol-5-yl, 1H-benzo[d]imidazol-6-yl, 1H-imidazo[4,5-b]pyridin-6-yl, 1H-imidazol-4-yl, 1H-indazol-5-yl, 1H-indazol-6-yl, 1H-indol-5-yl, 1H-pyrazol-3-yl, 1H-pyrazol-4-yl, (1H-pyrazol-5-yl)thiophen-2-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-phenyl-1H-pyrazol-4-yl, 2,3-dihydro-[1,4]dioxino[2,3-b]pyridin-7-yl, 2,3-dihydro-1H-benzo[d]imidazol-5-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzo[b][1,4]dioxin-6-yl, 2,3-dihydrobenzo[d]thiazol-6-yl, 2,3-dihydrobenzofuran-5-yl, 2,3-dihydrobenzofuran-7-yl, 2,3-dihydrofuro[2,3-b]pyridin-5-yl, 2-phenylthiazol-5-yl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-6-yl, 4'-(1,2,4-oxadiazol-3-yl)biphenyl-3-yl, 4-(2H-tetrazol-5-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5,6,7,8-tetrahydro-1,6-naphthyridin-3-yl, 5,6,7,8-tetrahydronaphthalen-1-yl, 5,6,7,8-tetrahydronaphthalen-2-yl, 5,6,7,8-tetrahydronaphthalenyl, 5,6,7,8-tetrahydroquinolin-3-yl, 5-phenyl-2,3-dihydrobenzofuran-7-yl, 5-phenylthiophen-2-yl, 6,7-dihydro-5H-cyclopenta[b]pyridin-3-yl, 6,7-dihydro-5H-pyrrolo[3,4-b]pyridin-3-yl, 7,8-dihydro-5H-pyrano[4,3-b]pyridin-3-yl, benzo[c][1,2,5]oxadiazol-4-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, biphenyl-2-yl, biphenyl-3-yl, biphenyl-4-yl, chroman-6-yl, furan-3-yl, imidazo[1,2-a]pyridin-6-yl, imidazo[2,1-b]thiazol-5-yl, indolin-5-yl, isoxazol-4-yl, naphthalen-1-yl, naphthalen-2-yl, phenyl, pyridin-2-yl, pyridin-3-yl, pyrimidin-5-yl, quinolin-3-yl, quinolin-6-yl, quinolin-8-yl, thiophen-2-yl, and thiophen-3-yl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, hydroxycarbamimidoyl, hydroxyl, hydroxymethyl, isobutyl, isopropoxy, isopropyl, methoxy, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl.

In some embodiments, $R^1$ is selected from: (dimethylcarbamoyl)phenyl, 1-(2-(benzyloxy)ethyl)-2,3-dihydro-1H-pyrido[2,3-b][1,4]oxazin-7-yl, 1-(2-hydroxyethyl)-2,3-dihydro-1H-pyrido[2,3-b][1,4]oxazin-7-yl, 1-(2-methoxyethyl)-2,3-dihydro-1H-pyrido[2,3-b][1,4]oxazin-7-yl, 1-(carboxymethyl)-4-oxo-1,4-dihydroquinolin-3-yl, 1,2-dimethyl-1H-imidazol-4-yl, 1,3,3-trimethyl-2,3-dihydro-1H-pyrido[2,3-b][1,4]oxazin-7-yl, 1,3-dimethyl-2,3-dihydro-1H-pyrido[2,3-b][1,4]oxazin-7-yl, 1,5-naphthyridin-3-yl, 1,6-dimethyl-2,3-dihydro-1H-pyrido[2,3-b][1,4]oxazin-7-yl, 1,8-dimethyl-2,3-dihydro-1H-pyrido[2,3-b][1,4]oxazin-7-yl, 1-ethyl-2,3-dihydro-1H-pyrido[2,3-b][1,4]oxazin-7-yl, 1-ethyl-4-oxo-1,4-dihydropyridin-3-yl, 1-ethyl-4-oxo-1,4-dihydroquinolin-3-yl, 1-ethyl-5-methyl-1H-pyrazol-4-yl, 1-ethyl-6-fluoro-4-oxo-1,4-dihydroquinolin-3-yl, 1-ethyl-6-methyl-4-oxo-1,4-dihydroquinolin-3-yl, 1-ethyl-7-fluoro-4-oxo-1,4-dihydroquinolin-3-yl, 1-ethyl-7-methyl-4-oxo-1,4-dihydroquinolin-3-yl, 1-ethyl-8-fluoro-4-oxo-1,4-dihydroquinolin-3-yl, 1-ethyl-8-methyl-4-oxo-1,4-dihydroquinolin-3-yl, 1H-benzo[d]imidazol-5-yl, 1H-benzo[d]imidazol-6-yl, 1H-imidazo[4,5-b]pyridin-6-yl, 1H-indazol-5-yl, 1H-indazol-6-yl, 1H-pyrazol-4-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-isopropyl-2,3-dihydro-1H-pyrido[2,3-b][1,4]oxazin-7-yl, 1-methyl-1,2,3,4-tetrahydropyrido[2,3-b][1,4]oxazepin-8-yl, 1'-methyl-1',2'-dihydrospiro[cyclopropane-1,3'-pyrido[2,3-b][1,4]oxazine]-7'-yl, 1-methyl-1H-imidazo[4,5-b]pyridin-6-yl, 1-methyl-1H-imidazol-4-yl, 1-methyl-H-indol-5-yl, 1-methyl-1H-pyrazol-3-yl, 1-methyl-1H-pyrrolo[3,2-b]pyridin-6-yl, 1-methyl-2,3-dihydro-1H-pyrido[2,3-b][1,4]oxazin-7-yl, 1-methyl-2-oxo-2,3-dihydro-1H-imidazo[4,5-b]pyridin-6-yl, 1-methyl-3-(trifluoromethyl)-1H-pyrazol-4-yl, 1-methyl-4-oxo-1,4-dihydroquinolin-3-yl, 1-methyl-6-(methylamino)-2,3-dihydro-1H-pyrido[2,3-b][1,4]oxazin-7-yl, 1-phenyl-1H-pyrazol-4-yl, 1-propyl-2,3-dihydro-1H-pyrido[2,3-b][1,4]oxazin-7-yl, 2-(dimethylamino)pyridin-3-yl, 2-(methylsulfonyl)phenyl, 2-(pyridin-4-yl)ethyl, 2-(trifluoromethoxy)phenyl, 2-(trifluoromethyl)phenyl, 2,2-dimethylchroman-6-yl, 2,3-dichlorophenyl, 2,3-difluorophenyl, 2,3-dihydro-[1,4]dioxino[2,3-b]pyridin-7-yl, 2,3-dihydro-1H-pyrido[2,3-b][1,4]oxazin-7-yl, 2,3-dihydrobenzo[b][1,4]dioxin-6-yl, 2,3-dihydrobenzofuran-5-yl, 2,3-dihydrofuro[2,3-b]pyridin-5-yl, 2,3-dimethylphenyl, 2,3-dioxoindolin-5-yl, 2,4-dichlorophenyl, 2,4-difluorophenyl, 2,5-dichlorophenyl, 2,5-difluorophenyl, 2,5-dimethylphenyl, 2,6-difluorophenyl, 2-bromophenyl, 2-chloro-3-fluorophenyl, 2-chloro-4-cyanophenyl, 2-chloro-4-fluorophenyl, 2-chloro-5-(methylsulfonyl)phenyl, 2-chloro-5-(trifluoromethyl)phenyl, 2-chloro-5-fluorophenyl, 2-chlorophenyl, 2-cyano-5-methoxyphenyl, 2-cyano-5-methylphenyl, 2-cyanophenyl, 2-ethyl-3H-imidazo[4,5-b]pyridin-6-yl, 2-fluoro-3-methylphenyl, 2-fluoro-5-methoxyphenyl, 2-fluoro-5-methylphenyl, 2-fluorophenyl, 2-hydroxypyrimidin-5-yl, 2-methoxy-4-methylphenyl, 2-methoxy-5-methylphenyl, 2-methoxyphenyl, 2-methyl-1H-benzo[d]imidazol-5-yl, 2-methyl-H-imidazo[4,5-b]pyridin-6-yl, 2-methyl-3H-imidazo[4,5-b]pyridin-6-yl, 2-morpholinopyridin-3-yl, 2-oxo-2,3-dihydro-1H-benzo[d]imidazol-5-yl, 2-oxo-2,3-dihydro-1H-imidazo[4,5-b]pyridin-6-yl, 2-oxo-2,3-dihydro-1H-pyrido[2,3-b][1,4]oxazin-6-yl, 2-oxo-2,3-dihydro-1H-pyrrolo[2,3-b]pyridin-5-yl, 2-oxo-2,3-dihydrobenzo[d]thiazol-6-yl, 2-oxoindolin-5-yl, 3'-((dimethylamino)methyl)biphenyl-3-yl, 3-(1-(2-hydroxyethyl)-1H-pyrazol-4-yl)phenyl, 3-(1-(cyclopropylmethyl)-1H-pyrazol-4-yl)phenyl, 3-(1,3-dimethyl-1H-pyrazol-4-yl)phenyl, 3-(1,3-dimethyl-2,4-dioxo-1,2,3,4-tetrahydropyrimidin-5-yl)phenyl, 3-(1-benzyl-1H-pyrazol-4-yl)phenyl, 3-(1-ethyl-1H-pyrazol-4-yl)phenyl, 3-(1H-pyrazol-3-yl)phenyl, 3-(1H-pyrazol-4-yl)phenyl, 3-(1H-pyrrol-3-yl)phenyl, 3-(1-isobutyl-1H-pyrazol-4-yl)phenyl, 3-(1-methyl-1H-pyrazol-4-yl)phenyl, 3-(1-methyl-1H-pyrrol-3-yl)phenyl, 3-(1-methyl-3-(trifluoromethyl)-1H-pyrazol-4-yl)phenyl, 3-(1-propyl-1H-pyrazol-4-yl)phenyl, 3-(2-(trifluoromethyl)phenoxy)phenyl, 3-(2,4-dimethylthiazol-5-yl)phenyl, 3-(2H-tetrazol-5-yl)phenyl, 3-(2-methoxypyrimidin-5-yl)phenyl, 3-(2-methylpyridin-4-yl)phenyl, 3-(3,5-dimethylisoxazol-4-yl)phenyl, 3-(3-methylthiophen-2-yl)phenyl, 3-(4-(trifluoromethyl)phenoxy)phenyl, 3-(4-methylthiophen-3-yl)phenyl, 3-(5-(aminomethyl)thiophen-2-yl)phenyl, 3-(5-cyanopyridin-3-yl)phenyl, 3-(5-methylpyridin-3-yl)phenyl, 3-(6-(2-morpholinoethylamino)pyridin-3-yl)phenyl, 3-(6-(3-(dimethylamino)propoxy)pyridin-3-yl)phenyl, 3-(6-(aminomethyl)pyridin-3-yl)phenyl, 3-(6-aminopyridin-3-yl)phenyl, 3-(6-methylpyridin-3-yl)phenyl, 3'-(aminomethyl)biphenyl-3-yl, 3-(aminomethyl)phenyl, 3'-(carboxy)biphenyl-3-yl, 3'-(dimethylamino)biphenyl-3-yl, 3-(furan-2-yl)phenyl, 3'-(hydroxymethyl)biphenyl-3-yl, 3-(hydroxymethyl)phenyl, 3'-(methoxymethyl)biphenyl-3-yl, 3'-(methylsulfonyl)biphenyl-3-yl, 3'-(N,N-dimethylsulfamoyl)biphenyl-3-yl, 3-(pyridin-2-yl)phenyl, 3-(pyridin-3-yl)phenyl, 3-(pyridin-4-yl)phenyl, 3-(pyrimidin-5-yl)phenyl, 3-(thiophen-3-yl)phenyl, 3-(trifluoromethyl)-1H-pyrrolo[2,3-b]pyridin-5-yl, 3-(trifluoromethyl)phenyl, 3,4-difluorophenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3,4-dimethoxyphenyl, 3,4-dimethylphenyl, 3,5-dichlorophenyl, 3,5-dimethyl-1-phenyl-1H-pyrazol-4-yl, 3,5-dimethylisoxazol-4-yl, 3,5-dimethylphenyl, 3-bromo-4-methylphenyl, 3-bromo-5-methylphenyl, 3-bromophenyl, 3-carboxyphenyl, 3-chloro-1H-pyrrolo[2,3-b]pyridin-5-yl, 3-chloro-1-methyl-1H-pyrrolo[2,3-b]pyridin-5-yl, 3-chloro-1-methyl-1H-pyrrolo[3,2-b]pyridin-6-yl, 3-chloro-2-fluorophenyl, 3-chloro-2-methyl-1H-pyrrolo[2,3-b]pyridin-5-yl, 3-chloro-2-methylphenyl, 3-chloro-4-cyanophenyl, 3-chloro-4-methoxyphenyl, 3-chlorophenyl, 3-cyano-1H-pyrrolo[2,3-b]pyridin-5-yl, 3-cyano-4-methylphenyl, 3'-cyanobiphenyl-3-yl, 3-cyanophenyl, 3-ethyl-3H-imidazo[4,5-b]pyridin-6-yl, 3-fluoro-4-methoxyphenyl, 3-fluoro-5-methylphenyl, 3-fluorophenyl, 3-methoxyphenyl, 3-methyl-1H-pyrazolo[3,4-b]pyridin-5-yl, 3-methyl-1H-pyrrolo[2,3-b]pyridin-5-yl, 3-methyl-2-oxo-2,3-dihydro-1H-imidazo[4,5-b]pyridin-6-yl, 3-methyl-3H-imidazo[4,5-b]pyridin-6-yl, 3-oxo-3,4-dihydro-2H-benzo[b][1,4]oxazin-6-yl, 3-phenoxyphenyl, 4'-((1-amino-3-hydroxy-1-oxopropan-2-yl)(methyl)amino)biphenyl-3-yl, 4'-((2-(dimethylamino)ethylamino)methyl)biphenyl-3-yl, 4'-((2,2,2-trifluoroethylamino)methyl)biphenyl-3-yl, 4'-((2,2-difluoroethylamino)methyl)biphenyl-3-yl, 4'-((2-acetamidoethyl)(methyl)amino)biphenyl-3-yl, 4'-((2-amino-2-oxoacetamido)methyl)biphenyl-3-yl, 4'-((2-aminoacetamido)methyl)biphenyl-3-yl, 4'-((2-fluoroethylamino)methyl)biphenyl-3-yl, 4'-((2-hydroxyethylamino)methyl)biphenyl-3-yl, 4'-((2-methoxyethylamino)methyl)biphenyl-3-yl, 4'-((cyanomethylamino)methyl)biphenyl-3-yl, 4'-((dimethylamino)methyl)biphenyl-4-yl, 4'-((ethylamino)methyl)biphenyl-3-yl, 4'-((isobutylamino)methyl)biphenyl-3-yl, 4'-((isopentylamino)methyl)biphenyl-3-yl, 4'-((isopropylamino)methyl)biphenyl-3-yl, 4'-((methylamino)methyl)biphenyl-3-yl, 4'-(1-aminocyclopropyl)-6-methoxybiphenyl-3-yl, 4'-(1-aminocyclopropyl)biphenyl-3-yl, 4'-(2-carboxy-N-methylacetamido)biphenyl-3-yl, 4-(2H-tetrazol-5-yl)phenyl, 4-(3-methoxyphenyl)pyrimidin-2-yl, 4-carboxypyrimidin-2-yl, 4'-(5-methyl-1,2,4-oxadiazol-3-yl)biphenyl-3-yl, 4'-(aminomethyl)-2-methoxybiphenyl-3-yl, 4'-(aminomethyl)-2-methylbiphenyl-3-yl, 4'-(aminomethyl)-3-(trifluoromethoxy)biphenyl-4-yl, 4'-(aminomethyl)-4-(trifluoromethoxy)biphenyl-3-yl, 4'-(aminomethyl)-4-chlorobiphenyl-3-yl, 4'-(aminomethyl)-4-ethoxybiphenyl-3-yl, 4'-(aminomethyl)-4-methoxybiphenyl-3-yl, 4'-(aminomethyl)-4-methylbiphenyl-3-yl, 4'-(aminomethyl)-5-(trifluoromethyl)biphenyl-3-yl, 4'-(aminomethyl)-5-methoxybiphenyl-3-yl, 4'-(aminomethyl)-5-methylbiphenyl-3-yl, 4'-(aminomethyl)-6-methoxybiphenyl-3-yl, 4'-(aminomethyl)-6-methylbiphenyl-3-yl, 4'-(aminomethyl)biphenyl-2-yl, 4'-(aminomethyl)biphenyl-3-yl, 4'-(aminomethyl)biphenyl-4-yl, 4-(aminomethyl)phenyl, 4'-(carboxymethyl)biphenyl-3-yl, 4'-(cyanomethoxy)biphenyl-3-yl, 4'-(cyanomethyl)biphenyl-3-yl, 4-(hydroxymethyl)phenyl, 4'-(methylsulfonamido)biphenyl-3-yl, 4-(methylsulfonyl)phenyl, 4'-(N'-hydroxycarbamimidoyl)-biphenyl-3-yl, 4-(phenylsulfonyl)thiophen-2-yl, 4-(pyridin-2-yl)phenyl, 4-(pyridin-3-yl)phenyl, 4-(pyridin-4-yl)phenyl, 4'-(sulfamoyl)biphenyl-3-yl, 4'-(thiazolidin-3-ylmethyl)biphenyl-3-yl, 4-(trifluoromethoxy)phenyl, 4'-(trifluoromethyl)biphenyl-4-yl, 4-(trifluoromethyl)phenyl, 4-(trifluoromethyl)pyrimidin-2-yl, 4,5-dichlorothiophen-2-yl, 4,6-dimethoxypyrimidin-2-yl, 4,6-dimethylpyrimidin-2-yl, 4-acetamidophenyl, 4-acetylphenyl, 4-aminopyrimidin-2-yl, 4-benzylpyrimidin- 2-yl, 4-bromo-3-chlorophenyl, 4-bromo-3-methylphenyl, 4-bromophenyl, 4'-carbamimidoyl-biphenyl-3-yl, 4'-carbamoyl-biphenyl-3-yl, 4-carboxyphenyl, 4-chloro-3-methoxyphenyl, 4-chloro-3-methylphenyl, 4-chlorophenyl, 4-chloropyridin-2-yl, 4-cyanophenyl, 4-ethoxy-4'-((isopropylamino)methyl)biphenyl-3-yl, 4-ethoxyphenyl, 4-ethyl-3,4-dihydro-2H-benzo[b][1,4]oxazin-6-yl, 4-fluoro-3-methylphenyl, 4'-fluorobiphenyl-4-yl, 4-fluorophenyl, 4-hydroxy-6-methylquinolin-3-yl, 4-hydroxy-6-methylquinolin-8-yl, 4-hydroxy-7-methylquinolin-3-yl, 4-hydroxy-8-methylquinolin-3-yl, 4-hydroxyquinolin-3-yl, 4-isobutyl-3,4-dihydro-2H-benzo[b][1,4]oxazin-6-yl,
4-isopropoxyphenyl, 4-isopropyl-3,4-dihydro-2H-benzo[b][1,4]oxazin-6-yl, 4-methoxy-1H-indazol-5-yl, 4-methoxy-2,3-dimethylphenyl, 4-methoxy-2-methylphenyl, 4-methoxy-3-methylphenyl, 4-methoxy-5,6,7,8-tetrahydronaphthalen-1-yl, 4-methoxynaphthalen-1-yl, 4-methoxyphenyl, 4-methoxypyrimidin-2-yl, 4-methyl-2-phenylthiazol-5-yl, 4-methyl-3,4-dihydro-2H-benzo[b][1,4]oxazin-6-yl, 4-methyl-3,4-dihydro-2H-pyrido[3,2-b][1,4]oxazin-7-yl, 4-methyl-6-phenylpyrimidin-2-yl, 4-methylpyrimidin-2-yl, 4-oxo-1-propyl-1,4-dihydroquinolin-3-yl, 4-phenylpyrimidin-2-yl, 4-sec-butylphenyl, 4-tert-butylphenyl, 4-tert-pentylphenyl, 5-(1-methyl-1H-pyrazol-4-yl)pyridin-3-yl, 5-(1-methyl-3-(trifluoromethyl)-1H-pyrazol-5-yl)thiophen-2-yl, 5-(4-(aminomethyl)phenyl)-2,3-dihydrobenzofuran-7-yl, 5-(4-(aminomethyl)phenyl)pyridin-3-yl, 5-(5-(trifluoromethyl)isoxazol-3-yl)thiophen-2-yl, 5-(methoxycarbonyl)pyrimidin-2-yl, 5-(trifluoromethyl)pyrazin-2-yl, 5-(trifluoromethyl)pyrimidin-2-yl, 5,6,7,8-tetrahydro-1,6-naphthyridin-3-yl, 5,6,7,8-tetrahydronaphthalen-2-yl, 5,6,7,8-tetrahydroquinolin-3-yl, 5-benzylpyrimidin-2-yl, 5-bromo-2-(2-(pyrrolidin-1-yl)ethoxy)phenyl, 5-bromo-2,3-dihydrobenzofuran-7-yl, 5-bromo-2-chlorophenyl, 5-bromo-2-methoxyphenyl, 5-bromo-2-methylphenyl, 5-bromopyridin-3-yl, 5-chloro-1,3-dimethyl-1H-pyrazol-4-yl, 5-chloro-2-cyanophenyl, 5-chloro-2-fluorophenyl, 5-chloro-2-methoxyphenyl, 5-chloro-2-methylphenyl, 5-chlorobenzo[c][1,2,5]oxadiazol-4-yl, 5-chloronaphthalen-2-yl, 5-chlorothiophen-2-yl, 5-cyano-2-methylphenyl, 5-ethylpyrimidin-2-yl, 5-fluoro-2-methoxyphenyl, 5-fluoro-2-methylphenyl, 5-heptylpyrimidin-2-yl, 5-methoxy-2-methylpyridin-3-yl, 5-methoxypyridin-3-yl, 5-methyl-1-phenyl-1H-pyrazol-4-yl, 5-methyl-2-(trifluoromethyl)furan-3-yl, 5-methyl-3H-imidazo[4,5-b]pyridin-6-yl, 5-methylbenzo[c][1,2,5]oxadiazol-4-yl, 5-oxo-6,7-dihydro-5H-pyrrolo[3,4-b]pyridin-3-yl, 5-phenylpyrimidin-2-yl, 5-phenylthiophen-2-yl, 5-propylpyrimidin-2-yl, 6-(2-aminoethylamino)pyridin-3-yl, 6-(2-hydroxyethylamino)pyridin-3-yl, 6-(2-methoxyethylamino)pyridin-3-yl, 6'-(aminomethyl)-3,3'-bipyridin-5-yl, 6-(dimethylamino)-1-methyl-2,3-dihydro-1H-pyrido[2,3-b][1,4]oxazin-7-yl, 6-(dimethylamino)pyridin-3-yl, 6-(piperazin-1-yl)pyridin-3-yl, 6-(piperidin-1-yl)pyridin-3-yl, 6,7-dihydro-5H-cyclopenta[b]pyridin-3-yl, 6,7-dihydro-5H-pyrrolo[3,4-b]pyridin-3-yl, 6-amino-1-methyl-2,3-dihydro-1H-pyrido[2,3-b][1,4]oxazin-7-yl, 6-chloro-1-methyl-2,3-dihydro-1H-pyrido[2,3-b][1,4]oxazin-7-yl, 6-chloroimidazo[2,1-b]thiazol-5-yl, 6-chloronaphthalen-2-yl, 6-ethoxy-1-methyl-2,3-dihydro-1H-pyrido[2,3-b][1,4]oxazin-7-yl, 6-ethoxypyridin-3-yl, 6-fluoro-4-hydroxyquinolin-3-yl, 6-fluoro-4-oxo-1,4-dihydroquinolin-3-yl, 6-hydroxy-1-methyl-2,3-dihydro-1H-pyrido[2,3-b][1,4]oxazin-7-yl, 6-hydroxypyridin-3-yl, 6-methoxy-1-methyl-2,3-dihydro-1H-pyrido[2,3-b][1,4]oxazin-7-yl, 6-methoxynaphthalen-2-yl, 6-methoxypyridin-3-yl, 6-morpholinopyridin-3-yl, 6-phenoxypyridin-3-yl, 7,8-dihydro-5H-pyrano[4,3-b]pyridin-3-yl, 7-amino-1,8-naphthyridin-3-yl, 7-chlorobenzo[c][1,2,5]oxadiazol-4-yl, 7-fluoro-4-hydroxyquinolin-3-yl, 7-fluoro-4-oxo-1,4-dihydroquinolin-3-yl, 7-methoxybenzo[c][1,2,5]oxadiazol-4-yl, 7-methyl-3H-imidazo[4,5-b]pyridin-6-yl, 8-fluoro-5-b]pyridin-6-yl, 8-fluoro-4-hydroxyquinolin-3-yl, 8-fluoro-4-oxo-1,4-dihydroquinolin-3-yl, 8-methyl-4-oxo-1,4-dihydroquinolin-3-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, benzyl, biphenyl-2-yl, biphenyl-3-yl, biphenyl-4-yl, chroman-6-yl, cyclohexyl, furan-3-yl, imidazo[1,2-a]pyridin-6-yl, m-tolyl, naphthalen-1-yl, naphthalen-2-yl, phenyl, p-tolyl, pyrazin-2-yl, pyridin-2-yl, pyridin-3-yl, pyridin-3-yl N-oxide, pyrimidin-2-yl, pyrimidin-4-yl, quinolin-3-yl, quinolin-6-yl, and thiophen-3-yl.

The $R^1$ Group (Aryl)

One aspect of the present invention relates to wherein $R^1$ is aryl optionally substituted with one or more substituents as described herein.

In some embodiments, $R^1$ is aryl optionally substituted with one or more substituents selected from: $C_1$-$C_6$ alkoxy, $C_1$-$C_7$ alkyl, $C_1$-$C_6$ alkylcarboxamide, $C_1$-$C_6$ alkylsulfonamido, $C_1$-$C_6$ alkylsulfonyl, aryloxy, carboxamide, carbamimidoyl, carboxy, cyano, $C_3$-$C_7$ cycloalkyl, $C_2$-$C_8$ dialkylamino, $C_2$-$C_5$ dialkylsulfamoyl, $C_1$-$C_6$ haloalkoxy, $C_1$-$C_6$ haloalkyl, halogen, hydroxycarbamimidoyl, and sulfamoyl; and wherein said $C_1$-$C_6$ alkoxy, $C_1$-$C_7$ alkyl, aryloxy, and $C_2$-$C_8$ dialkylamino are each optionally substituted with one or more substituents selected from: amino, $C_1$-$C_6$ alkoxy, $C_1$-$C_6$ alkylamino, $C_1$-$C_6$ alkylcarboxamide, carboxy, —Y—$C_1$-$C_6$-alkylene-Z optionally substituted with oxo, cyano, $C_2$-$C_6$ dialkylamino, $C_1$-$C_6$ haloalkyl, $C_1$-$C_6$ haloalkylamino, heterocyclyl, hydroxyl, and oxo;

Y is —NH—; and

Z is selected from: $C_1$-$C_6$ alkoxy, amino, cyano, $C_2$-$C_6$ dialkylamino, and hydroxyl.

In some embodiments, $R^1$ is selected from: 5,6,7,8-tetrahydronaphthalenyl, biphenylyl, naphthalenyl, and phenyl; each optionally substituted with one or more substituents selected from: (2-ethyl)(methyl)amino, 4-(trifluoromethyl)phenoxy, acetamido, bromo, carbamimidoyl, carboxamide, carboxy, chloro, cyano, cyclopropyl, dimethylamino, dimethylcarbamoyl, ethoxy, ethyl, fluoro, hydroxycarbamimidoyl, isopropoxy, isopropyl(methyl)amino, methoxy, methyl, methyl(propyl)amino, methylsulfonamido, methylsulfonyl, N,N-dimethylsulfamoyl, phenoxy, sec-butyl, sulfamoyl, tert-butyl, tert-pentyl, trifluoromethoxy, and trifluoromethyl; and wherein (2-ethyl)(methyl)amino, cyclopropyl, ethoxy, ethyl, isopropyl(methyl)amino, methoxy, methyl, methyl(propyl)amino, and phenoxy; are each optionally substituted with one or more substituents selected from: 2-(dimethylamino)ethylamino, 2,2,2-trifluoroethylamino, 2,2-difluoroethylamino, 2-amino-2-oxoacetamido, 2-aminoacetamido, 2-fluoroethylamino, 2-hydroxyethylamino, 2-methoxyethylamino, acetamido, amino, carboxy, cyano, cyanomethylamino, dimethylamino, ethylamino, hydroxyl, isobutylamino, isopentylamino, isopropylamino, methoxy, methylamino, oxo, pyrrolidin-1-yl, thiazolidin-3-yl, and trifluoromethyl.

In some embodiments, $R^1$ is selected from: 5,6,7,8-tetrahydronaphthalen-1-yl, 5,6,7,8-tetrahydronaphthalen-2-yl, biphenyl-2-yl, biphenyl-3-yl, biphenyl-4-yl, naphthalen-1-yl, naphthalen-2-yl, and phenyl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(pyrrolidin-1-yl)ethoxy, 2-(trifluoromethyl)phenoxy, 2-carboxy-N-methylacetamido, 4-(trifluoromethyl)phenoxy, acetamido, acetyl, aminomethyl, bromo, carbamimidoyl, carboxamide, carboxy, carboxymethyl, chloro, cyano, cyanomethoxy, cyanomethyl, dimethylamino, dimethylcarbamoyl, ethoxy, fluoro, hydroxycarbamimidoyl, hydroxymethyl, isopropoxy, methoxy, methoxymethyl, methyl, methylsulfonamido, methylsulfonyl, N,N-dimethylsulfamoyl, phenoxy, sec-butyl, sulfamoyl, tert-butyl, tert-pentyl, thiazolidin-3-ylmethyl, trifluoromethoxy, and trifluoromethyl.

In some embodiments, $R^1$ is selected from: (dimethylcarbamoyl)phenyl, 2-(methylsulfonyl)phenyl, 2-(trifluoromethoxy)phenyl, 2-(trifluoromethyl)phenyl, 2,3-dichlorophenyl, 2,3-difluorophenyl, 2,3-dimethylphenyl, 2,4-dichlorophenyl, 2,4-difluorophenyl, 2,5-dichlorophenyl, 2,5-difluorophenyl, 2,5-dimethylphenyl, 2,6-difluorophenyl, 2-bromophenyl, 2-chloro-3-fluorophenyl, 2-chloro-4-cyanophenyl, 2-chloro-4-fluorophenyl, 2-chloro-5-(methylsulfonyl)phenyl, 2-chloro-5-(trifluoromethyl)phenyl, 2-chloro-5-fluorophenyl, 2-chlorophenyl, 2-cyano-5-methoxyphenyl, 2-cyano-5-methylphenyl, 2-cyanophenyl, 2-fluoro-3-methylphenyl, 2-fluoro-5-methoxyphenyl, 2-fluoro-5-methylphenyl, 2-fluorophenyl, 2-methoxy-4-methylphenyl, 2-methoxy-5-methylphenyl, 2-methoxyphenyl, 3'-((dimethylamino)methyl)biphenyl-3-yl, 3-(2-(trifluoromethyl)phenoxy)phenyl, 3-(4-(trifluoromethyl)phenoxy)phenyl, 3'-(aminomethyl)biphenyl-3-yl, 3-(aminomethyl)phenyl, 3'-(carboxy)biphenyl-3-yl, 3'-(dimethylamino)biphenyl-3-yl, 3'-(hydroxymethyl)biphenyl-3-yl, 3-(hydroxymethyl)phenyl, 3'-(methoxymethyl)biphenyl-3-yl, 3'-(methylsulfonyl)biphenyl-3-yl, 3'-(N,N-dimethylsulfamoyl)biphenyl-3-yl, 3-(trifluoromethyl)phenyl, 3,4-difluorophenyl, 3,4-dimethoxyphenyl, 3,4-dimethylphenyl, 3,5-dichlorophenyl, 3,5-dimethylphenyl, 3-bromo-4-methylphenyl, 3-bromo-5-methylphenyl, 3-bromophenyl, 3-carboxyphenyl, 3-chloro-2-fluorophenyl, 3-chloro-2-methylphenyl, 3-chloro-4-cyanophenyl, 3-chloro-4-methoxyphenyl, 3-chlorophenyl, 3-cyano-4-methylphenyl, 3'-cyanobiphenyl-3-yl, 3-cyanophenyl, 3-fluoro-4-methoxyphenyl, 3-fluoro-5-methylphenyl, 3-fluorophenyl, 3-methoxyphenyl, 3-phenoxyphenyl, 4'-((1-amino-3-hydroxy-1-oxopropan-2-yl)(methyl)amino)biphenyl-3-yl, 4'-((2-(dimethylamino)ethylamino)methyl)biphenyl-3-yl, 4'-((2,2,2-trifluoroethylamino)methyl)biphenyl-3-yl, 4'-((2,2-difluoroethylamino)methyl)biphenyl-3-yl, 4'-((2-acetamidoethyl)(methyl)amino)biphenyl-3-yl, 4'-((2-amino-2-oxoacetamido)methyl)biphenyl-3-yl, 4'-((2-aminoacetamido)methyl)biphenyl-3-yl, 4'-((2-fluoroethylamino)methyl)biphenyl-3-yl, 4'-((2-hydroxyethylamino)methyl)biphenyl-3-yl, 4'-((2-methoxyethylamino)methyl)biphenyl-3-yl, 4'-((cyanomethylamino)methyl)biphenyl-3-yl, 4'-((dimethylamino)methyl)biphenyl-4-yl, 4'-((ethylamino)methyl)biphenyl-3-yl, 4'-((isobutylamino)methyl)biphenyl-3-yl, 4'-((isopentylamino)methyl)biphenyl-3-yl, 4'-((isopropylamino)methyl)biphenyl-3-yl, 4'-((methylamino)methyl)biphenyl-3-yl, 4'-(1-aminocyclopropyl)-6-methoxybiphenyl-3-yl, 4'-(1-aminocyclopropyl)biphenyl-3-yl, 4'-(2-carboxy-N-methylacetamido)biphenyl-3-yl, 4'-(aminomethyl)-2-methoxybiphenyl-3-yl, 4'-(aminomethyl)-2-methylbiphenyl-3-yl, 4'-(aminomethyl)-3-(trifluoromethoxy)biphenyl-4-yl, 4'-(aminomethyl)-4-(trifluoromethoxy)biphenyl-3-yl, 4'-(aminomethyl)-4-chlorobiphenyl-3-yl, 4'-(aminomethyl)-4-ethoxybiphenyl-3-yl, 4'-(aminomethyl)-4-methoxybiphenyl-3-yl, 4'-(aminomethyl)-4-methylbiphenyl-3-yl, 4'-(aminomethyl)-5-(trifluoromethyl)biphenyl-3-yl, 4'-(aminomethyl)-5-methoxybiphenyl-3-yl, 4'-(aminomethyl)-5-methylbiphenyl-3-yl, 4'-(aminomethyl)-6-methoxybiphenyl-3-yl, 4'-(aminomethyl)-6-methylbiphenyl-3-yl, 4'-(aminomethyl)biphenyl-2-yl, 4'-(aminomethyl)biphenyl-3-yl, 4'-(aminomethyl)biphenyl-4-yl, 4-(aminomethyl)phenyl, 4'-(carboxymethyl)biphenyl-3-yl, 4'-(cyanomethoxy)biphenyl-3-yl, 4'-(cyanomethyl)biphenyl-3-yl, 4-(hydroxymethyl)phenyl, 4'-(methylsulfonamido)biphenyl-3-yl, 4-(methylsulfonyl)phenyl, 4'-(N'-hydroxycarbamimidoyl)-biphenyl-3-yl, 4'-(sulfamoyl)biphenyl-3-yl, 4'-(thiazolidin-3-ylmethyl)biphenyl-3-yl, 4-(trifluoromethoxy)phenyl, 4'-(trifluoromethyl)biphenyl-4-yl, 4-(trifluoromethyl)phenyl, 4-acetamidophenyl, 4-acetylphenyl, 4-bromo-3-chlorophenyl, 4-bromo-3-methylphenyl, 4-bromophenyl, 4'-carbamimidoyl-biphenyl-3-yl, 4'-carbamoyl-biphenyl-3-yl, 4-carboxyphenyl, 4-chloro-3-methoxyphenyl, 4-chloro-3-methylphenyl, 4-chlorophenyl, 4-cyanophenyl, 4-ethoxy-4'-((isopropylamino)methyl)biphenyl-3-yl, 4-ethoxyphenyl, 4-fluoro-3-methylphenyl, 4'-fluorobiphenyl-4-yl, 4-fluorophenyl, 4-isopropoxyphenyl, 4-methoxy-2,3-dimethylphenyl, 4-methoxy-2-methylphenyl, 4-methoxy-3-methylphenyl, 4-methoxy-5,6,7,8-tetrahydronaphthalen-1-yl, 4-methoxynaphthalen-1-yl, 4-methoxyphenyl, 4-sec-butylphenyl, 4-tert-butylphenyl, 4-tert-pentylphenyl, 5,6,7,8-tetrahydronaphthalen-2-yl, 5-bromo-2-(2-(pyrrolidin-1-yl)ethoxy)phenyl, 5-bromo-2-chlorophenyl, 5-bromo-2-methoxyphenyl, 5-bromo-2-methylphenyl, 5-chloro-2-cyanophenyl, 5-chloro-2-fluorophenyl, 5-chloro-2-methoxyphenyl, 5-chloro-2-methylphenyl, 5-chloronaphthalen-2-yl, 5-cyano-2-methylphenyl, 5-fluoro-2-methoxyphenyl, 5-fluoro-2-methylphenyl, 6-chloronaphthalen-2-yl, 6-methoxynaphthalen-2-yl, biphenyl-2-yl, biphenyl-3-yl, biphenyl-4-yl, m-tolyl, naphthalen-1-yl, naphthalen-2-yl, phenyl, and p-tolyl.

The $R^1$ Group (Heteroaryl)

One aspect of the present invention relates to wherein $R^1$ is heteroaryl optionally substituted with one or more substituents as described herein.

In some embodiments, $R^1$ is heteroaryl optionally substituted with one or more substituents selected from: $C_1$-$C_6$ alkoxy, $C_1$-$C_6$ alkoxycarbonyl, $C_1$-$C_7$ alkyl, $C_1$-$C_6$ alkylamino, amino, aryloxy, arylsulfonyl, carboxy, cyano, $C_2$-$C_5$ dialkylamino, $C_1$-$C_6$ haloalkyl, halogen, heterocyclyl, hydroxyl, and oxo; and wherein said $C_1$-$C_6$ alkoxy, $C_1$-$C_7$ alkyl, and $C_1$-$C_6$ alkylamino are each optionally substituted with one or more substituents selected from: amino, $C_1$-$C_6$ alkoxy, carboxy, —Y—$C_1$-$C_6$-alkylene-Z optionally substituted with oxo, $C_3$-$C_7$ cycloalkyl, $C_2$-$C_6$ dialkylamino, heterocyclyl, hydroxyl, and phenyl;

Y is —O—; and

Z is phenyl.

In some embodiments, $R^1$ is selected from: (1,2,3,4-tetrahydropyrimidin-5-yl)phenyl, (5-isoxazol-3-yl)thiophen-2-yl, (5-isoxazol-3-yl)thiophen-3-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-2-yl, (1H-pyrazol-5-yl)thiophen-3-yl, 1H-pyrazolo[3,4-b]pyridinyl, 1H-pyrazolo[4,3-b]pyridinyl, 1H-pyrazolyl, 1H-pyrrolo[2, 3-b]pyridinyl, 1H-pyrrolo[3,2-b]pyridinyl, 1-phenyl-1H-pyrazolyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(phenyl)pyrimidinyl, 4-(pyridin-3-yl)phenyl, 4-(pyridin-4-yl)phenyl, 4-phenylpyrimidinyl, 5-(1H-pyrazol-4-yl)pyridin-3-yl, 5-(phenyl)pyridinyl, 5,6,7,8-tetrahydro-1,6-naphthyridinyl, 5,6,7,8-tetrahydroquinolinyl, 5-phenyl-2,3-dihydrobenzofuranyl, 5-phenylpyrimidinyl, 5-phenylthiophen-2-yl, 5-phenylthiophen-3-yl, 6,7-dihydro-5H-cyclopenta[b]pyridinyl, 6,7-dihydro-5H-pyrrolo[3,4-b]pyridinyl, 6-phenylpyrimidinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, chromanyl, furanyl, imidazo[1,2-a]pyridinyl, imidazo[2,1-b]thiazolyl, indolinyl, isoxazolyl, pyrazinyl, pyridinyl, pyrimidinyl, quinolinyl, thiophen-2-yl, and thiophen-3-yl; each optionally substituted with one or more substituents selected from: amino, bromo, carboxy, chloro, cyano, dimethylamino, ethoxy, ethyl, ethylamino, fluoro, heptyl, hydroxyl, isobutyl, isopropyl, methoxy, methoxycarbonyl, methyl, methylamino, morpholino, oxo, phenoxy, phenylsulfonyl, piperazin-1-yl, piperidin-1-yl, propoxy, propyl, and trifluoromethyl; and wherein ethyl, ethylamino, methyl, and propoxy; are each optionally substituted with one or more substituents selected from: amino, benzyloxy, carboxy, cyclopropyl, dimethylamino, hydroxyl, methoxy, morpholino, and phenyl.

In some embodiments, $R^1$ is selected from: (1,2,3,4-tetrahydropyrimidin-5-yl)phenyl, (5-isoxazol-3-yl)thiophen-2-yl, (pyridin-2-yl)phenyl, [3,3'-bipyridin]-5-yl, 1,2,3,4-tetrahydropyrido[2,3-b][1,4]oxazepin-8-yl, 1',2'-dihydrospiro[cyclopropane-1,3'-pyrido[2,3-b][1,4]oxazine]-7'-yl, 1,4-dihydroquinolin-3-yl, 1,5-naphthyridin-3-yl, 1,8-naphthyridin-3-yl, 1H-benzo[d]imidazol-5-yl, 1H-benzo[d]imidazol-6-yl, 1H-imidazo[4,5-b]pyridin-6-yl, 1H-imidazol-4-yl, 1H-indazol-5-yl, 1H-indazol-6-yl, 1H-indol-5-yl, 1H-pyrazol-3-yl, 1H-pyrazol-4-yl, 5-(1H-pyrazol-5-yl)thiophen-2-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-phenyl-1H-pyrazol-4-yl, 2,3-dihydro-[1,4]dioxino[2,3-b]pyridin-7-yl, 2,3-dihydro-1H-benzo[d]imidazol-5-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzo[b][1,4]dioxin-6-yl, 2,3-dihydrobenzo[d]thiazol-6-yl, 2,3-dihydrobenzofuran-5-yl, 2,3-dihydrobenzofuran-7-yl, 2,3-dihydrofuro[2,3-b]pyridin-5-yl, 2-phenylthiazol-5-yl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-6-yl, 4'-(1,2,4-oxadiazol-3-yl)biphenyl-3-yl, 4-(2H-tetrazol-5-yl)phenyl, 4-(phenyl)pyrimidin-2-yl, 4-(pyridin-3-yl)phenyl, 4-(pyridin-4-yl)phenyl, 4-phenylpyrimidin-2-yl, 5-(1H-pyrazol-4-yl)pyridin-3-yl, 5-(phenyl)pyridin-3-yl, 5,6,7,8-tetrahydro-1,6-naphthyridin-3-yl, 5,6,7,8-tetrahydroquinolin-3-yl, 5-phenyl-2,3-dihydrobenzofuran-7-yl, 5-phenylpyrimidin-2-yl, 5-phenylthiophen-2-yl, 6,7-dihydro-5H-cyclopenta[b]pyridin-3-yl, 6,7-dihydro-5H-pyrrolo[3,4-b]pyridin-3-yl, 6-phenylpyrimidin-2-yl, 7,8-dihydro-5H-pyrano[4,3-b]pyridin-3-yl, benzo[c][1,2,5]oxadiazol-4-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, chroman-6-yl, furan-3-yl, imidazo[1,2-a]pyridin-6-yl, imidazo[2,1-b]thiazol-5-yl, indolin-5-yl, isoxazol-4-yl, pyrazin-2-yl, pyridin-2-yl, pyridin-3-yl, pyrimidin-2-yl, pyrimidin-4-yl, pyrimidin-5-yl, quinolin-3-yl, quinolin-6-yl, quinolin-8-yl, thiophen-2-yl, and thiophen-3-yl; each optionally substituted with one or more substituents selected from: 2-(benzyloxy)ethyl, 2-aminoethylamino, 2-hydroxyethyl, 2-hydroxyethylamino, 2-methoxyethyl, 2-methoxyethylamino, 2-morpholinoethylamino, 3-(dimethylamino)propoxy, amino, aminomethyl, benzyl, bromo, carboxy, carboxymethyl, chloro, cyano, cyclopropylmethyl, dimethylamino, ethoxy, ethyl, fluoro, heptyl, hydroxyl, isobutyl, isopropyl, methoxy, methoxycarbonyl, methyl, methylamino, morpholino, oxo, phenoxy, phenylsulfonyl, piperazin-1-yl, piperidin-1-yl, and propyl, trifluoromethyl.

In some embodiments, $R^1$ is selected from: 1-(2-(benzyloxy)ethyl)-2,3-dihydro-1H-pyrido[2,3-b][1,4]oxazin-7-yl, 1-(2-hydroxyethyl)-2,3-dihydro-1H-pyrido[2,3-b][1,4]oxazin-7-yl, 1-(2-methoxyethyl)-2,3-dihydro-1H-pyrido[2,3-b][1,4]oxazin-7-yl, 1-(carboxymethyl)-4-oxo-1,4-dihydroquinolin-3-yl, 1,2-dimethyl-1H-imidazol-4-yl, 1,3,3-trimethyl-2,3-dihydro-1H-pyrido[2,3-b][1,4]oxazin-7-yl, 1,3-dimethyl-2,3-dihydro-1H-pyrido[2,3-b][1,4]oxazin-7-yl, 1,5-naphthyridin-3-yl, 1,6-dimethyl-2,3-dihydro-1H-pyrido[2,3-b][1,4]oxazin-7-yl, 1,8-dimethyl-2,3-dihydro-1H-pyrido[2,3-b][1,4]oxazin-7-yl, 1-ethyl-2,3-dihydro-1H-pyrido[2,3-b][1,4]oxazin-7-yl, 1-ethyl-4-oxo-1,4-dihydroquinolin-3-yl, 1-ethyl-5-methyl-H-pyrazol-4-yl, 1-ethyl-6-fluoro-4-oxo-1,4-dihydroquinolin-3-yl, 1-ethyl-6-methyl-4-oxo-1,4-dihydroquinolin-3-yl, 1-ethyl-7-fluoro-4-oxo-1,4-dihydroquinolin-3-yl, 1-ethyl-7-methyl-4-oxo-1,4-dihydroquinolin-3-yl, 1-ethyl-8-fluoro-4-oxo-1,4-dihydroquinolin-3-yl, 1-ethyl-8-methyl-4-oxo-1,4-dihydroquinolin-3-yl, 1H-benzo[d]imidazol-5-yl, 1H-benzo[d]imidazol-6-yl, 1H-imidazo[4,5-b]pyridin-6-yl, 1H-indazol-5-yl, 1H-indazol-6-yl, 1H-pyrazol-4-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-isopropyl-2,3-dihydro-1H-pyrido[2,3-b][1,4]oxazin-7-yl, 1-methyl-1,2,3,4-tetrahydropyrido[2,3-b][1,4]oxazepin-8-yl, 1'-methyl-1',2'-dihydrospiro[cyclopropane-1,3'-pyrido[2,3-b][1,4]oxazine]-7'-yl, 1-methyl-1H-imidazo[4,5-b]pyridin-6-yl, 1-methyl-1H-imidazol-4-yl, 1-methyl-1H-indol-5-yl, 1-methyl-1H-pyrazol-3-yl, 1-methyl-1H-pyrrolo[3,2-b]pyridin-6-yl, 1-methyl-2,3-dihydro-1H-pyrido[2,3-b][1,4]oxazin-7-yl, 1-methyl-2-oxo-2,3-dihydro-1H-imidazo[4,5-b]pyridin-6-yl, 1-methyl-3-(trifluoromethyl)-1H-pyrazol-4-yl, 1-methyl-4-oxo-1,4-dihydroquinolin-3-yl, 1-methyl-6-(methylamino)-2,3- dihydro-1H-pyrido[2,3-b][1,4]oxazin-7-yl, 1-phenyl-1H-pyrazol-4-yl, 1-propyl-2,3-dihydro-1H-pyrido[2,3-b][1,4]oxazin-7-yl, 2-(dimethylamino)pyridin-3-yl, 2,2-dimethylchroman-6-yl, 2,3-dihydro-[1,4]dioxino[2,3-b]pyridin-7-yl, 2,3-dihydro-1H-pyrido[2,3-b][1,4]oxazin-7-yl, 2,3-dihydrobenzo[b][1,4]dioxin-6-yl, 2,3-dihydrobenzofuran-5-yl, 2,3-dihydrofuro[2,3-b]pyridin-5-yl, 2,3-dioxoindolin-5-yl, 2-ethyl-3H-imidazo[4,5-b]pyridin-6-yl, 2-hydroxypyrimidin-5-yl, 2-methyl-1H-benzo[d]imidazol-5-yl, 2-methyl-1H-imidazo[4,5-b]pyridin-6-yl, 2-methyl-3H-imidazo[4,5-b]pyridin-6-yl, 2-morpholinopyridin-3-yl, 2-oxo-2,3-dihydro-1H-benzo[d]imidazol-5-yl, 2-oxo-2,3-dihydro-1H-imidazo[4,5-b]pyridin-6-yl, 2-oxo-2,3-dihydro-1H-pyrido[2,3-b][1,4]oxazin-6-yl, 2-oxo-2,3-dihydro-1H-pyrrolo[2,3-b]pyridin-5-yl, 2-oxo-2,3-dihydrobenzo[d]thiazol-6-yl, 2-oxoindolin-5-yl, 3-(1-(2-hydroxyethyl)-1H-pyrazol-4-yl)phenyl, 3-(1-(cyclopropylmethyl)-1H-pyrazol-4-yl)phenyl, 3-(1,3-dimethyl-1H-pyrazol-4-yl)phenyl, 3-(1,3-dimethyl-2,4-dioxo-1,2,3,4-tetrahydropyrimidin-5-yl)phenyl, 3-(1-benzyl-1H-pyrazol-4-yl)phenyl, 3-(1-ethyl-1H-pyrazol-4-yl)phenyl, 3-(1H-pyrazol-3-yl)phenyl, 3-(1H-pyrazol-4-yl)phenyl, 3-(1H-pyrrol-3-yl)phenyl, 3-(1-isobutyl-1H-pyrazol-4-yl)phenyl, 3-(1-methyl-1H-pyrazol-4-yl)phenyl, 3-(1-methyl-1H-pyrrol-3-yl)phenyl, 3-(1-methyl-3-(trifluoromethyl)-1H-pyrazol-4-yl)phenyl, 3-(1-propyl-1H-pyrazol-4-yl)phenyl, 3-(2,4-dimethylthiazol-5-yl)phenyl, 3-(2H-tetrazol-5-yl)phenyl, 3-(2-methoxypyrimidin-5-yl)phenyl, 3-(2-methylpyridin-4-yl)phenyl, 3-(3,5-dimethylisoxazol-4-yl)phenyl, 3-(3-methylthiophen-2-yl)phenyl, 3-(4-methylthiophen-3-yl)phenyl, 3-(5-(aminomethyl)thiophen-2-yl)phenyl, 3-(5-cyanopyridin-3-yl)phenyl, 3-(5-methylpyridin-3-yl)phenyl, 3-(6-(2-morpholinoethylamino)pyridin-3-yl)phenyl, 3-(6-(3-(dimethylamino)propoxy)pyridin-3-yl)phenyl, 3-(6-(aminomethyl)pyridin-3-yl)phenyl, 3-(6-aminopyridin-3-yl)phenyl, 3-(6-methylpyridin-3-yl)phenyl, 3-(furan-2-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiophen-3-yl)phenyl, 3-(trifluoromethyl)-1H-pyrrolo[2,3-b]pyridin-5-yl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3,5-dimethyl-1-phenyl-1H-pyrazol-4-yl, 3,5-dimethylisoxazol-4-yl, 3-chloro-1H-pyrrolo[2,3-b]pyridin-5-yl, 3-chloro-1-methyl-1H-pyrrolo[2,3-b]pyridin-5-yl, 3-chloro-1-methyl-1H-pyrrolo[3,2-b]pyridin-6-yl, 3-chloro-2-methyl-1H-pyrrolo[2,3-b]pyridin-5-yl, 3-cyano-1H-pyrrolo[2,3-b]pyridin-5-yl, 3-ethyl-3H-imidazo[4,5-b]pyridin-6-yl, 3-methyl-H-pyrazolo[3,4-b]pyridin-5-yl, 3-methyl-1H-pyrrolo[2,3-b]pyridin-5-yl, 3-methyl-2-oxo-2,3-dihydro-1H-imidazo[4,5-b]pyridin-6-yl, 3-methyl-3H-imidazo[4,5-b]pyridin-6-yl, 3-oxo-3,4-dihydro-2H-benzo[b][1,4]oxazin-6-yl, 4-(2H-tetrazol-5-yl)phenyl, 4-(3-methoxyphenyl)pyrimidin-2-yl, 4-carboxypyrimidin-2-yl, 4'-(5-methyl-1,2,4-oxadiazol-3-yl)biphenyl-3-yl, 4-(phenylsulfonyl)thiophen-2-yl, 4-(pyridin-2-yl)phenyl, 4-(pyridin-3-yl)phenyl, 4-(pyridin-4-yl)phenyl, 4-(trifluoromethyl)pyrimidin-2-yl, 4,5-dichlorothiophen-2-yl, 4,6-dimethoxypyrimidin-2-yl, 4,6-dimethylpyrimidin-2-yl, 4-aminopyrimidin-2-yl, 4-benzylpyrimidin-2-yl, 4-chloropyridin-2-yl, 4-ethyl-3,4-dihydro-2H-benzo[b][1,4]oxazin-6-yl, 4-hydroxy-6-methylquinolin-3-yl, 4-hydroxy-6-methylquinolin-8-yl, 4-hydroxy-7-methylquinolin-3-yl, 4-hydroxy-8-methylquinolin-3-yl, 4-hydroxyquinolin-3-yl, 4-isobutyl-3,4-dihydro-2H-benzo[b][1,4]oxazin-6-yl, 4-isopropyl-3,4-dihydro-2H-benzo[b][1,4]oxazin-6-yl, 4-methoxy-1H-indazol-5-yl, 4-methoxypyrimidin-2-yl, 4-methyl-2-phenylthiazol-5-yl, 4-methyl-3,4-dihydro-2H-benzo[b][1,4]oxazin-6-yl, 4-methyl-3,4-dihydro-2H-pyrido[3,2-b][1,4]oxazin-7-yl, 4-methyl-6-phenylpyrimidin-2-yl, 4-methylpyrimidin-2-yl, 4-oxo-1-propyl-1,4-dihydroquinolin-3-yl, 4-phenylpyrimidin-2-yl, 5-(1-methyl-1H-pyrazol-4-yl)pyridin-3-yl, 5-(1-methyl-3-(trifluoromethyl)-1H-pyrazol-5-yl)thiophen-2-yl, 5-(4-(aminomethyl)phenyl)-2,3-dihydrobenzofuran-7-yl, 5-(4-(aminomethyl)phenyl)pyridin-3-yl, 5-(5-(trifluoromethyl)isoxazol-3-yl)thiophen-2-yl, 5-(methoxycarbonyl)pyrimidin-2-yl, 5-(trifluoromethyl)pyrazin-2-yl, 5-(trifluoromethyl)pyrimidin-2-yl, 5,6,7,8-tetrahydro-1,6-naphthyridin-3-yl, 5,6,7,8-tetrahydroquinolin-3-yl, 5-benzylpyrimidin-2-yl, 5-bromo-2,3-dihydrobenzofuran-7-yl, 5-bromopyridin-3-yl, 5-chloro-1,3-dimethyl-1H-pyrazol-4-yl, 5-chlorobenzo[c][1,2,5]oxadiazol-4-yl, 5-chlorothiophen-2-yl, 5-ethylpyrimidin-2-yl, 5-heptylpyrimidin-2-yl, 5-methoxy-2-methylpyridin-3-yl, 5-methoxypyridin-3-yl, 5-methyl-1-phenyl-1H-pyrazol-4-yl, 5-methyl-2-(trifluoromethyl)furan-3-yl, 5-methyl-3H-imidazo[4,5-b]pyridin-6-yl, 5-methylbenzo[c][1,2,5]oxadiazol-4-yl, 5-oxo-6,7-dihydro-5H-pyrrolo[3,4-b]pyridin-3-yl, 5-phenylpyrimidin-2-yl, 5-phenylthiophen-2-yl, 5-propylpyrimidin-2-yl, 6-(2-aminoethylamino)pyridin-3-yl, 6-(2-hydroxyethylamino)pyridin-3-yl, 6-(2-methoxyethylamino)pyridin-3-yl, 6'-(aminomethyl)-3,3'-bipyridin-5-yl, 6-(dimethylamino)-1-methyl-2,3-dihydro-1H-pyrido[2,3-b][1,4]oxazin-7-yl, 6-(dimethylamino)pyridin-3-yl, 6-(piperazin-1-yl)pyridin-3-yl, 6-(piperidin-1-yl)pyridin-3-yl, 6,7-dihydro-5H-cyclopenta[b]pyridin-3-yl, 6,7-dihydro-5H-pyrrolo[3,4-b]pyridin-3-yl, 6-amino-1-methyl-2,3-dihydro-1H-pyrido[2,3-b][1,4]oxazin-7-yl, 6-chloro-1-methyl-2,3-dihydro-1H-pyrido[2,3-b][1,4]oxazin-7-yl, 6-chloroimidazo[2,1-b]thiazol-5-yl, 6-ethoxy-1-methyl-2,3-dihydro-1H-pyrido[2,3-b][1,4]oxazin-7-yl, 6-ethoxypyridin-3-yl, 6-fluoro-4-hydroxyquinolin-3-yl, 6-fluoro-4-oxo-1,4-dihydroquinolin-3-yl, 6-hydroxy-1-methyl-2,3-dihydro-1H-pyrido[2,3-b][1,4]oxazin-7-yl, 6-hydroxypyridin-3-yl, 6-methoxy-1-methyl-2,3-dihydro-1H-pyrido[2,3-b][1,4]oxazin-7-yl, 6-methoxypyridin-3-yl, 6-morpholinopyridin-3-yl, 6-phenoxypyridin-3-yl, 7,8-dihydro-5H-pyrano[4,3-b]pyridin-3-yl, 7-amino-1,8-naphthyridin-3-yl, 7-chlorobenzo[c][1,2,5]oxadiazol-4-yl, 7-fluoro-4-hydroxyquinolin-3-yl, 7-fluoro-4-oxo-1,4-dihydroquinolin-3-yl, 7-methoxybenzo[c][1,2,5]oxadiazol-4-yl, 7-methyl-3H-imidazo[4,5-b]pyridin-6-yl, 8-fluoro-4-hydroxyquinolin-3-yl, 8-fluoro-4-oxo-1,4-dihydroquinolin-3-yl, 8-methyl-4-oxo-1,4-dihydroquinolin-3-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, chroman-6-yl, furan-3-yl, imidazo[1,2-a]pyridin-6-yl, pyrazin-2-yl, pyridin-2-yl, pyridin-3-yl, pyridin-3-yl N-oxide, pyrimidin-2-yl, pyrimidin-4-yl, quinolin-3-yl, quinolin-6-yl, and thiophen-3-yl.

In some embodiments, $R^1$ is heteroaryl optionally substituted with one or more substituents selected from: $C_1$-$C_7$ alkyl, cyano, $C_1$-$C_6$ haloalkyl, halogen, hydroxyl, and oxo.

In some embodiments, $R^1$ is selected from: 1H-pyrrolo[3,2-b]pyridinyl, quinolinyl, 1,4-dihydroquinolinyl, 1H-pyrrolo[2,3-b]pyridinyl, and 2,3-dihydro-1H-pyrido[2,3-b][1,4]oxazinyl; each optionally substituted with one or more substituents selected from: ethyl, methyl, cyano, trifluoromethyl, fluoro, hydroxyl, and oxo.

In some embodiments, $R^1$ is selected from: 1H-pyrrolo[3,2-b]pyridin-6-yl, quinolin-3-yl, 1,4-dihydroquinolin-3-yl, 1H-pyrrolo[2,3-b]pyridin-5-yl, and 2,3-dihydro-1H-pyrido[2,3-b][1,4]oxazin-7-yl; each optionally substituted with one or more substituents selected from: ethyl, methyl, cyano, trifluoromethyl, fluoro, hydroxyl, and oxo.

In some embodiments, $R^1$ is selected from: 1H-pyrrolo[3,2-b]pyridin-6-yl, 4-hydroxyquinolin-3-yl, 1-ethyl-4-oxo-1,4-dihydroquinolin-3-yl, 3-cyano-1H-pyrrolo[2,3-b]pyridin-5-yl, 1,3-dimethyl-2,3-dihydro-1H-pyrido[2,3-b][1,4]oxazin-7-yl, and 3-(trifluoromethyl)-1H-pyrrolo[2,3-b]pyridin-5-yl.

Certain $R^1$ Groups

One aspect of the present invention relates to certain $R^1$ groups as described herein. In some embodiments, $R^1$ is (dimethylcarbamoyl)phenyl. In some embodiments, $R^1$ is 1-(2-(benzyloxy)ethyl)-2,3-dihydro-1H-pyrido[2,3-b][1,4]oxazin-7-yl. In some embodiments, $R^1$ is 1-(2-hydroxyethyl)-2,3-dihydro-1H-pyrido[2,3-b][1,4]oxazin-7-yl. In some embodiments, $R^1$ is 1-(2-methoxyethyl)-2,3-dihydro-1H-pyrido[2,3-b][1,4]oxazin-7-yl. In some embodiments, $R^1$ is 1-(carboxymethyl)-4-oxo-1,4-dihydroquinolin-3-yl. In some embodiments, $R^1$ is 1,2-dimethyl-1H-imidazol-4-yl. In some embodiments, $R^1$ is 1,3,3-trimethyl-2,3-dihydro-1H-pyrido[2,3-b][1,4]oxazin-7-yl. In some embodiments, $R^1$ is 1,3-dimethyl-2,3-dihydro-1H-pyrido[2,3-b][1,4]oxazin-7-yl. In some embodiments, $R^1$ is 1,5-naphthyridin-3-yl. In some embodiments, $R^1$ is 1,6-dimethyl-2,3-dihydro-1H-pyrido[2,3-b][1,4]oxazin-7-yl. In some embodiments, $R^1$ is 1,8-dimethyl-2,3-dihydro-1H-pyrido[2,3-b][1,4]oxazin-7-yl. In some embodiments, $R^1$ is 1-ethyl-2,3-dihydro-1H-pyrido[2,3-b][1,4]oxazin-7-yl. In some embodiments, $R^1$ is 1-ethyl-4-oxo-1,4-dihydropyridin-3-yl. In some embodiments, $R^1$ is 1-ethyl-4-oxo-1,4-dihydroquinolin-3-yl. In some embodiments, $R^1$ is 1-ethyl-5-methyl-1H-pyrazol-4-yl. In some embodiments, $R^1$ is 1-ethyl-6-fluoro-4-oxo-1,4-dihydroquinolin-3-yl. In some embodiments, $R^1$ is 1-ethyl-6-methyl-4-oxo-1,4-dihydroquinolin-3-yl. In some embodiments, $R^1$ is 1-ethyl-7-fluoro-4-oxo-1,4-dihydroquinolin-3-yl. In some embodiments, $R^1$ is 1-ethyl-7-methyl-4-oxo-1,4-dihydroquinolin-3-yl. In some embodiments, $R^1$ is 1-ethyl-8-fluoro-4-oxo-1,4-dihydroquinolin-3-yl. In some embodiments, $R^1$ is 1-ethyl-8-methyl-4-oxo-1,4-dihydroquinolin-3-yl. In some embodiments, $R^1$ is 1H-benzo[d]imidazol-5-yl. In some embodiments, $R^1$ is 1H-benzo[d]imidazol-6-yl. In some embodiments, $R^1$ is 1H-imidazo[4,5-b]pyridin-6-yl. In some embodiments, $R^1$ is 1H-indazol-5-yl. In some embodiments, $R^1$ is 1H-indazol-6-yl. In some embodiments, $R^1$ is 1H-pyrazol-4-yl. In some embodiments, $R^1$ is 1H-pyrazolo[3,4-b]pyridin-5-yl. In some embodiments, $R^1$ is 1H-pyrazolo[4,3-b]pyridin-6-yl. In some embodiments, $R^1$ is 1H-pyrrolo[2,3-b]pyridin-3-yl. In some embodiments, $R^1$ is 1H-pyrrolo[2,3-b]pyridin-5-yl. In some embodiments, $R^1$ is 1H-pyrrolo[3,2-b]pyridin-3-yl. In some embodiments, $R^1$ is 1H-pyrrolo[3,2-b]pyridin-6-yl. In some embodiments, $R^1$ is 1-isopropyl-2,3-dihydro-1H-pyrido[2,3-b][1,4]oxazin-7-yl. In some embodiments, $R^1$ is 1-methyl-1,2,3,4-tetrahydropyrido[2,3-b][1,4]oxazepin-8-yl. In some embodiments, $R^1$ is 1'-methyl-1',2'-dihydrospiro[cyclopropane-1,3'-pyrido[2,3-b][1,4]oxazine]-7'-yl. In some embodiments, $R^1$ is 1-methyl-1H-imidazo[4,5-b]pyridin-6-yl. In some embodiments, $R^1$ is 1-methyl-1H-imidazol-4-yl. In some embodiments, $R^1$ is 1-methyl-1H-indol-5-yl. In some embodiments, $R^1$ is 1-methyl-1H-pyrazol-3-yl. In some embodiments, $R^1$ is 1-methyl-1H-pyrrolo[3,2-b]pyridin-6-yl. In some embodiments, $R^1$ is 1-methyl-2,3-dihydro-1H-pyrido[2,3-b][1,4]oxazin-7-yl. In some embodiments, $R^1$ is 1-methyl-2-oxo-2,3-dihydro-1H-imidazo[4,5-b]pyridin-6-yl. In some embodiments, $R^1$ is 1-methyl-3-(trifluoromethyl)-1H-pyrazol-4-yl. In some embodiments, $R^1$ is 1-methyl-4-oxo-1,4-dihydroquinolin-3-yl. In some embodiments, $R^1$ is 1-methyl-6-(methylamino)-2,3-dihydro-1H-pyrido[2,3-b][1,4]oxazin-7-yl. In some embodiments, $R^1$ is 1-phenyl-1H-pyrazol-4-yl. In some embodiments, $R^1$ is 1-propyl-2,3-dihydro-1H-pyrido[2,3-b][1,4]oxazin-7-yl. In some embodiments, $R^1$ is 2-(dimethylamino)pyridin-3-yl. In some embodiments, $R^1$ is 2-(methylsulfonyl)phenyl. In some embodiments, $R^1$ is 2-(pyridin-4-yl)ethyl. In some embodiments, $R^1$ is 2-(trifluoromethoxy)phenyl. In some embodiments, $R^1$ is 2-(trifluoromethyl)phenyl. In some embodiments, $R^1$ is 2,2-dimethylchroman-6-yl. In some embodiments, $R^1$ is 2,3-dichlorophenyl. In some embodiments, $R^1$ is 2,3-difluorophenyl. In some embodiments, $R^1$ is 2,3-dihydro-[1,4]dioxino[2,3-b]pyridin-7-yl. In some embodiments, $R^1$ is 2,3-dihydro-1H-pyrido[2,3-b][1,4]oxazin-7-yl. In some embodiments, $R^1$ is 2,3-dihydrobenzo[b][1,4]dioxin-6-yl. In some embodiments, $R^1$ is 2,3-dihydrobenzofuran-5-yl. In some embodiments, $R^1$ is 2,3-dihydrofuro[2,3-b]pyridin-5-yl. In some embodiments, $R^1$ is 2,3-dimethylphenyl. In some embodiments, $R^1$ is 2,3-dioxoindolin-5-yl. In some embodiments, $R^1$ is 2,4-dichlorophenyl. In some embodiments, $R^1$ is 2,4-difluorophenyl. In some embodiments, $R^1$ is 2,5-dichlorophenyl. In some embodiments, $R^1$ is 2,5-difluorophenyl. In some embodiments, $R^1$ is 2,5-dimethylphenyl. In some embodiments, $R^1$ is 2,6-difluorophenyl. In some embodiments, $R^1$ is 2-bromophenyl. In some embodiments, $R^1$ is 2-chloro-3-fluorophenyl. In some embodiments, $R^1$ is 2-chloro-4-cyanophenyl. In some embodiments, $R^1$ is 2-chloro-4-fluorophenyl. In some embodiments, $R^1$ is 2-chloro-5-(methylsulfonyl)phenyl. In some embodiments, $R^1$ is 2-chloro-5-(trifluoromethyl)phenyl. In some embodiments, $R^1$ is 2-chloro-5-fluorophenyl. In some embodiments, $R^1$ is 2-chlorophenyl. In some embodiments, $R^1$ is 2-cyano-5-methoxyphenyl. In some embodiments, $R^1$ is 2-cyano-5-methylphenyl. In some embodiments, $R^1$ is 2-cyanophenyl. In some embodiments, $R^1$ is 2-ethyl-3H-imidazo[4,5-b]pyridin-6-yl. In some embodiments, $R^1$ is 2-fluoro-3-methylphenyl. In some embodiments, $R^1$ is 2-fluoro-5-methoxyphenyl. In some embodiments, $R^1$ is 2-fluoro-5-methylphenyl. In some embodiments, $R^1$ is 2-fluorophenyl. In some embodiments, $R^1$ is 2-hydroxypyrimidin-5-yl. In some embodiments, $R^1$ is 2-methoxy-4-methylphenyl. In some embodiments, $R^1$ is 2-methoxy-5-methylphenyl. In some embodiments, $R^1$ is 2-methoxyphenyl. In some embodiments, $R^1$ is 2-methyl-1H-benzo[d]imidazol-5-yl. In some embodiments, $R^1$ is 2-methyl-1H-imidazo[4,5-b]pyridin-6-yl. In some embodiments, $R^1$ is 2-methyl-3H-imidazo[4,5-b]pyridin-6-yl. In some embodiments, $R^1$ is 2-morpholinopyridin-3-yl. In some embodiments, $R^1$ is 2-oxo-2,3-dihydro-1H-benzo[d]imidazol-5-yl. In some embodiments, $R^1$ is 2-oxo-2,3-dihydro-1H-imidazo[4,5-b]pyridin-6-yl. In some embodiments, $R^1$ is 2-oxo-2,3-dihydro-1H-pyrido[2,3-b][1,4]oxazin-6-yl. In some embodiments, $R^1$ is 2-oxo-2,3-dihydro-1H-pyrrolo[2,3-b]pyridin-5-yl. In some embodiments, $R^1$ is 2-oxo-2,3-dihydrobenzo[d]thiazol-6-yl. In some embodiments, $R^1$ is 2-oxoindolin-5-yl. In some embodiments, $R^1$ is 3'-((dimethylamino)methyl)biphenyl-3-yl. In some embodiments, $R^1$ is 3-(1-(2-hydroxyethyl)-1H-pyrazol-4-yl)phenyl. In some embodiments, $R^1$ is 3-(1-(cyclopropylmethyl)-1H-pyrazol-4-yl)phenyl. In some embodiments, $R^1$ is 3-(1,3-dimethyl-1H-pyrazol-4-yl)phenyl. In some embodiments, $R^1$ is 3-(1,3-dimethyl-2,4-dioxo-1,2,3,4-tetrahydropyrimidin-5-yl)phenyl. In some embodiments, $R^1$ is 3-(1-benzyl-1H-pyrazol-4-yl)phenyl. In some embodiments, $R^1$ is 3-(1-ethyl-1H-pyrazol-4-yl)phenyl. In some embodiments, $R^1$ is 3-(1H-pyrazol-3-yl)phenyl. In some embodiments, $R^1$ is 3-(1H-pyrazol-4-yl)phenyl. In some embodiments, $R^1$ is 3-(1H-pyrrol-3-yl)phenyl. In some embodiments, $R^1$ is 3-(1-isobutyl-1H-pyrazol-4-yl)phenyl.

In some embodiments, R¹ is 3-(1-methyl-1H-pyrazol-4-yl)phenyl. In some embodiments, R¹ is 3-(1-methyl-1H-pyrrol-3-yl)phenyl. In some embodiments, R¹ is 3-(1-methyl-3-(trifluoromethyl)-1H-pyrazol-4-yl)phenyl. In some embodiments, R¹ is 3-(1-propyl-1H-pyrazol-4-yl)phenyl. In some embodiments, R¹ is 3-(2-(trifluoromethyl)phenoxy)phenyl. In some embodiments, R¹ is 3-(2,4-dimethylthiazol-5-yl)phenyl. In some embodiments, R¹ is 3-(2H-tetrazol-5-yl)phenyl. In some embodiments, R¹ is 3-(2-methoxypyrimidin-5-yl)phenyl. In some embodiments, R¹ is 3-(2-methylpyridin-4-yl)phenyl. In some embodiments, R¹ is 3-(3,5-dimethylisoxazol-4-yl)phenyl. In some embodiments, R¹ is 3-(3-methylthiophen-2-yl)phenyl. In some embodiments, R¹ is 3-(4-(trifluoromethyl)phenoxy)phenyl. In some embodiments, R¹ is 3-(4-methylthiophen-3-yl)phenyl. In some embodiments, R¹ is 3-(5-(aminomethyl)thiophen-2-yl)phenyl. In some embodiments, R¹ is 3-(5-cyanopyridin-3-yl)phenyl. In some embodiments, R¹ is 3-(5-methylpyridin-3-yl)phenyl. In some embodiments, R¹ is 3-(6-(2-morpholinoethylamino)pyridin-3-yl)phenyl. In some embodiments, R¹ is 3-(6-(3-(dimethylamino)propoxy)pyridin-3-yl)phenyl. In some embodiments, R¹ is 3-(6-(aminomethyl)pyridin-3-yl)phenyl. In some embodiments, R¹ is 3-(6-aminopyridin-3-yl)phenyl. In some embodiments, R¹ is 3-(6-methylpyridin-3-yl)phenyl. In some embodiments, R¹ is 3'-(aminomethyl)biphenyl-3-yl. In some embodiments, R¹ is 3-(aminomethyl)phenyl. In some embodiments, R¹ is 3'-(carboxy)biphenyl-3-yl. In some embodiments, R¹ is 3'-(dimethylamino)biphenyl-3-yl. In some embodiments, R¹ is 3-(furan-2-yl)phenyl. In some embodiments, R¹ is 3'-(hydroxymethyl)biphenyl-3-yl. In some embodiments, R¹ is 3-(hydroxymethyl)phenyl. In some embodiments, R¹ is 3'-(methoxymethyl)biphenyl-3-yl. In some embodiments, R¹ is 3'-(methylsulfonyl)biphenyl-3-yl. In some embodiments, R¹ is 3'-(N,N-dimethylsulfamoyl)biphenyl-3-yl. In some embodiments, R¹ is 3-(pyridin-2-yl)phenyl. In some embodiments, R¹ is 3-(pyridin-3-yl)phenyl. In some embodiments, R¹ is 3-(pyridin-4-yl)phenyl. In some embodiments, R¹ is 3-(pyrimidin-5-yl)phenyl. In some embodiments, R¹ is 3-(thiophen-3-yl)phenyl. In some embodiments, R¹ is 3-(trifluoromethyl)-1H-pyrrolo[2,3-b]pyridin-5-yl. In some embodiments, R¹ is 3-(trifluoromethyl)phenyl. In some embodiments, R¹ is 3,4-difluorophenyl. In some embodiments, R¹ is 3,4-dihydro-2H-benzo[b][1,4]oxazin-6-yl. In some embodiments, R¹ is 3,4-dihydro-2H-pyrano[2,3-b]pyridin-6-yl. In some embodiments, R¹ is 3,4-dihydro-2H-pyrido[3,2-b][1,4]oxazin-7-yl. In some embodiments, R¹ is 3,4-dimethoxyphenyl. In some embodiments, R¹ is 3,4-dimethylphenyl. In some embodiments, R¹ is 3,5-dichlorophenyl. In some embodiments, R¹ is 3,5-dimethyl-1-phenyl-1H-pyrazol-4-yl. In some embodiments, R¹ is 3,5-dimethylisoxazol-4-yl. In some embodiments, R¹ is 3,5-dimethylphenyl. In some embodiments, R¹ is 3-bromo-4-methylphenyl. In some embodiments, R¹ is 3-bromo-5-methylphenyl. In some embodiments, R¹ is 3-bromophenyl. In some embodiments, R¹ is 3-carboxyphenyl. In some embodiments, R¹ is 3-chloro-1H-pyrrolo[2,3-b]pyridin-5-yl. In some embodiments, R¹ is 3-chloro-1-methyl-1H-pyrrolo[2,3-b]pyridin-5-yl. In some embodiments, R¹ is 3-chloro-1-methyl-1H-pyrrolo[3,2-b]pyridin-6-yl. In some embodiments, R¹ is 3-chloro-2-fluorophenyl. In some embodiments, R¹ is 3-chloro-2-methyl-1H-pyrrolo[2,3-b]pyridin-5-yl. In some embodiments, R¹ is 3-chloro-2-methylphenyl. In some embodiments, R¹ is 3-chloro-4-cyanophenyl. In some embodiments, R¹ is 3-chloro-4-methoxyphenyl. In some embodiments, R¹ is 3-chlorophenyl. In some embodiments, R¹ is 3-cyano-1H-pyrrolo[2,3-b]pyridin-5-yl. In some embodiments, R¹ is 3-cyano-4-methylphenyl. In some embodiments, R¹ is 3'-cyanobiphenyl-3-yl. In some embodiments, R¹ is 3-cyanophenyl. In some embodiments, R¹ is 3-ethyl-3H-imidazo[4,5-b]pyridin-6-yl. In some embodiments, R¹ is 3-fluoro-4-methoxyphenyl. In some embodiments, R¹ is 3-fluoro-5-methylphenyl. In some embodiments, R¹ is 3-fluorophenyl. In some embodiments, R¹ is 3-methoxyphenyl. In some embodiments, R¹ is 3-methyl-1H-pyrazolo[3,4-b]pyridin-5-yl. In some embodiments, R¹ is 3-methyl-1H-pyrrolo[2,3-b]pyridin-5-yl. In some embodiments, R¹ is 3-methyl-2-oxo-2,3-dihydro-1H-imidazo[4,5-b]pyridin-6-yl. In some embodiments, R¹ is 3-methyl-3H-imidazo[4,5-b]pyridin-6-yl. In some embodiments, R¹ is 3-oxo-3,4-dihydro-2H-benzo[b][1,4]oxazin-6-yl. In some embodiments, R¹ is 3-phenoxyphenyl. In some embodiments, R¹ is 4'-((1-amino-3-hydroxy-1-oxopropan-2-yl)(methyl)amino)biphenyl-3-yl. In some embodiments, R¹ is 4'-((2-(dimethylamino)ethylamino)methyl)biphenyl-3-yl. In some embodiments, R¹ is 4'-((2,2,2-trifluoroethylamino)methyl)biphenyl-3-yl. In some embodiments, R¹ is 4'-((2,2-difluoroethylamino)methyl)biphenyl-3-yl. In some embodiments, R¹ is 4'-((2-acetamidoethyl)(methyl)amino)biphenyl-3-yl. In some embodiments, R¹ is 4'-((2-amino-2-oxoacetamido)methyl)biphenyl-3-yl. In some embodiments, R¹ is 4'-((2-aminoacetamido)methyl)biphenyl-3-yl. In some embodiments, R¹ is 4'-((2-fluoroethylamino)methyl)biphenyl-3-yl. In some embodiments, R¹ is 4'-((2-hydroxyethylamino)methyl)biphenyl-3-yl. In some embodiments, R¹ is 4'-((2-methoxyethylamino)methyl)biphenyl-3-yl. In some embodiments, R¹ is 4'-((cyanomethylamino)methyl)biphenyl-3-yl. In some embodiments, R¹ is 4'-((dimethylamino)methyl)biphenyl-4-yl. In some embodiments, R¹ is 4'-((ethylamino)methyl)biphenyl-3-yl. In some embodiments, R¹ is 4'-((isobutylamino)methyl)biphenyl-3-yl. In some embodiments, R¹ is 4'-((isopentylamino)methyl)biphenyl-3-yl. In some embodiments, R¹ is 4'-((isopropylamino)methyl)biphenyl-3-yl. In some embodiments, R¹ is 4'-((methylamino)methyl)biphenyl-3-yl. In some embodiments, R¹ is 4'-(1-aminocyclopropyl)-6-methoxybiphenyl-3-yl. In some embodiments, R¹ is 4'-(1-aminocyclopropyl)biphenyl-3-yl. In some embodiments, R¹ is 4'-(2-carboxy-N-methylacetamido)biphenyl-3-yl. In some embodiments, R¹ is 4-(2H-tetrazol-5-yl)phenyl. In some embodiments, R¹ is 4-(3-methoxyphenyl)pyrimidin-2-yl. In some embodiments, R¹ is 4-carboxypyrimidin-2-yl. In some embodiments, R¹ is 4'-(5-methyl-1,2,4-oxadiazol-3-yl)biphenyl-3-yl. In some embodiments, R¹ is 4'-(aminomethyl)-2-methoxybiphenyl-3-yl. In some embodiments, R¹ is 4'-(aminomethyl)-2-methylbiphenyl-3-yl. In some embodiments, R¹ is 4'-(aminomethyl)-3-(trifluoromethoxy)biphenyl-4-yl. In some embodiments, R¹ is 4'-(aminomethyl)-4-(trifluoromethoxy)biphenyl-3-yl. In some embodiments, R¹ is 4'-(aminomethyl)-4-chlorobiphenyl-3-yl. In some embodiments, R¹ is 4'-(aminomethyl)-4-ethoxybiphenyl-3-yl. In some embodiments, R¹ is 4'-(aminomethyl)-4-methoxybiphenyl-3-yl. In some embodiments, R¹ is 4'-(aminomethyl)-4-methylbiphenyl-3-yl. In some embodiments, R¹ is 4'-(aminomethyl)-5-(trifluoromethyl)biphenyl-3-yl. In some embodiments, R¹ is 4'-(aminomethyl)-5-methoxybiphenyl-3-yl. In some embodiments, R¹ is 4'-(aminomethyl)-5-methylbiphenyl-3-yl. In some embodiments, R¹ is 4'-(aminomethyl)-6-methoxybiphenyl-3-yl. In some embodiments, R¹ is 4'-(aminomethyl)-6-methylbiphenyl-3-yl. In some embodiments, R¹ is 4'-(aminomethyl)biphenyl-2-yl. In some embodiments, R¹ is 4'-(aminomethyl)biphenyl-3-yl. In some embodiments, R¹ is 4'-(aminomethyl)biphenyl-4-yl. In some embodiments, $R^1$ is 4-(aminomethyl)phenyl. In some embodiments, $R^1$ is 4'-(carboxymethyl)biphenyl-3-yl. In some embodiments, $R^1$ is 4'-(cyanomethoxy)biphenyl-3-yl. In some embodiments, $R^1$ is 4'-(cyanomethyl)biphenyl-3-yl. In some embodiments, $R^1$ is 4-(hydroxymethyl)phenyl. In some embodiments, $R^1$ is 4'-(methylsulfonamido)biphenyl-3-yl. In some embodiments, $R^1$ is 4-(methylsulfonyl)phenyl. In some embodiments, $R^1$ is 4'-(N'-hydroxycarbamimidoyl)-biphenyl-3-yl. In some embodiments, $R^1$ is 4-(phenylsulfonyl)thiophen-2-yl. In some embodiments, $R^1$ is 4-(pyridin-2-yl)phenyl. In some embodiments, $R^1$ is 4-(pyridin-3-yl)phenyl. In some embodiments, $R^1$ is 4-(pyridin-4-yl)phenyl. In some embodiments, $R^1$ is 4'-(sulfamoyl)biphenyl-3-yl. In some embodiments, $R^1$ is 4'-(thiazolidin-3-ylmethyl)biphenyl-3-yl. In some embodiments, $R^1$ is 4-(trifluoromethoxy)phenyl. In some embodiments, $R^1$ is 4'-(trifluoromethyl)biphenyl-4-yl. In some embodiments, $R^1$ is 4-(trifluoromethyl)phenyl. In some embodiments, $R^1$ is 4-(trifluoromethyl)pyrimidin-2-yl. In some embodiments, $R^1$ is 4,5-dichlorothiophen-2-yl. In some embodiments, $R^1$ is 4,6-dimethoxypyrimidin-2-yl. In some embodiments, $R^1$ is 4,6-dimethylpyrimidin-2-yl. In some embodiments, $R^1$ is 4-acetamidophenyl. In some embodiments, $R^1$ is 4-acetylphenyl. In some embodiments, $R^1$ is 4-aminopyrimidin-2-yl. In some embodiments, $R^1$ is 4-benzylpyrimidin-2-yl. In some embodiments, $R^1$ is 4-bromo-3-chlorophenyl. In some embodiments, $R^1$ is 4-bromo-3-methylphenyl. In some embodiments, $R^1$ is 4-bromophenyl. In some embodiments, $R^1$ is 4'-carbamimidoyl-biphenyl-3-yl. In some embodiments, $R^1$ is 4'-carbamoyl-biphenyl-3-yl. In some embodiments, $R^1$ is 4-carboxyphenyl. In some embodiments, $R^1$ is 4-chloro-3-methoxyphenyl. In some embodiments, $R^1$ is 4-chloro-3-methylphenyl. In some embodiments, $R^1$ is 4-chlorophenyl. In some embodiments, $R^1$ is 4-chloropyridin-2-yl. In some embodiments, $R^1$ is 4-cyanophenyl. In some embodiments, $R^1$ is 4-ethoxy-4'-((isopropylamino)methyl)biphenyl-3-yl. In some embodiments, $R^1$ is 4-ethoxyphenyl. In some embodiments, $R^1$ is 4-ethyl-3,4-dihydro-2H-benzo[b][1,4]oxazin-6-yl. In some embodiments, $R^1$ is 4-fluoro-3-methylphenyl. In some embodiments, $R^1$ is 4'-fluorobiphenyl-4-yl. In some embodiments, $R^1$ is 4-fluorophenyl. In some embodiments, $R^1$ is 4-hydroxy-6-methylquinolin-3-yl. In some embodiments, $R^1$ is 4-hydroxy-6-methylquinolin-8-yl. In some embodiments, $R^1$ is 4-hydroxy-7-methylquinolin-3-yl. In some embodiments, $R^1$ is 4-hydroxy-8-methylquinolin-3-yl. In some embodiments, $R^1$ is 4-hydroxyquinolin-3-yl. In some embodiments, $R^1$ is 4-isobutyl-3,4-dihydro-2H-benzo[b][1,4]oxazin-6-yl. In some embodiments, $R^1$ is 4-isopropoxyphenyl. In some embodiments, $R^1$ is 4-isopropyl-3,4-dihydro-2H-benzo[b][1,4]oxazin-6-yl. In some embodiments, $R^1$ is 4-methoxy-1H-indazol-5-yl. In some embodiments, $R^1$ is 4-methoxy-2,3-dimethylphenyl. In some embodiments, $R^1$ is 4-methoxy-2-methylphenyl. In some embodiments, $R^1$ is 4-methoxy-3-methylphenyl. In some embodiments, $R^1$ is 4-methoxy-5,6,7,8-tetrahydronaphthalen-1-yl. In some embodiments, $R^1$ is 4-methoxynaphthalen-1-yl. In some embodiments, $R^1$ is 4-methoxyphenyl. In some embodiments, $R^1$ is 4-methoxypyrimidin-2-yl. In some embodiments, $R^1$ is 4-methyl-2-phenylthiazol-5-yl. In some embodiments, $R^1$ is 4-methyl-3,4-dihydro-2H-benzo[b][1,4]oxazin-6-yl. In some embodiments, $R^1$ is 4-methyl-3,4-dihydro-2H-pyrido[3,2-b][1,4]oxazin-7-yl. In some embodiments, $R^1$ is 4-methyl-6-phenylpyrimidin-2-yl. In some embodiments, $R^1$ is 4-methylpyrimidin-2-yl. In some embodiments, $R^1$ is 4-oxo-1-propyl-1,4-dihydroquinolin-3-yl. In some embodiments, $R^1$ is 4-phenylpyrimidin-2-yl. In some embodiments, $R^1$ is 4-sec-butylphenyl. In some embodiments, $R^1$ is 4-tert-butylphenyl. In some embodiments, $R^1$ is 4-tert-pentylphenyl. In some embodiments, $R^1$ is 5-(1-methyl-1H-pyrazol-4-yl)pyridin-3-yl. In some embodiments, $R^1$ is 5-(1-methyl-3-(trifluoromethyl)-1H-pyrazol-5-yl)thiophen-2-yl. In some embodiments, $R^1$ is 5-(4-(aminomethyl)phenyl)-2,3-dihydrobenzofuran-7-yl. In some embodiments, $R^1$ is 5-(4-(aminomethyl)phenyl)pyridin-3-yl. In some embodiments, $R^1$ is 5-(5-(trifluoromethyl)isoxazol-3-yl)thiophen-2-yl. In some embodiments, $R^1$ is 5-(methoxycarbonyl)pyrimidin-2-yl. In some embodiments, $R^1$ is 5-(trifluoromethyl)pyrazin-2-yl. In some embodiments, $R^1$ is 5-(trifluoromethyl)pyrimidin-2-yl. In some embodiments, $R^1$ is 5,6,7,8-tetrahydro-1,6-naphthyridin-3-yl. In some embodiments, $R^1$ is 5,6,7,8-tetrahydronaphthalen-2-yl. In some embodiments, $R^1$ is 5,6,7,8-tetrahydroquinolin-3-yl. In some embodiments, $R^1$ is 5-benzylpyrimidin-2-yl. In some embodiments, $R^1$ is 5-bromo-2-(2-(pyrrolidin-1-yl)ethoxy)phenyl. In some embodiments, $R^1$ is 5-bromo-2,3-dihydrobenzofuran-7-yl. In some embodiments, $R^1$ is 5-bromo-2-chlorophenyl. In some embodiments, $R^1$ is 5-bromo-2-methoxyphenyl. In some embodiments, $R^1$ is 5-bromo-2-methylphenyl. In some embodiments, $R^1$ is 5-bromopyridin-3-yl. In some embodiments, $R^1$ is 5-chloro-1,3-dimethyl-1H-pyrazol-4-yl. In some embodiments, $R^1$ is 5-chloro-2-cyanophenyl. In some embodiments, $R^1$ is 5-chloro-2-fluorophenyl. In some embodiments, $R^1$ is 5-chloro-2-methoxyphenyl. In some embodiments, $R^1$ is 5-chloro-2-methylphenyl. In some embodiments, $R^1$ is 5-chlorobenzo[c][1,2,5]oxadiazol-4-yl. In some embodiments, $R^1$ is 5-chloronaphthalen-2-yl. In some embodiments, $R^1$ is 5-chlorothiophen-2-yl. In some embodiments, $R^1$ is 5-cyano-2-methylphenyl. In some embodiments, $R^1$ is 5-ethylpyrimidin-2-yl. In some embodiments, $R^1$ is 5-fluoro-2-methoxyphenyl. In some embodiments, $R^1$ is 5-fluoro-2-methylphenyl. In some embodiments, $R^1$ is 5-heptylpyrimidin-2-yl. In some embodiments, $R^1$ is 5-methoxy-2-methylpyridin-3-yl. In some embodiments, $R^1$ is 5-methoxypyridin-3-yl. In some embodiments, $R^1$ is 5-methyl-1-phenyl-1H-pyrazol-4-yl. In some embodiments, $R^1$ is 5-methyl-2-(trifluoromethyl)furan-3-yl. In some embodiments, $R^1$ is 5-methyl-3H-imidazo[4,5-b]pyridin-6-yl. In some embodiments, $R^1$ is 5-methylbenzo[c][1,2,5]oxadiazol-4-yl. In some embodiments, $R^1$ is 5-oxo-6,7-dihydro-5H-pyrrolo[3,4-b]pyridin-3-yl. In some embodiments, $R^1$ is 5-phenylpyrimidin-2-yl. In some embodiments, $R^1$ is 5-phenylthiophen-2-yl. In some embodiments, $R^1$ is 5-propylpyrimidin-2-yl. In some embodiments, $R^1$ is 6-(2-aminoethylamino)pyridin-3-yl. In some embodiments, $R^1$ is 6-(2-hydroxyethylamino)pyridin-3-yl. In some embodiments, $R^1$ is 6-(2-methoxyethylamino)pyridin-3-yl. In some embodiments, $R^1$ is 6'-(aminomethyl)-3,3'-bipyridin-5-yl. In some embodiments, $R^1$ is 6-(dimethylamino)-1-methyl-2,3-dihydro-1H-pyrido[2,3-b][1,4]oxazin-7-yl. In some embodiments, $R^1$ is 6-(dimethylamino)pyridin-3-yl. In some embodiments, $R^1$ is 6-(piperazin-1-yl)pyridin-3-yl. In some embodiments, $R^1$ is 6-(piperidin-1-yl)pyridin-3-yl. In some embodiments, $R^1$ is 6,7-dihydro-5H-cyclopenta[b]pyridin-3-yl. In some embodiments, $R^1$ is 6,7-dihydro-5H-pyrrolo[3,4-b]pyridin-3-yl. In some embodiments, $R^1$ is 6-amino-1-methyl-2,3-dihydro-1H-pyrido[2,3-b][1,4]oxazin-7-yl. In some embodiments, $R^1$ is 6-chloro-1-methyl-2,3-dihydro-1H-pyrido[2,3-b][1,4]oxazin-7-yl. In some embodiments, $R^1$ is 6-chloroimidazo[2,1-b]thiazol-5-yl. In some embodiments, $R^1$ is 6-chloronaphthalen-2-yl. In some embodiments, $R^1$ is 6-ethoxy-1-methyl-2,3-dihydro-1H-pyrido[2,3-b][1,4]oxazin-7-yl. In some embodiments, $R^1$ is 6-ethoxypyridin- 3-yl. In some embodiments, $R^1$ is 6-fluoro-4-hydroxyquinolin-3-yl. In some embodiments, $R^1$ is 6-fluoro-4-oxo-1,4-dihydroquinolin-3-yl. In some embodiments, $R^1$ is 6-hydroxy-1-methyl-2,3-dihydro-1H-pyrido[2,3-b][1,4]oxazin-7-yl. In some embodiments, $R^1$ is 6-hydroxypyridin-3-yl. In some embodiments, $R^1$ is 6-methoxy-1-methyl-2,3-dihydro-1H-pyrido[2,3-b][1,4]oxazin-7-yl. In some embodiments, $R^1$ is 6-methoxynaphthalen-2-yl. In some embodiments, $R^1$ is 6-methoxypyridin-3-yl. In some embodiments, $R^1$ is 6-morpholinopyridin-3-yl. In some embodiments, $R^1$ is 6-phenoxypyridin-3-yl. In some embodiments, $R^1$ is 7,8-dihydro-5H-pyrano[4,3-b]pyridin-3-yl. In some embodiments, $R^1$ is 7-amino-1,8-naphthyridin-3-yl. In some embodiments, $R^1$ is 7-chlorobenzo[c][1,2,5]oxadiazol-4-yl. In some embodiments, $R^1$ is 7-fluoro-4-hydroxyquinolin-3-yl. In some embodiments, $R^1$ is 7-fluoro-4-oxo-1,4-dihydroquinolin-3-yl. In some embodiments, $R^1$ is 7-methoxybenzo[c][1,2,5]oxadiazol-4-yl. In some embodiments, $R^1$ is 7-methyl-3H-imidazo[4,5-b]pyridin-6-yl. In some embodiments, $R^1$ is 8-fluoro-4-hydroxyquinolin-3-yl. In some embodiments, $R^1$ is 8-fluoro-4-oxo-1,4-dihydroquinolin-3-yl. In some embodiments, $R^1$ is 8-methyl-4-oxo-1,4-dihydroquinolin-3-yl. In some embodiments, $R^1$ is benzo[c][1,2,5]thiadiazol-4-yl. In some embodiments, $R^1$ is benzo[c][1,2,5]thiadiazol-5-yl. In some embodiments, $R^1$ is benzo[d]isoxazol-5-yl. In some embodiments, $R^1$ is benzofuran-2-yl. In some embodiments, $R^1$ is benzofuran-5-yl. In some embodiments, $R^1$ is benzyl. In some embodiments, $R^1$ is biphenyl-2-yl. In some embodiments, $R^1$ is biphenyl-3-yl. In some embodiments, $R^1$ is biphenyl-4-yl. In some embodiments, $R^1$ is chroman-6-yl. In some embodiments, $R^1$ is cyclohexyl. In some embodiments, $R^1$ is furan-3-yl. In some embodiments, $R^1$ is imidazo[1,2-a]pyridin-6-yl. In some embodiments, $R^1$ is m-tolyl. In some embodiments, $R^1$ is naphthalen-1-yl. In some embodiments, $R^1$ is naphthalen-2-yl. In some embodiments, $R^1$ is phenyl. In some embodiments, $R^1$ is p-tolyl. In some embodiments, $R^1$ is pyrazin-2-yl. In some embodiments, $R^1$ is pyridin-2-yl. In some embodiments, $R^1$ is pyridin-3-yl. In some embodiments, $R^1$ is pyridin-3-yl N-oxide. In some embodiments, $R^1$ is pyrimidin-2-yl. In some embodiments, $R^1$ is pyrimidin-4-yl. In some embodiments, $R^1$ is quinolin-3-yl. In some embodiments, $R^1$ is quinolin-6-yl. In some embodiments, $R^1$ is thiophen-3-yl.

The $R^2$ Groups ($R^{2a}$ and $R^{2b}$)

In some embodiments, $R^{2a}$ is H or selected from: $C_1$-$C_6$ alkoxy, $C_1$-$C_6$ alkyl, $C_3$-$C_7$ cycloalkyl, and heterocyclyl; each optionally substituted with one or more substituents selected from: $C_1$-$C_6$ alkoxy, $C_1$-$C_6$ alkylamino, $C_1$-$C_6$ alkyl, $C_1$-$C_6$ alkylenehydroxyl, amino, $C_3$-$C_7$ cycloalkyl, cyano, $C_2$-$C_8$ dialkylamino, heterocyclyl optionally substituted with one oxo group, halogen, hydroxyl, and oxo.

In some embodiments, $R^{2a}$ is H or $C_1$-$C_6$ alkyl optionally substituted with one or more substituents selected from: $C_1$-$C_6$ alkoxy, $C_1$-$C_6$ alkylamino, $C_1$-$C_6$ alkyl, $C_1$-$C_6$ alkylenehydroxyl, amino, $C_3$-$C_7$ cycloalkyl, cyano, $C_2$-$C_8$ dialkylamino, heterocyclyl optionally substituted with one oxo group, halogen, hydroxyl, and oxo.

In some embodiments, $R^{2a}$ is H or selected from: $C_1$-$C_6$ alkoxy, $C_1$-$C_6$ alkyl, $C_3$-$C_7$ cycloalkyl, and heterocyclyl; each optionally substituted with one or more substituents selected from: amino, cyano, cyclopropyl, dimethylamino, ethoxy, ethyl, fluoro, hydroxyl, hydroxymethyl, methoxy, methylamino, oxo, oxopyrrolidinyl, and piperidinyl.

In some embodiments, $R^{2a}$ is H or selected from: 2-methylpropanyl, butanyl, cyclobutyl, cyclohexyl, cyclopentyl, cyclopropyl, dimethylbutanyl, ethyl, ethylbutyl, isopentyl, isopropyl, methoxy, methyl, pentyl, piperidinyl, propanyl, propyl, sec-butyl, tert-butyl, and tetrahydro-2H-pyranyl; each optionally substituted with one or more substituents selected from: $C_1$-$C_6$ alkoxy, $C_1$-$C_6$ alkylamino, $C_1$-$C_6$ alkyl, $C_1$-$C_6$ alkylenehydroxyl, amino, $C_3$-$C_7$ cycloalkyl, cyano, $C_2$-$C_5$ dialkylamino, heterocyclyl optionally substituted with one oxo group, halogen, hydroxyl, and oxo.

In some embodiments, $R^{2a}$ is H or selected from: 2-methylpropanyl, butanyl, cyclobutyl, cyclohexyl, cyclopentyl, cyclopropyl, dimethylbutanyl, ethyl, ethylbutyl, isopentyl, isopropyl, methoxy, methyl, pentyl, piperidinyl, propanyl, propyl, sec-butyl, tert-butyl, and tetrahydro-2H-pyranyl; each optionally substituted with one or more substituents selected from: amino, cyano, cyclopropyl, dimethylamino, ethoxy, ethyl, fluoro, hydroxyl, hydroxymethyl, methoxy, methylamino, oxo, oxopyrrolidinyl, and piperidinyl.

In some embodiments, $R^{2a}$ is selected from: H, methyl, propyl, pentyl, (2,2,2-trifluoroethyl), isopropyl, cyclopropylmethyl, 2,2-difluoroethyl, sec-butyl, methoxy, 2-hydroxyethyl, 2-methoxyethyl, 2-hydroxypropyl, 2-ethoxyethyl, 1-hydroxypropan-2-yl, 1-hydroxy-2-methylpropan-2-yl, tetrahydro-2H-pyran-4-yl, 3-hydroxypropyl, cyclopropyl, 3-methoxypropyl, 3,3-difluorocyclobutyl, 2-aminoethyl, 3-hydroxy-1-(methylamino)-1-oxobutan-2-yl, 1-cyclopropylethyl, tert-butyl, 1,3-dihydroxypropan-2-yl, 2-ethylbutyl, isopentyl, 1-(hydroxymethyl)cyclopropyl, 3,3-dimethylbutan-2-yl, ethyl, 2-(2-oxopyrrolidin-1-yl)ethyl, 1-ethylpiperidin-4-yl, 2,3-dihydroxypropyl, 2-(dimethylamino)ethyl, piperidin-3-ylmethyl, 3-(dimethylamino)propyl, acetyl, 2-fluoroethyl, 2-hydroxycyclopentyl, 2-hydroxycyclohexyl, and cyanomethyl.

In some embodiments, $R^{2a}$ is H or $C_1$-$C_6$ alkyl.

In some embodiments, $R^{2a}$ is H, ethyl, or methyl.

In some embodiments, $R^{2a}$ is H. In some embodiments, $R^{2a}$ is methyl. In some embodiments, $R^{2a}$ is propyl. In some embodiments, $R^{2a}$ is pentyl. In some embodiments, $R^{2a}$ is (2,2,2-trifluoroethyl). In some embodiments, $R^{2a}$ is isopropyl. In some embodiments, $R^{2a}$ is cyclopropylmethyl. In some embodiments, $R^{2a}$ is 2,2-difluoroethyl. In some embodiments, $R^{2a}$ is sec-butyl. In some embodiments, $R^{2a}$ is methoxy. In some embodiments, $R^{2a}$ is 2-hydroxyethyl. In some embodiments, $R^{2a}$ is 2-methoxyethyl. In some embodiments, $R^{2a}$ is 2-hydroxypropyl. In some embodiments, $R^{2a}$ is 2-ethoxyethyl. In some embodiments, $R^{2a}$ is 1-hydroxypropan-2-yl. In some embodiments, $R^{2a}$ is 1-hydroxy-2-methylpropan-2-yl. In some embodiments, $R^{2a}$ is tetrahydro-2H-pyran-4-yl. In some embodiments, $R^{2a}$ is 3-hydroxypropyl. In some embodiments, $R^{2a}$ is cyclopropyl. In some embodiments, $R^{2a}$ is 3-methoxypropyl. In some embodiments, $R^{2a}$ is 3,3-difluorocyclobutyl. In some embodiments, $R^{2a}$ is 2-aminoethyl. In some embodiments, $R^{2a}$ is 3-hydroxy-1-(methylamino)-1-oxobutan-2-yl. In some embodiments, $R^{2a}$ is 1-cyclopropylethyl. In some embodiments, $R^{2a}$ is tert-butyl. In some embodiments, $R^{2a}$ is 1,3-dihydroxypropan-2-yl. In some embodiments, $R^{2a}$ is 2-ethylbutyl. In some embodiments, $R^{2a}$ is isopentyl. In some embodiments, $R^{2a}$ is 1-(hydroxymethyl)cyclopropyl. In some embodiments, $R^{2a}$ is 3,3-dimethylbutan-2-yl. In some embodiments, $R^{2a}$ is ethyl. In some embodiments, $R^{2a}$ is 2-(2-oxopyrrolidin-1-yl)ethyl. In some embodiments, $R^{2a}$ is 1-ethylpiperidin-4-yl. In some embodiments, $R^{2a}$ is 2,3-dihydroxypropyl. In some embodiments, $R^{2a}$ is 2-(dimethylamino)ethyl. In some embodiments, $R^{2a}$ is piperidin-3-ylmethyl. In some embodiments, $R^{2a}$ is 3-(dimethylamino)propyl. In some embodiments, $R^{2a}$ is acetyl. In some embodiments, $R^{2a}$ is 2-fluoroethyl. In some embodiments, $R^{2a}$ is 2-hydroxycyclopentyl. In some embodiments, $R^{2a}$ is 2-hydroxycyclohexyl. In some embodiments, $R^{2a}$ is cyanomethyl.

In some embodiments, $R^{2b}$ is H or $C_1$-$C_6$ alkyl.

In some embodiments, $R^{2b}$ is selected from: H, ethyl, isopropyl, and methyl. In some embodiments, $R^{2b}$ is selected from: H and methyl. In some embodiments, $R^{2b}$ is H.

Certain Combinations

One aspect of the present invention pertains to compounds of Formula (Ic) and pharmaceutically acceptable salts, solvates, and hydrates thereof:

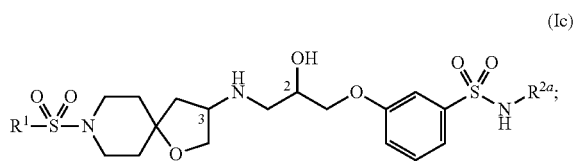

wherein: $R^1$ (as well as Y and Z that are both related to $R^1$), $R^{2a}$, and $R^{2b}$ all have the same definitions as described herein, supra and infra.

One aspect of the present invention pertains to compounds of Formula (Ic) and pharmaceutically acceptable salts, solvates, and hydrates thereof:

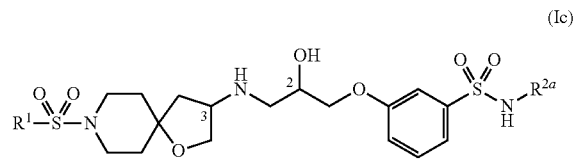

wherein:

$R^1$ is selected from: aryl, heteroaryl, and heterocyclyl; each optionally substituted with one or more substituents selected from: $C_1$-$C_6$ alkoxy, $C_1$-$C_7$ alkyl, $C_1$-$C_6$ alkylamino, $C_1$-$C_6$ alkylcarboxamide, $C_1$-$C_6$ alkylsulfonamido, $C_1$-$C_6$ alkylsulfonyl, amino, aryloxy, arylsulfonyl, carboxamide, carbamimidoyl, carboxy, cyano, $C_3$-$C_7$ cycloalkyl, $C_2$-$C_5$ dialkylamino, $C_2$-$C_8$ dialkylsulfamoyl, $C_1$-$C_6$ haloalkoxy, $C_1$-$C_6$ haloalkyl, halogen, heterocyclyl, hydroxycarbamimidoyl, hydroxyl, oxo, and sulfamoyl; and wherein said $C_1$-$C_6$ alkoxy, $C_1$-$C_7$ alkyl, $C_1$-$C_6$ alkylamino, aryloxy, $C_3$-$C_7$ cycloalkyl, and $C_2$-$C_5$ dialkylamino are each optionally substituted with one or more substituents selected from: amino, $C_1$-$C_6$ alkoxy, $C_1$-$C_6$ alkylamino, $C_1$-$C_6$ alkylcarboxamide, carboxy, —Y—$C_1$-$C_6$-alkylene-Z optionally substituted with oxo, $C_3$-$C_7$ cycloalkyl, cyano, $C_2$-$C_6$ dialkylamino, $C_1$-$C_6$ haloalkyl, $C_1$-$C_6$ haloalkylamino, heterocyclyl, hydroxyl, oxo, and phenyl;

Y is selected from: —O— and —NH—;

Z is selected from: $C_1$-$C_6$ alkoxy, amino, cyano, $C_2$-$C_6$ dialkylamino, hydroxyl, and phenyl; and $R^{2a}$ is H, ethyl, or methyl.

One aspect of the present invention pertains to compounds of Formula (Ic) and pharmaceutically acceptable salts, solvates, and hydrates thereof:

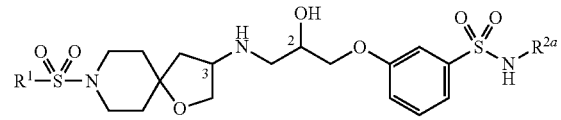

wherein:

$R^1$ is selected from: aryl, heteroaryl, and heterocyclyl; each optionally substituted with one or more substituents selected from: (2-ethyl)(methyl)amino, acetamido, amino, bromo, carbamimidoyl, carboxamide, carboxy, chloro, cyano, cyclopropyl, dimethylamino, dimethylcarbamoyl, ethoxy, ethyl, ethylamino, fluoro, hydroxycarbamimidoyl, hydroxyl, isobutyl, isopropoxy, isopropyl, isopropyl(methyl)amino, methoxy, methyl, methyl(propyl)amino, methylamino, methylsulfonamido, methylsulfonyl, morpholino, N,N-dimethylsulfamoyl, oxo, phenoxy, phenylsulfonyl, piperazin-1-yl, piperidin-1-yl, propoxy, propyl, sec-butyl, sulfamoyl, tert-butyl, tert-pentyl, trifluoromethoxy, and trifluoromethyl; and wherein (2-ethyl)(methyl)amino, cyclopropyl, ethoxy, ethyl, ethylamino, isopropyl(methyl)amino, methoxy, methyl, methyl(propyl)amino, phenoxy, and propoxy are each optionally substituted with one or more substituents selected from: 2-(dimethylamino)ethylamino, 2,2,2-trifluoroethylamino, 2,2-difluoroethylamino, 2-amino-2-oxoacetamido, 2-aminoacetamido, 2-fluoroethylamino, 2-hydroxyethylamino, 2-methoxyethylamino, acetamido, amino, benzyloxy, carboxy, cyano, cyanomethylamino, cyclopropyl, dimethylamino, ethylamino, hydroxyl, isobutylamino, isopentylamino, isopropylamino, methoxy, methylamino, morpholino, oxo, phenyl, pyrrolidin-1-yl, thiazolidin-3-yl, and trifluoromethyl; and $R^{2a}$ is H, ethyl, or methyl.

One aspect of the present invention pertains to compounds of Formula (Ic) and pharmaceutically acceptable salts, solvates, and hydrates thereof:

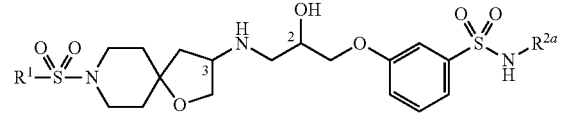

wherein:

$R^1$ is selected from: aryl, heteroaryl, and heterocyclyl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, hydroxycarbamimidoyl, hydroxyl, hydroxyethyl, isobutyl, isopropoxy, isopropyl, methoxy, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl; and
$R^{2a}$ is H, ethyl, or methyl.

One aspect of the present invention pertains to compounds of Formula (Ic) and pharmaceutically acceptable salts, solvates, and hydrates thereof:

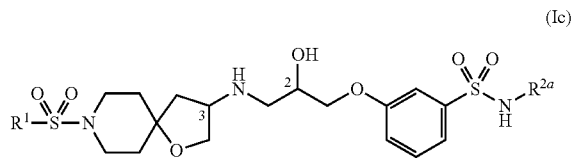

(Ic)

wherein:

$R^1$ is selected from: (1,2,3,4-tetrahydropyrimidin-5-yl)phenyl, (5-isoxazol-3-yl)thiophen-2-yl, (5-isoxazol-3-yl)thiophen-3-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydropyridinyl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-2-yl, (1H-pyrazol-5-yl)thiophen-3-yl, 1H-pyrazolo[3,4-b]pyridinyl, 1H-pyrazolo[4,3-b]pyridinyl, 1H-pyrazolyl, 1H-pyrrolo[2,3-b]pyridinyl, 1H-pyrrolo[3,2-b]pyridinyl, 1-phenyl-1H-pyrazolyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(pyridin-3-yl)phenyl, 4-(pyridin-4-yl)phenyl, 5-(1H-pyrazol-4-yl)pyridinyl, 5-(phenyl)pyridinyl, 5,6,7,8-tetrahydro-1,6-naphthyridinyl, 5,6,7,8-tetrahydronaphthalenyl, 5,6,7,8-tetrahydroquinolinyl, 5-phenyl-2,3-dihydrobenzofuranyl, 5-phenylthiophen-2-yl, 5-phenylthiophen-3-yl, 6,7-dihydro-5H-cyclopenta[b]pyridinyl, 6,7-dihydro-5H-pyrrolo[3,4-b]pyridinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, biphenylyl, chromanyl, furanyl, imidazo[1,2-a]pyridinyl, imidazo[2,1-b]thiazolyl, indolinyl, isoxazolyl, naphthalenyl, phenyl, pyridinyl, pyrimidinyl, quinolinyl, thiophen-2-yl, and thiophen-3-yl; $R^1$ is selected from: aryl, heteroaryl, and heterocyclyl; each optionally substituted with one or more substituents selected from:
(2-ethyl)(methyl)amino, acetamido, amino, bromo, carbamimidoyl, carboxamide, carboxy, chloro, cyano, cyclopropyl, dimethylamino, dimethylcarbamoyl, ethoxy, ethyl, ethylamino, fluoro, hydroxycarbamimidoyl, hydroxyl, isobutyl, isopropoxy, isopropyl, isopropyl(methyl)amino, methoxy, methyl, methyl(propyl)amino, methylamino, methylsulfonamido, methylsulfonyl, morpholino, N,N-dimethylsulfamoyl, oxo, phenoxy, phenylsulfonyl, piperazin-1-yl, piperidin-1-yl, propoxy, propyl, sec-butyl, sulfamoyl, tert-butyl, tert-pentyl, trifluoromethoxy, and trifluoromethyl; and
wherein (2-ethyl)(methyl)amino, cyclopropyl, ethoxy, ethyl, ethylamino, isopropyl(methyl)amino, methoxy, methyl, methyl(propyl)amino, phenoxy, and propoxy are each optionally substituted with one or more substituents selected from: 2-(dimethylamino)ethylamino, 2,2,2-trifluoroethylamino, 2,2-difluoroethylamino, 2-amino-2-oxoacetamido, 2-aminoacetamido, 2-fluoroethylamino, 2-hydroxyethylamino, 2-methoxyethylamino, acetamido, amino, benzyloxy, carboxy, cyano, cyanomethylamino, cyclopropyl, dimethylamino, ethylamino, hydroxyl, isobutylamino, isopentylamino, isopropylamino, methoxy, methylamino, morpholino, oxo, phenyl, pyrrolidin-1-yl, thiazolidin-3-yl, and trifluoromethyl; and
$R^{2a}$ is H, ethyl, or methyl.

One aspect of the present invention pertains to compounds of Formula (Ic) and pharmaceutically acceptable salts, solvates, and hydrates thereof:

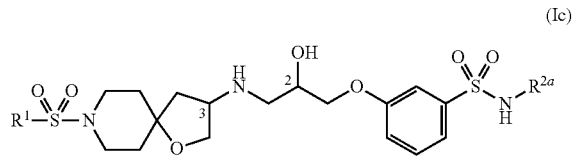

(Ic)

wherein:

$R^1$ is selected from: (1,2,3,4-tetrahydropyrimidin-5-yl)phenyl, (5-isoxazol-3-yl)thiophen-2-yl, (5-isoxazol-3-yl)thiophen-3-yl, (pyridin-2-yl)phenyl, [3,3'-bipyridin]yl, 1,2,3,4-tetrahydropyrido[2,3-b][1,4]oxazepinyl, 1',2'-dihydrospiro[cyclopropane-1,3'-pyrido[2,3-b][1,4]oxazine]-7'-yl, 1,4-dihydropyridinyl, 1,4-dihydroquinolinyl, 1,5-naphthyridinyl, 1,8-naphthyridinyl, 1H-benzo[d]imidazolyl, 1H-imidazo[4,5-b]pyridinyl, 1H-imidazolyl, 1H-indazolyl, 1H-indolyl, (1H-pyrazol-5-yl)thiophen-2-yl, (1H-pyrazol-5-yl)thiophen-3-yl, 1H-pyrazolo[3,4-b]pyridinyl, 1H-pyrazolo[4,3-b]pyridinyl, 1H-pyrazolyl, 1H-pyrrolo[2,3-b]pyridinyl, 1H-pyrrolo[3,2-b]pyridinyl, 1-phenyl-1H-pyrazolyl, 2,3-dihydro-[1,4]dioxino[2,3-b]pyridinyl, 2,3-dihydro-1H-benzo[d]imidazolyl, 2,3-dihydro-1H-imidazo[4,5-b]pyridinyl, 2,3-dihydro-1H-pyrido[2,3-b][1,4]oxazinyl, 2,3-dihydro-1H-pyrrolo[2,3-b]pyridinyl, 2,3-dihydrobenzo[b][1,4]dioxinyl, 2,3-dihydrobenzo[d]thiazolyl, 2,3-dihydrobenzofuranyl, 2,3-dihydrofuro[2,3-b]pyridinyl, 2-phenylthiazolyl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazinyl, 3,4-dihydro-2H-pyrano[2,3-b]pyridinyl, 3,4-dihydro-2H-pyrido[3,2-b][1,4]oxazinyl, 3H-imidazo[4,5-b]pyridinyl, 4'-(1,2,4-oxadiazol-3-yl)biphenylyl, 4-(2H-tetrazol-5-yl)phenyl, 4-(pyridin-3-yl)phenyl, 4-(pyridin-4-yl)phenyl, 5-(1H-pyrazol-4-yl)pyridinyl, 5-(phenyl)pyridinyl, 5,6,7,8-tetrahydro-1,6-naphthyridinyl, 5,6,7,8-tetrahydronaphthalenyl, 5,6,7,8-tetrahydroquinolinyl, 5-phenyl-2,3-dihydrobenzofuranyl, 5-phenylthiophen-2-yl, 5-phenylthiophen-3-yl, 6,7-dihydro-5H-cyclopenta[b]pyridinyl, 6,7-dihydro-5H-pyrrolo[3,4-b]pyridinyl, 7,8-dihydro-5H-pyrano[4,3-b]pyridinyl, benzo[c][1,2,5]oxadiazolyl, benzo[c][1,2,5]thiadiazolyl, benzo[d]isoxazolyl, benzofuranyl, biphenylyl, chromanyl, furanyl, imidazo[1,2-a]pyridinyl, imidazo[2,1-b]thiazolyl, indolinyl, isoxazolyl, naphthalenyl, phenyl, pyridinyl, pyrimidinyl, quinolinyl, thiophen-2-yl, and thiophen-3-yl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, hydroxycarbamimidoyl, hydroxyl, hydroxymethyl, isobutyl, isopropoxy, isopropyl, methoxy, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl; and $R^{2a}$ is H, ethyl, or methyl.

One aspect of the present invention pertains to compounds of Formula (Ic) and pharmaceutically acceptable salts, solvates, and hydrates thereof:

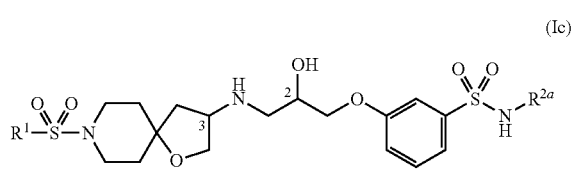

(Ic)

wherein:

$R^1$ is selected from: (1,2,3,4-tetrahydropyrimidin-5-yl)phenyl, (5-isoxazol-3-yl)thiophen-2-yl, (pyridin-2-yl)phenyl, [3,3'-bipyridin]-5-yl, 1,2,3,4-tetrahydropyrido[2,3-b][1,4]oxazepin-8-yl, 1',2'-dihydrospiro[cyclopropane-1,3'-pyrido[2,3-b][1,4]oxazine]-7'-yl, 1,4-dihydropyridin-3-yl, 1,4-dihydroquinolin-3-yl, 1,5-naphthyridin-3-yl, 1,8-naphthyridin-3-yl, 1H-benzo[d]imidazol-5-yl, 1H-benzo[d]imidazol-6-yl, 1H-imidazo[4,5-b]pyridin-6-yl, 1H-imidazol-4-yl, 1H-indazol-5-yl, 1H-indazol-6-yl, 1H-indol-5-yl, 1H-pyrazol-3-yl, 1H-pyrazol-4-yl, (1H-pyrazol-5-yl)thiophen-2-yl, 1H-pyrazolo[3,4-b]pyridin-5-yl, 1H-pyrazolo[4,3-b]pyridin-6-yl, 1H-pyrrolo[2,3-b]pyridin-3-yl, 1H-pyrrolo[2,3-b]pyridin-5-yl, 1H-pyrrolo[3,2-b]pyridin-3-yl, 1H-pyrrolo[3,2-b]pyridin-6-yl, 1-phenyl-1H-pyrazol-4-yl, 2,3-dihydro-[1,4]dioxino[2,3-b]pyridin-7-yl, 2,3-dihydro-1H-benzo[d]imidazol-5-yl, 2,3-dihydro-1H-imidazo[4,5-b]pyridin-6-yl, 2,3-dihydro-1H-pyrido[2,3-b][1,4]oxazin-6-yl, 2,3-dihydro-1H-pyrido[2,3-b][1,4]oxazin-7-yl, 2,3-dihydro-1H-pyrrolo[2,3-b]pyridin-5-yl, 2,3-dihydrobenzo[b][1,4]dioxin-6-yl, 2,3-dihydrobenzo[d]thiazol-6-yl, 2,3-dihydrobenzofuran-5-yl, 2,3-dihydrobenzofuran-7-yl, 2,3-dihydrofuro[2,3-b]pyridin-5-yl, 2-phenylthiazol-5-yl, 3-(1H-pyrazol-3-yl)phenyl, 3-(1H-pyrazol-4-yl)phenyl, 3-(1H-pyrrol-3-yl)phenyl, 3-(2H-tetrazol-5-yl)phenyl, 3-(furan-2-yl)phenyl, 3-(isoxazol-4-yl)phenyl, 3-(pyridin-2-yl)phenyl, 3-(pyridin-3-yl)phenyl, 3-(pyridin-4-yl)phenyl, 3-(pyrimidin-5-yl)phenyl, 3-(thiazol-5-yl)phenyl, 3-(thiophen-2-yl)phenyl, 3-(thiophen-3-yl)phenyl, 3,4-dihydro-2H-benzo[b][1,4]oxazin-6-yl, 3,4-dihydro-2H-pyrano[2,3-b]pyridin-6-yl, 3,4-dihydro-2H-pyrido[3,2-b][1,4]oxazin-7-yl, 3H-imidazo[4,5-b]pyridin-6-yl, 4'-(1,2,4-oxadiazol-3-yl)biphenyl-3-yl, 4-(2H-tetrazol-5-yl)phenyl, 4-(pyridin-3-yl)phenyl, 4-(pyridin-4-yl)phenyl, 5-(1H-pyrazol-4-yl)pyridin-3-yl, 5-(phenyl)pyridin-3-yl, 5,6,7,8-tetrahydro-1,6-naphthyridin-3-yl, 5,6,7,8-tetrahydronaphthalen-1-yl, 5,6,7,8-tetrahydronaphthalen-2-yl, 5,6,7,8-tetrahydronaphthalenyl, 5,6,7,8-tetrahydroquinolin-3-yl, 5-phenyl-2,3-dihydrobenzofuran-7-yl, 5-phenylthiophen-2-yl, 6,7-dihydro-5H-cyclopenta[b]pyridin-3-yl, 6,7-dihydro-5H-pyrrolo[3,4-b]pyridin-3-yl, 7,8-dihydro-5H-pyrano[4,3-b]pyridin-3-yl, benzo[c][1,2,5]oxadiazol-4-yl, benzo[c][1,2,5]thiadiazol-4-yl, benzo[c][1,2,5]thiadiazol-5-yl, benzo[d]isoxazol-5-yl, benzofuran-2-yl, benzofuran-5-yl, biphenyl-2-yl, biphenyl-3-yl, biphenyl-4-yl, chroman-6-yl, furan-3-yl, imidazo[1,2-a]pyridin-6-yl, imidazo[2,1-b]thiazol-5-yl, indolin-5-yl, isoxazol-4-yl, naphthalen-1-yl, naphthalen-2-yl, phenyl, pyridin-2-yl, pyridin-3-yl, pyrimidin-5-yl, quinolin-3-yl, quinolin-6-yl, quinolin-8-yl, thiophen-2-yl, and thiophen-3-yl; each optionally substituted with one or more substituents selected from: (1-amino-3-hydroxy-1-oxopropan-2-yl)(methyl)amino, (2-(dimethylamino)ethylamino)methyl, (2,2,2-trifluoroethylamino)methyl, (2,2-difluoroethylamino)methyl, (2-acetamidoethyl)(methyl)amino, (2-amino-2-oxoacetamido)methyl, (2-aminoacetamido)methyl, (2-fluoroethylamino)methyl, (2-hydroxyethylamino)methyl, (2-methoxyethylamino)methyl, (cyanomethylamino)methyl, (dimethylamino)methyl, (ethylamino)methyl, (isobutylamino)methyl, (isopentylamino)methyl, (isopropylamino)methyl, (methylamino)methyl, 1-aminocyclopropyl, 2-(benzyloxy)ethyl, 2-(pyrrolidin-1-yl)ethoxy, 2-(trifluoromethyl)phenoxy, 2-aminoethylamino, 2-carboxy-N-methylacetamido, 2-hydroxyethyl, 2-hydroxyethylamino, 2-methoxyethyl, 2-methoxyethylamino, 2-morpholinoethylamino, 3-(dimethylamino)propoxy, 4-(trifluoromethyl)phenoxy, acetamido, acetyl, amino, aminomethyl, benzyl, bromo, carbamimidoyl, carboxamide, carboxy, carboxymethyl, chloro, cyano, cyanomethoxy, cyanomethyl, cyclopropylmethyl, dimethylamino, dimethylcarbamoyl, ethoxy, ethyl, fluoro, hydroxycarbamimidoyl, hydroxyl, hydroxymethyl, isobutyl, isopropoxy, isopropyl, methoxy, methoxymethyl, methyl, methylamino, methylsulfonamido, methylsulfonyl, morpholino, N,N-dimethylsulfamoyl, oxo, phenoxy, phenylsulfonyl, piperazin-1-yl, piperidin-1-yl, propyl, sec-butyl, sulfamoyl, tert-butyl, tert-pentyl, thiazolidin-3-ylmethyl, trifluoromethoxy, and trifluoromethyl; and $R^{2a}$ is H, ethyl, or methyl.

One aspect of the present invention pertains to compounds of Formula (Ic) and pharmaceutically acceptable salts, solvates, and hydrates thereof:

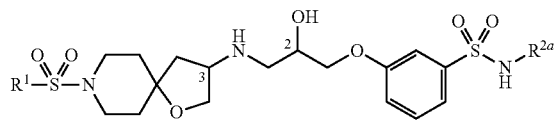

(Ic)

wherein:

$R^1$ is heteroaryl optionally substituted with one or more substituents selected from: $C_1$-$C_7$ alkyl, cyano, $C_1$-$C_6$ haloalkyl, halogen, hydroxyl, and oxo; and $R^{2a}$ is H or $C_1$-$C_6$ alkyl.

One aspect of the present invention pertains to compounds of Formula (Ic) and pharmaceutically acceptable salts, solvates, and hydrates thereof:

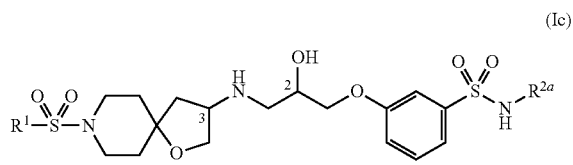

(Ic)

wherein:

$R^1$ is selected from: 1H-pyrrolo[3,2-b]pyridinyl, quinolinyl, 1,4-dihydroquinolinyl, 1H-pyrrolo[2,3-b]pyridinyl, and 2,3-dihydro-1H-pyrido[2,3-b][1,4]oxazinyl; each optionally substituted with one or more substituents selected from: ethyl, methyl, cyano, trifluoromethyl, fluoro, hydroxyl, and oxo; and $R^{2a}$ is H or $C_1$-$C_6$ alkyl.

One aspect of the present invention pertains to compounds of Formula (Ic) and pharmaceutically acceptable salts, solvates, and hydrates thereof:

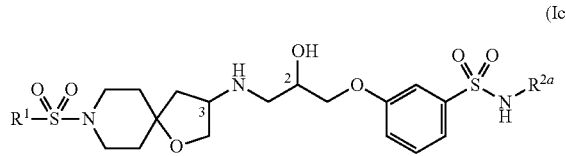

(Ic)

wherein:

$R^1$ is selected from: 1H-pyrrolo[3,2-b]pyridin-6-yl, quinolin-3-yl, 1,4-dihydroquinolin-3-yl, 1H-pyrrolo[2,3-b]pyridin-5-yl, and 2,3-dihydro-1H-pyrido[2,3-b][1,4]oxazin-7-yl; each optionally substituted with one or more substituents selected from: ethyl, methyl, cyano, trifluoromethyl, fluoro, hydroxyl, and oxo; and $R^{2a}$ is H, ethyl, or methyl.

One aspect of the present invention pertains to compounds of Formula (Ic) and pharmaceutically acceptable salts, solvates, and hydrates thereof:

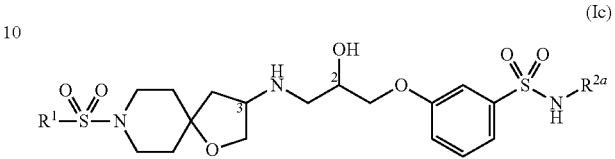

(Ic)

wherein:

$R^1$ is selected from: 1H-pyrrolo[3,2-b]pyridin-6-yl, 4-hydroxyquinolin-3-yl, 1-ethyl-4-oxo-1,4-dihydroquinolin-3-yl, 3-cyano-1H-pyrrolo[2,3-b]pyridin-5-yl, 1,3-dimethyl-2,3-dihydro-1H-pyrido[2,3-b][1,4]oxazin-7-yl, and 3-(trifluoromethyl)-1H-pyrrolo[2,3-b]pyridin-5-yl; and $R^{2a}$ is H or methyl.

Some embodiments of the present invention include every combination of one or more compounds and pharmaceutically acceptable salts, solvates, and hydrates thereof selected from the following group, wherein the Compound Number in bold directly preceding the chemical name is used elsewhere in this disclosure: Compound 1: 3-((2S)-2-hydroxy-3-(8-(naphthalen-2-ylsulfonyl)-1-oxa-8-azaspiro[4.5]decan-3-ylamino)propoxy)-N-methylbenzenesulfonamide; Compound 2: 3-((2S)-2-hydroxy-3-(8-(naphthalen-2-ylsulfonyl)-1-oxa-8-azaspiro[4.5]decan-3-ylamino)propoxy)-N-propylbenzenesulfonamide; Compound 3: 3-((2S)-2-hydroxy-3-(8-(naphthalen-2-ylsulfonyl)-1-oxa-8-azaspiro[4.5]decan-3-ylamino)propoxy)-N-pentylbenzenesulfonamide; Compound 4: 3-((2S)-2-hydroxy-3-(8-(naphthalen-2-ylsulfonyl)-1-oxa-8-azaspiro[4.5]decan-3-ylamino)propoxy)-N,N-dimethylbenzenesulfonamide; Compound 5: 3-((2S)-2-hydroxy-3-(8-(naphthalen-2-ylsulfonyl)-1-oxa-8-azaspiro[4.5]decan-3-ylamino)propoxy)-N-(2,2,2-trifluoroethyl)benzenesulfonamide; Compound 6: 3-((2S)-2-hydroxy-3-(8-(naphthalen-2-ylsulfonyl)-1-oxa-8-azaspiro[4.5]decan-3-ylamino)propoxy)-N-isopropylbenzenesulfonamide; Compound 7: N-ethyl-3-((2S)-2-hydroxy-3-(8-(naphthalen-2-ylsulfonyl)-1-oxa-8-azaspiro[4.5]decan-3-ylamino)propoxy)-N-isopropylbenzenesulfonamide; Compound 8: N-(cyclopropylmethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 9: N-(2,2-difluoroethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 10: N-sec-butyl-3-((2S)-2-hydroxy-3-(8-(naphthalen-2-ylsulfonyl)-1-oxa-8-azaspiro[4.5]decan-3-ylamino)propoxy)benzenesulfonamide; Compound 11: 3-((2S)-2-hydroxy-3-(8-(naphthalen-2-ylsulfonyl)-1-oxa-8-azaspiro[4.5]decan-3-ylamino)propoxy)-N-methoxybenzenesulfonamide; Compound 12: 3-((2S)-2-hydroxy-3-(8-(naphthalen-2-ylsulfonyl)-1-oxa-8-azaspiro[4.5]decan-3-ylamino)propoxy)-N-(2-hydroxyethyl)benzenesulfonamide; Compound 13: 3-((2S)-2-hydroxy-3-(8-(naphthalen-2-ylsulfonyl)-1-oxa-8-azaspiro[4.5]decan-3-ylamino)propoxy)-N-(2-methoxyethyl)benzenesulfonamide; Compound 14: 3-((2S)-2-hydroxy-3-(8-(phenylsulfonyl)-1-oxa-8-azaspiro[4.5]decan-3-ylamino)propoxy)-N-methylbenzenesulfonamide; Compound 15:

3-((2S)-3-(8-(3-chlorophenylsulfonyl)-1-oxa-8-azaspiro[4.5]decan-3-ylamino)-2-hydroxypropoxy)-N-methylbenzenesulfonamide; Compound 16: 3-((2S)-2-hydroxy-3-(8-(5,6,7,8-tetrahydronaphthalen-2-ylsulfonyl)-1-oxa-8-azaspiro[4.5]decan-3-ylamino)propoxy)-N-methylbenzenesulfonamide; Compound 17: 3-((2S)-3-(8-(4-chlorophenylsulfonyl)-1-oxa-8-azaspiro[4.5]decan-3-ylamino)-2-hydroxypropoxy)-N-methylbenzenesulfonamide; Compound 18: 3-((2S)-2-hydroxy-3-(8-(4-methoxyphenylsulfonyl)-1-oxa-8-azaspiro[4.5]decan-3-ylamino)propoxy)-N-methylbenzenesulfonamide; Compound 19: 3-((2S)-3-(8-(3,4-dimethylphenylsulfonyl)-1-oxa-8-azaspiro[4.5]decan-3-ylamino)-2-hydroxypropoxy)-N-methylbenzenesulfonamide; Compound 20: 3-((2S)-3-(8-(3-bromophenylsulfonyl)-1-oxa-8-azaspiro[4.5]decan-3-ylamino)-2-hydroxypropoxy)-N-methylbenzenesulfonamide; Compound 21: 3-((2S)-2-hydroxy-3-(8-(m-tolylsulfonyl)-1-oxa-8-azaspiro[4.5]decan-3-ylamino)propoxy)-N-methylbenzenesulfonamide; Compound 22: 3-((2S)-3-(8-(4-sec-butylphenylsulfonyl)-1-oxa-8-azaspiro[4.5]decan-3-ylamino)-2-hydroxypropoxy)-N-methylbenzenesulfonamide; Compound 23: 3-((2S)-3-(8-(3,5-dimethylsulfonyl)-1-oxa-8-azaspiro[4.5]decan-3-ylamino)-2-hydroxypropoxy)-N-methylbenzenesulfonamide; Compound 24: 4-(3-((S)-2-hydroxy-3-(3-(N-methylsulfamoyl)phenoxy)propylamino)-1-oxa-8-azaspiro[4.5]decan-8-ylsulfonyl)-N,N-dimethylbenzamide; Compound 25: 3-((2S)-3-(8-(4-acetylphenylsulfonyl)-1-oxa-8-azaspiro[4.5]decan-3-ylamino)-2-hydroxypropoxy)-N-methylbenzenesulfonamide; Compound 26: 3-((2S)-3-(8-(4-fluorophenylsulfonyl)-1-oxa-8-azaspiro[4.5]decan-3-ylamino)-2-hydroxypropoxy)-N-methylbenzenesulfonamide; Compound 27: 3-((2S)-2-hydroxy-3-(8-(3-methoxyphenylsulfonyl)-1-oxa-8-azaspiro[4.5]decan-3-ylamino)propoxy)-N-methylbenzenesulfonamide; Compound 28: 3-((2S)-3-(8-(3-fluorophenylsulfonyl)-1-oxa-8-azaspiro[4.5]decan-3-ylamino)-2-hydroxypropoxy)-N-methylbenzenesulfonamide; Compound 29: 3-((S)-2-hydroxy-3-((S)-8-(naphthalen-2-ylsulfonyl)-1-oxa-8-azaspiro[4.5]decan-3-ylamino)propoxy)-N-methylbenzenesulfonamide; Compound 30: 3-((S)-2-hydroxy-3-((R)-8-(naphthalen-2-ylsulfonyl)-1-oxa-8-azaspiro[4.5]decan-3-ylamino)propoxy)-N-methylbenzenesulfonamide; Compound 31: 3-((2S)-3-(8-(biphenyl-3-ylsulfonyl)-1-oxa-8-azaspiro[4.5]decan-3-ylamino)-2-hydroxypropoxy)-N-methylbenzenesulfonamide; Compound 32: 3-((2S)-3-(8-(3-cyanophenylsulfonyl)-1-oxa-8-azaspiro[4.5]decan-3-ylamino)-2-hydroxypropoxy)-N-methylbenzenesulfonamide; Compound 33: 3-((2S)-2-hydroxy-3-(8-(2-(trifluoromethyl)phenylsulfonyl)-1-oxa-8-azaspiro[4.5]decan-3-ylamino)propoxy)-N-methylbenzenesulfonamide; Compound 34: 3-((2S)-3-(8-(2-fluorophenylsulfonyl)-1-oxa-8-azaspiro[4.5]decan-3-ylamino)-2-hydroxypropoxy)-N-methylbenzenesulfonamide; Compound 35: 3-((2S)-3-(8-(2-chlorophenylsulfonyl)-1-oxa-8-azaspiro[4.5]decan-3-ylamino)-2-hydroxypropoxy)-N-methylbenzenesulfonamide; Compound 36: 3-((2S)-3-(8-(4-tert-butylphenylsulfonyl)-1-oxa-8-azaspiro[4.5]decan-3-ylamino)-2-hydroxypropoxy)-N-methylbenzenesulfonamide; Compound 37: 3-((2S)-2-hydroxy-3-(8-(4-(methylsulfonyl)phenylsulfonyl)-1-oxa-8-azaspiro[4.5]decan-3-ylamino)propoxy)-N-methylbenzenesulfonamide; Compound 38: 3-((2S)-2-hydroxy-3-(8-(3-(trifluoromethyl)phenylsulfonyl)-1-oxa-8-azaspiro[4.5]decan-3-ylamino)propoxy)-N-methylbenzenesulfonamide; Compound 39: 3-((2S)-3-(8-(2-cyanophenylsulfonyl)-1-oxa-8-azaspiro[4.5]decan-3-ylamino)-2-hydroxypropoxy)-N-methylbenzenesulfonamide; Compound 40: 4-(3-((S)-2-hydroxy-3-(3-(N-methylsulfamoyl)phenoxy)propylamino)-1-oxa-8-azaspiro[4.5]decan-8-ylsulfonyl)benzoic acid; Compound 41: 3-((2S)-3-(8-(chroman-6-ylsulfonyl)-1-oxa-8-azaspiro[4.5]decan-3-ylamino)-2-hydroxypropoxy)-N-methylbenzenesulfonamide; Compound 42: N-(4-(3-((S)-2-hydroxy-3-(3-(N-methylsulfamoyl)phenoxy)propylamino)-1-oxa-8-azaspiro[4.5]decan-8-ylsulfonyl)phenyl)acetamide; Compound 43: 3-((2S)-2-hydroxy-3-(8-(2-(methylsulfonyl)phenylsulfonyl)-1-oxa-8-azaspiro[4.5]decan-3-ylamino)propoxy)-N-methylbenzenesulfonamide; Compound 44: 3-((2S)-3-(8-(4-cyanophenylsulfonyl)-1-oxa-8-azaspiro[4.5]decan-3-ylamino)-2-hydroxypropoxy)-N-methylbenzenesulfonamide; Compound 45: 3-((2S)-2-hydroxy-3-(8-(4-(trifluoromethyl)phenylsulfonyl)-1-oxa-8-azaspiro[4.5]decan-3-ylamino)propoxy)-N-methylbenzenesulfonamide; Compound 46: 3-((2S)-2-hydroxy-3-(8-(naphthalen-2-ylsulfonyl)-1-oxa-8-azaspiro[4.5]decan-3-ylamino)propoxy)-N-(2-hydroxypropyl)benzenesulfonamide; Compound 47: N-(2-ethoxyethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 48: 3-((2S)-2-hydroxy-3-(8-(naphthalen-2-ylsulfonyl)-1-oxa-8-azaspiro[4.5]decan-3-ylamino)propoxy)-N—((S)-1-hydroxypropan-2-yl)benzenesulfonamide; Compound 49: N-(1-hydroxy-2-methylpropan-2-yl)-3-((2S)-2-hydroxy-3-(8-(naphthalen-2-ylsulfonyl)-1-oxa-8-azaspiro[4.5]decan-3-ylamino)propoxy)benzenesulfonamide; Compound 50: 3-((2S)-2-hydroxy-3-(8-(naphthalen-2-ylsulfonyl)-1-oxa-8-azaspiro[4.5]decan-3-ylamino)propoxy)-N-(tetrahydro-2H-pyran-4-yl)benzenesulfonamide; Compound 51: 3-((2S)-2-hydroxy-3-(8-(naphthalen-2-ylsulfonyl)-1-oxa-8-azaspiro[4.5]decan-3-ylamino)propoxy)-N-(3-hydroxypropyl)benzenesulfonamide; Compound 52: 3-((2S)-3-(8-(4-bromophenylsulfonyl)-1-oxa-8-azaspiro[4.5]decan-3-ylamino)-2-hydroxypropoxy)-N-methylbenzenesulfonamide; Compound 53: 3-((2S)-2-hydroxy-3-(8-tosyl-1-oxa-8-azaspiro[4.5]decan-3-ylamino)propoxy)-N-methylbenzenesulfonamide; Compound 54: 3-((2S)-3-(8-(2-bromophenylsulfonyl)-1-oxa-8-azaspiro[4.5]decan-3-ylamino)-2-hydroxypropoxy)-N-methylbenzenesulfonamide; Compound 55: 3-((2S)-2-hydroxy-3-(8-(naphthalen-1-ylsulfonyl)-1-oxa-8-azaspiro[4.5]decan-3-ylamino)propoxy)-N-methylbenzenesulfonamide; Compound 56: 3-(3-((S)-2-hydroxy-3-(3-(N-methylsulfamoyl)phenoxy)propylamino)-1-oxa-8-azaspiro[4.5]decan-8-ylsulfonyl)benzoic acid; Compound 57: 3-((2S)-2-hydroxy-3-(8-(4-(trifluoromethoxy)phenylsulfonyl)-1-oxa-8-azaspiro[4.5]decan-3-ylamino)propoxy)-N-methylbenzenesulfonamide; Compound 58: 3-((2S)-2-hydroxy-3-(8-(2-oxo-2,3-dihydrobenzo[d]thiazol-6-ylsulfonyl)-1-oxa-8-azaspiro[4.5]decan-3-ylamino)propoxy)-N-methylbenzenesulfonamide; Compound 59: 3-((2S)-3-(8-(3-(3,5-dimethylisoxazol-4-yl)phenylsulfonyl)-1-oxa-8-azaspiro[4.5]decan-3-ylamino)-2-hydroxypropoxy)-N-methylbenzenesulfonamide; Compound 60: 3-((2S)-2-hydroxy-3-(8-(naphthalen-2-ylsulfonyl)-1-oxa-8-azaspiro[4.5]decan-3-ylamino)propoxy)-N-(2-methoxyethyl)-N-methylbenzenesulfonamide; Compound 61: 3-((2S)-2-hydroxy-3-(8-(3-(1-methyl-1H-pyrazol-4-yl)phenylsulfonyl)-1-oxa-8-azaspiro[4.5]decan-3-ylamino)

propoxy)-N-methylbenzenesulfonamide; Compound 62: 3-((2S)-2-hydroxy-3-(8-(3-(1-methyl-3-(trifluoromethyl)-1H-pyrazol-4-yl)phenylsulfonyl)-1-oxa-8-azaspiro[4.5]decan-3-ylamino)propoxy)-N-methylbenzenesulfonamide; Compound 63: 3-((2S)-3-(8-(3-(1H-pyrrol-3-yl)phenylsulfonyl)-1-oxa-8-azaspiro[4.5]decan-3-ylamino)-2-hydroxypropoxy)-N-methylbenzenesulfonamide; Compound 64: 3-((2S)-3-(8-(3-(1H-pyrazol-4-yl)phenylsulfonyl)-1-oxa-8-azaspiro[4.5]decan-3-ylamino)-2-hydroxypropoxy)-N-methylbenzenesulfonamide; Compound 65: 3-((2S)-2-hydroxy-3-(8-(3'-(methoxymethyl)biphenyl-3-ylsulfonyl)-1-oxa-8-azaspiro[4.5]decan-3-ylamino)propoxy)-N-methylbenzenesulfonamide; Compound 66:3-((2S)-2-hydroxy-3-(8-(3-(thiophen-3-yl)phenylsulfonyl)-1-oxa-8-azaspiro[4.5]decan-3-ylamino)propoxy)-N-methylbenzenesulfonamide; Compound 67: 3-((2S)-3-(8-(3'-(aminomethyl)biphenyl-3-ylsulfonyl)-1-oxa-8-azaspiro[4.5]decan-3-ylamino)-2-hydroxypropoxy)-N-methylbenzenesulfonamide; Compound 68: 3-((2S)-3-(8-(3-(1,3-dimethyl-1H-pyrazol-4-yl)phenylsulfonyl)-1-oxa-8-azaspiro[4.5]decan-3-ylamino)-2-hydroxypropoxy)-N-methylbenzenesulfonamide; Compound 69: 3-((2S)-3-(8-(3-(1-ethyl-1H-pyrazol-4-yl)phenylsulfonyl)-1-oxa-8-azaspiro[4.5]decan-3-ylamino)-2-hydroxypropoxy)-N-methylbenzenesulfonamide; Compound 70: 3-((2S)-2-hydroxy-3-(8-(3-(1-(2-hydroxyethyl)-1H-pyrazol-4-yl)phenylsulfonyl)-1-oxa-8-azaspiro[4.5]decan-3-ylamino)propoxy)-N-methylbenzenesulfonamide; Compound 71: 3-((2S)-2-hydroxy-3-(8-(3'-(methylsulfonyl)biphenyl-3-ylsulfonyl)-1-oxa-8-azaspiro[4.5]decan-3-ylamino)propoxy)-N-methylbenzenesulfonamide; Compound 72:3-((2S)-3-(8-(3'-cyanobiphenyl-3-ylsulfonyl)-1-oxa-8-azaspiro[4.5]decan-3-ylamino)-2-hydroxypropoxy)-N-methylbenzenesulfonamide; Compound 73: 3-((2S)-3-(8-(3-(2,4-dimethylthiazol-5-yl)phenylsulfonyl)-1-oxa-8-azaspiro[4.5]decan-3-ylamino)-2-hydroxypropoxy)-N-methylbenzenesulfonamide; Compound 74: N-cyclopropyl-3-((2S)-2-hydroxy-3-(8-(naphthalen-2-ylsulfonyl)-1-oxa-8-azaspiro[4.5]decan-3-ylamino)propoxy)benzenesulfonamide; Compound 75: 3-((2S)-2-hydroxy-3-(8-(naphthalen-2-ylsulfonyl)-1-oxa-8-azaspiro[4.5]decan-3-ylamino)propoxy)-N-(3-methoxypropyl)benzenesulfonamide; Compound 76: 3-((2S)-2-hydroxy-3-(8-(3-(1-methyl-1H-pyrrol-3-yl)phenylsulfonyl)-1-oxa-8-azaspiro[4.5]decan-3-ylamino)propoxy)-N-methylbenzenesulfonamide; Compound 77: 3-((2S)-3-(8-(3-(1-benzyl-1H-pyrazol-4-yl)phenylsulfonyl)-1-oxa-8-azaspiro[4.5]decan-3-ylamino)-2-hydroxypropoxy)-N-methylbenzenesulfonamide; Compound 78: 3-((2S)-3-(8-(3-(furan-2-yl)phenylsulfonyl)-1-oxa-8-azaspiro[4.5]decan-3-ylamino)-2-hydroxypropoxy)-N-methylbenzenesulfonamide; Compound 79: 3-((2S)-3-(8-(4'-(aminomethyl)biphenyl-3-ylsulfonyl)-1-oxa-8-azaspiro[4.5]decan-3-ylamino)-2-hydroxypropoxy)-N-methylbenzenesulfonamide; Compound 80: 3-((2S)-2-hydroxy-3-(8-(3-(1-propyl-1H-pyrazol-4-yl)phenylsulfonyl)-1-oxa-8-azaspiro[4.5]decan-3-ylamino)propoxy)-N-methylbenzenesulfonamide; Compound 81: 3-((2S)-2-hydroxy-3-(8-(3-(1-isobutyl-1H-pyrazol-4-yl)phenylsulfonyl)-1-oxa-8-azaspiro[4.5]decan-3-ylamino)propoxy)-N-methylbenzenesulfonamide; Compound 82: 3-((2S)-3-(8-(3-(1-(cyclopropylmethyl)-1H-pyrazol-4-yl)phenylsulfonyl)-1-oxa-8-azaspiro[4.5]decan-3-ylamino)-2-hydroxypropoxy)-N-methylbenzenesulfonamide; Compound 83: 3-((2S)-3-(8-(3'-(dimethylamino)biphenyl-3-ylsulfonyl)-1-oxa-8-azaspiro[4.5]decan-3-ylamino)-2-hydroxypropoxy)-N-methylbenzenesulfonamide; Compound 84: 3-((2S)-3-(8-(3-(1H-pyrazol-3-yl)phenylsulfonyl)-1-oxa-8-azaspiro[4.5]decan-3-ylamino)-2-hydroxypropoxy)-N-methylbenzenesulfonamide; Compound 85: 3'-(3-((S)-2-hydroxy-3-(3-(N-methylsulfamoyl)phenoxy)propylamino)-1-oxa-8-azaspiro[4.5]decan-8-ylsulfonyl)biphenyl-4-sulfonamide; Compound 86: 3-((2S)-2-hydroxy-3-(8-(4'-(methylsulfonamido)biphenyl-3-ylsulfonyl)-1-oxa-8-azaspiro[4.5]decan-3-ylamino)propoxy)-N-methylbenzenesulfonamide; Compound 87: 2-(3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl) acetic acid; Compound 88: 3-((2S)-2-hydroxy-3-(8-(3-(pyridin-3-yl)phenylsulfonyl)-1-oxa-8-azaspiro[4.5]decan-3-ylamino)propoxy)-N-methylbenzenesulfonamide; Compound 89: N-(3,3-difluorocyclobutyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 90: N-cyclopropyl-3-((2S)-2-hydroxy-3-(8-(naphthalen-2-ylsulfonyl)-1-oxa-8-azaspiro[4.5]decan-3-ylamino)propoxy)-N-methylbenzenesulfonamide; Compound 91: N-(2-aminoethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 92: (2S,3R)-3-hydroxy-2-(3-((2S)-2-hydroxy-3-(8-(naphthalen-2-ylsulfonyl)-1-oxa-8-azaspiro[4.5]decan-3-ylamino)propoxy)phenylsulfonamido)-N-methylbutanamide; Compound 93: N—((R)-1-cyclopropylethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 94: N-tert-butyl-3-((2S)-2-hydroxy-3-(8-(naphthalen-2-ylsulfonyl)-1-oxa-8-azaspiro[4.5]decan-3-ylamino)propoxy)benzenesulfonamide; Compound 95: N-(1,3-dihydroxypropan-2-yl)-3-((2S)-2-hydroxy-3-(8-(naphthalen-2-ylsulfonyl)-1-oxa-8-azaspiro[4.5]decan-3-ylamino)propoxy)benzenesulfonamide; Compound 96: 3-((2S)-2-hydroxy-3-(8-(naphthalen-2-ylsulfonyl)-1-oxa-8-azaspiro[4.5]decan-3-ylamino)propoxy)-N—((R)-1-hydroxypropan-2-yl)benzenesulfonamide; Compound 97: N-(2-ethylbutyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 98: 3-((2S)-2-hydroxy-3-(8-(naphthalen-2-ylsulfonyl)-1-oxa-8-azaspiro[4.5]decan-3-ylamino)propoxy)-N-isopentylbenzenesulfonamide; Compound 99: 3-((2S)-2-hydroxy-3-(8-(naphthalen-2-ylsulfonyl)-1-oxa-8-azaspiro[4.5]decan-3-ylamino)propoxy)-N-(1-(hydroxymethyl)cyclopropyl)benzenesulfonamide; Compound 100: N—((R)-3,3-dimethylbutan-2-yl)-3-((2S)-2-hydroxy-3-(8-(naphthalen-2-ylsulfonyl)-1-oxa-8-azaspiro[4.5]decan-3-ylamino)propoxy)benzenesulfonamide; Compound 101: N-ethyl-3-((2S)-2-hydroxy-3-(8-(naphthalen-2-ylsulfonyl)-1-oxa-8-azaspiro[4.5]decan-3-ylamino)propoxy)benzenesulfonamide; Compound 102: 3-((2S)-2-hydroxy-3-(8-(3-(pyridin-2-yl)phenylsulfonyl)-1-oxa-8-azaspiro[4.5]decan-3-ylamino)propoxy)-N-methylbenzenesulfonamide; Compound 103: 3-((2S)-3-(8-(3-(6-aminopyridin-3-yl)phenylsulfonyl)-1-oxa-8-azaspiro[4.5]decan-3-ylamino)-2-hydroxypropoxy)-N-methylbenzenesulfonamide; Compound 104: 3-((2S)-2-hydroxy-3-(8-(3-(pyrimidin-5-yl)phenylsulfonyl)-1-oxa-8-azaspiro[4.5]decan-3-ylamino)propoxy)-N-methylbenzenesulfonamide; Compound 105: 3-((2S)-3-(8-(3'-((dimethylamino)methyl)biphenyl-3-ylsulfonyl)-1-oxa-8-azaspiro[4.5]decan-3-ylamino)-2-hydroxypropoxy)-N-methylbenzenesulfonamide; Compound 106: 3-((2S)-2-hydroxy-3-(8-(3-(pyridin-4-yl)phenylsulfonyl)-1-oxa-8-azaspiro[4.5]decan-3-ylamino)propoxy)-N-methylbenzenesulfonamide; Compound 107: 3-((2S)-2-hydroxy-3-(8-(3-(2-methylpyridin-4-yl)phenylsulfonyl)-1-oxa-8-azaspiro[4.5]decan-3-ylamino)propoxy)-N-methylbenzenesulfonamide; Compound 108: 3-((2S)-2-hydroxy-3-(8-(3-(2-methoxypyrimidin-5-yl)phenylsulfonyl)-1-oxa-8-azaspiro[4.5]decan-3-ylamino)propoxy)-N-methylbenzenesulfonamide; Compound 109: 3-((2S)-2-hydroxy-3-(8-(3-(4-methylthiophen-3-yl)phenylsulfonyl)-1-oxa-8-azaspiro[4.5]decan-3-ylamino)propoxy)-N-methylbenzenesulfonamide; Compound 110: 3-((2S)-2-hydroxy-3-(8-(3-(5-methylpyridin-3-yl)phenylsulfonyl)-1-oxa-8-azaspiro[4.5]decan-3-ylamino)propoxy)-N-methylbenzenesulfonamide; Compound 111: 3-((2S)-2-hydroxy-3-(8-(3-(6-methylpyridin-3-yl)phenylsulfonyl)-1-oxa-8-azaspiro[4.5]decan-3-ylamino)propoxy)-N-methylbenzenesulfonamide; Compound 112: 3'-(3-((S)-2-hydroxy-3-(3-(N-methylsulfamoyl)phenoxy)propylamino)-1-oxa-8-azaspiro[4.5]decan-8-ylsulfonyl)biphenyl-3-carboxylic acid; Compound 113: 3-((2S)-3-(8-(3-(1,3-dimethyl-2,4-dioxo-1,2,3,4-tetrahydropyrimidin-5-yl)phenylsulfonyl)-1-oxa-8-azaspiro[4.5]decan-3-ylamino)-2-hydroxypropoxy)-N-methylbenzenesulfonamide; Compound 114: 3-((2S)-3-(8-(4'-(cyanomethoxy)biphenyl-3-ylsulfonyl)-1-oxa-8-azaspiro[4.5]decan-3-ylamino)-2-hydroxypropoxy)-N-methylbenzenesulfonamide; Compound 115: 3'-(3-((S)-2-hydroxy-3-(3-(N-methylsulfamoyl)phenoxy)propylamino)-1-oxa-8-azaspiro[4.5]decan-8-ylsulfonyl)-N,N-dimethylbiphenyl-3-sulfonamide; Compound 116: 3-((2S)-2-hydroxy-3-(8-(3-(3-methylthiophen-2-yl)phenylsulfonyl)-1-oxa-8-azaspiro[4.5]decan-3-ylamino)propoxy)-N-methylbenzenesulfonamide; Compound 117: 3-((2S)-3-(8-(4'-(cyanomethyl)biphenyl-3-ylsulfonyl)-1-oxa-8-azaspiro[4.5]decan-3-ylamino)-2-hydroxypropoxy)-N-methylbenzenesulfonamide; Compound 118: 3-((2S)-2-hydroxy-3-(8-(3'-(hydroxymethyl)biphenyl-3-ylsulfonyl)-1-oxa-8-azaspiro[4.5]decan-3-ylamino)propoxy)-N-methylbenzenesulfonamide; Compound 119: 3-((2S)-3-(8-(1,2-dimethyl-1H-imidazol-4-ylsulfonyl)-1-oxa-8-azaspiro[4.5]decan-3-ylamino)-2-hydroxypropoxy)-N-methylbenzenesulfonamide; Compound 120: 3-((2S)-2-hydroxy-3-(8-(4-tert-pentylphenylsulfonyl)-1-oxa-8-azaspiro[4.5]decan-3-ylamino)propoxy)-N-methylbenzenesulfonamide; Compound 121: 3-((2S)-2-hydroxy-3-(8-(4'-(trifluoromethyl)biphenyl-4-ylsulfonyl)-1-oxa-8-azaspiro[4.5]decan-3-ylamino)propoxy)-N-methylbenzenesulfonamide; Compound 122: 3-((2S)-3-(8-(4'-fluorobiphenyl-4-ylsulfonyl)-1-oxa-8-azaspiro[4.5]decan-3-ylamino)-2-hydroxypropoxy)-N-methylbenzenesulfonamide; Compound 123: 3-((2S)-3-(8-(biphenyl-4-ylsulfonyl)-1-oxa-8-azaspiro[4.5]decan-3-ylamino)-2-hydroxypropoxy)-N-methylbenzenesulfonamide; Compound 124: 3-((2S)-2-hydroxy-3-(8-(3-phenoxyphenylsulfonyl)-1-oxa-8-azaspiro[4.5]decan-3-ylamino)propoxy)-N-methylbenzenesulfonamide; Compound 125: 3-((2S)-3-(8-(cyclohexylsulfonyl)-1-oxa-8-azaspiro[4.5]decan-3-ylamino)-2-hydroxypropoxy)-N-methylbenzenesulfonamide; Compound 126: 3-((2S)-2-hydroxy-3-(8-(3-oxo-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 127: 3-((2S)-3-(8-(2,2-dimethylchroman-6-ylsulfonyl)-1-oxa-8-azaspiro[4.5]decan-3-ylamino)-2-hydroxypropoxy)-N-methylbenzenesulfonamide; Compound 128: 3-((2S)-3-(8-(benzo[c][1,2,5]thiadiazol-4-ylsulfonyl)-1-oxa-8-azaspiro[4.5]decan-3-ylamino)-2-hydroxypropoxy)-N-methylbenzenesulfonamide; Compound 129: 3-((2S)-3-(8-(6-chloroimidazo[2,1-b]thiazol-5-ylsulfonyl)-1-oxa-8-azaspiro[4.5]decan-3-ylamino)-2-hydroxypropoxy)-N-methylbenzenesulfonamide; Compound 130: 3-((2S)-2-hydroxy-3-(8-(6-phenoxypyridin-3-ylsulfonyl)-1-oxa-8-azaspiro[4.5]decan-3-ylamino)propoxy)-N-methylbenzenesulfonamide; Compound 131: 3-((2S)-3-(8-(1H-pyrazol-4-ylsulfonyl)-1-oxa-8-azaspiro[4.5]decan-3-ylamino)-2-hydroxypropoxy)-N-methylbenzenesulfonamide; Compound 132: 3-((2S)-2-hydroxy-3-(8-(5-methyl-1-phenyl-1H-pyrazol-4-ylsulfonyl)-1-oxa-8-azaspiro[4.5]decan-3-ylamino)propoxy)-N-methylbenzenesulfonamide; Compound 133: 3-((2S)-3-(8-(2-chloro-5-(trifluoromethyl)phenylsulfonyl)-1-oxa-8-azaspiro[4.5]decan-3-ylamino)-2-hydroxypropoxy)-N-methylbenzenesulfonamide; Compound 134: 3-((2S)-3-(8-(2,4-difluorophenylsulfonyl)-1-oxa-8-azaspiro[4.5]decan-3-ylamino)-2-hydroxypropoxy)-N-methylbenzenesulfonamide; Compound 135: 3-((2S)-2-hydroxy-3-(8-(2-methoxy-4-methylphenylsulfonyl)-1-oxa-8-azaspiro[4.5]decan-3-ylamino)propoxy)-N-methylbenzenesulfonamide; Compound 136: 3-((2S)-3-(8-(4-ethoxyphenylsulfonyl)-1-oxa-8-azaspiro[4.5]decan-3-ylamino)-2-hydroxypropoxy)-N-methylbenzenesulfonamide; Compound 137: 3-((2S)-2-hydroxy-3-(8-(4-isopropoxyphenylsulfonyl)-1-oxa-8-azaspiro[4.5]decan-3-ylamino)propoxy)-N-methylbenzenesulfonamide; Compound 138: 3-((2S)-3-(8-(3,5-dichlorophenylsulfonyl)-1-oxa-8-azaspiro[4.5]decan-3-ylamino)-2-hydroxypropoxy)-N-methylbenzenesulfonamide; Compound 139: 3-((2S)-3-(8-(3-chloro-2-fluorophenylsulfonyl)-1-oxa-8-azaspiro[4.5]decan-3-ylamino)-2-hydroxypropoxy)-N-methylbenzenesulfonamide; Compound 140: 3-((2S)-3-(8-(2,5-dichlorophenylsulfonyl)-1-oxa-8-azaspiro[4.5]decan-3-ylamino)-2-hydroxypropoxy)-N-methylbenzenesulfonamide; Compound 141: 3-((2S)-3-(8-(3,4-difluorophenylsulfonyl)-1-oxa-8-azaspiro[4.5]decan-3-ylamino)-2-hydroxypropoxy)-N-methylbenzenesulfonamide; Compound 142: 3-((2S)-3-(8-(2,3-dichlorophenylsulfonyl)-1-oxa-8-azaspiro[4.5]decan-3-ylamino)-2-hydroxypropoxy)-N-methylbenzenesulfonamide; Compound 143: 3-((2S)-3-(8-(3-chloro-2-methylphenylsulfonyl)-1-oxa-8-azaspiro[4.5]decan-3-ylamino)-2-hydroxypropoxy)-N-methylbenzenesulfonamide; Compound 144: 3-((2S)-3-(8-(5-chloro-2-fluorophenylsulfonyl)-1-oxa-8-azaspiro[4.5]decan-3-ylamino)-2-hydroxypropoxy)-N-methylbenzenesulfonamide; Compound 145: 3-((2S)-3-(8-(5-chloro-2-cyanophenylsulfonyl)-1-oxa-8-azaspiro[4.5]decan-3-ylamino)-2-hydroxypropoxy)-N-methylbenzenesulfonamide; Compound 146: 3-((2S)-3-(8-(1H-benzo[d]imidazol-6-ylsulfonyl)-1-oxa-8-azaspiro[4.5]decan-3-ylamino)-2-hydroxypropoxy)-N-methylbenzenesulfonamide; Compound 147: 3-((2S)-2-hydroxy-3-(8-(4-methoxy-3-methylphenylsulfonyl)-1-oxa-8-azaspiro[4.5]decan-3-ylamino)propoxy)-N-methylbenzenesulfonamide; Compound 148: 3-((2S)-3-(8-(5-chloro-2-methoxyphenylsulfonyl)-1-oxa-8-azaspiro[4.5]decan-3-ylamino)-2-hydroxypropoxy)-N-methylbenzenesulfonamide; Compound 149: 3-((2S)-3-(8-(4-fluoro-3-methylphenylsulfonyl)-1-oxa-8-azaspiro[4.5]decan-3-ylamino)-2-hydroxypropoxy)-N-methylbenzenesulfonamide; Compound 150: 3-((2S)-3-(8-(2-fluoro-5-methylphenylsulfonyl)-1-oxa-8-azaspiro[4.5]decan-3-ylamino)-2-hydroxypropoxy)-N-methylbenzenesulfonamide; Compound 151: 3-((2S)-3-(8-(4-chloro-3-methylphenylsulfonyl)-1-oxa-8-azaspiro[4.5]decan-3-ylamino)-2-hydroxypropoxy)-N-methylbenzenesulfonamide; Compound 152: 3-((2S)-2- hydroxy-3-(8-(1-methyl-3-(trifluoromethyl)-1H-pyrazol-4-ylsulfonyl)-1-oxa-8-azaspiro[4.5]decan-3-ylamino)propoxy)-N-methylbenzenesulfonamide; Compound 153: 3-((2S)-3-(8-(3,4-dimethoxyphenylsulfonyl)-1-oxa-8-azaspiro[4.5]decan-3-ylamino)-2-hydroxypropoxy)-N-methylbenzenesulfonamide; Compound 154: 3-((2S)-3-(8-(2,5-dimethylphenylsulfonyl)-1-oxa-8-azaspiro[4.5]decan-3-ylamino)-2-hydroxypropoxy)-N-methylbenzenesulfonamide; Compound 155: 3-((2S)-3-(8-(4-bromo-3-chlorophenylsulfonyl)-1-oxa-8-azaspiro[4.5]decan-3-ylamino)-2-hydroxypropoxy)-N-methylbenzenesulfonamide; Compound 156: 3-((2S)-3-(8-(2,6-difluorophenylsulfonyl)-1-oxa-8-azaspiro[4.5]decan-3-ylamino)-2-hydroxypropoxy)-N-methylbenzenesulfonamide; Compound 157: 3-((2S)-3-(8-(2-chloro-4-cyanophenylsulfonyl)-1-oxa-8-azaspiro[4.5]decan-3-ylamino)-2-hydroxypropoxy)-N-methylbenzenesulfonamide; Compound 158: 3-((2S)-3-(8-(2,4-dichlorophenylsulfonyl)-1-oxa-8-azaspiro[4.5]decan-3-ylamino)-2-hydroxypropoxy)-N-methylbenzenesulfonamide; Compound 159: 3-((2S)-3-(8-(4-bromo-3-methylphenylsulfonyl)-1-oxa-8-azaspiro[4.5]decan-3-ylamino)-2-hydroxypropoxy)-N-methylbenzenesulfonamide; Compound 160: 3-((2S)-3-(8-(2-fluoro-3-methylphenylsulfonyl)-1-oxa-8-azaspiro[4.5]decan-3-ylamino)-2-hydroxypropoxy)-N-methylbenzenesulfonamide; Compound 161: 3-((2S)-2-hydroxy-3-(8-(3-(4-(trifluoromethyl)phenoxy)phenylsulfonyl)-1-oxa-8-azaspiro[4.5]decan-3-ylamino)propoxy)-N-methylbenzenesulfonamide; Compound 162: 3-((2S)-2-hydroxy-3-(8-(5-methyl-2-(trifluoromethyl)furan-3-ylsulfonyl)-1-oxa-8-azaspiro[4.5]decan-3-ylamino)propoxy)-N-methylbenzenesulfonamide; Compound 163: 3-((2S)-3-(8-(5-chloro-1,3-dimethyl-1H-pyrazol-4-ylsulfonyl)-1-oxa-8-azaspiro[4.5]decan-3-ylamino)-2-hydroxypropoxy)-N-methylbenzenesulfonamide; Compound 164: 3-((2S)-2-hydroxy-3-(8-(naphthalen-2-ylsulfonyl)-1-oxa-8-azaspiro[4.5]decan-3-ylamino)propoxy)-N-(2-(2-oxopyrrolidin-1-yl)ethyl)benzenesulfonamide; Compound 165: N-(1-ethylpiperidin-4-yl)-3-((2S)-2-hydroxy-3-(8-(naphthalen-2-ylsulfonyl)-1-oxa-8-azaspiro[4.5]decan-3-ylamino)propoxy)benzenesulfonamide; Compound 166: N—((S)-2,3-dihydroxypropyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 167: N-(2-(dimethylamino)ethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 168: 3-((2S)-2-hydroxy-3-(8-(naphthalen-2-ylsulfonyl)-1-oxa-8-azaspiro[4.5]decan-3-ylamino)propoxy)-N-(piperidin-3-ylmethyl)benzenesulfonamide; Compound 169: 3-((2S)-2-hydroxy-3-(8-(6-methoxynaphthalen-2-ylsulfonyl)-1-oxa-8-azaspiro[4.5]decan-3-ylamino)propoxy)-N-methylbenzenesulfonamide; Compound 170: 3-((2S)-2-hydroxy-3-(8-(3-(2-(trifluoromethyl)phenoxy)phenylsulfonyl)-1-oxa-8-azaspiro[4.5]decan-3-ylamino)propoxy)-N-methylbenzenesulfonamide; Compound 171: 3-((2S)-2-hydroxy-3-(8-(2-(trifluoromethoxy)phenylsulfonyl)-1-oxa-8-azaspiro[4.5]decan-3-ylamino)propoxy)-N-methylbenzenesulfonamide; Compound 172: 3-((2S)-3-(8-(benzylsulfonyl)-1-oxa-8-azaspiro[4.5]decan-3-ylamino)-2-hydroxypropoxy)-N-methylbenzenesulfonamide; Compound 173: 3-((2S)-2-hydroxy-3-(8-(7-methoxybenzo[c][1,2,5]oxadiazol-4-ylsulfonyl)-1-oxa-8-azaspiro[4.5]decan-3-ylamino)propoxy)-N-methylbenzenesulfonamide; Compound 174: 3-((2S)-3-(8-(biphenyl-2-ylsulfonyl)-1-oxa-8-azaspiro[4.5]decan-3-ylamino)-2-hydroxypropoxy)-N-methylbenzenesulfonamide; Compound 175: 3-((2S)-2-hydroxy-3-(8-(5-methylbenzo[c][1,2,5]oxadiazol-4-ylsulfonyl)-1-oxa-8-azaspiro[4.5]decan-3-ylamino)propoxy)-N-methylbenzenesulfonamide; Compound 176: 3-((2S)-2-hydroxy-3-(8-(2-methoxy-5-methylphenylsulfonyl)-1-oxa-8-azaspiro[4.5]decan-3-ylamino)propoxy)-N-methylbenzenesulfonamide; Compound 177: 3-((2S)-3-(8-(benzo[c][1,2,5]thiadiazol-5-ylsulfonyl)-1-oxa-8-azaspiro[4.5]decan-3-ylamino)-2-hydroxypropoxy)-N-methylbenzenesulfonamide; Compound 178: 3-((2S)-3-(8-(4,5-dichlorothiophen-2-ylsulfonyl)-1-oxa-8-azaspiro[4.5]decan-3-ylamino)-2-hydroxypropoxy)-N-methylbenzenesulfonamide; Compound 179: 3-((2S)-3-(8-(3-fluoro-5-methylphenylsulfonyl)-1-oxa-8-azaspiro[4.5]decan-3-ylamino)-2-hydroxypropoxy)-N-methylbenzenesulfonamide; Compound 180: 3-((2S)-3-(8-(2-cyano-5-methylphenylsulfonyl)-1-oxa-8-azaspiro[4.5]decan-3-ylamino)-2-hydroxypropoxy)-N-methylbenzenesulfonamide; Compound 181: 3-((2S)-3-(8-(5-chlorothiophen-2-ylsulfonyl)-1-oxa-8-azaspiro[4.5]decan-3-ylamino)-2-hydroxypropoxy)-N-methylbenzenesulfonamide; Compound 182: 3-((2S)-2-hydroxy-3-(8-(2-oxoindolin-5-ylsulfonyl)-1-oxa-8-azaspiro[4.5]decan-3-ylamino)propoxy)-N-methylbenzenesulfonamide; Compound 183: 3-((S)-3-((S)-8-(chroman-6-ylsulfonyl)-1-oxa-8-azaspiro[4.5]decan-3-ylamino)-2-hydroxypropoxy)-N-methylbenzenesulfonamide; Compound 184: 3-((S)-3-((R)-8-(chroman-6-ylsulfonyl)-1-oxa-8-azaspiro[4.5]decan-3-ylamino)-2-hydroxypropoxy)-N-methylbenzenesulfonamide; Compound 185: 3-((2S)-3-(8-(7-chlorobenzo[c][1,2,5]oxadiazol-4-ylsulfonyl)-1-oxa-8-azaspiro[4.5]decan-3-ylamino)-2-hydroxypropoxy)-N-methylbenzenesulfonamide; Compound 186: 3-((2S)-2-hydroxy-3-(8-(4-methyl-2-phenylthiazol-5-ylsulfonyl)-1-oxa-8-azaspiro[4.5]decan-3-ylamino)propoxy)-N-methylbenzenesulfonamide; Compound 187: 3-((2S)-2-hydroxy-3-(8-(5-phenylthiophen-2-ylsulfonyl)-1-oxa-8-azaspiro[4.5]decan-3-ylamino)propoxy)-N-methylbenzenesulfonamide; Compound 188: 3-((2S)-3-(8-(3,5-dimethylisoxazol-4-ylsulfonyl)-1-oxa-8-azaspiro[4.5]decan-3-ylamino)-2-hydroxypropoxy)-N-methylbenzenesulfonamide; Compound 189: 3-((2S)-2-hydroxy-3-(8-(4-methyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 190: 3-((2S)-2-hydroxy-3-(8-(4-(phenylsulfonyl)thiophen-2-ylsulfonyl)-1-oxa-8-azaspiro[4.5]decan-3-ylamino)propoxy)-N-methylbenzenesulfonamide; Compound 191: 3-((2S)-2-hydroxy-3-(8-(5-(1-methyl-3-(trifluoromethyl)-1H-pyrazol-5-yl)thiophen-2-ylsulfonyl)-1-oxa-8-azaspiro[4.5]decan-3-ylamino)propoxy)-N-methylbenzenesulfonamide; Compound 192: 3-((2S)-3-(8-(furan-3-ylsulfonyl)-1-oxa-8-azaspiro[4.5]decan-3-ylamino)-2-hydroxypropoxy)-N-methylbenzenesulfonamide; Compound 193: 3-((2S)-2-hydroxy-3-(8-(1-methyl-1H-pyrazol-3-ylsulfonyl)-1-oxa-8-azaspiro[4.5]decan-3-ylamino)propoxy)-N-methylbenzenesulfonamide; Compound 194: 3-((2S)-2-hydroxy-3-(8-(1-methyl-1H-imidazol-4-ylsulfonyl)-1-oxa-8-azaspiro[4.5]decan-3-ylamino)propoxy)-N-methylbenzenesulfonamide; Compound 195: 3-((2S)-3-(8-(3-fluoro-4-methoxyphenylsulfonyl)-1-oxa-8-azaspiro[4.5]decan-3-ylamino)-2-hydroxypropoxy)-N-methylbenzenesulfonamide; Compound 196: 3-((2S)-2-hydroxy-3-(8-(thiophen-3-ylsulfonyl)-1-oxa-8-azaspiro[4.5]decan-3-ylamino)propoxy)-N- methylbenzenesulfonamide; Compound 197: 3-((2S)-3-(8-(5-chlorobenzo[c][1,2,5]thiadiazol-4-ylsulfonyl)-1-oxa-8-azaspiro[4.5]decan-3-ylamino)-2-hydroxypropoxy)-N-methylbenzenesulfonamide; Compound 198: 3-((2S)-3-(8-(3-cyano-4-methylphenylsulfonyl)-1-oxa-8-azaspiro[4.5]decan-3-ylamino)-2-hydroxypropoxy)-N-methylbenzenesulfonamide; Compound 199: 3-((2S)-3-(8-(2-chloro-3-fluorophenylsulfonyl)-1-oxa-8-azaspiro[4.5]decan-3-ylamino)-2-hydroxypropoxy)-N-methylbenzenesulfonamide; Compound 200: 3-((2S)-3-(8-(2-chloro-4-fluorophenylsulfonyl)-1-oxa-8-azaspiro[4.5]decan-3-ylamino)-2-hydroxypropoxy)-N-methylbenzenesulfonamide; Compound 201: 3-((2S)-3-(8-(2,3-difluorophenylsulfonyl)-1-oxa-8-azaspiro[4.5]decan-3-ylamino)-2-hydroxypropoxy)-N-methylbenzenesulfonamide; Compound 202: 3-((2S)-3-(8-(2-chloro-5-fluorophenylsulfonyl)-1-oxa-8-azaspiro[4.5]decan-3-ylamino)-2-hydroxypropoxy)-N-methylbenzenesulfonamide; Compound 203: 3-((2S)-3-(8-(2-chloro-5-(methylsulfonyl)phenylsulfonyl)-1-oxa-8-azaspiro[4.5]decan-3-ylamino)-2-hydroxypropoxy)-N-methylbenzenesulfonamide; Compound 204: 3-((2S)-3-(8-(5-fluoro-2-methylphenylsulfonyl)-1-oxa-8-azaspiro[4.5]decan-3-ylamino)-2-hydroxypropoxy)-N-methylbenzenesulfonamide; Compound 205: 3-((2S)-3-(8-(2,5-difluorophenylsulfonyl)-1-oxa-8-azaspiro[4.5]decan-3-ylamino)-2-hydroxypropoxy)-N-methylbenzenesulfonamide; Compound 206: 3-((2S)-3-(8-(4-chloro-3-methoxyphenylsulfonyl)-1-oxa-8-azaspiro[4.5]decan-3-ylamino)-2-hydroxypropoxy)-N-methylbenzenesulfonamide; Compound 207: 3-((2S)-3-(8-(3-chloro-4-methoxyphenylsulfonyl)-1-oxa-8-azaspiro[4.5]decan-3-ylamino)-2-hydroxypropoxy)-N-methylbenzenesulfonamide; Compound 208: 3-((2S)-2-hydroxy-3-(8-(5-(5-(trifluoromethyl)isoxazol-3-yl)thiophen-2-ylsulfonyl)-1-oxa-8-azaspiro[4.5]decan-3-ylamino)propoxy)-N-methylbenzenesulfonamide; Compound 209: N-ethyl-3-((2S)-3-(8-(3-(1-ethyl-1H-pyrazol-4-yl)phenylsulfonyl)-1-oxa-8-azaspiro[4.5]decan-3-ylamino)-2-hydroxypropoxy)benzenesulfonamide; Compound 210: 3-((2S)-3-(8-(4'-(aminomethyl)biphenyl-3-ylsulfonyl)-1-oxa-8-azaspiro[4.5]decan-3-ylamino)-2-hydroxypropoxy)-N-ethylbenzenesulfonamide; Compound 211: 3'-((S)-3-(3-(N-ethylsulfamoyl)phenoxy)-2-hydroxypropylamino)-1-oxa-8-azaspiro[4.5]decan-8-ylsulfonyl)biphenyl-4-sulfonamide; Compound 212: 3-((2S)-3-(8-(3-(6-aminopyridin-3-yl)phenylsulfonyl)-1-oxa-8-azaspiro[4.5]decan-3-ylamino)-2-hydroxypropoxy)-N-ethylbenzenesulfonamide; Compound 213: 3-((2S)-3-(8-(4'-(cyanomethoxy)biphenyl-3-ylsulfonyl)-1-oxa-8-azaspiro[4.5]decan-3-ylamino)-2-hydroxypropoxy)-N-ethylbenzenesulfonamide; Compound 214: 3-((2S)-3-(8-(4'-(cyanomethyl)biphenyl-3-ylsulfonyl)-1-oxa-8-azaspiro[4.5]decan-3-ylamino)-2-hydroxypropoxy)-N-ethylbenzenesulfonamide; Compound 215: 3-((S)-2-hydroxy-3-((R)-8-(3-(1-methyl-1H-pyrazol-4-yl)phenylsulfonyl)-1-oxa-8-azaspiro[4.5]decan-3-ylamino)propoxy)-N-methylbenzenesulfonamide; Compound 216: 3-((S)-2-hydroxy-3-((S)-8-(3-(1-methyl-1H-pyrazol-4-yl)phenylsulfonyl)-1-oxa-8-azaspiro[4.5]decan-3-ylamino)propoxy)-N-methylbenzenesulfonamide; Compound 217: 3-((2S)-3-(8-(5-cyano-2-methylphenylsulfonyl)-1-oxa-8-azaspiro[4.5]decan-3-ylamino)-2-hydroxypropoxy)-N-methylbenzenesulfonamide; Compound 218: 3-((2S)-3-(8-(3-bromo-4-methylphenylsulfonyl)-1-oxa-8-azaspiro[4.5]decan-3-ylamino)-2-hydroxypropoxy)-N-methylbenzenesulfonamide; Compound 219: 3-((2S)-3-(8-(3-bromo-5-methylphenylsulfonyl)-1-oxa-8-azaspiro[4.5]decan-3-ylamino)-2-hydroxypropoxy)-N-methylbenzenesulfonamide; Compound 220: 3-((2S)-3-(8-(5-bromo-2-methoxyphenylsulfonyl)-1-oxa-8-azaspiro[4.5]decan-3-ylamino)-2-hydroxypropoxy)-N-methylbenzenesulfonamide; Compound 221: 3-((2S)-2-hydroxy-3-(8-(1-methyl-1H-indol-5-ylsulfonyl)-1-oxa-8-azaspiro[4.5]decan-3-ylamino)propoxy)-N-methylbenzenesulfonamide; Compound 222: 3-((2S)-2-hydroxy-3-(8-(4-methoxy-5,6,7,8-tetrahydronaphthalen-1-ylsulfonyl)-1-oxa-8-azaspiro[4.5]decan-3-ylamino)propoxy)-N-methylbenzenesulfonamide; Compound 223: 3-((2S)-3-(8-(5-chloronaphthalen-2-ylsulfonyl)-1-oxa-8-azaspiro[4.5]decan-3-ylamino)-2-hydroxypropoxy)-N-methylbenzenesulfonamide; Compound 224: 3-((2S)-3-(8-(3-chlorophenylsulfonyl)-1-oxa-8-azaspiro[4.5]decan-3-ylamino)-2-hydroxypropoxy)-N-ethylbenzenesulfonamide; Compound 225: N-ethyl-3-((2S)-2-hydroxy-3-(8-(4-methoxy-3-methylphenylsulfonyl)-1-oxa-8-azaspiro[4.5]decan-3-ylamino)propoxy)benzenesulfonamide; Compound 226: N-ethyl-3-((2S)-3-(8-(2-fluoro-5-methylphenylsulfonyl)-1-oxa-8-azaspiro[4.5]decan-3-ylamino)-2-hydroxypropoxy)benzenesulfonamide; Compound 227: 3-((2S)-3-(8-(4-bromo-3-methylphenylsulfonyl)-1-oxa-8-azaspiro[4.5]decan-3-ylamino)-2-hydroxypropoxy)-N-ethylbenzenesulfonamide; Compound 228: N-ethyl-3-((2S)-2-hydroxy-3-(8-(3-oxo-3,4-dihydro-2H-benzo[b][1,4]oxazin-6-ylsulfonyl)-1-oxa-8-azaspiro[4.5]decan-3-ylamino)propoxy)benzenesulfonamide; Compound 229: 3-((2S)-3-(8-(benzo[c][1,2,5]thiadiazol-5-ylsulfonyl)-1-oxa-8-azaspiro[4.5]decan-3-ylamino)-2-hydroxypropoxy)-N-ethylbenzenesulfonamide; Compound 230: N-ethyl-3-((2S)-2-hydroxy-3-(8-(5-methyl-1-phenyl-1H-pyrazol-4-ylsulfonyl)-1-oxa-8-azaspiro[4.5]decan-3-ylamino)propoxy)benzenesulfonamide; Compound 231: N-ethyl-3-((2S)-2-hydroxy-3-(8-(5,6,7,8-tetrahydronaphthalen-2-ylsulfonyl)-1-oxa-8-azaspiro[4.5]decan-3-ylamino)propoxy)benzenesulfonamide; Compound 232: 3-((2S)-3-(8-(3,5-dimethylisoxazol-4-ylsulfonyl)-1-oxa-8-azaspiro[4.5]decan-3-ylamino)-2-hydroxypropoxy)-N-ethylbenzenesulfonamide; Compound 233: N-ethyl-3-((2S)-2-hydroxy-3-(8-(5-phenylthiophen-2-ylsulfonyl)-1-oxa-8-azaspiro[4.5]decan-3-ylamino)propoxy)benzenesulfonamide; Compound 234: N-ethyl-3-((2S)-2-hydroxy-3-(8-(4-methyl-3,4-dihydro-2H-benzo[b][1,4]oxazin-6-ylsulfonyl)-1-oxa-8-azaspiro[4.5]decan-3-ylamino)propoxy)benzenesulfonamide; Compound 235: 3-((2S)-3-(8-(7-chlorobenzo[c][1,2,5]oxadiazol-4-ylsulfonyl)-1-oxa-8-azaspiro[4.5]decan-3-ylamino)-2-hydroxypropoxy)-N-ethylbenzenesulfonamide; Compound 236: 3-((2S)-2-hydroxy-3-(8-(4-methoxy-2-methylphenylsulfonyl)-1-oxa-8-azaspiro[4.5]decan-3-ylamino)propoxy)-N-methylbenzenesulfonamide; Compound 237: 3-((2S)-3-(8-(5-bromo-2-methylphenylsulfonyl)-1-oxa-8-azaspiro[4.5]decan-3-ylamino)-2-hydroxypropoxy)-N-methylbenzenesulfonamide; Compound 238: 3-((2S)-3-(8-(5-fluoro-2-methoxyphenylsulfonyl)-1-oxa-8-azaspiro[4.5]decan-3-ylamino)-2-hydroxypropoxy)-N-methylbenzenesulfonamide; Compound 239: 3-((2S)-3-(8-(3-chloro-4-cyanophenylsulfonyl)-1-oxa-8-azaspiro[4.5]decan-3-ylamino)-2-hydroxypropoxy)-N-methylbenzenesulfonamide; Compound 240: 3-((2S)-3-(8-(5-chloro-2-methylphenylsulfonyl)-1-oxa-8-azaspiro[4.5]decan-3-ylamino)-2-hydroxypropoxy)-N-methylbenzenesulfonamide; Compound 241: 3-((2S)-3-(8-(2-fluoro-5-methoxyphenylsulfonyl)-1-oxa-8-azaspiro[4.5]decan-3-ylamino)-2-hydroxypropoxy)-N- methylbenzenesulfonamide; Compound 242: 3-((2S)-2-hydroxy-3-(8-(4-methoxy-2,3-dimethylphenylsulfonyl)-1-oxa-8-azaspiro[4.5]decan-3-ylamino)propoxy)-N-methylbenzenesulfonamide; Compound 243: 3-((2S)-2-hydroxy-3-(8-(1-phenyl-1H-pyrazol-4-ylsulfonyl)-1-oxa-8-azaspiro[4.5]decan-3-ylamino)propoxy)-N-methylbenzenesulfonamide; Compound 244: 3-((S)-3-((S)-8-(benzo[c][1,2,5]thiadiazol-4-ylsulfonyl)-1-oxa-8-azaspiro[4.5]decan-3-ylamino)-2-hydroxypropoxy)-N-methylbenzenesulfonamide; Compound 245: 3-((S)-3-((R)-8-(benzo[c][1,2,5]thiadiazol-4-ylsulfonyl)-1-oxa-8-azaspiro[4.5]decan-3-ylamino)-2-hydroxypropoxy)-N-methylbenzenesulfonamide; Compound 246: 3-((2S)-3-(8-(3-chlorophenylsulfonyl)-1-oxa-8-azaspiro[4.5]decan-3-ylamino)-2-hydroxypropoxy)-N,N-dimethylbenzenesulfonamide; Compound 247: 3-((2S)-2-hydroxy-3-(8-(4-methoxy-3-methylphenylsulfonyl)-1-oxa-8-azaspiro[4.5]decan-3-ylamino)propoxy)-N,N-dimethylbenzenesulfonamide; Compound 248: 3-((2S)-3-(8-(2-fluoro-5-methylphenylsulfonyl)-1-oxa-8-azaspiro[4.5]decan-3-ylamino)-2-hydroxypropoxy)-N,N-dimethylbenzenesulfonamide; Compound 249: 3-((2S)-3-(8-(4-bromo-3-methylphenylsulfonyl)-1-oxa-8-azaspiro[4.5]decan-3-ylamino)-2-hydroxypropoxy)-N,N-dimethylbenzenesulfonamide; Compound 250: 3-((2S)-2-hydroxy-3-(8-(3-oxo-3,4-dihydro-2H-benzo[b][1,4]oxazin-6-ylsulfonyl)-1-oxa-8-azaspiro[4.5]decan-3-ylamino)propoxy)-N,N-dimethylbenzenesulfonamide; Compound 251: 3-((2S)-3-(8-(benzo[c][1,2,5]thiadiazol-5-ylsulfonyl)-1-oxa-8-azaspiro[4.5]decan-3-ylamino)-2-hydroxypropoxy)-N,N-dimethylbenzenesulfonamide; Compound 252: 3-((2S)-2-hydroxy-3-(8-(5-methyl-1-phenyl-1H-pyrazol-4-ylsulfonyl)-1-oxa-8-azaspiro[4.5]decan-3-ylamino)propoxy)-N,N-dimethylbenzenesulfonamide; Compound 253: 3-((2S)-2-hydroxy-3-(8-(5,6,7,8-tetrahydronaphthalen-2-ylsulfonyl)-1-oxa-8-azaspiro[4.5]decan-3-ylamino)propoxy)-N,N-dimethylbenzenesulfonamide; Compound 254: 3-((2S)-3-(8-(3,5-dimethylisoxazol-4-ylsulfonyl)-1-oxa-8-azaspiro[4.5]decan-3-ylamino)-2-hydroxypropoxy)-N,N-dimethylbenzenesulfonamide; Compound 255: 3-((2S)-2-hydroxy-3-(8-(5-phenylthiophen-2-ylsulfonyl)-1-oxa-8-azaspiro[4.5]decan-3-ylamino)propoxy)-N,N-dimethylbenzenesulfonamide; Compound 256: 3-((2S)-2-hydroxy-3-(8-(4-methyl-3,4-dihydro-2H-benzo[b][1,4]oxazin-6-ylsulfonyl)-1-oxa-8-azaspiro[4.5]decan-3-ylamino)propoxy)-N,N-dimethylbenzenesulfonamide; Compound 257: 3-((2S)-3-(8-(7-chlorobenzo[c][1,2,5]oxadiazol-4-ylsulfonyl)-1-oxa-8-azaspiro[4.5]decan-3-ylamino)-2-hydroxypropoxy)-N,N-dimethylbenzenesulfonamide; Compound 258: 3-((2S)-2-hydroxy-3-(8-(4-methoxynaphthalen-1-ylsulfonyl)-1-oxa-8-azaspiro[4.5]decan-3-ylamino)propoxy)-N-methylbenzenesulfonamide; Compound 259: 3-((2S)-3-(8-(5-bromo-2-chlorophenylsulfonyl)-1-oxa-8-azaspiro[4.5]decan-3-ylamino)-2-hydroxypropoxy)-N-methylbenzenesulfonamide; Compound 260: 3-((2S)-3-(8-(5-bromo-2,3-dihydrobenzofuran-7-ylsulfonyl)-1-oxa-8-azaspiro[4.5]decan-3-ylamino)-2-hydroxypropoxy)-N-methylbenzenesulfonamide; Compound 261: 3-((2S)-3-(8-(3,5-dimethyl-1-phenyl-1H-pyrazol-4-ylsulfonyl)-1-oxa-8-azaspiro[4.5]decan-3-ylamino)-2-hydroxypropoxy)-N-methylbenzenesulfonamide; Compound 262: 3-((2S)-3-(8-(5-chlorobenzo[c][1,2,5]oxadiazol-4-ylsulfonyl)-1-oxa-8-azaspiro[4.5]decan-3-ylamino)-2-hydroxypropoxy)-N-methylbenzenesulfonamide; Compound 263: 3-((2S)-3-(8-(2-cyano-5-methoxyphenylsulfonyl)-1-oxa-8-azaspiro[4.5]decan-3-ylamino)-2-hydroxypropoxy)-N-methylbenzenesulfonamide; Compound 264: 3-((2S)-3-(8-(6-chloronaphthalen-2-ylsulfonyl)-1-oxa-8-azaspiro[4.5]decan-3-ylamino)-2-hydroxypropoxy)-N-methylbenzenesulfonamide; Compound 265: 3-((2S)-3-(8-(2,3-dimethylphenylsulfonyl)-1-oxa-8-azaspiro[4.5]decan-3-ylamino)-2-hydroxypropoxy)-N-methylbenzenesulfonamide; Compound 266: 3-((S)-2-hydroxy-3-((S)-8-(4-methoxy-3-methylphenylsulfonyl)-1-oxa-8-azaspiro[4.5]decan-3-ylamino)propoxy)-N-methylbenzenesulfonamide; Compound 267: 3-((S)-2-hydroxy-3-((R)-8-(4-methoxy-3-methylphenylsulfonyl)-1-oxa-8-azaspiro[4.5]decan-3-ylamino)propoxy)-N-methylbenzenesulfonamide; Compound 268: 3-((S)-3-((S)-8-(2-fluoro-5-methylphenylsulfonyl)-1-oxa-8-azaspiro[4.5]decan-3-ylamino)-2-hydroxypropoxy)-N-methylbenzenesulfonamide; Compound 269: 3-((S)-3-((R)-8-(2-fluoro-5-methylphenylsulfonyl)-1-oxa-8-azaspiro[4.5]decan-3-ylamino)-2-hydroxypropoxy)-N-methylbenzenesulfonamide; Compound 270: 3-((S)-3-((S)-8-(4-bromo-3-methylphenylsulfonyl)-1-oxa-8-azaspiro[4.5]decan-3-ylamino)-2-hydroxypropoxy)-N-methylbenzenesulfonamide; Compound 271: 3-((S)-3-((R)-8-(4-bromo-3-methylphenylsulfonyl)-1-oxa-8-azaspiro[4.5]decan-3-ylamino)-2-hydroxypropoxy)-N-methylbenzenesulfonamide; Compound 272: 3-((2S)-3-(8-(3-(1-ethyl-1H-pyrazol-4-yl)phenylsulfonyl)-1-oxa-8-azaspiro[4.5]decan-3-ylamino)-2-hydroxypropoxy)-N,N-dimethylbenzenesulfonamide; Compound 273: 3-((2S)-3-(8-(4'-(aminomethyl)biphenyl-3-ylsulfonyl)-1-oxa-8-azaspiro[4.5]decan-3-ylamino)-2-hydroxypropoxy)-N,N-dimethylbenzenesulfonamide; Compound 274: 3'-(3-((S)-3-(3-(N,N-dimethylsulfamoyl)phenoxy)-2-hydroxypropylamino)-1-oxa-8-azaspiro[4.5]decan-8-ylsulfonyl)biphenyl-4-sulfonamide; Compound 275: 3-((2S)-3-(8-(3-(6-aminopyridin-3-yl)phenylsulfonyl)-1-oxa-8-azaspiro[4.5]decan-3-ylamino)-2-hydroxypropoxy)-N,N-dimethylbenzenesulfonamide; Compound 276: 3-((2S)-3-(8-(4'-(cyanomethoxy)biphenyl-3-ylsulfonyl)-1-oxa-8-azaspiro[4.5]decan-3-ylamino)-2-hydroxypropoxy)-N,N-dimethylbenzenesulfonamide; Compound 277: 3-((2S)-3-(8-(4'-(cyanomethyl)biphenyl-3-ylsulfonyl)-1-oxa-8-azaspiro[4.5]decan-3-ylamino)-2-hydroxypropoxy)-N,N-dimethylbenzenesulfonamide; Compound 278: 3-((S)-2-hydroxy-3-((S)-8-(3-oxo-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 279: 3-((S)-2-hydroxy-3-((R)-8-(3-oxo-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 280: 3-((S)-2-hydroxy-3-((S)-8-(5-methyl-1-phenyl-1H-pyrazol-4-ylsulfonyl)-1-oxa-8-azaspiro[4.5]decan-3-ylamino)propoxy)-N-methylbenzenesulfonamide; Compound 281: 3-((S)-2-hydroxy-3-((R)-8-(5-methyl-1-phenyl-1H-pyrazol-4-ylsulfonyl)-1-oxa-8-azaspiro[4.5]decan-3-ylamino)propoxy)-N-methylbenzenesulfonamide; Compound 282: 3-((S)-3-((S)-8-(3-(1-ethyl-1H-pyrazol-4-yl)phenylsulfonyl)-1-oxa-8-azaspiro[4.5]decan-3-ylamino)-2-hydroxypropoxy)-N-methylbenzenesulfonamide; Compound 283: 3-((S)-3-((R)-8-(3-(1-ethyl-1H-pyrazol-4-yl)phenylsulfonyl)-1-oxa-8-azaspiro[4.5]decan-3-ylamino)-2-hydroxypropoxy)-N-methylbenzenesulfonamide; Compound 284: 3-((S)-2-hydroxy-3-((S)-8-(3-(pyridin-3-yl)phenylsulfonyl)-1-oxa-8-azaspiro[4.5]decan-3-ylamino)propoxy)-N-methylbenzenesulfonamide; Compound 285: 3-((S)-2-hydroxy-3-((R)-8-(3-(pyridin-3-yl)phenylsulfonyl)-1-oxa-8-azaspiro[4.5]decan-3-ylamino)propoxy)-N-methylbenzenesulfonamide; Compound 286: 3-((S)-3-((S)-

8-(3-(6-aminopyridin-3-yl)phenylsulfonyl)-1-oxa-8-azaspiro[4.5]decan-3-ylamino)-2-hydroxypropoxy)-N-methylbenzenesulfonamide; Compound 287: 3-((S)-3-((R)-8-(3-(6-aminopyridin-3-yl)phenylsulfonyl)-1-oxa-8-azaspiro[4.5]decan-3-ylamino)-2-hydroxypropoxy)-N-methylbenzenesulfonamide; Compound 288: 3-((S)-3-((S)-8-(4'-(aminomethyl)biphenyl-3-ylsulfonyl)-1-oxa-8-azaspiro[4.5]decan-3-ylamino)-2-hydroxypropoxy)-N-methylbenzenesulfonamide; Compound 289: 3-((S)-3-((R)-8-(4'-(aminomethyl)biphenyl-3-ylsulfonyl)-1-oxa-8-azaspiro[4.5]decan-3-ylamino)-2-hydroxypropoxy)-N-methylbenzenesulfonamide; Compound 290: 3-((2S)-3-(8-(4-(aminomethyl)phenylsulfonyl)-1-oxa-8-azaspiro[4.5]decan-3-ylamino)-2-hydroxypropoxy)-N,N-dimethylbenzenesulfonamide; Compound 291: 3'-((S)-3-((S)-2-hydroxy-3-(3-(N-methylsulfamoyl)phenoxy)propylamino)-1-oxa-8-azaspiro[4.5]decan-8-ylsulfonyl)biphenyl-4-sulfonamide; Compound 292: 3'-((R)-3-((S)-2-hydroxy-3-(3-(N-methylsulfamoyl)phenoxy)propylamino)-1-oxa-8-azaspiro[4.5]decan-8-ylsulfonyl)biphenyl-4-sulfonamide; Compound 293: 3-((S)-3-((S)-8-(4'-(cyanomethyl)biphenyl-3-ylsulfonyl)-1-oxa-8-azaspiro[4.5]decan-3-ylamino)-2-hydroxypropoxy)-N-methylbenzenesulfonamide; Compound 294: 3-((S)-3-((R)-8-(4'-(cyanomethyl)biphenyl-3-ylsulfonyl)-1-oxa-8-azaspiro[4.5]decan-3-ylamino)-2-hydroxypropoxy)-N-methylbenzenesulfonamide; Compound 295: 3-((S)-3-((S)-8-(3-(1H-pyrazol-3-yl)phenylsulfonyl)-1-oxa-8-azaspiro[4.5]decan-3-ylamino)-2-hydroxypropoxy)-N-methylbenzenesulfonamide; Compound 296: 3-((S)-3-((R)-8-(3-(1H-pyrazol-3-yl)phenylsulfonyl)-1-oxa-8-azaspiro[4.5]decan-3-ylamino)-2-hydroxypropoxy)-N-methylbenzenesulfonamide; Compound 297: 3-((S)-3-((S)-8-(4'-(cyanomethoxy)biphenyl-3-ylsulfonyl)-1-oxa-8-azaspiro[4.5]decan-3-ylamino)-2-hydroxypropoxy)-N-methylbenzenesulfonamide; Compound 298: 3-((S)-3-((R)-8-(4'-(cyanomethoxy)biphenyl-3-ylsulfonyl)-1-oxa-8-azaspiro[4.5]decan-3-ylamino)-2-hydroxypropoxy)-N-methylbenzenesulfonamide; Compound 299: 3-((S)-2-hydroxy-3-((S)-8-(4-methyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 300: 3-((S)-2-hydroxy-3-((R)-8-(4-methyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 301: 3-((2S)-2-hydroxy-3-(8-(4'-((methylamino)methyl)biphenyl-3-ylsulfonyl)-1-oxa-8-azaspiro[4.5]decan-3-ylamino)propoxy)-N-methylbenzenesulfonamide; Compound 302: 3-((2S)-3-(8-(4'-((ethylamino)methyl)biphenyl-3-ylsulfonyl)-1-oxa-8-azaspiro[4.5]decan-3-ylamino)-2-hydroxypropoxy)-N-methylbenzenesulfonamide; Compound 303: 3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide; Compound 304: 3-((2S)-2-hydroxy-3-(8-(4'-((2-hydroxyethylamino)methyl)biphenyl-3-ylsulfonyl)-1-oxa-8-azaspiro[4.5]decan-3-ylamino)propoxy)-N-methylbenzenesulfonamide; Compound 305: 3-((2S)-3-(8-(4'-((2-(dimethylamino)ethylamino)methyl)biphenyl-3-ylsulfonyl)-1-oxa-8-azaspiro[4.5]decan-3-ylamino)-2-hydroxypropoxy)-N-methylbenzenesulfonamide; Compound 306: 3-((2S)-2-hydroxy-3-(8-(naphthalen-2-ylsulfonyl)-1-oxa-8-azaspiro[4.5]decan-3-ylamino)propoxy)benzenesulfonamide; Compound 307: 3-((2S)-3-(8-(3-chlorophenylsulfonyl)-1-oxa-8-azaspiro[4.5]decan-3-ylamino)-2-hydroxypropoxy)-N-(3-(dimethylamino)propyl)benzenesulfonamide; Compound 308: N-(3-(dimethylamino)propyl)-3-((2S)-2-hydroxy-3-(8-(4-methoxy-3-methylphenylsulfonyl)-1-oxa-8-azaspiro[4.5]decan-3-ylamino)propoxy)benzenesulfonamide; Compound 309: N-(3-(dimethylamino)propyl)-3-((2S)-3-(8-(2-fluoro-5-methylphenylsulfonyl)-1-oxa-8-azaspiro[4.5]decan-3-ylamino)-2-hydroxypropoxy)benzenesulfonamide; Compound 310: 3-((2S)-3-(8-(4-bromo-3-methylphenylsulfonyl)-1-oxa-8-azaspiro[4.5]decan-3-ylamino)-2-hydroxypropoxy)-N-(3-(dimethylamino)propyl)benzenesulfonamide; Compound 311: N-(3-(dimethylamino)propyl)-3-((2S)-2-hydroxy-3-(8-(3-oxo-3,4-dihydro-2H-benzo[b][1,4]oxazin-6-ylsulfonyl)-1-oxa-8-azaspiro[4.5]decan-3-ylamino)propoxy)benzenesulfonamide; Compound 312: 3-((2S)-3-(8-(benzo[c][1,2,5]thiadiazol-5-ylsulfonyl)-1-oxa-8-azaspiro[4.5]decan-3-ylamino)-2-hydroxypropoxy)-N-(3-(dimethylamino)propyl)benzenesulfonamide; Compound 313: N-(3-(dimethylamino)propyl)-3-((2S)-2-hydroxy-3-(8-(5-methyl-1-phenyl-1H-pyrazol-4-ylsulfonyl)-1-oxa-8-azaspiro[4.5]decan-3-ylamino)propoxy)benzenesulfonamide; Compound 314: N-(3-(dimethylamino)propyl)-3-((2S)-2-hydroxy-3-(8-(5,6,7,8-tetrahydronaphthalen-2-ylsulfonyl)-1-oxa-8-azaspiro[4.5]decan-3-ylamino)propoxy)benzenesulfonamide; Compound 315: N-(3-(dimethylamino)propyl)-3-((2S)-2-hydroxy-3-(8-(5-phenylthiophen-2-ylsulfonyl)-1-oxa-8-azaspiro[4.5]decan-3-ylamino)propoxy)benzenesulfonamide; Compound 316: N-(3-(dimethylamino)propyl)-3-((2S)-2-hydroxy-3-(8-(4-methyl-3,4-dihydro-2H-benzo[b][1,4]oxazin-6-ylsulfonyl)-1-oxa-8-azaspiro[4.5]decan-3-ylamino)propoxy)benzenesulfonamide; Compound 317: N-(3-(dimethylamino)propyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 318: N-(3-((2S)-2-hydroxy-3-(8-(naphthalen-2-ylsulfonyl)-1-oxa-8-azaspiro[4.5]decan-3-ylamino)propoxy)phenylsulfonyl)acetamide; Compound 319: 3-((2S)-2-hydroxy-3-(8-(4'-((isobutylamino)methyl)biphenyl-3-ylsulfonyl)-1-oxa-8-azaspiro[4.5]decan-3-ylamino)propoxy)-N-methylbenzenesulfonamide; Compound 320: 3-((2S)-2-hydroxy-3-(8-(4'-((isopentylamino)methyl)biphenyl-3-ylsulfonyl)-1-oxa-8-azaspiro[4.5]decan-3-ylamino)propoxy)-N-methylbenzenesulfonamide; Compound 321: 3-((2S)-2-hydroxy-3-(8-(4'-((2,2,2-trifluoroethylamino)methyl)biphenyl-3-ylsulfonyl)-1-oxa-8-azaspiro[4.5]decan-3-ylamino)propoxy)-N-methylbenzenesulfonamide; Compound 322: 3-((2S)-2-hydroxy-3-(8-(pyridin-2-ylsulfonyl)-1-oxa-8-azaspiro[4.5]decan-3-ylamino)propoxy)-N-methylbenzenesulfonamide; Compound 323: 3-((2S)-2-hydroxy-3-(8-(quinolin-6-ylsulfonyl)-1-oxa-8-azaspiro[4.5]decan-3-ylamino)propoxy)-N-methylbenzenesulfonamide; Compound 324: 3-((2S)-2-hydroxy-3-(8-(pyridin-3-ylsulfonyl)-1-oxa-8-azaspiro[4.5]decan-3-ylamino)propoxy)-N-methylbenzenesulfonamide; Compound 325: 3-((2S)-3-(8-(1H-indazol-5-ylsulfonyl)-1-oxa-8-azaspiro[4.5]decan-3-ylamino)-2-hydroxypropoxy)-N-methylbenzenesulfonamide; Compound 326: 3-((2S)-3-(8-(benzofuran-2-ylsulfonyl)-1-oxa-8-azaspiro[4.5]decan-3-ylamino)-2-hydroxypropoxy)-N-methylbenzenesulfonamide; Compound 327: 3-((2S)-3-(8-(benzo[d]isoxazol-5-ylsulfonyl)-1-oxa-8-azaspiro[4.5]decan-3-ylamino)-2-hydroxypropoxy)-N-methylbenzenesulfonamide; Compound 328: 3-((2S)-3-(8-(1H-indazol-6-ylsulfonyl)-1-oxa-8-azaspiro[4.5]decan-3-ylamino)-2-hydroxypropoxy)-N-methylbenzenesulfonamide; Compound 329: 3-((2S)-3-(8-(1-ethyl-5-methyl-1H-pyrazol-4-ylsulfonyl)-1-oxa-8- azaspiro[4.5]decan-3-ylamino)-2-hydroxypropoxy)-N-methylbenzenesulfonamide; Compound 330: 3-((2S)-3-(8-(2,3-dihydrobenzofuran-5-ylsulfonyl)-1-oxa-8-azaspiro[4.5]decan-3-ylamino)-2-hydroxypropoxy)-N-methylbenzenesulfonamide; Compound 331: 3-((2S)-3-(8-(benzofuran-5-ylsulfonyl)-1-oxa-8-azaspiro[4.5]decan-3-ylamino)-2-hydroxypropoxy)-N-methylbenzenesulfonamide; Compound 332: 3-((2S)-3-(8-(2,3-dihydrobenzo[b][1,4]dioxin-6-ylsulfonyl)-1-oxa-8-azaspiro[4.5]decan-3-ylamino)-2-hydroxypropoxy)-N-methylbenzenesulfonamide; Compound 333: 3-((2S)-3-(8-(4-ethyl-3,4-dihydro-2H-benzo[b][1,4]oxazin-6-ylsulfonyl)-1-oxa-8-azaspiro[4.5]decan-3-ylamino)-2-hydroxypropoxy)-N-methylbenzenesulfonamide; Compound 334: 3-((2S)-2-hydroxy-3-(8-(4-isopropyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 335: 3-((S)-2-hydroxy-3-((S)-8-(quinolin-3-ylsulfonyl)-1-oxa-8-azaspiro[4.5]decan-3-ylamino)propoxy)-N-methylbenzenesulfonamide; Compound 336: 3-((S)-2-hydroxy-3-((R)-8-(quinolin-3-ylsulfonyl)-1-oxa-8-azaspiro[4.5]decan-3-ylamino)propoxy)-N-methylbenzenesulfonamide; Compound 337: 3-((2S)-3-(8-(5-bromopyridin-3-ylsulfonyl)-1-oxa-8-azaspiro[4.5]decan-3-ylamino)-2-hydroxypropoxy)-N-methylbenzenesulfonamide; Compound 338: 3-((2S)-3-(8-(4'-((cyanomethylamino)methyl)biphenyl-3-ylsulfonyl)-1-oxa-8-azaspiro[4.5]decan-3-ylamino)-2-hydroxypropoxy)-N-methylbenzenesulfonamide; Compound 339: 3-((2S)-3-(8-(4'-((2,2-difluoroethylamino)methyl)biphenyl-3-ylsulfonyl)-1-oxa-8-azaspiro[4.5]decan-3-ylamino)-2-hydroxypropoxy)-N-methylbenzenesulfonamide; Compound 340: 3-((2S)-2-hydroxy-3-(8-(4'-((2-methoxyethylamino)methyl)biphenyl-3-ylsulfonyl)-1-oxa-8-azaspiro[4.5]decan-3-ylamino)propoxy)-N-methylbenzenesulfonamide; Compound 341: 3-((2S)-3-(8-(5-(4-(aminomethyl)phenyl)pyridin-3-ylsulfonyl)-1-oxa-8-azaspiro[4.5]decan-3-ylamino)-2-hydroxypropoxy)-N-methylbenzenesulfonamide; Compound 342: 3-((2S)-2-hydroxy-3-(8-(5-(1-methyl-1H-pyrazol-4-yl)pyridin-3-ylsulfonyl)-1-oxa-8-azaspiro[4.5]decan-3-ylamino)propoxy)-N-methylbenzenesulfonamide; Compound 343: 3-((S)-2-hydroxy-3-((S)-8-(quinolin-6-ylsulfonyl)-1-oxa-8-azaspiro[4.5]decan-3-ylamino)propoxy)-N-methylbenzenesulfonamide; Compound 344: 3-((S)-2-hydroxy-3-((R)-8-(quinolin-6-ylsulfonyl)-1-oxa-8-azaspiro[4.5]decan-3-ylamino)propoxy)-N-methylbenzenesulfonamide; Compound 345: (2S)-3-hydroxy-2-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methylamino)propanamide; Compound 346: 3-((2S)-2-hydroxy-3-(8-(4'-(thiazolidin-3-ylmethyl)biphenyl-3-ylsulfonyl)-1-oxa-8-azaspiro[4.5]decan-3-ylamino)propoxy)-N-methylbenzenesulfonamide; Compound 347: 3-((2S)-3-(8-(4'-((2-fluoroethylamino)methyl)biphenyl-3-ylsulfonyl)-1-oxa-8-azaspiro[4.5]decan-3-ylamino)-2-hydroxypropoxy)-N-methylbenzenesulfonamide; Compound 348: N-(2-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methylamino)ethyl)acetamide; Compound 349: 3-((2S)-2-hydroxy-3-(8-(4-isobutyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 350: 3-((S)-3-((S)-8-(4-ethyl-3,4-dihydro-2H-benzo[b][1,4]oxazin-6-ylsulfonyl)-1-oxa-8-azaspiro[4.5]decan-3-ylamino)-2-hydroxypropoxy)-N-methylbenzenesulfonamide; Compound 351: 3-((S)-3-((R)-8-(4-ethyl-3,4-dihydro-2H-benzo[b][1,4]oxazin-6-ylsulfonyl)-1-oxa-8-azaspiro[4.5]decan-3-ylamino)-2-hydroxypropoxy)-N-methylbenzenesulfonamide; Compound 352: 3-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methylamino)-3-oxopropanoic acid; Compound 353: 2-amino-N-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)acetamide; Compound 354: $N^1$-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide; Compound 355: 3-((2S)-3-(8-(3,4-dihydro-2H-benzo[b][1,4]oxazin-6-ylsulfonyl)-1-oxa-8-azaspiro[4.5]decan-3-ylamino)-2-hydroxypropoxy)-N-methylbenzenesulfonamide; Compound 356: N-(2-fluoroethyl)-3-((2S)-2-hydroxy-3-(8-(naphthalen-2-ylsulfonyl)-1-oxa-8-azaspiro[4.5]decan-3-ylamino)propoxy)benzenesulfonamide; Compound 357: 3-((2S)-3-(8-(4'-(aminomethyl)-4-methoxybiphenyl-3-ylsulfonyl)-1-oxa-8-azaspiro[4.5]decan-3-ylamino)-2-hydroxypropoxy)-N-methylbenzenesulfonamide; Compound 358: 3-((2S)-3-(8-(5-(4-(aminomethyl)phenyl)-2,3-dihydrobenzofuran-7-ylsulfonyl)-1-oxa-8-azaspiro[4.5]decan-3-ylamino)-2-hydroxypropoxy)-N-methylbenzenesulfonamide; Compound 359: 3-((S)-2-hydroxy-3-((S)-8-(4'-((isopropylamino)methyl)biphenyl-3-ylsulfonyl)-1-oxa-8-azaspiro[4.5]decan-3-ylamino)propoxy)-N-methylbenzenesulfonamide; Compound 360: 3-((S)-2-hydroxy-3-((S)-8-(4'-((isobutylamino)methyl)biphenyl-3-ylsulfonyl)-1-oxa-8-azaspiro[4.5]decan-3-ylamino)propoxy)-N-methylbenzenesulfonamide; Compound 361: 3-((S)-2-hydroxy-3-((S)-8-(4'-((isopentylamino)methyl)biphenyl-3-ylsulfonyl)-1-oxa-8-azaspiro[4.5]decan-3-ylamino)propoxy)-N-methylbenzenesulfonamide; Compound 362: 3-((S)-2-hydroxy-3-((R)-8-(4'-((isopropylamino)methyl)biphenyl-3-ylsulfonyl)-1-oxa-8-azaspiro[4.5]decan-3-ylamino)propoxy)-N-methylbenzenesulfonamide; Compound 363: 3-((S)-2-hydroxy-3-((R)-8-(4'-((isobutylamino)methyl)biphenyl-3-ylsulfonyl)-1-oxa-8-azaspiro[4.5]decan-3-ylamino)propoxy)-N-methylbenzenesulfonamide; Compound 364: 3-((S)-2-hydroxy-3-((R)-8-(4'-((isopentylamino)methyl)biphenyl-3-ylsulfonyl)-1-oxa-8-azaspiro[4.5]decan-3-ylamino)propoxy)-N-methylbenzenesulfonamide; Compound 365: 3-((2S)-3-(8-(4'-(aminomethyl)-4-methylbiphenyl-3-ylsulfonyl)-1-oxa-8-azaspiro[4.5]decan-3-ylamino)-2-hydroxypropoxy)-N-methylbenzenesulfonamide; Compound 366: 3-((2S)-3-(8-(4'-(aminomethyl)-6-methoxybiphenyl-3-ylsulfonyl)-1-oxa-8-azaspiro[4.5]decan-3-ylamino)-2-hydroxypropoxy)-N-methylbenzenesulfonamide; Compound 367: 3-((2S)-3-(8-(4'-(aminomethyl)-5-(trifluoromethyl)biphenyl-3-ylsulfonyl)-1-oxa-8-azaspiro[4.5]decan-3-ylamino)-2-hydroxypropoxy)-N-methylbenzenesulfonamide; Compound 368: 3'-(3-((S)-2-hydroxy-3-(3-(N-methylsulfamoyl)phenoxy)propylamino)-1-oxa-8-azaspiro[4.5]decan-8-ylsulfonyl)biphenyl-4-carboxamide; Compound 369: 3-((2S)-3-(8-(3-(5-(aminomethyl)thiophen-2-yl)phenylsulfonyl)-1-oxa-8-azaspiro[4.5]decan-3-ylamino)-2-hydroxypropoxy)-N-methylbenzenesulfonamide; Compound 370: 3-((2S)-3-(8-(3-(5-cyanopyridin-3-yl)phenylsulfonyl)-1-oxa-8-azaspiro[4.5]decan-3-ylamino)-2-hydroxypropoxy)-N-methylbenzenesulfonamide; Compound 371: 3-((2S)-2-hydroxy-3-(8-(3-(6-(2-morpholinoethylamino)pyridin-3-yl)phenylsulfonyl)-1-oxa-8-azaspiro[4.5]decan-3-ylamino)propoxy)-N-methylbenzenesulfonamide; Compound 372: 3-((2S)-3-(8-(3-(6-(3-(dimethylamino)propoxy)

pyridin-3-yl)phenylsulfonyl)-1-oxa-8-azaspiro[4.5]decan-3-ylamino)-2-hydroxypropoxy)-N-methylbenzenesulfonamide; Compound 373: 3-((2S)-3-(8-(4'-(aminomethyl)-5-methylbiphenyl-3-ylsulfonyl)-1-oxa-8-azaspiro[4.5]decan-3-ylamino)-2-hydroxypropoxy)-N-methylbenzenesulfonamide; Compound 374: 3-((S)-3-((S)-8-(5-(4-(aminomethyl)phenyl)pyridin-3-ylsulfonyl)-1-oxa-8-azaspiro[4.5]decan-3-ylamino)-2-hydroxypropoxy)-N-methylbenzenesulfonamide; Compound 375: 3-((S 3-((R)-8-(5-(4-(aminomethyl)phenyl)pyridin-3-ylsulfonyl)-1-oxa-8-azaspiro[4.5]decan-3-ylamino)-2-hydroxypropoxy)-N-methylbenzenesulfonamide; Compound 376: 3-((2S)-3-(8-(4'-(aminomethyl)-6-methylbiphenyl-3-ylsulfonyl)-1-oxa-8-azaspiro[4.5]decan-3-ylamino)-2-hydroxypropoxy)-N-methylbenzenesulfonamide; Compound 377: 3-((2S)-3-(8-(4'-(aminomethyl)-4-chlorobiphenyl-3-ylsulfonyl)-1-oxa-8-azaspiro[4.5]decan-3-ylamino)-2-hydroxypropoxy)-N-methylbenzenesulfonamide; Compound 378: 3-((2S)-2-hydroxy-3-(8-(2-(pyridin-4-yl)ethylsulfonyl)-1-oxa-8-azaspiro[4.5]decan-3-ylamino)propoxy)-N-methylbenzenesulfonamide; Compound 379: (Z)—N'-hydroxy-3'-(3-((S)-2-hydroxy-3-(3-(N-methylsulfamoyl)phenoxy)propylamino)-1-oxa-8-azaspiro[4.5]decan-8-ylsulfonyl)biphenyl-4-carboximidamide; Compound 380: 3-((2S)-2-hydroxy-3-(8-(4'-(5-methyl-1,2,4-oxadiazol-3-yl)biphenyl-3-ylsulfonyl)-1-oxa-8-azaspiro[4.5]decan-3-ylamino)propoxy)-N-methylbenzenesulfonamide; Compound 381: 3-((2S)-3-(8-(4'-(aminomethyl)biphenyl-2-ylsulfonyl)-1-oxa-8-azaspiro[4.5]decan-3-ylamino)-2-hydroxypropoxy)-N-methylbenzenesulfonamide; Compound 382: 3-((2S)-3-(8-(4'-(aminomethyl)biphenyl-4-ylsulfonyl)-1-oxa-8-azaspiro[4.5]decan-3-ylamino)-2-hydroxypropoxy)-N-methylbenzenesulfonamide; Compound 383: 3'-(3-((S)-2-hydroxy-3-(3-(N-methylsulfamoyl)phenoxy)propylamino)-1-oxa-8-azaspiro[4.5]decan-8-ylsulfonyl)biphenyl-4-carboximidamide; Compound 384: 3-((S)-3-((S)-8-(4'-(aminomethyl)-4-methoxybiphenyl-3-ylsulfonyl)-1-oxa-8-azaspiro[4.5]decan-3-ylamino)-2-hydroxypropoxy)-N-methylbenzenesulfonamide; Compound 385: 3-((S)-3-((R)-8-(4'-(aminomethyl)-4-methoxybiphenyl-3-ylsulfonyl)-1-oxa-8-azaspiro[4.5]decan-3-ylamino)-2-hydroxypropoxy)-N-methylbenzenesulfonamide; Compound 386: 3-((2S)-2-hydroxy-3-(8-(5-methoxypyridin-3-ylsulfonyl)-1-oxa-8-azaspiro[4.5]decan-3-ylamino)propoxy)-N-methylbenzenesulfonamide; Compound 387: 3-((2S)-3-(8-(3-(6-(aminomethyl)pyridin-3-yl)phenylsulfonyl)-1-oxa-8-azaspiro[4.5]decan-3-ylamino)-2-hydroxypropoxy)-N-methylbenzenesulfonamide; Compound 388: 3-((2S)-3-(8-(6'-(aminomethyl)-3,3'-bipyridin-5-ylsulfonyl)-1-oxa-8-azaspiro[4.5]decan-3-ylamino)-2-hydroxypropoxy)-N-methylbenzenesulfonamide; Compound 389:3-((2S)-3-(8-(3-(aminomethyl)phenylsulfonyl)-1-oxa-8-azaspiro[4.5]decan-3-ylamino)-2-hydroxypropoxy)-N-methylbenzenesulfonamide; Compound 390: 3-((2S)-2-hydroxy-3-(8-(3-(hydroxymethyl)phenylsulfonyl)-1-oxa-8-azaspiro[4.5]decan-3-ylamino)propoxy)-N-methylbenzenesulfonamide; Compound 391: 3-((2S)-3-(8-(4-(aminomethyl)phenylsulfonyl)-1-oxa-8-azaspiro[4.5]decan-3-ylamino)-2-hydroxypropoxy)-N-methylbenzenesulfonamide; Compound 392: 3-((2S)-2-hydroxy-3-(8-(4-(hydroxymethyl)phenylsulfonyl)-1-oxa-8-azaspiro[4.5]decan-3-ylamino)propoxy)-N-methylbenzenesulfonamide; Compound 393: N-(2-fluoroethyl)-3-((S)-2-hydroxy-3-((R)-8-(quinolin-6-ylsulfonyl)-1-oxa-8-azaspiro[4.5]decan-3-ylamino)propoxy)benzenesulfonamide; Compound 394: N-(2-fluoroethyl)-3-((S)-2-hydroxy-3-((R)-8-(quinolin-3-ylsulfonyl)-1-oxa-8-azaspiro[4.5]decan-3-ylamino)propoxy)benzenesulfonamide; Compound 395: 3-((2S)-2-hydroxy-3-(8-(6-hydroxypyridin-3-ylsulfonyl)-1-oxa-8-azaspiro[4.5]decan-3-ylamino)propoxy)-N-methylbenzenesulfonamide; Compound 396: 3-((2S)-2-hydroxy-3-(8-(6-methoxypyridin-3-ylsulfonyl)-1-oxa-8-azaspiro[4.5]decan-3-ylamino)propoxy)-N-methylbenzenesulfonamide; Compound 397: 3-((2S)-2-hydroxy-3-(8-(5-methoxy-2-methylpyridin-3-ylsulfonyl)-1-oxa-8-azaspiro[4.5]decan-3-ylamino)propoxy)-N-methylbenzenesulfonamide; Compound 398: 3-((2S)-2-hydroxy-3-(8-(2-methoxyphenylsulfonyl)-1-oxa-8-azaspiro[4.5]decan-3-ylamino)propoxy)-N-methylbenzenesulfonamide; Compound 399: 3-((2S)-2-hydroxy-3-(8-(1-methyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 400: 3-((2S)-3-(8-(6-chloro-1-methyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 401: 3-((2S)-3-(8-(6-ethoxy-1-methyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 402: 3-((2S)-2-hydroxy-3-(8-(4-(pyridin-2-yl)phenylsulfonyl)-1-oxa-8-azaspiro[4.5]decan-3-ylamino)propoxy)-N-methylbenzenesulfonamide; Compound 403: 3-((2S)-3-(8-(4'-(aminomethyl)-3-(trifluoromethoxy)biphenyl-4-ylsulfonyl)-1-oxa-8-azaspiro[4.5]decan-3-ylamino)-2-hydroxypropoxy)-N-methylbenzenesulfonamide; Compound 404: 3-((2S)-3-(8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide; Compound 405: 3-((S)-3-((R)-8-(4'-((dimethylamino)methyl)biphenyl-4-ylsulfonyl)-1-oxa-8-azaspiro[4.5]decan-3-ylamino)-2-hydroxypropoxy)-N-methylbenzenesulfonamide; Compound 406: 3-((2S)-2-hydroxy-3-(8-(6-morpholinopyridin-3-ylsulfonyl)-1-oxa-8-azaspiro[4.5]decan-3-ylamino)propoxy)-N-methylbenzenesulfonamide; Compound 407: 3-((2S)-2-hydroxy-3-(8-(4-(pyridin-3-yl)phenylsulfonyl)-1-oxa-8-azaspiro[4.5]decan-3-ylamino)propoxy)-N-methylbenzenesulfonamide; Compound 408: 3-((2S)-2-hydroxy-3-(8-(4-(pyridin-4-yl)phenylsulfonyl)-1-oxa-8-azaspiro[4.5]decan-3-ylamino)propoxy)-N-methylbenzenesulfonamide; Compound 409: 3-((2S)-3-(8-(3-(2H-tetrazol-5-yl)phenylsulfonyl)-1-oxa-8-azaspiro[4.5]decan-3-ylamino)-2-hydroxypropoxy)-N-methylbenzenesulfonamide; Compound 410: 3-((2S)-3-(8-(4-(2H-tetrazol-5-yl)phenylsulfonyl)-1-oxa-8-azaspiro[4.5]decan-3-ylamino)-2-hydroxypropoxy)-N-methylbenzenesulfonamide; Compound 411: 3-((2S)-3-(8-(4'-(aminomethyl)-4-(trifluoromethoxy)biphenyl-3-ylsulfonyl)-1-oxa-8-azaspiro[4.5]decan-3-ylamino)-2-hydroxypropoxy)-N-methylbenzenesulfonamide; Compound 412: 3-((2S)-3-(8-(5-bromo-2-(2-(pyrrolidin-1-yl)ethoxy)phenylsulfonyl)-1-oxa-8-azaspiro[4.5]decan-3-ylamino)-2-hydroxypropoxy)-N-methylbenzenesulfonamide; Compound 413: 3-((S)-2-hydroxy-3-((S)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 414: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 415: 3-((S)-3-((S)-8-(4'-(aminomethyl)-4-(trifluoromethoxy)biphenyl-3-ylsulfonyl)-1-oxa-8-azaspiro[4.5]decan-3-ylamino)-2-hydroxypropoxy)-N-methylbenzenesulfonamide; Compound 416: 3-((S)-3-((R)-8-(4'-(aminomethyl)-4-(trifluoromethoxy)biphenyl-3-ylsulfonyl)-1-oxa-8-azaspiro[4.5]decan-3-ylamino)-2-hydroxypropoxy)-N-methylbenzenesulfonamide; Compound 417: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-(2-hydroxyethyl)benzenesulfonamide; Compound 418: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N—((R)-1-hydroxypropan-2-yl)benzenesulfonamide; Compound 419: 3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide; Compound 420: 3-((S)-3-((R)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide; Compound 421: 3-((2S)-2-hydroxy-3-(8-(6-(piperidin-1-yl)pyridin-3-ylsulfonyl)-1-oxa-8-azaspiro[4.5]decan-3-ylamino)propoxy)-N-methylbenzenesulfonamide; Compound 422: 3-((2S)-3-(8-(6-(dimethylamino)pyridin-3-ylsulfonyl)-1-oxa-8-azaspiro[4.5]decan-3-ylamino)-2-hydroxypropoxy)-N-methylbenzenesulfonamide; Compound 423: 3-((2S)-3-(8-(1-ethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 424: 3-((S)-3-((S)-8-(4'-(aminomethyl)biphenyl-3-ylsulfonyl)-1-oxa-8-azaspiro[4.5]decan-3-ylamino)-2-hydroxypropoxy)-N—((R)-1-hydroxypropan-2-yl)benzenesulfonamide; Compound 425: 3-((2S)-2-hydroxy-3-(8-(2-hydroxypyrimidin-5-ylsulfonyl)-1-oxa-8-azaspiro[4.5]decan-3-ylamino)propoxy)-N-methylbenzenesulfonamide; Compound 426: 3-((2S)-2-hydroxy-3-(8-(6-(2-methoxyethylamino)pyridin-3-ylsulfonyl)-1-oxa-8-azaspiro[4.5]decan-3-ylamino)propoxy)-N-methylbenzenesulfonamide; Compound 427: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1S,2S)-2-hydroxycyclopentyl)benzenesulfonamide; Compound 428: 3-((2S)-2-hydroxy-3-(8-(6-(2-hydroxyethylamino)pyridin-3-ylsulfonyl)-1-oxa-8-azaspiro[4.5]decan-3-ylamino)propoxy)-N-methylbenzenesulfonamide; Compound 429: 3-((2S)-3-(8-(6-(2-aminoethylamino)pyridin-3-ylsulfonyl)-1-oxa-8-azaspiro[4.5]decan-3-ylamino)-2-hydroxypropoxy)-N-methylbenzenesulfonamide; Compound 430: 3-((2S)-2-hydroxy-3-(8-(6-(piperazin-1-yl)pyridin-3-ylsulfonyl)-1-oxa-8-azaspiro[4.5]decan-3-ylamino)propoxy)-N-methylbenzenesulfonamide; Compound 431: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1S,2S)-2-hydroxycyclohexyl)benzenesulfonamide; Compound 432: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N—((S)-1-hydroxypropan-2-yl)benzenesulfonamide; Compound 433: 3-((2S)-3-(8-(4-chloropyridin-2-yl)-1-oxa-8-azaspiro[4.5]decan-3-ylamino)-2-hydroxypropoxy)-N-methylbenzenesulfonamide; Compound 434: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N—(S)-2-hydroxypropyl)benzenesulfonamide; Compound 435: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1R,2S)-2-hydroxycyclohexyl)benzenesulfonamide; Compound 436: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N—((R)-2-hydroxypropyl)benzenesulfonamide; Compound 437: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1R,2S)-2-hydroxycyclopentyl)benzenesulfonamide; Compound 438: 3-((S)-3-((S)-8-(4-ethoxy-4'-((isopropylamino)methyl)biphenyl-3-ylsulfonyl)-1-oxa-8-azaspiro[4.5]decan-3-ylamino)-2-hydroxypropoxy)-N-methylbenzenesulfonamide; Compound 439: 3-((S)-3-((R)-8-(4-ethoxy-4'-((isopropylamino)methyl)biphenyl-3-ylsulfonyl)-1-oxa-8-azaspiro[4.5]decan-3-ylamino)-2-hydroxypropoxy)-N-methylbenzenesulfonamide; Compound 440: 3-((S)-2-hydroxy-3-((R)-8-(4'-((isopropylamino)methyl)biphenyl-3-ylsulfonyl)-1-oxa-8-azaspiro[4.5]decan-3-ylamino)propoxy)benzenesulfonamide; Compound 441: 3-((2S)-3-(8-(2-(dimethylamino)pyridin-3-ylsulfonyl)-1-oxa-8-azaspiro[4.5]decan-3-ylamino)-2-hydroxypropoxy)-N-methylbenzenesulfonamide; Compound 442: 3-((2S)-2-hydroxy-3-(8-(2-morpholinopyridin-3-ylsulfonyl)-1-oxa-8-azaspiro[4.5]decan-3-ylamino)propoxy)-N-methylbenzenesulfonamide; Compound 443: 3-((S)-2-hydroxy-3-((R)-8-(2-oxo-2,3-dihydro-1H-pyrido[2,3-b][1,4]oxazin-6-ylsulfonyl)-1-oxa-8-azaspiro[4.5]decan-3-ylamino)propoxy)-N-methylbenzenesulfonamide; Compound 444: 3-((S)-3-((R)-8-(2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 445: 3-((2S)-3-(8-(6-ethoxypyridin-3-ylsulfonyl)-1-oxa-8-azaspiro[4.5]decan-3-ylamino)-2-hydroxypropoxy)-N-methylbenzenesulfonamide; Compound 446: 3-((S)-3-((S)-8-(4'-(1-aminocyclopropyl)biphenyl-3-ylsulfonyl)-1-oxa-8-azaspiro[4.5]decan-3-ylamino)-2-hydroxypropoxy)-N-methylbenzenesulfonamide; Compound 447: 3-((S)-3-((S)-8-(4'-(aminomethyl)-2-methylbiphenyl-3-ylsulfonyl)-1-oxa-8-azaspiro[4.5]decan-3-ylamino)-2-hydroxypropoxy)-N-methylbenzenesulfonamide; Compound 448: 3-((S)-3-((S)-8-(4'-(aminomethyl)-2-methoxybiphenyl-3-ylsulfonyl)-1-oxa-8-azaspiro[4.5]decan-3-ylamino)-2-hydroxypropoxy)-N-methylbenzenesulfonamide; Compound 449: 3-((S)-3-((S)-8-(4'-(aminomethyl)-5-methoxybiphenyl-3-ylsulfonyl)-1-oxa-8-azaspiro[4.5]decan-3-ylamino)-2-hydroxypropoxy)-N-methylbenzenesulfonamide; Compound 450: 3-((S)-3-((S)-8-(6-ethoxy-1-methyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 451: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-methoxybenzenesulfonamide; Compound 452: 3-((S)-2-hydroxy-3-((R)-8-(1-methyl-6-(methylamino)-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 453: 3-((S)-3-((R)-8-(6-(dimethylamino)-1-methyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 454: 3-((S)-2-hydroxy-3-((R)-8-(6-hydroxy-1-methyl-2,3-dihydro-1H-pyrido[2,3-b][1,4]oxazin-7-ylsulfonyl)-1-oxa-8-azaspiro[4.5]decan-3-ylamino)propoxy)-N- methylbenzenesulfonamide; Compound 455: 3-((S)-3-((R)-8-(6-amino-1-methyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 456: N-ethyl-3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)benzenesulfonamide; Compound 457: N-(2-fluoroethyl)-3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)benzenesulfonamide; Compound 458: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)benzenesulfonamide; Compound 459: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-(2-methoxyethyl)benzenesulfonamide; Compound 460: N-(cyanomethyl)-3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)benzenesulfonamide; Compound 461: N-(2,2-difluoroethyl)-3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)benzenesulfonamide; Compound 462: 3-((S)-3-((R)-8-(1-(2-(benzyloxy)ethyl)-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 463: 3-((S)-3-((S)-8-(4'-(1-aminocyclopropyl)-6-methoxybiphenyl-3-ylsulfonyl)-1-oxa-8-azaspiro[4.5]decan-3-ylamino)-2-hydroxypropoxy)-N-methylbenzenesulfonamide; Compound 464: 3-((S)-3-((R)-8-(4'-(1-aminocyclopropyl)-6-methoxybiphenyl-3-ylsulfonyl)-1-oxa-8-azaspiro[4.5]decan-3-ylamino)-2-hydroxypropoxy)-N-methylbenzenesulfonamide; Compound 465: 3-((S)-2-hydroxy-3-((R)-8-(1-(2-hydroxyethyl)-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 466: 3-((S)-3-((R)-8-(1,6-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 467: 3-((S)-3-((R)-8-(1,8-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 468: 3-((S)-3-((R)-8-((R)-1,3-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 469: 3-((S)-2-hydroxy-3-((R)-8-(1-isopropyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 470: 3-((S)-2-hydroxy-3-((R)-8-(1-propyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 471: 3-((S)-2-hydroxy-3-((R)-8-(1-(2-methoxyethyl)-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 472: 3-((S)-3-((R)-8-((S)-1,3-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 473: 3-((S)-2-hydroxy-3-((R)-8-(1,3,3-trimethyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 474: 3-((S)-2-hydroxy-3-((R)-8-(1'-methyl-1',2'-dihydrospiro[cyclopropane-1,3'-pyrido[2,3-b][1,4]oxazine]-7'-ylsulfonyl)-1-oxa-8-azaspiro[4.5]decan-3-ylamino)propoxy)-N-methylbenzenesulfonamide; Compound 475: 3-((S)-2-hydroxy-3-((R)-8-(3-methyl-3H-imidazo[4,5-b]pyridin-6-ylsulfonyl)-1-oxa-8-azaspiro[4.5]decan-3-ylamino)propoxy)-N-methylbenzenesulfonamide; Compound 476: 3-((S)-2-hydroxy-3-((R)-8-(6-methoxy-1-methyl-2,3-dihydro-1H-pyrido[2,3-b][1,4]oxazin-7-ylsulfonyl)-1-oxa-8-azaspiro[4.5]decan-3-ylamino)propoxy)-N-methylbenzenesulfonamide; Compound 477: 3-((S)-2-hydroxy-3-((R)-8-(2-oxo-2,3-dihydro-1H-imidazo[4,5-b]pyridin-6-ylsulfonyl)-1-oxa-8-azaspiro[4.5]decan-3-ylamino)propoxy)-N-methylbenzenesulfonamide; Compound 478: 3-((S)-2-hydroxy-3-((R)-8-(5-oxo-6,7-dihydro-5H-pyrrolo[3,4-b]pyridin-3-ylsulfonyl)-1-oxa-8-azaspiro[4.5]decan-3-ylamino)propoxy)-N-methylbenzenesulfonamide; Compound 479: 3-((S)-2-hydroxy-3-((R)-8-(5,6,7,8-tetrahydroquinolin-3-ylsulfonyl)-1-oxa-8-azaspiro[4.5]decan-3-ylamino)propoxy)-N-methylbenzenesulfonamide; Compound 480: 3-((S)-3-((R)-8-(2,3-dihydro-[1,4]dioxino[2,3-b]pyridin-7-ylsulfonyl)-1-oxa-8-azaspiro[4.5]decan-3-ylamino)-2-hydroxypropoxy)-N-methylbenzenesulfonamide; Compound 481: 3-((S)-2-hydroxy-3-((R)-8-(4-methyl-3,4-dihydro-2H-pyrido[3,2-b][1,4]oxazin-7-ylsulfonyl)-1-oxa-8-azaspiro[4.5]decan-3-ylamino)propoxy)-N-methylbenzenesulfonamide; Compound 482: 3-((S)-3-((R)-8-(6,7-dihydro-5H-pyrrolo[3,4-b]pyridin-3-ylsulfonyl)-1-oxa-8-azaspiro[4.5]decan-3-ylamino)-2-hydroxypropoxy)-N-methylbenzenesulfonamide; Compound 483: 3-((S)-3-((R)-8-(3,4-dihydro-2H-pyrano[2,3-b]pyridin-6-ylsulfonyl)-1-oxa-8-azaspiro[4.5]decan-3-ylamino)-2-hydroxypropoxy)-N-methylbenzenesulfonamide; Compound 484: 3-((S)-2-hydroxy-3-((R)-8-(5,6,7,8-tetrahydro-1,6-naphthyridin-3-ylsulfonyl)-1-oxa-8-azaspiro[4.5]decan-3-ylamino)propoxy)-N-methylbenzenesulfonamide; Compound 485: 3-((S)-3-((R)-8-(1,5-naphthyridin-3-ylsulfonyl)-1-oxa-8-azaspiro[4.5]decan-3-ylamino)-2-hydroxypropoxy)-N-methylbenzenesulfonamide; Compound 486: 3-((S)-2-hydroxy-3-((R)-8-(2-methyl-1H-imidazo[4,5-b]pyridin-6-ylsulfonyl)-1-oxa-8-azaspiro[4.5]decan-3-ylamino)propoxy)-N-methylbenzenesulfonamide; Compound 487: 3-((S)-2-hydroxy-3-((R)-8-(1-methyl-1,2,3,4-tetrahydropyrido[2,3-b][1,4]oxazepin-8-ylsulfonyl)-1-oxa-8-azaspiro[4.5]decan-3-ylamino)propoxy)-N-methylbenzenesulfonamide; Compound 488: 3-((S)-3-((R)-8-(7,8-dihydro-5H-pyrano[4,3-b]pyridin-3-ylsulfonyl)-1-oxa-8-azaspiro[4.5]decan-3-ylamino)-2-hydroxypropoxy)-N-methylbenzenesulfonamide; Compound 489: 3-((S)-3-((R)-8-(7-amino-1,8-naphthyridin-3-ylsulfonyl)-1-oxa-8-azaspiro[4.5]decan-3-ylamino)-2-hydroxypropoxy)-N-methylbenzenesulfonamide; Compound 490: 3-((S)-3-((R)-8-(1H-pyrazolo[3,4-b]pyridin-5-ylsulfonyl)-1-oxa-8-azaspiro[4.5]decan-3-ylamino)-2-hydroxypropoxy)-N-methylbenzenesulfonamide; Compound 491: 3-((S)-3-((R)-8-(6,7-dihydro-5H-cyclopenta[b]pyridin-3-ylsulfonyl)-1-oxa-8-azaspiro[4.5]decan-3-ylamino)-2-hydroxypropoxy)-N-methylbenzenesulfonamide; Compound 492: 3-((S)-3-((R)-8-(1-ethyl-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 493: 3-((S)-3-((R)-8-(3-cyano-H-pyrrolo[2,3-b]pyridin-5-ylsulfonyl)-1-oxa-8-azaspiro[4.5]decan-3-ylamino)-2-hydroxypropoxy)-N-methylbenzenesulfonamide; Compound 494: 3-((S)-2-hydroxy-3-((R)-8-(1-methyl-4-oxo-1,4-dihydroquinolin-3- ylsulfonyl)-1-oxa-8-azaspiro[4.5]decan-3-ylamino)propoxy)-N-methylbenzenesulfonamide; Compound 495: 3-((S)-3-((R)-8-(1H-imidazo[4,5-b]pyridin-6-ylsulfonyl)-1-oxa-8-azaspiro[4.5]decan-3-ylamino)-2-hydroxypropoxy)-N-methylbenzenesulfonamide; Compound 496: 3-((R)-3-((S)-2-hydroxy-3-(3-(N-methylsulfamoyl)phenoxy)propylamino)-1-oxa-8-azaspiro[4.5]decan-8-ylsulfonyl) pyridine 1-oxide; Compound 497: 3-((S)-2-hydroxy-3-((R)-8-(3-methyl-1H-pyrazolo[3,4-b]pyridin-5-ylsulfonyl)-1-oxa-8-azaspiro[4.5]decan-3-ylamino)propoxy)-N-methylbenzenesulfonamide; Compound 498: 3-((S)-3-((R)-8-(2,3-dioxoindolin-5-ylsulfonyl)-1-oxa-8-azaspiro[4.5]decan-3-ylamino)-2-hydroxypropoxy)-N-methylbenzenesulfonamide; Compound 499: 3-((S)-2-hydroxy-3-((R)-8-(2-oxo-2,3-dihydro-1H-benzo[d]imidazol-5-ylsulfonyl)-1-oxa-8-azaspiro[4.5]decan-3-ylamino)propoxy)-N-methylbenzenesulfonamide; Compound 500: 3-((S)-3-((R)-8-(3,4-dihydro-2H-pyrido[3,2-b][1,4]oxazin-7-ylsulfonyl)-1-oxa-8-azaspiro[4.5]decan-3-ylamino)-2-hydroxypropoxy)-N-methylbenzenesulfonamide; Compound 501: 3-((S)-2-hydroxy-3-((R)-8-(2-methyl-1H-benzo[d]imidazol-5-ylsulfonyl)-1-oxa-8-azaspiro[4.5]decan-3-ylamino)propoxy)-N-methylbenzenesulfonamide; Compound 502: 3-((S)-3-((R)-8-(1H-pyrazolo[4,3-b]pyridin-6-ylsulfonyl)-1-oxa-8-azaspiro[4.5]decan-3-ylamino)-2-hydroxypropoxy)-N-methylbenzenesulfonamide; Compound 503: 3-((S)-3-((R)-8-(1H-benzo[d]imidazol-5-ylsulfonyl)-1-oxa-8-azaspiro[4.5]decan-3-ylamino)-2-hydroxypropoxy)-N-methylbenzenesulfonamide; Compound 504: 3-((S)-3-((R)-8-(2,3-dihydrofuro[2,3-b]pyridin-5-ylsulfonyl)-1-oxa-8-azaspiro[4.5]decan-3-ylamino)-2-hydroxypropoxy)-N-methylbenzenesulfonamide; Compound 505: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide; Compound 506: 3-((S)-3-((R)-8-(1H-pyrrolo[2,3-b]pyridin-5-ylsulfonyl)-1-oxa-8-azaspiro[4.5]decan-3-ylamino)-2-hydroxypropoxy)-N-methylbenzenesulfonamide; Compound 507: 3-((S)-3-((R)-8-(1H-pyrrolo[2,3-b]pyridin-3-ylsulfonyl)-1-oxa-8-azaspiro[4.5]decan-3-ylamino)-2-hydroxypropoxy)-N-methylbenzenesulfonamide; Compound 508: 3-((S)-2-hydroxy-3-((R)-8-(4-methoxy-1H-indazol-5-ylsulfonyl)-1-oxa-8-azaspiro[4.5]decan-3-ylamino)propoxy)-N-methylbenzenesulfonamide; Compound 509: 3-((S)-2-hydroxy-3-((R)-8-(3-(trifluoromethyl)-1H-pyrrolo[2,3-b]pyridin-5-ylsulfonyl)-1-oxa-8-azaspiro[4.5]decan-3-ylamino)propoxy)-N-methylbenzenesulfonamide; Compound 510: 3-((S)-3-((R)-8-(3-chloro-1H-pyrrolo[2,3-b]pyridin-5-ylsulfonyl)-1-oxa-8-azaspiro[4.5]decan-3-ylamino)-2-hydroxypropoxy)-N-methylbenzenesulfonamide; Compound 511: 3-((S)-3-((R)-8-(3-ethyl-3H-imidazo[4,5-b]pyridin-6-ylsulfonyl)-1-oxa-8-azaspiro[4.5]decan-3-ylamino)-2-hydroxypropoxy)-N-methylbenzenesulfonamide; Compound 512: 3-((S)-2-hydroxy-3-((R)-8-(3-methyl-H-pyrrolo[2,3-b]pyridin-5-ylsulfonyl)-1-oxa-8-azaspiro[4.5]decan-3-ylamino)propoxy)-N-methylbenzenesulfonamide; Compound 513: 3-((S)-3-((R)-8-(3-chloro-1-methyl-H-pyrrolo[2,3-b]pyridin-5-ylsulfonyl)-1-oxa-8-azaspiro[4.5]decan-3-ylamino)-2-hydroxypropoxy)-N-methylbenzenesulfonamide; Compound 514: 3-((S)-2-hydroxy-3-((R)-8-(2-oxo-2,3-dihydro-1H-pyrrolo[2,3-b]pyridin-5-ylsulfonyl)-1-oxa-8-azaspiro[4.5]decan-3-ylamino)propoxy)-N-methylbenzenesulfonamide; Compound 515: 3-((S)-3-((R)-8-(2-ethyl-3H-imidazo[4,5-b]pyridin-6-ylsulfonyl)-1-oxa-8-azaspiro[4.5]decan-3-ylamino)-2-hydroxypropoxy)-N-methylbenzenesulfonamide; Compound 516: 3-((S)-2-hydroxy-3-((R)-8-(5-methyl-3H-imidazo[4,5-b]pyridin-6-ylsulfonyl)-1-oxa-8-azaspiro[4.5]decan-3-ylamino)propoxy)-N-methylbenzenesulfonamide; Compound 517: 3-((S)-3-((R)-8-(3-chloro-2-methyl-1H-pyrrolo[2,3-b]pyridin-5-ylsulfonyl)-1-oxa-8-azaspiro[4.5]decan-3-ylamino)-2-hydroxypropoxy)-N-methylbenzenesulfonamide; Compound 518: 3-((S)-2-hydroxy-3-((R)-8-(3-methyl-2-oxo-2,3-dihydro-1H-imidazo[4,5-b]pyridin-6-ylsulfonyl)-1-oxa-8-azaspiro[4.5]decan-3-ylamino)propoxy)-N-methylbenzenesulfonamide; Compound 519: 3-((S)-2-hydroxy-3-((R)-8-(7-methyl-3H-imidazo[4,5-b]pyridin-6-ylsulfonyl)-1-oxa-8-azaspiro[4.5]decan-3-ylamino)propoxy)-N-methylbenzenesulfonamide; Compound 520: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-ethylbenzenesulfonamide; Compound 521: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-(2-hydroxyethyl)benzenesulfonamide; Compound 522: 3-((S)-2-hydroxy-3-((R)-8-(1-methyl-2-oxo-2,3-dihydro-1H-imidazo[4,5-b]pyridin-6-ylsulfonyl)-1-oxa-8-azaspiro[4.5]decan-3-ylamino)propoxy)-N-methylbenzenesulfonamide; Compound 523: 3-((S)-2-hydroxy-3-((R)-8-(1-methyl-H-imidazo[4,5-b]pyridin-6-ylsulfonyl)-1-oxa-8-azaspiro[4.5]decan-3-ylamino)propoxy)-N-methylbenzenesulfonamide; Compound 524: 3-((S)-2-hydroxy-3-((R)-8-(4-oxo-1-propyl-1,4-dihydroquinolin-3-ylsulfonyl)-1-oxa-8-azaspiro[4.5]decan-3-ylamino)propoxy)-N-methylbenzenesulfonamide; Compound 525: 3-((S)-3-((R)-8-(1-ethyl-8-fluoro-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 526: 3-((S)-2-hydroxy-3-((R)-8-(1-methyl-1H-pyrrolo[3,2-b]pyridin-6-ylsulfonyl)-1-oxa-8-azaspiro[4.5]decan-3-ylamino)propoxy)-N-methylbenzenesulfonamide; Compound 527: 3-((S)-3-((R)-8-(3-chloro-1-methyl-H-pyrrolo[3,2-b]pyridin-6-ylsulfonyl)-1-oxa-8-azaspiro[4.5]decan-3-ylamino)-2-hydroxypropoxy)-N-methylbenzenesulfonamide; Compound 528: 3-((S)-2-hydroxy-3-((R)-8-(4-hydroxy-8-methylquinolin-3-ylsulfonyl)-1-oxa-8-azaspiro[4.5]decan-3-ylamino)propoxy)-N-methylbenzenesulfonamide; Compound 529: 3-((S)-3-((R)-8-(1H-pyrrolo[3,2-b]pyridin-3-ylsulfonyl)-1-oxa-8-azaspiro[4.5]decan-3-ylamino)-2-hydroxypropoxy)-N-methylbenzenesulfonamide; Compound 530: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-(2-methoxyethyl)benzenesulfonamide; Compound 531: 3-((S)-3-((R)-8-(1-ethyl-7-methyl-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 532: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)benzenesulfonamide; Compound 533: 3-((S)-2-hydroxy-3-((R)-8-(4-hydroxy-6-methylquinolin-3-ylsulfonyl)-1-oxa-8-azaspiro[4.5]decan-3-ylamino)propoxy)-N-methylbenzenesulfonamide; Compound 534: 3-((S)-3-((R)-8-(6-fluoro-4-hydroxyquinolin-3-ylsulfonyl)-1-oxa-8-azaspiro[4.5]decan-3-ylamino)-2-hydroxypropoxy)-N-methylbenzenesulfonamide; Compound 535: 3-((S)-3-((R)-8-(1-ethyl-6-methyl-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 536: 3-((S)-3-((R)-8-(1-ethyl-6-fluoro-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 537: 3-((S)-2-hydroxy-3-((R)-8-(imidazo[1,2-a]pyridin-6-ylsulfonyl)-1-oxa-8-azaspiro[4.5]decan-3-ylamino)propoxy)-N-methylbenzenesulfonamide; Compound 538: 3-((S)-2-hydroxy-3-((R)-8-(4-hydroxy-7-methylquinolin-3-ylsulfonyl)-1-oxa-8-azaspiro[4.5]decan-3-ylamino)propoxy)-N-methylbenzenesulfonamide; Compound 539: 3-((S)-3-((R)-8-(7-fluoro-4-hydroxyquinolin-3-ylsulfonyl)-1-oxa-8-azaspiro[4.5]decan-3-ylamino)-2-hydroxypropoxy)-N-methylbenzenesulfonamide; Compound 540: 3-((S)-3-((R)-8-(8-fluoro-4-hydroxyquinolin-3-ylsulfonyl)-1-oxa-8-azaspiro[4.5]decan-3-ylamino)-2-hydroxypropoxy)-N-methylbenzenesulfonamide; Compound 541: 3-((S)-2-hydroxy-3-((R)-8-(4-hydroxyquinolin-3-ylsulfonyl)-1-oxa-8-azaspiro[4.5]decan-3-ylamino)propoxy)-N-methylbenzenesulfonamide; Compound 542: 3-((S)-2-hydroxy-3-((R)-8-(4-hydroxy-7-methylquinolin-3-ylsulfonyl)-1-oxa-8-azaspiro[4.5]decan-3-ylamino)propoxy)benzenesulfonamide; Compound 543: 3-((S)-3-((R)-8-(1-ethyl-7-fluoro-4-oxo-1,4-dihydroquinolin-3-ylsulfonyl)-1-oxa-8-azaspiro[4.5]decan-3-ylamino)-2-hydroxypropoxy)benzenesulfonamide; Compound 544: 2-(3-((R)-3-((S)-2-hydroxy-3-(3-(N-methylsulfamoyl)phenoxy)propylamino)-1-oxa-8-azaspiro[4.5]decan-8-ylsulfonyl)-4-oxoquinolin-1(4H)-yl)acetic acid; Compound 545: 3-((S)-3-((R)-8-(1-ethyl-8-methyl-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 546: 3-((S)-3-((R)-8-(1-ethyl-7-fluoro-4-oxo-1,4-dihydroquinolin-3-ylsulfonyl)-1-oxa-8-azaspiro[4.5]decan-3-ylamino)-2-hydroxypropoxy)-N-methylbenzenesulfonamide; Compound 547: 3-((S)-2-hydroxy-3-((R)-8-(4-hydroxy-6-methylquinolin-8-ylsulfonyl)-1-oxa-8-azaspiro[4.5]decan-3-ylamino)propoxy)-N-methylbenzenesulfonamide; Compound 548: 3-((S)-2-hydroxy-3-((R)-8-(4-hydroxyquinolin-3-ylsulfonyl)-1-oxa-8-azaspiro[4.5]decan-3-ylamino)propoxy)benzenesulfonamide; Compound 549: 3-((S)-2-hydroxy-3-((R)-8-(1-methyl-4-oxo-1,4-dihydroquinolin-3-ylsulfonyl)-1-oxa-8-azaspiro[4.5]decan-3-ylamino)propoxy)benzenesulfonamide; Compound 550: 3-((S)-3-((R)-8-(1-ethyl-4-oxo-1,4-dihydroquinolin-3-ylsulfonyl)-1-oxa-8-azaspiro[4.5]decan-3-ylamino)-2-hydroxypropoxy)benzenesulfonamide; Compound 551: 3-((S)-2-hydroxy-3-((R)-8-(4-oxo-1-propyl-1,4-dihydroquinolin-3-ylsulfonyl)-1-oxa-8-azaspiro[4.5]decan-3-ylamino)propoxy)benzenesulfonamide; Compound 552: 3-((S)-3-((R)-8-(6-fluoro-4-oxo-1,4-dihydroquinolin-3-ylsulfonyl)-1-oxa-8-azaspiro[4.5]decan-3-ylamino)-2-hydroxypropoxy)benzenesulfonamide; Compound 553: 3-((S)-2-hydroxy-3-((R)-8-(8-methyl-4-oxo-1,4-dihydroquinolin-3-ylsulfonyl)-1-oxa-8-azaspiro[4.5]decan-3-ylamino)propoxy)benzenesulfonamide; Compound 554: 3-((S)-3-((R)-8-(8-fluoro-4-oxo-1,4-dihydroquinolin-3-ylsulfonyl)-1-oxa-8-azaspiro[4.5]decan-3-ylamino)-2-hydroxypropoxy)benzenesulfonamide; Compound 555: 3-((S)-3-((R)-8-(7-fluoro-4-oxo-1,4-dihydroquinolin-3-ylsulfonyl)-1-oxa-8-azaspiro[4.5]decan-3-ylamino)-2-hydroxypropoxy)benzenesulfonamide; Compound 556: 3-((S)-2-hydroxy-3-((R)-8-(5,6,7,8-tetrahydronaphthalen-2-ylsulfonyl)-1-oxa-8-azaspiro[4.5]decan-3-ylamino)propoxy)benzenesulfonamide; Compound 557: 3-((S)-3-((R)-8-(1-ethyl-7-methyl-4-oxo-1,4-dihydroquinolin-3-ylsulfonyl)-1-oxa-8-azaspiro[4.5]decan-3-ylamino)-2-hydroxypropoxy)benzenesulfonamide; Compound 558: 3-((S)-2-hydroxy-3-((R)-8-(3-methyl-1H-pyrrolo[2,3-b]pyridin-5-ylsulfonyl)-1-oxa-8-azaspiro[4.5]decan-3-ylamino)propoxy)benzenesulfonamide; Compound 559: 3-((S)-2-hydroxy-3-((R)-8-(2-methyl-3H-imidazo[4,5-b]pyridin-6-ylsulfonyl)-1-oxa-8-azaspiro[4.5]decan-3-ylamino)propoxy)benzenesulfonamide; Compound 560: 3-((S)-2-hydroxy-3-((R)-8-(naphthalen-2-ylsulfonyl)-1-oxa-8-azaspiro[4.5]decan-3-ylamino)propoxy)benzenesulfonamide; Compound 561: 3-((S)-3-((R)-8-(pyridin-2-yl)-1-oxa-8-azaspiro[4.5]decan-3-ylamino)propoxy)-N-methylbenzenesulfonamide; Compound 562: 3-((S)-2-hydroxy-3-((R)-8-(quinolin-3-ylsulfonyl)-1-oxa-8-azaspiro[4.5]decan-3-ylamino)propoxy)benzenesulfonamide; Compound 563: 3-((S)-3-((S)-8-(1H-pyrrolo[3,2-b]pyridin-6-ylsulfonyl)-1-oxa-8-azaspiro[4.5]decan-3-ylamino)-2-hydroxypropoxy)benzenesulfonamide; Compound 564: 3-((S)-2-hydroxy-3-((R)-8-(3-methyl-1H-pyrazolo[3,4-b]pyridin-5-ylsulfonyl)-1-oxa-8-azaspiro[4.5]decan-3-ylamino)propoxy)benzenesulfonamide; Compound 565: 3-((S)-3-((R)-8-(chroman-6-ylsulfonyl)-1-oxa-8-azaspiro[4.5]decan-3-ylamino)-2-hydroxypropoxy)benzenesulfonamide; Compound 566: 3-((S)-2-hydroxy-3-((R)-8-(quinolin-6-ylsulfonyl)-1-oxa-8-azaspiro[4.5]decan-3-ylamino)propoxy)benzenesulfonamide; Compound 567: 3-((S)-3-((R)-8-(4'-(aminomethyl)-4-ethoxybiphenyl-3-ylsulfonyl)-1-oxa-8-azaspiro[4.5]decan-3-ylamino)-2-hydroxypropoxy)benzenesulfonamide; Compound 568: 3-((S)-2-hydroxy-3-((R)-8-(4-methoxypyrimidin-2-yl)-1-oxa-8-azaspiro[4.5]decan-3-ylamino)propoxy)-N-methylbenzenesulfonamide; Compound 569: 3-((S)-3-((R)-8-(4-aminopyrimidin-2-yl)-1-oxa-8-azaspiro[4.5]decan-3-ylamino)-2-hydroxypropoxy)-N-methylbenzenesulfonamide; Compound 570: 3-((S)-3-((R)-8-(5-benzylpyrimidin-2-yl)-1-oxa-8-azaspiro[4.5]decan-3-ylamino)-2-hydroxypropoxy)-N-methylbenzenesulfonamide; Compound 571: 3-((S)-3-((R)-8-(5-ethylpyrimidin-2-yl)-1-oxa-8-azaspiro[4.5]decan-3-ylamino)-2-hydroxypropoxy)-N-methylbenzenesulfonamide; Compound 572: 3-((S)-2-hydroxy-3-((R)-8-(4-phenylpyrimidin-2-yl)-1-oxa-8-azaspiro[4.5]decan-3-ylamino)propoxy)-N-methylbenzenesulfonamide; Compound 573: 3-((S)-3-((R)-8-(4-benzylpyrimidin-2-yl)-1-oxa-8-azaspiro[4.5]decan-3-ylamino)-2-hydroxypropoxy)-N-methylbenzenesulfonamide; Compound 574: 3-((S)-2-hydroxy-3-((R)-8-(4-(trifluoromethyl)pyrimidin-2-yl)-1-oxa-8-azaspiro[4.5]decan-3-ylamino)propoxy)-N-methylbenzenesulfonamide; Compound 575: 3-((S)-2-hydroxy-3-((R)-8-(4-methylpyrimidin-2-yl)-1-oxa-8-azaspiro[4.5]decan-3-ylamino)propoxy)-N-methylbenzenesulfonamide; Compound 576: 3-((S)-2-hydroxy-3-((R)-8-(pyrimidin-2-yl)-1-oxa-8-azaspiro[4.5]decan-3-ylamino)propoxy)-N-methylbenzenesulfonamide; Compound 577: 3-((S)-3-((R)-8-(4,6-dimethylpyrimidin-2-yl)-1-oxa-8-azaspiro[4.5]decan-3-ylamino)-2-hydroxypropoxy)-N-methylbenzenesulfonamide; Compound 578: 3-((S)-3-((R)-8-(5-heptylpyrimidin-2-yl)-1-oxa-8-azaspiro[4.5]decan-3-ylamino)-2-hydroxypropoxy)-N-methylbenzenesulfonamide; Compound 579: 3-((S)-2-hydroxy-3-((R)-8-(5-propylpyrimidin-2-yl)-1-oxa-8-azaspiro[4.5]decan-3-ylamino)propoxy)-N-methylbenzenesulfonamide; Compound 580: 3-((S)-2-hydroxy-3-((R)-8-(5-phenylpyrimidin-2-yl)-1-oxa-8-azaspiro[4.5]decan-3-ylamino)propoxy)-N-methylbenzenesulfonamide; Compound 581: methyl 2-((R)-3-((S)-2-hydroxy-3-(3-(N-methylsulfamoyl)phenoxy)propylamino)-1-oxa-8-azaspiro[4.5]decan-8-yl)pyrimidine-5-carboxylate; Compound 582: 2-((R)-3-((S)-2-hydroxy-3-(3-(N-methylsulfamoyl)phenoxy)propylamino)-1-oxa-8-azaspiro[4.5]decan-8-yl)pyrimidine-4-carboxylic acid; Compound 583: 3-((S)-2-hydroxy-3-((R)-8-(5-(trifluoromethyl)pyrimidin-2-yl)-1-oxa-8-azaspiro[4.5]decan-3-ylamino)propoxy)-N-methylbenzenesulfonamide; Compound 584: 3-((S)-3-((R)-8-(4,6-dimethoxypyrimidin-2-yl)-1-oxa-8-azaspiro[4.5]decan-3-ylamino)-2-hydroxypropoxy)-N-methylbenzenesulfonamide; Compound 585: 3-((S)-2-hydroxy-3-((R)-8-(5-(trifluoromethyl)pyrazin-2-yl)-1-oxa-8-azaspiro[4.5]decan-3-ylamino)propoxy)-N-methylbenzenesulfonamide; Compound 586: 3-((S)-2-hydroxy-3-((R)-8-(pyrazin-2-yl)-1-oxa-8-azaspiro[4.5]decan-3-ylamino)propoxy)-N-methylbenzenesulfonamide; Compound 587: 3-((S)-3-((R)-8-(1-ethyl-4-oxo-1,4-dihydropyridin-3-ylsulfonyl)-1-oxa-8-azaspiro[4.5]decan-3-ylamino)-2-hydroxypropoxy)benzenesulfonamide; Compound 588: 3-((S)-3-((R)-8-(1-ethyl-4-oxo-1,4-dihydropyridin-3-ylsulfonyl)-1-oxa-8-azaspiro[4.5]decan-3-ylamino)-2-hydroxypropoxy)-N-methylbenzenesulfonamide; Compound 589: 3-((S)-2-hydroxy-3-((R)-8-(pyrimidin-4-yl)-1-oxa-8-azaspiro[4.5]decan-3-ylamino)propoxy)-N-methylbenzenesulfonamide; Compound 590: 3-((S)-3-((R)-8-(4-bromo-3-methylphenylsulfonyl)-1-oxa-8-azaspiro[4.5]decan-3-ylamino)-2-hydroxypropoxy)benzenesulfonamide; Compound 591: 3-((S)-3-((R)-8-(3-chlorophenylsulfonyl)-1-oxa-8-azaspiro[4.5]decan-3-ylamino)-2-hydroxypropoxy)benzenesulfonamide; Compound 592: 3-((S)-3-((R)-8-(3-chlorophenylsulfonyl)-1-oxa-8-azaspiro[4.5]decan-3-ylamino)-2-hydroxypropoxy)-N-methylbenzenesulfonamide; Compound 593: 3-((S)-2-hydroxy-3-((R)-8-(4-(3-methoxyphenyl)pyrimidin-2-yl)-1-oxa-8-azaspiro[4.5]decan-3-ylamino)propoxy)-N-methylbenzenesulfonamide; and Compound 594: 3-((S)-2-hydroxy-3-((R)-8-(4-methyl-6-phenylpyrimidin-2-yl)-1-oxa-8-azaspiro[4.5]decan-3-ylamino)propoxy)-N-methylbenzenesulfonamide.

Some embodiments of the present invention include every combination of one or more compounds and pharmaceutically acceptable salts, solvates, and hydrates thereof selected from the following group, wherein the Compound Number in bold directly preceding the chemical name is used elsewhere in this disclosure: Compound 61: 3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methylbenzenesulfonamide; Compound 172: 3-((2S)-3-(8-(benzylsulfonyl)-1-oxa-8-azaspiro[4.5]decan-3-ylamino)-2-hydroxypropoxy)-N-methylbenzenesulfonamide; Compound 300: 3-((S)-2-hydroxy-3-((R)-8-(4-methyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide; Compound 303: 3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide; Compound 320: 3-((2S)-2-hydroxy-3-(8-(4'-((isopentylamino)methyl)biphenyl-3-ylsulfonyl)-1-oxa-8-azaspiro[4.5]decan-3-ylamino)propoxy)-N-methylbenzenesulfonamide; Compound 336: 3-((S)-2-hydroxy-3-((R)-8-(quinolin-3-ylsulfonyl)-1-oxa-8-azaspiro[4.5]decan-3-ylamino)propoxy)-N-methylbenzenesulfonamide; Compound 339: 3-((2S)-3-(8-(4'-((2,2-difluoroethylamino)methyl)biphenyl-3-ylsulfonyl)-1-oxa-8-azaspiro[4.5]decan-3-ylamino)-2-hydroxypropoxy)-N-methylbenzenesulfonamide; Compound 344: 3-((S)-2-hydroxy-3-((R)-8-(quinolin-6-ylsulfonyl)-1-oxa-8-azaspiro[4.5]decan-3-ylamino)propoxy)-N-methylbenzenesulfonamide; Compound 354: N¹-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide; Compound 419: 3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide;

Compound 437: 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1R,2S)-2-hydroxycyclopentyl)benzenesulfonamide; Compound 468: 3-((S)-3-((R)-8-((R)-1,3-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide; Compound 493: 3-((S)-3-((R)-8-(3-cyano-1H-pyrrolo[2,3-b]pyridin-5-ylsulfonyl)-1-oxa-8-azaspiro[4.5]decan-3-ylamino)-2-hydroxypropoxy)-N-methylbenzenesulfonamide; Compound 496: 3-((R)-3-((S)-2-hydroxy-3-(3-(N-methylsulfamoyl)phenoxy)propylamino)-1-oxa-8-azaspiro[4.5]decan-8-ylsulfonyl)pyridine 1-oxide; Compound 505: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide; Compound 509: 3-((S)-2-hydroxy-3-((R)-8-(3-(trifluoromethyl)-1H-pyrrolo[2,3-b]pyridin-5-ylsulfonyl)-1-oxa-8-azaspiro[4.5]decan-3-ylamino)propoxy)-N-methylbenzenesulfonamide; Compound 532: 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)benzenesulfonamide; Compound 541: 3-((S)-2-hydroxy-3-((R)-8-(4-hydroxyquinolin-3-ylsulfonyl)-1-oxa-8-azaspiro[4.5]decan-3-ylamino)propoxy)-N-methylbenzenesulfonamide; Compound 548: 3-((S)-2-hydroxy-3-((R)-8-(4-hydroxyquinolin-3-ylsulfonyl)-1-oxa-8-azaspiro[4.5]decan-3-ylamino)propoxy)benzenesulfonamide; Compound 550: 3-((S)-3-((R)-8-(1-ethyl-4-oxo-1,4-dihydroquinolin-3-ylsulfonyl)-1-oxa-8-azaspiro[4.5]decan-3-ylamino)-2-hydroxypropoxy)benzenesulfonamide; Compound 568: 3-((S)-2-hydroxy-3-((R)-8-(4-methoxypyrimidin-2-yl)-1-oxa-8-azaspiro[4.5]decan-3-ylamino)propoxy)-N-methylbenzenesulfonamide; and Compound 573: 3-((S)-3-((R)-8-(4-benzylpyrimidin-2-yl)-1-oxa-8-azaspiro[4.5]decan-3-ylamino)-2-hydroxypropoxy)-N-methylbenzenesulfonamide.

Additionally, chemical genera of the present invention and individual compounds, for example those compounds found in Table A, including diastereoisomers and enantiomers thereof, encompass all pharmaceutically acceptable salts, solvates, hydrates, and N-oxides thereof.

The compounds of Formula (Ia) of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each isomer, each diastereoisomer, each enantiomer and mixtures thereof of each compound and generic formulae disclosed herein just as if they were each individually disclosed with the specific stereochemical designation for each chiral carbon.

Individual isomers and enantiomers can be prepared by selective synthesis, such as, by enantiomeric selective syntheses; or they can be obtained using separation techniques which are well known to practitioners in the art, such as, by HPLC (including, normal phase, reverse phase, and chiral), recrystallization (i.e., diastereoisomeric mixtures) and like techniques.

Disorders and Methods of Treatment

The compounds disclosed herein are useful in the treatment or prevention of several diseases, disorders, conditions, and/or indications (which are cumulatively referred to herein as "disorders"). One of skill in the art will recognize that when a disorder, or a method of treatment or prevention, is disclosed herein, such disclosure encompasses second medical uses (e.g., a compound for use in the treatment of the disorder, use of a compound for the treatment of the disorder, and use of a compound in the manufacture of a medicament for the treatment of the disorder).

In some embodiments, the compounds disclosed herein are useful for the treatment or prevention of a disorder. In some embodiments, the compounds disclosed herein are useful for the treatment or prevention of a subtype of a disorder. In some embodiments, the compounds disclosed herein are useful for the treatment or prevention of a symptom of a disorder.

Provided herein are methods for treating or preventing a beta-3 adrenergic receptor-mediated disorder. In some embodiments, the compounds disclosed herein are useful for the prevention of a beta-3 adrenergic receptor-mediated disorder. In some embodiments, the compounds disclosed herein are useful for the treatment or prevention of a beta-3 adrenergic receptor-mediated disorder.

One aspect of the present invention relates to methods for treating or preventing a beta-3 adrenergic receptor-mediated disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing heart failure in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating a hypotensive patient or a borderline hypotensive patient, comprising administering to the patient in need thereof, a therapeutically effective amount of a compound of the present invention; a pharmaceutical product of the present invention; or a pharmaceutical composition of the present invention. One aspect of the present invention relates to uses of a compound of the present invention in the manufacture of a medicament for treating or preventing a beta-3 adrenergic receptor-mediated disorder in an individual.

One aspect of the present invention relates to uses of a compound of the present invention in the manufacture of a medicament for treating or preventing heart failure in an individual.

One aspect of the present invention relates to uses of a compound of the present invention in the manufacture of a medicament for treating a hypotensive patient or a borderline hypotensive patient.

One aspect of the present invention relates to uses of a compound of the present invention in the manufacture of a medicament for treating a normotensive patient.

One aspect of the present invention relates to uses of a compound of the present invention in the manufacture of a medicament for treating a hypertensive patient.

One aspect of the present invention relates to uses of a compound of the present invention in the manufacture of a medicament for treating a patient following myocardial infarction.

One aspect of the present invention relates to compounds of the present invention; a pharmaceutical product of the present invention; or a pharmaceutical composition of the present invention; for use in a method of treatment of the human or animal body by therapy.

One aspect of the present invention relates to compounds of the present invention; pharmaceutical products of the present invention; or pharmaceutical compositions of the present invention; for use in a method for treating or preventing a beta-3 adrenergic receptor-mediated disorder in an individual.

In some embodiments, the beta-3 adrenergic receptor-mediated disorder is selected from the list consisting of: heart failure; reduced cardiac performance in heart failure; mortality, reinfarction, and/or hospitalization in connection with heart failure; acute heart failure; acute decompensated heart failure; congestive heart failure; severe congestive heart failure; organ damage associated with heart failure (e.g., kidney damage or failure, heart valve problems, heart rhythm problems, and/or liver damage); heart failure due to left ventricular dysfunction; heart failure with normal ejection fraction; cardiovascular mortality following myocardial infarction; cardiovascular mortality in patients with left ventricular failure or left ventricular dysfunction; a condition following myocardial infarction; left ventricular failure; left ventricular dysfunction; class II heart failure using the New York Heart Association (NYHA) classification system; class III heart failure using the New York Heart Association (NYHA) classification system; class IV heart failure using the New York Heart Association (NYHA) classification system; LVEF<40% by radionuclide ventriculography; and LVEF≤35% by echocardiography or ventricular contrast angiography.

In some embodiments, the beta-3 adrenergic receptor-mediated disorder is heart failure.

In some embodiments, the beta-3 adrenergic receptor-mediated disorder is reduced cardiac performance in heart failure.

In some embodiments, the beta-3 adrenergic receptor-mediated disorder is mortality, reinfarction, and/or hospitalization in connection with heart failure.

In some embodiments, the beta-3 adrenergic receptor-mediated disorder is acute heart failure.

In some embodiments, the beta-3 adrenergic receptor-mediated disorder is acute decompensated heart failure.

In some embodiments, the beta-3 adrenergic receptor-mediated disorder is congestive heart failure.

In some embodiments, the beta-3 adrenergic receptor-mediated disorder is severe congestive heart failure.

In some embodiments, the beta-3 adrenergic receptor-mediated disorder is organ damage associated with heart failure (e.g., kidney damage or failure, heart valve problems, heart rhythm problems, and/or liver damage).

In some embodiments, the beta-3 adrenergic receptor-mediated disorder is heart failure due to left ventricular dysfunction.

In some embodiments, the beta-3 adrenergic receptor-mediated disorder is heart failure with normal ejection fraction.

In some embodiments, the beta-3 adrenergic receptor-mediated disorder is cardiovascular mortality following myocardial infarction. In some embodiments, the beta-3 adrenergic receptor-mediated disorder is reducing or a reduction of cardiovascular mortality following myocardial infarction.

In some embodiments, the beta-3 adrenergic receptor-mediated disorder is cardiovascular mortality in patients with left ventricular failure or left ventricular dysfunction.

In some embodiments, the beta-3 adrenergic receptor-mediated disorder is following myocardial infarction.

In some embodiments, the beta-3 adrenergic receptor-mediated disorder is left ventricular failure.

In some embodiments, the beta-3 adrenergic receptor-mediated disorder is left ventricular dysfunction.

Doctors can classify the patient's heart failure according to the severity of their symptoms. The table below describes the most commonly used classification system, the New York Heart Association (NYHA) Functional Classification. It places patients in one of four categories based on how much they are limited during physical activity.

| Class | Patient Symptoms |
| --- | --- |
| I | No limitation of physical activity. Ordinary physical activity does not cause undue fatigue, palpitation, dyspnea (shortness of breath). |
| II | Slight limitation of physical activity. Comfortable at rest. Ordinary physical activity results in fatigue, palpitation, dyspnea (shortness of breath). |
| III | Marked limitation of physical activity. Comfortable at rest. Less than ordinary activity causes fatigue, palpitation, or dyspnea. |
| IV | Unable to carry on any physical activity without discomfort. Symptoms of heart failure at rest. If any physical activity is undertaken, discomfort increases. |

Accordingly, in some embodiments, the beta-3 adrenergic receptor-mediated disorder is class II heart failure using the New York Heart Association (NYHA) classification system.

In some embodiments, the beta-3 adrenergic receptor-mediated disorder is class III heart failure using the New York Heart Association (NYHA) classification system.

In some embodiments, the beta-3 adrenergic receptor-mediated disorder is class IV heart failure using the New York Heart Association (NYHA) classification system.

In some embodiments, the beta-3 adrenergic receptor-mediated disorder is LVEF<40% by radionuclide ventriculography.

In some embodiments, the beta-3 adrenergic receptor-mediated disorder is LVEF≤35% by echocardiography or ventricular contrast angiography.

Polymorphs and Pseudopolymorphs

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly published a polymorph screen of 245 compounds consisting of a "wide variety of structural types" that revealed about 90% of them exhibited multiple solid forms. Overall, approximately half of the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026).

Isotopes

The present disclosure includes all isotopes of atoms occurring in the compounds provided herein. Isotopes include those atoms having the same atomic number but different mass numbers. It is appreciated that certain features of the invention(s) include every combination of one or more atoms in the compounds provided herein that is replaced with an atom having the same atomic number but a different mass number. One such example is the replacement of an atom that is the most naturally abundant isotope, such as $^1$H or $^{12}$C, found in one of the compounds provided herein with a different atom that is not the most naturally abundant isotope, such as $^2$H or $^3$H (replacing $^1$H), or $^{11}$C, $^{13}$C, or $^{14}$C (replacing $^{12}$C). A compound wherein such a replacement has taken place is commonly referred to as being isotopically-labeled. Isotopic-labeling of the present compounds can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$O. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Also provided are compositions, such as, those prepared during synthesis, preformulation, and the like, and pharmaceutical compositions, such as, those prepared with the intent of using in a mammal for the treatment of one or more of the disorders described herein, comprising one or more of the present compounds, wherein the naturally occurring distribution of the isotopes in the composition is perturbed. Also provided herein are compositions and pharmaceutical compositions comprising compounds of the invention as described herein, wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

One challenge in drug development is improving absorption, distribution, metabolism, excretion, and toxicity (ADMET) properties while maintaining a desired pharmacological profile. Structural changes to improve ADMET properties often alter the pharmacology of a lead compound. While the effects of deuterium substitution on ADMET properties are unpredictable, in select cases deuterium can improve a compound's ADMET properties with minimal perturbation of its pharmacology. Two examples where deuterium has enabled improvements in therapeutic entities are: CTP-347 and CTP-354. CTP-347 is a deuterated version of paroxetine with a reduced liability for mechanism-based inactivation of CYP2D6 that is observed clinically with paroxetine. CTP-354 is a deuterated version of a promising preclinical gamma-aminobutyric acid A receptor (GABAA) modulator (L-838417) that was not developed due to poor pharmacokinetic (PK) properties. In both cases, deuterium substitution resulted in improved ADMET profiles that provide the potential for improved safety, efficacy, and/or tolerability without significantly altering the biochemical potency and selectivity versus the all-hydrogen compounds. Provided are deuterium substituted compounds of the present invention with improved ADMET profiles and substantially similar biochemical potency and selectivity versus the corresponding all-hydrogen compounds.

Other Utilities

Another object of the present invention relates to radio-labeled compounds of the present invention that would be useful not only in radio-imaging but also in assays, both in vitro and in vivo, for localizing and quantitating beta-3 adrenergic receptors in tissue samples, including human and for identifying beta-3 adrenergic receptor ligands by inhibition binding of a radio-labeled compound. It is a further object of this invention to develop novel beta-3 adrenergic receptor assays of which comprise such radio-labeled compounds.

The present disclosure includes all isotopes of atoms occurring in the present compounds, intermediates, salts and crystalline forms thereof. Isotopes include those atoms having the same atomic number but different mass numbers. One aspect of the present invention includes every combination of one or more atoms in the present compounds, intermediates, salts, and crystalline forms thereof that is replaced with an atom having the same atomic number but a different mass number. One such example is the replacement of an atom that is the most naturally abundant isotope, such as $^1H$ or $^{12}C$, found in one the present compounds, intermediates, salts, and crystalline forms thereof, with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being an isotopically-labeled compound. Isotopic-labeling of the present compounds, intermediates, salts, and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, intermediates, salts, and crystalline forms thereof, wherein the naturally occurring distribution of the isotopes in the composition is perturbed. Another aspect of the present invention includes compositions and pharmaceutical compositions comprising compounds as described herein wherein the compound is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. Representative synthetic methods for incorporating activity levels of tritium into target molecules include, for example:

A. Catalytic Reduction with Tritium Gas: This procedure normally yields high specific activity products and requires halogenated or unsaturated precursors.

B. Reduction with Sodium Borohydride [$^3H$]: This procedure is rather inexpensive and requires precursors containing reducible functional groups such as aldehydes, ketones, lactones, esters and the like.

C. Reduction with Lithium Aluminum Hydride [$^3H$]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3H$]: This procedure is usually employed to prepare O-methyl or N-methyl ($^3H$) products by treating appropriate precursors with high specific activity methyl iodide ($^3H$). This method in general allows for higher specific activity, such as for example, about 70-90 Ci/mmol.

Synthetic methods for incorporating activity levels of $^{125}I$ into target molecules include:

A. Sandmeyer and like reactions: This procedure transforms an aryl amine or a heteroaryl amine into a diazonium salt, such as a diazonium tetrafluoroborate salt and subsequently to $^{125}I$ labeled compound using Na$^{125}I$. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}I$ at the ortho position of a phenol as reported by Collier, T. L. and co-workers in *J. Labelled Compd. Radiopharm.*, 1999, 42, S264-S266.

C. Aryl and heteroaryl bromide exchange with $^{125}I$: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled beta-3 adrenergic receptor compound of Formula (Ia) can be used in a screening assay to identify/evaluate compounds. In general terms, a newly synthesized or identified compound (i.e., test compound) can be evaluated for its ability to reduce binding of the "radiolabeled compound of Formula (Ia)" to a beta-3 adrenergic receptor. Accordingly, the ability of a test compound to compete with the "radiolabeled compound of Formula (Ia)" for the binding to a beta-3 adrenergic receptor directly correlates to its binding affinity.

Certain labeled compounds of the present invention bind to certain beta-3 adrenergic receptors. In one embodiment the labeled compound has an $IC_{50}$ less than about 500 µM, in another embodiment the labeled compound has an $IC_{50}$ less than about 100 µM, in yet another embodiment the labeled compound has an $IC_{50}$ less than about 10 µM, in yet another embodiment the labeled compound has an $IC_{50}$ less than about 1 µM and in still yet another embodiment the labeled compound has an $IC_{50}$ less than about 0.1 µM.

Compositions and Formulations

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound provided herein in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro et. al.).

While it is possible that, for use in the prophylaxis or treatment, a compound provided herein may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds provided herein or a salt, solvate, or hydrate thereof can be used as active ingredients in pharmaceutical compositions, specifically as beta-3 adrenergic receptor modulators. The term "active ingredient", defined in the context of a "pharmaceutical composition"," refers to a component of a pharmaceutical composition that provides the primary pharmacological effect, as opposed to an "inactive ingredient" which would generally be recognized as providing no pharmaceutical benefit.

The dose when using the compounds provided herein can vary within wide limits and as is customary and is known to the physician or other clinician, it is to be tailored to the individual conditions in each individual case. It depends, for example, on the nature and severity of the illness to be treated, on the condition of the patient, on the compound employed or on whether an acute or chronic disease state is treated, or prophylaxis conducted, or on whether further active compounds are administered in addition to the compounds provided herein. Representative doses include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3, or 4 doses. Depending on the individual and as deemed appropriate from the healthcare provider it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated, or prophylaxis conducted, or on whether further active compounds are administered in addition to the compounds provided herein and as part of a drug combination. The dosage regimen for treating a disease condition with the compounds and/or compositions provided herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods provided herein.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations. The daily dose can be divided, especially when relatively large amounts are administered as deemed appropriate, into several, for example two, three, or four-part administrations. If appropriate, depending on individual behavior, it may be necessary to deviate upward or downward from the daily dose indicated.

The compounds provided herein can be administered in a wide variety of oral and parenteral dosage forms. It will be obvious to those skilled in the art that the dosage forms may comprise, as the active component, either a compound provided herein or a pharmaceutically acceptable salt, hydrate, or solvate of a compound provided herein.

For preparing pharmaceutical compositions from the compounds provided herein, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is admixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethyl cellulose, a low melting wax, cocoa butter and the like. The term "preparation" refers to the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams, or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds provided herein may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethyl cellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds provided herein may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds provided herein or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds provided herein as an aerosol can be prepared by processes well known to the person skilled in the art. For their preparation, for example, solutions or dispersions of the compounds provided herein in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds provided herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds provided herein which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino)hexane-1,2,3,4,5-pentaol), procaine (2-(diethylamino)ethyl 4-aminobenzoate), and the like. Certain pharmaceutically acceptable salts are listed in Berge, et. al., Journal of Pharmaceutical Sciences, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds provided herein may form solvates with standard low molecular weight solvents using methods known to the skilled artisan.

Compounds provided herein can be converted to "prodrugs." The term "pro-drugs" refers to compounds that have been modified with specific chemical groups known in the art and when administered into an individual these groups undergo biotransformation to give the parent compound. Pro-drugs can thus be viewed as compounds provided herein containing one or more specialized non-toxic protective groups used in a transient manner to alter or to eliminate a property of the compound. In one general aspect, the "prodrug" approach is utilized to facilitate oral absorption. A thorough discussion is provided in T. Higuchi and V. Stella, Pro-drugs as Novel Delivery Systems Vol. 14 of the A.C.S. Symposium Series; and in Bioreversible Carriers in Drug Design, ed. Edward B. Roche, American Pharmaceutical Association and Pergamon Press, 1987.

Some embodiments include a method of producing a pharmaceutical composition for "combination-therapy" comprising admixing at least one compound according to any of the compound embodiments disclosed herein, together with at least one known pharmaceutical agent and a pharmaceutically acceptable carrier.

It is noted that when the beta-3 adrenergic receptor modulators are utilized as active ingredients in pharmaceutical compositions, these are not intended for use in humans only, but in non-human mammals as well. Recent advances in the area of animal health-care mandate that consideration be given for the use of active agents, such as beta-3 adrenergic receptor modulators, for the treatment of a beta-3 adrenergic receptor-associated disease or disorder in companionship animals (e.g., cats, dogs, etc.) and in livestock animals (e.g., horses, cows, etc.) Those of ordinary skill in the art are readily credited with understanding the utility of such compounds in such settings.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses of Compounds of the Present Invention

The compounds disclosed herein and their syntheses are further illustrated by the following examples. Additional illustrated syntheses for compounds of the present invention are shown in FIGS. 1 to 19 where the symbols have the same definitions as used throughout this disclosure. The following examples are provided to further define the invention without, however, limiting the invention to the particulars of these examples. The compounds described herein, supra and infra, are named according to CS ChemDraw Ultra Version 9.0.7, or ChemDraw Professional 16.0.0.82 (68). In certain instances common names are used and it is understood that these common names would be recognized by those skilled in the art.

Chemistry: Proton nuclear magnetic resonance ($^1$H NMR) spectra were recorded on a Bruker Avance III-400 equipped with a 5 mm BBFO probe. Chemical shifts are given in parts per million (ppm) with the residual solvent signal used as reference. NMR abbreviations are used as follows: s=singlet, d=doublet, dd=doublet of doublets, ddd=doublet of doublet of doublets, dddd=doublet of doublet of doublet of doublets, dt=doublet of triplets, t=triplet, q=quartet, m=multiplet, bs=broad singlet, sxt=sextet. Microwave irradiations were carried out using an Initiator$^{+TM}$ (Biotage®). Thin-layer chromatography (TLC) was performed on silica gel 60 F$_{254}$ (Merck), preparatory thin-layer chromatography (prep TLC) was performed on PK6F silica gel 60 Å 1 mm plates (Whatman) and column chromatography was carried out on a silica gel column using Kieselgel 60, 0.063-0.200 mm (Merck). Evaporation was done under reduced pressure on a Büchi rotary evaporator. Celite® 545 was used for filtration of palladium.

LCMS spec: HPLC-Agilent 1200; pumps: G1312A; DAD:G1315B; Autosampler: G1367B; Mass spectrometer-Agilent G1956A; ionization source: ESI; Drying Gas Flow: 10 L/min; Nebulizer Pressure: 40 psig; Drying Gas Temperature: 350° C.; Capillary Voltage: 2500 V) Software: Agilent Chemstation Rev.B.04.03.

Example 1.1: Preparation of benzyl 3-((tert-butoxycarbonyl)amino)-1-oxa-8-azaspiro[4.5]decane-8-carboxylate Step A: Preparation of benzyl 4-allyl-4-hydroxypiperidine-1-carboxylate To a mixture of benzyl 4-oxopiperidine-1-carboxylate (51 g, 218.6 mmol) in THF (36.44 mL) were added 3-bromoprop-1-ene (54.72 mL, 655.92 mmol) and saturated NH$_4$Cl (114 mL, 218.6 mmol) aqueous solution. Then zinc dust (31.59 g, 483.1 mmol) was added portion wise while the internal reaction temperature was kept below 40° C. The reaction was stirred at room temperature overnight. After the reaction was completed, it was quenched with H$_2$SO$_4$ (10%, 225 mL). The reaction mixture was filtered through a pad of Celite® and washed with MTBE (1 L). The aqueous layer was extracted with MBTE (2×) and EtOAc (lx). The combined organic layers were washed with water and brine, and then dried over MgSO$_4$, filtered and concentrated to give the title compound (62.39 g, 103.6%). This material was used in the next step without further purification. LC/MS m/z=276.2 [M+H]$^+$; $^1$H NMR (400 MHz, CDCl$_3$) δ ppm 1.55-1.63 (m, 5H), 2.24 (d, J=7.33 Hz, 2H), 3.25 (br. s., 2H), 3.93 (br. s., 2H), 5.14 (s, 2H), 5.21 (td, J=9.54, 1.89 Hz, 1H), 5.79-5.93 (m, J=17.27, 10.01, 7.58, 7.58 Hz, 1H), 7.33 (dd, J=5.18, 3.41 Hz, 1H), 7.35-7.40 (m, 4H).

Step B: Preparation of benzyl 4-(2,3-dihydroxypropyl)-4-hydroxypiperidine-1-carboxylate A mixture of K$_3$Fe(CN)$_6$ (62.64 g, 190.3 mmol), K$_2$CO$_3$ (26.29 g, 190.3 mmol), quinuclidine (0.25 g, 2.25 mmol), K$_2$OsO$_2$(OH)$_4$ (0.20 g, 0.53 mmol) was dissolved in H$_2$O (354.0 mL) and then stirred at room temperature for 20 min. (Note: Not all of the salts dissolved in water). A solution of benzyl 4-allyl-4-hydroxypiperidine-1-carboxylate (14.72 g, 53.44 mmol) in t-BuOH (354 mL) was prepared then added into the aqueous salt solution via addition funnel portion wise at room temperature. (Note: All of the salts went into the solution as benzyl 4-allyl-4-hydroxypiperidine-1-carboxylate solution was added.) Then methanesulfonamide (5.08 g, 53.44 mmol) was added. The reaction mixture changed color from reddish to green, and was stirred at room temperature for 5 h. The reaction was quenched with Na$_2$SO$_3$ (51.5 g). The organic layer was separated and concentrated. The residue was dissolved in EtOAc and extracted with water and brine, then dried over MgSO$_4$, filtered and concentrated to give the title compound (19 g, 115%) as an oil which was used in the next step without further purification. LC/MS m/z=310.4 [M+H]$^+$; $^1$H NMR (400 MHz, CDCl$_3$) δ ppm 1.47 (dd, J=14.65, 2.27 Hz, 1H), 1.57 (s, 2H), 1.72 (dd, J=14.65, 11.12 Hz, 1H), 1.81 (d, J=12.63 Hz, 1H), 1.88 (t, J=5.43 Hz, 1H), 3.12 (s, 2H), 3.16-3.23 (m, 1H), 3.25-3.37 (m, 1H), 3.48 (ddd, J=10.86, 6.95, 5.68 Hz, 1H), 3.65 (ddd, J=10.80, 4.61, 3.54 Hz, 1H), 3.92 (br. s., 2H), 4.14 (br. s., 1H), 4.68 (br. s., 1H), 5.14 (s, 2H), 7.29-7.40 (m, 5H).

Step C: Preparation of benzyl 3-hydroxy-1-oxa-8-azaspiro[4.5]decane-8-carboxylate To a solution of benzyl 4-(2,3-dihydroxypropyl)-4-hydroxypiperidine-1-carboxylate (17.80 g, 57.55 mmol) in CH$_2$Cl$_2$ (16 mL) and Pyridine (8.90 mL) under nitrogen were added N,N-dimethylpyridin-4-amine (1.41 g, 11.51 mmol) and 4-methylbenzene-1-sulfonyl chloride (12.07 g, 63.30 mmol) at 0° C. The reaction was stirred at room temperature overnight. After the reaction was completed, it was quenched with water then extracted with DCM (5×). The combined organic layers were washed with 1M HCl aqueous solution, water and brine, then dried over MgSO$_4$ and concentrated. The residue was purified by silica gel column chromatography to give the title compound (12.5 g, 75%) as a yellow oil. LC/MS m/z=292.2 [M+H]$^+$; $^1$H NMR (400 MHz, CD$_3$D) δ ppm 1.53-1.60 (m, 2H), 1.63-1.72 (m, 1H), 1.79 (ddd, J=13.52, 1.26, 1.14 Hz, 1H), 1.82-1.89 (m, 1H), 1.98 (dd, J=13.52, 6.44 Hz, 1H), 3.41 (br. s., 2H), 3.67 (dd, J=12.51, 6.44 Hz, 2H), 3.74 (ddd, J=9.60, 2.53, 1.01 Hz, 1H), 3.90 (dd, J=9.60, 4.55 Hz, 1H), 4.39-4.48 (m, J=6.57, 4.55, 2.53, 2.53 Hz, 1H), 5.11 (s, 2H), 7.26-7.39 (m, 5H).

Step D: Preparation of benzyl 3-azido-1-oxa-8-azaspiro[4.5]decane-8-carboxylate

Benzyl 3-hydroxy-1-oxa-8-azaspiro[4.5]decane-8-carboxylate (10 g, 34.31 mmol) was dissolved in Pyridine (22 mL) under nitrogen then cooled down to 0° C. Methanesulfonyl chloride (8.76 mL, 113.2 mmol) was added. The reaction mixture was stirred at room temperature overnight. (Note: Precipitation was formed.). After the reaction was completed, it was diluted with EtOAc then washed with H$_2$O (40 mL), HCl (1N, 30 mL), and brine (30 mL). The aqueous layers were back extracted with EtOAc (2×). The combined organic layers were dried over MgSO$_4$, filtered and concentrated to give benzyl 3-((methylsulfonyl)oxy)-1-oxa-8-azaspiro[4.5]decane-8-carboxylate as a brown oil which was used in the next step without further purification. LC/MS m/z=370.0 [M+H]$^+$.

Benzyl 3-((methylsulfonyl)oxy)-1-oxa-8-azaspiro[4.5]decane-8-carboxylate from the previous step was dissolved in DMF (30 mL) under nitrogen. Sodium azide (5.13 g, 78.91 mmol) was added. The reaction was heated at 50° C. overnight. After the reaction was cooled down to room temperature, it was diluted with EtOAc and washed water and brine. The aqueous layer was back extracted with EtOAc (2×). The combined organic layers were dried over MgSO$_4$, filtered and concentrated. The residue was purified by silica gel column chromatography to give the title compound (10.02 g, 92%). LC/MS m/z=317.2 [M+H]$^+$; $^1$H NMR (400 MHz, CDCl$_3$) δ ppm 1.57-1.70 (m, 3H), 1.83 (d, J=12.88 Hz, 1H), 1.88 (dd, J=13.64, 2.27 Hz, 1H), 2.03 (dd, J=13.64, 7.07 Hz, 1H), 3.30-3.41 (m, 2H), 3.78 (br. s., 2H), 3.85 (dd, J=10.36, 2.78 Hz, 1H), 3.97 (dd, J=9.09, 6.32 Hz, 1H), 4.15-4.21 (m, 1H), 5.14 (s, 2H), 7.29-7.41 (m, 5H).

Step E: Preparation of benzyl 3-((tert-butoxycarbonyl)amino)-1-oxa-8-azaspiro[4.5]decane-8-carboxylate To a solution of benzyl 3-azido-1-oxa-8-azaspiro[4.5]decane-8-carboxylate (13.11 g, 41.43 mmol) in THF (220 mL) were added acetic acid (16.59 mL, 290.0 mmol) and zinc dust (10.84 g, 165.7 mmol). The reaction was heated at 70° C. for 1 h. After the reaction was cooled down to room temperature, it was neutralized with NaHCO$_3$ to pH 7 then passed through a pad of Celite®, and washed with EtOAc and IPA/DCM (30%). The aqueous layer was back extracted with EtOAc (3×). (Note: The product was still remained in the aqueous layer which was then back extracted with IPA/DCM (30%). The combined extracts were dried over MgSO$_4$ and concentrated to give benzyl 3-amino-1-oxa-8-azaspiro[4.5]decane-8-carboxylate, as a white gummy solid which was used in the next step without further purification. LC/MS m/z=291.2 [M+H]$^+$.

The benzyl 3-amino-1-oxa-8-azaspiro[4.5]decane-8-carboxylate from the previous step was dissolved in CH$_2$Cl$_2$ (220 mL) followed by addition of DIEA (14.43 mL, 82.86 mmol) and Boc$_2$O (13.56 g, 62.15 mmol). The reaction mixture was stirred at room temperature overnight. After the reaction was completed, the solvent was removed then the residue was purified by flash column chromatography to give the title compound (11.55 g, 71%) as a white solid. LC/MS m/z=391.4 [M+H]$^+$; $^1$H NMR (400 MHz, CD$_3$OD) δ ppm 1.43 (s, 9H), 1.52-1.58 (m, 1H), 1.59-1.76 (m, 4H), 2.10 (dd, J=13.14, 8.08 Hz, 1H), 3.39 (br. s., 2H), 3.58 (dd, J=9.09, 5.56 Hz, 1H), 3.63-3.72 (m, 2H), 3.99 (dd, J=8.97, 6.19 Hz, 1H), 4.10-4.20 (m, 1H), 5.11 (s, 2H), 6.85 (br. s., 1H), 7.26-7.40 (m, 5H).

Step F: Chiral HPLC Resolution of Enantiomers of benzyl 3-((tert-butoxycarbonyl)amino)-1-oxa-8-azaspiro[4.5]decane-8-carboxylate The racemic benzyl 3-((tert-butoxycarbonyl)amino)-1-oxa-8-azaspiro[4.5]decane-8-carboxylate (11.55 g, 29.58 mmol) was resolved to give two enantiomers by normal phase preparative chiral HPLC under the following conditions:

Column: Chiralcel OD, 5 cm×50 cm ID, 20 μm particle size

Eluent: EtOH/Hex (10%) with TEA (0.1%)

Injection: 800 mg/6 mL per injection

Gradient: isocratic

Flow rate: 60 m/min

Detector: 250 nm

Retention time: 1$^{st}$ enantiomer 28.978 min, 2$^{nd}$ enantiomer 39.382 min

The 1$^{st}$ enantiomer (28.978 min on Chiralcel OD column) and 2$^{nd}$ enantiomer (39.382 min on Chiralcel OD column) was checked by analytical normal phase preparative chiral HPLC under the following conditions:

Column: ChiralPak IC, 250×20 mm ID, 5 μm particle size

Eluent: EtOH/Hex (10%) with TEA (0.1%)

Injection: 2 mg/mL per injection

Gradient: isocratic

Flow rate: 1 mL/min

Detector: 250 nm

Retention time of 1$^{st}$ enantiomer (28.978 min on Chiralcel OD column) & % ee: 31.13 min; 100% ee.

Retention time of 2$^{nd}$ enantiomer (39.382 min on Chiralcel OD column) & % ee: 28.14 min; 100% ee.

(S)-benzyl 3-((tert-butoxycarbonyl)amino)-1-oxa-8-azaspiro[4.5]decane-8-carboxylate (1$^{st}$ enantiomer, 5.14 g, 45% yield, 100% ee). $^1$H NMR (400 MHz, CD$_3$OD-d) ppm 1.43 (s, 9H), 1.49-1.59 (m, 1H), 1.59-1.75 (m, 4H), 2.10 (dd, J=13.14, 8.08 Hz, 1H), 3.38 (br. s., 2H), 3.58 (dd, J=9.09, 5.56 Hz, 1H), 3.63-3.72 (m, 2H), 3.99 (dd, J=9.09, 6.32 Hz, 1H), 4.10-4.20 (m, 1H), 5.11 (s, 2H), 7.26-7.39 (m, 5H).

(R)-benzyl 3-((tert-butoxycarbonyl)amino)-1-oxa-8-azaspiro[4.5]decane-8-carboxylate (2$^{nd}$ enantiomer, 4.86 g, 42% yield, 100% ee): $^1$H NMR (400 MHz, CD$_3$OD-d) ppm 1.43 (s, 9H), 1.49-1.58 (m, 1H), 1.60-1.75 (m, 4H), 2.10 (dd, J=13.14, 8.08 Hz, 1H), 3.37 (br. s., 2H), 3.58 (dd, J=9.09, 5.56 Hz, 1H), 3.63-3.72 (m, 2H), 3.99 (dd, J=9.09, 6.32 Hz, 1H), 4.10-4.20 (m, 1H), 5.11 (s, 2H), 7.24-7.40 (m, 5H).

The stereochemistry was elucidated using Mosher amide as show in Example 1.2 and Example 1.3, respectively.

Example 1.2: Preparation of (S)-3,3,3-trifluoro-2-methoxy-N—((S)-8-(naphthalen-2-ylsulfonyl)-1-oxa-8-azaspiro[4.5]decan-3-yl)-2-phenylpropanamide and (R)-3,3,3-trifluoro-2-methoxy-N—((S)-8-(naphthalen-2-ylsulfonyl)-1-oxa-8-azaspiro[4.5]decan-3-yl)-2-phenylpropanamide Step A: Preparation of One Enantiomer of tert-butyl (8-(naphthalen-2-ylsulfonyl)-1-oxa-8-azaspiro[4.5]decan-3-yl)carbamate (from $1^{st}$ Enantiomer)

The $1^{st}$ enantiomer of benzyl 3-((tert-butoxycarbonyl)amino)-1-oxa-8-azaspiro[4.5]decane-8-carboxylate (1.13 g, 2.89 mmol) from chiral HPLC in Example 1.1 was dissolved in MeOH (10 mL). palladium/C (30.72 mg, 0.289 mmol) and a $H_2$ balloon were applied. The reaction was stirred at room temperature overnight at room temperature. The next day, the $H_2$ balloon was removed. The reaction mixture was filtered through a pad of Celite®, washed with EtOAc and MeOH, and concentrated to give an enantiomer of tert-butyl 1-oxa-8-azaspiro[4.5]decan-3-ylcarbamate (0.64 g, 86%) as a colorless gum which was used in the next step without further purification. LC/MS m/z=257.4 [M+H]$^+$; $^1$H NMR (400 MHz, DMSO-$d_6$) δ ppm 1.37 (s, 9H), 1.39-1.42 (m, 2H), 1.46-1.59 (m, 4H), 1.95 (dd, J=12.63, 8.34 Hz, 1H), 2.70-2.82 (m, 2H), 3.17 (d, J=2.78 Hz, 1H), 3.40 (dd, J=8.59, 6.57 Hz, 1H), 3.84 (t, J=8.00 Hz, 1H), 3.93-4.10 (m, 1H), 6.99 (d, J=5.56 Hz, 1H).

The above obtained enantiomer of tert-butyl 1-oxa-8-azaspiro[4.5]decan-3-ylcarbamate (0.64 g, 2.49 mmol) was dissolved in $CH_2Cl_2$ (12 mL). DIEA (1.00 mL, 5.77 mmol) was added then the resulting mixture was cooled on an ice bath. To the cooled solution was added naphthalene-2-sulfonyl chloride (0.92 g, 4.04 mmol). The reaction was warmed up to room temperature and stirred overnight. The reaction mixture was concentrated. The residue was purified by silica gel column chromatography to give the title compound (1.12 g, 87%) as a white solid. LC/MS m/z=447.4 [M+H]$^+$; $^1$H NMR (400 MHz, DMSO-$d_6$) δ ppm 1.34 (s, 9H), 1.52 (dd, J=13.01, 6.44 Hz, 1H), 1.57-1.63 (m, 2H), 1.64-1.71 (m, 2H), 1.89 (dd, J=12.88, 8.34 Hz, 1H), 2.53-2.56 (m, 1H), 2.59-2.71 (m, 2H), 3.33 (d, J=1.77 Hz, 2H), 3.70 (dd, J=8.97, 6.44 Hz, 1H), 3.93 (br. s., 1H), 6.97 (br. s., 1H), 7.66-7.78 (m, 3H), 8.08 (d, J=8.08 Hz, 1H), 8.17 (d, J=8.84 Hz, 1H), 8.21 (d, J=7.83 Hz, 1H), 8.42 (d, J=1.52 Hz, 1H).

Step B: Preparation of One Enantiomer of 8-(naphthalen-2-ylsulfonyl)-1-oxa-8-azaspiro[4.5]decan-3-amine To a solution of tert-butyl (8-(naphthalen-2-ylsulfonyl)-1-oxa-8-azaspiro[4.5]decan-3-yl)carbamate (1.12 g, 2.50 mmol) in $CH_2Cl_2$ (20 mL) at room temperature was added 4N HCl (in dioxane, 6.25 mL, 25.01 mmol). The reaction mixture was stirred at room temperature for 16 h. After the reaction was completed, it was concentrated to give the title compound (1.19 g, 125%) as a white solid which was used in the next step without further purification. LC/MS m/z=347.0 [M+H]$^+$; $^1$H NMR (400 MHz, DMSO-$d_6$) δ ppm 1.52-1.72 (m, 3H), 1.73-1.90 (m, 2H), 2.06 (dd, J=13.64, 8.08 Hz, 1H), 2.53-2.70 (m, 2H), 3.33-3.44 (m, 2H), 3.58 (dd, J=9.60, 4.29 Hz, 1H), 3.69-3.82 (m, 2H), 7.64-7.83 (m, 3H), 8.09 (d, J=8.08 Hz, 1H), 8.13-8.27 (m, 5H), 8.44 (d, J=1.52 Hz, 1H).

Step C: Preparation of (S)-3,3,3-trifluoro-2-methoxy-N—((S)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 μmol) and DIEA (7.542 μL, 43.30 μmol) in THF (1 mL) was added (R)-3,3,3-trifluoro-2-methoxy-2-phenylpropanoyl chloride (7.92 mg, 31.34 μmol) then stirred for 1.5 h. The reaction was quenched with water then extracted with DCM. The aqueous layer was back extracted with DCM (3×). The combined organics were dried over $MgSO_4$, filtered and concentrated. The residue was purified by flash column chromatography to give the title compound (12 mg, 82%) as a white solid. The stereochemistry of the title compound was elucidated by NMR. LC/MS m/z=563.4 [M+H]$^+$; $^1$H NMR (400 MHz, CDCl$_3$) δ ppm 1.53-1.64 (m, 3H), 1.67-1.76 (m, 2H), 2.07 (dd, J=13.52, 7.45 Hz, 1H), 2.79 (qd, J=5.68, 3.41 Hz, 2H), 3.39 (t, J=1.52 Hz, 3H), 3.49 (td, J=11.62, 8.59 Hz, 2H), 3.59 (dd, J=9.73, 3.41 Hz, 1H), 3.89 (dd, J=9.73, 5.43 Hz, 1H), 4.42-4.51 (m, J=7.52, 5.37, 3.66, 3.66 Hz, 1H), 6.81 (d, J=7.33 Hz, 1H), 7.36-7.43 (m, 3H), 7.46 (d, J=2.27 Hz, 2H), 7.64 (qd, J=7.71, 7.45 Hz, 2H), 7.75 (dd, J=8.59, 1.77 Hz, 1H), 7.93 (d, J=7.83 Hz, 1H), 7.98 (d, J=8.34 Hz, 2H), 8.33 (d, J=1.26 Hz, 1H).

Step D: Preparation of (R)-3,3,3-trifluoro-2-methoxy-N—((S)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 μmol) and DIEA (6.82 μL, 39.17 μmol) in THF (1 mL) was added (S)-3,3,3-trifluoro-2-methoxy-2-phenylpropanoyl chloride (7.92 mg, 31.34 μmol). The reaction was stirred at room temperature for 1.5 h. It was quenched with water then extracted with DCM. The aqueous layer was back extracted with DCM (3×). The combined organic layers were dried over $MgSO_4$, filtered and concentrated. The residue was purified by flash column chromatography to give the title compound (12 mg, 82%) as a white solid. The stereochemistry of the title compound was elucidated by NMR. LC/MS m/z=563.4 [M+H]$^1$; $^1$H NMR (400 MHz, CDCl$_3$) δ ppm 1.64-1.80 (m, 4H), 1.82-1.92 (m, 1H), 2.13 (dd, J=13.52, 7.45 Hz, 1H), 2.78-2.90 (m, 2H), 3.33 (d, J=1.26 Hz, 3H), 3.47-3.60 (m, 3H), 3.88 (dd, J=9.85, 5.56 Hz, 1H), 4.48 (dq, J=5.24, 3.81 Hz, 1H), 6.98 (d, J=7.33 Hz, 1H), 7.39 (d, J=2.78 Hz, 3H), 7.42-7.48 (m, 2H), 7.64 (qd, J=7.71, 7.45 Hz, 2H), 7.76 (dd, J=8.59, 1.77 Hz, 1H), 7.93 (d, J=8.08 Hz, 1H), 7.98 (d, J=8.34 Hz, 2H), 8.34 (d, J=1.26 Hz, 1H).

Example 1.3: Preparation of (S)-3,3,3-trifluoro-2-methoxy-N—((R)-8-(naphthalen-2-ylsulfonyl)-1-oxa-8-azaspiro[4.5]decan-3-yl)-2-phenylpropanamide and (R)-3,3,3-trifluoro-2-methoxy-N—((R)-8-(naphthalen-2-ylsulfonyl)-1-oxa-8-azaspiro[4.5]decan-3-yl)-2-phenylpropanamide Step A: Preparation of One Enantiomer of tert-butyl (8-(naphthalen-2-ylsulfonyl)-1-oxa-8-azaspiro[4.5]decan-3-yl)carbamate (from $2^{nd}$ Enantiomer)

The $2^{nd}$ enantiomer of benzyl 3-((tert-butoxycarbonyl)amino)-1-oxa-8-azaspiro[4.5]decane-8-carboxylate (1.14 g, 2.92 mmol) from chiral HPLC in Example 1.1 was dissolved in MeOH (10 mL). To the resulting solution palladium/C (31.07 mg, 0.29 mmol) and balloon $H_2$ were applied. The reaction was stirred at room temperature for 16 h. The next day the $H_2$ balloon was removed. The reaction mixture was filtered through a pad of Celite®, washed with EtOAc and MeOH, and concentrated to give an enantiomer of tert-butyl 1-oxa-8-azaspiro[4.5]decan-3-ylcarbamate (Peak 2, 735 mg, 98%) as a colorless gum which was used in the next step without further purification. LC/MS m/z=257.4 [M+H]$^+$; $^1$H NMR (400 MHz, DMSO-$d_6$) δ ppm 1.34-1.45 (m, 11H), 1.52 (dd, J=6.69, 3.41 Hz, 4H), 1.96 (dd, J=12.63, 8.34 Hz, 1H), 2.51-2.59 (m, 2H), 2.71-2.84 (m, 2H), 3.41 (dd, J=8.59, 6.57 Hz, 1H), 3.83 (dd, J=8.59, 6.82 Hz, 1H), 3.91-4.07 (m, 1H), 6.99 (br. s., 1H).

The above obtained enantiomer of tert-butyl 1-oxa-8-azaspiro[4.5]decan-3-ylcarbamate was re-dissolved in $CH_2Cl_2$ (12 mL) following by addition of DIEA (1.02 mL, 5.84 mmol). The reaction was cooled on an ice bath then naphthalene-2-sulfonyl chloride (0.93 g, 4.09 mmol) was added. The resulting mixture was stirred at room temperature overnight then concentrated. The residue was purified by silica gel column chromatography to yield the title compound (1.07 g, 82%) as a white solid. LC/MS m/z=447.4 [M+H]$^+$; $^1$H NMR (400 MHz, DMSO-$d_6$) δ ppm 1.34 (s, 9H), 1.52 (dd, J=12.88, 6.32 Hz, 1H), 1.60 (t, J=4.55 Hz, 2H), 1.65-1.72 (m, 2H), 1.89 (dd, J=12.88, 8.34 Hz, 1H), 2.60-2.72 (m, 2H), 3.70 (dd, J=8.72, 6.44 Hz, 1H), 3.88-3.99 (m, 1H), 6.98 (br. s., 1H), 7.66-7.77 (m, 3H), 8.08 (d, J=8.34 Hz, 1H), 8.17 (d, J=8.84 Hz, 1H), 8.21 (d, J=8.08 Hz, 1H), 8.42 (d, J=1.26 Hz, 1H).

Step B: Preparation of One Enantiomer of 8-(naphthalen-2-ylsulfonyl)-1-oxa-8-azaspiro[4.5]decan-3-amine To a solution of tert-butyl (8-(naphthalen-2-ylsulfonyl)-1-oxa-8-azaspiro[4.5]decan-3-yl)carbamate (1.07 g, 2.39 mmol) in DCM at room temperature was added HCl (4N in dioxane, 5.97 mL, 23.89 mmol).

The reaction was stirred at room temperature for 16 h. After the reaction was completed, it was concentrated to give the title compound (934 mg, 102%) as a white solid which was used in the next step without further purification. LC/MS m/z=347.2 [M+H]$^+$; $^1$H NMR (400 MHz, DMSO-$d_6$) δ ppm 1.53-1.72 (m, 3H), 1.80 (d, J=3.79 Hz, 2H), 2.01-2.12 (m, 1H), 2.54-2.73 (m, 6H), 3.39 (d, J=15.41 Hz, 3H), 3.57 (d, J=5.05 Hz, 1H), 3.76 (d, J=8.84 Hz, 2H), 7.66-7.80 (m, 3H), 8.09 (d, J=8.08 Hz, 1H), 8.17 (d, J=8.84 Hz, 1H), 8.21 (d, J=8.08 Hz, 1H), 8.44 (s, 1H).

Step C: Preparation of (S)-3,3,3-trifluoro-2-methoxy-N—((R)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 μmol) and DIEA (7.54 μL, 43.30 μmol) in THF (1 mL) was added (R)-3,3,3-trifluoro-2-methoxy-2-phenylpropanoyl chloride (7.92 mg, 31.34 μmol). The reaction was stirred for 1.5 h at room temperature. Then the reaction was quenched with water and extracted with DCM. The aqueous layer was back extracted with DCM (3×). The combined organics were dried over MgSO$_4$, filtered and concentrated. The residue was purified by flash column chromatography to yield the title compound (11 mg, 75%) as a white solid. The stereochemistry of the title compound was elucidated by NMR. LC/MS m/z=563.2 [M+H]$^+$; $^1$H NMR (400 MHz, CDCl$_3$) δ ppm 1.65-1.79 (m, 4H), 1.85 (dd, J=10.99, 4.42 Hz, 1H), 2.13 (dd, J=13.64, 7.58 Hz, 1H), 2.79-2.90 (m, 2H), 3.33 (d, J=1.52 Hz, 3H), 3.47-3.60 (m, 3H), 3.88 (dd, J=9.73, 5.43 Hz, 1H), 4.48 (dq, J=5.24, 3.81 Hz, 1H), 6.98 (d, J=7.33 Hz, 1H), 7.39 (d, J=2.78 Hz, 3H), 7.44 (q, J=3.79 Hz, 2H), 7.64 (quin, J=7.64 Hz, 2H), 7.76 (dd, J=8.72, 1.89 Hz, 1H), 7.93 (d, J=7.83 Hz, 1H), 7.98 (d, J=8.34 Hz, 2H), 8.34 (d, J=1.26 Hz, 1H).

Step D: Preparation of (R)-3,3,3-trifluoro-2-methoxy-N—((R)-8-(naphthalen-2-ylsulfonyl)-1-oxa-8-azaspiro[4.5]decan-3-yl)-2-phenylpropanamide To a solution of the above obtained 8-(naphthalen-2-ylsulfonyl)-1-oxa-8-azaspiro[4.5]decan-3-amine (10 mg, 26.12 μmol) and DIEA (7.54 μL, 43.30 μmol) in THF (1 mL) was added (S)-3,3,3-trifluoro-2-methoxy-2-phenylpropanoyl chloride (7.92 mg, 31.34 μmol). The reaction was stirred at room temperature for 1.5 h. Then it was quenched with water and extracted with DCM. The aqueous was back extracted with DCM (3×). The combined organic layers were dried over MgSO$_4$, filtered and concentrated. The residue was purified by flash column chromatography to give the title compound (12 mg, 82%) as a white solid. The stereochemistry of the title compound was elucidated by NMR. LC/MS m/z=563.2 [M+H]$^+$; $^1$H NMR (400 MHz, CDCl$_3$) δ ppm 1.52-1.66 (m, 2H), 1.67-1.79 (m, 3H), 2.07 (dd, J=13.52, 7.45 Hz, 1H), 2.72-2.89 (m, J=5.81, 5.62, 5.62, 3.41 Hz, 2H), 3.39 (s, 3H), 3.49 (ddd, J=15.98, 11.94, 3.92 Hz, 2H), 3.59 (dd, J=9.60, 3.54 Hz, 1H), 3.89 (dd, J=9.73, 5.43 Hz, 1H), 4.39-4.54 (m, 1H), 6.81 (d, J=7.33 Hz, 1H), 7.35-7.44 (m, 3H), 7.46 (d, J=2.27 Hz, 2H), 7.66 (dd, J=7.71, 1.39 Hz, 2H), 7.75 (dd, J=8.59, 1.77 Hz, 1H), 7.93 (d, J=7.83 Hz, 1H), 7.97 (d, J=8.34 Hz, 2H), 8.33 (s, 1H).

Example 1.4: Preparation of (R)-benzyl 3-((tert-butoxycarbonyl)amino)-1-oxa-8-azaspiro[4.5]decane-8-carboxylate Step A: Preparation of (R)-benzyl 3-amino-1-oxa-8-azaspiro[4.5]decane-8-carboxylate To a solution of benzyl 3-amino-1-oxa-8-azaspiro[4.5]decane-8-carboxylate (126 g, 434 mmol, 1.0 eq.) in MeOH (2.5 L) was added di-p-toluoyl-D-tartaric acid (37 g, 95.5 mmol, 0.44 eq.) and the mixture was heated to 78° C. After stirred at this temperature for 5 h, the mixture was cooled to 25° C. slowly and stirred at this temperature for 1 h. The white solid was collected by filtration and the solid was washed with MeOH (500 mL). The filter cake was added to NaHCO$_3$ aqueous solution (500 mL) and extracted with DCM (1 L×2). The combined organics were washed with brine, dried over Na$_2$SO$_4$, filtered and concentrated to give the title compound (54 g) which was analyzed by SFC (AD-3S_4_25_3ML Column: Chiralpak AD-3 100×4.6 mm I.D., 3 um Mobile phase: 25% isopropanol (0.05% DEA) in CO$_2$ Flow rate: 3 mL/min Wavelength: 220 nm) to have an ee value of 93%. The above material (42 g, 145 mmol, 1.0 eq.) was dissolved with MeOH (800 mL), followed by the addition of di-p-toluoyl-D-tartaric acid (27 g, 69 mmol, 0.96 eq.). The mixture was heated to 78° C. After stirred at this temperature for 5 h, the mixture was cooled to 25° C. slowly and stirred at this temperature for 1 h. The white solid was collected by filtration, washed with EtOH (500 mL). The cake was added to NaHCO₃ aqueous (500 mL) and extracted with DCM (1 L×2). The combined organics were washed with brine, dried over Na₂SO₄, filtered and concentrated to give the title compound (36 g, 97.5% ee) as colorless oil.

Step B: Preparation of (R)-benzyl 3-((tert-butoxycarbonyl)amino)-1-oxa-8-azaspiro[4.5]decane-8-carboxylate To a solution of (R)-benzyl 3-amino-1-oxa-8-azaspiro[4.5]decane-8-carboxylate (36 g, 124 mmol, 1.0 eq.) in DCM (600 mL) were added TEA (25 g, 248 mmol, 2.0 eq.) and Boc₂O (30 g, 136 mmol, 1.1 eq.). The reaction was stirred at 20° C. for 6 h. The mixture was washed with cold HC aqueous solution (1N, 200 mL) and brine, dried over Na₂SO₄, filtered and concentrated. The residue was triturated with petroleum ether to give the title compound (44 g, 113 mmol, 91%) as a white solid. LC/MS m/z=335.1 (M-tBu+H); $^1$H NMR (400 MHz, DMSO-d₆) δ 7.38-7.32 (m, 5H), 7.10-7.09 (d, J=6.0 Hz, 1H), 5.06 (s, 2H), 4.04 (m, 1H), 3.89 (t, J=6.4 Hz, 1H), 3.53-3. (m, 3H), 3.39-3.36 (m, 2H), 2.69 (m, 2H), 1.99 (m, 1H), 1.62-1.48 (m, 5H), 1.38 (s, 9H).

SFC: EW2734-5-P1D (AD-3S_5_40_3ML Column: Chiralpak AD-3 100×4.6 mm I.D., 3 um Mobile phase: 40% ethanol (0.05% DEA) in CO₂ Flow rate: 3 mL/min Wave length: 220 nm) 100% ee.

Example 1.5: Preparation of (S)-benzyl 3-((tert-butoxycarbonyl)amino)-1-oxa-8-azaspiro[4.5]decane-8-carboxylate Step A: Preparation of (S)-benzyl 3-amino-1-oxa-8-azaspiro[4.5]decane-8-carboxylate To a solution of benzyl 3-amino-1-oxa-8-azaspiro[4.5]decane-8-carboxylate (97 g, 0.334 mol, 1.0 eq.) in MeOH (2.5 L) was added di-p-toluoyl-L-tartaric acid (40 g, 104 mmol, 0.62 eq.) and the mixture was heated to 78° C. After stirred at this temperature for 5 h, the mixture was cooled to 25° C. slowly and stirred at this temperature for 1 h. The white solid was collected by filtration and the solid was washed with MeOH (250 mL). The filter cake was added to NaHCO₃ aqueous solution (300 mL) and extracted with DCM (500 mL×2). The combined organics were washed with brine, dried over Na₂SO₄, filtered and concentrated to give the residue (45 g) which was analyzed by SFC (AD-3S_4_25_3ML Column: Chiralpak AD-3 100×4.6 mm I.D., 3 um Mobile phase: 25% isopropanol (0.05% DEA) in CO₂ Flow rate: 3 mL/min, wavelength: 220 nm) to have an ee value of 95%. The above material (45 g, 150 mmol, 1.0 eq.) was dissolved with MeOH (1.2 L), followed by the addition of di-p-toluoyl-L-tartaric acid (28 g, 72 mmol, 0.96 eq.) and the mixture was heated to 78° C. After stirred at this temperature for 5 h, the mixture was cooled to 25° C. slowly and stirred at this temperature for 1 h. The white solid was collected by filtration, washed with EtOH (500 mL). The cake was added to NaHCO₃ aqueous solution (300 mL) and extracted with DCM (500 mL×2). The combined organics were washed with brine, dried over Na₂SO₄, filtered and concentrated to give the title compound (40 g, 97.5% ee) as a colorless oil.

Step B: Preparation of (S)-benzyl 3-((tert-butoxycarbonyl)amino)-1-oxa-8-azaspiro[4.5]decane-8-carboxylate To a solution of (S)-benzyl 3-amino-1-oxa-8-azaspiro[4.5]decane-8-carboxylate (40 g, 138 mmol, 1.0 eq.) in DCM (600 mL) were added TEA (28 g, 276 mmol, 2.0 eq.) and Boc₂O (33 g, 152 mmol, 1.1 eq.). The reaction was stirred at 20° C. for 6 h. The mixture was washed with cold HCl aq. (1 N, 200 mL) and brine, dried over Na₂SO₄, filtered and concentrated. The residue was triturated with petroleum ether to give the title compound (51 g, 131 mmol, 95%) as a white solid. LC/MS m/z=335.1 (M-tBu+H); $^1$H NMR (400 MHz DMSO-d₆) δ 7.38-7.32 (m, 5H), 7.10-7.09 (d, J=6.0 Hz, 1H), 5.06 (s, 2H), 4.04 (m, 1H), 3.89 (t, J=6.4 Hz, 1H), 3.53-3. (m, 3H), 3.39-3.36 (m, 2H), 2.69 (m, 2H), 1.99 (m, 1H), 1.62-1.48 (m, 5H), 1.38 (s, 9H).

SFC: EW2734-5-P1C (AD-3S_5_40_3ML Column: Chiralpak AD-3 100×4.6 mm I.D., 3 um Mobile phase: 40% ethanol (0.05% DEA) in CO₂ Flow rate: 3 mL/min Wave length: 220 nm) 100% ee.

Example 1.6: Preparation of (S)—N-methyl-3-(oxiran-2-ylmethoxy)benzenesulfonamide Step A: Preparation of 3-methoxy-N-methylbenzenesulfonamide 3-Methoxybenzene-1-sulfonyl chloride (2.831 mL, 20 mmol) was added slowly to 40% aqueous methanamine (34.43 mL, 400.0 mmol) via syringe. The reaction was stirred for 1 hour, concentrated under vacuum, and diluted with EtOAc. The organic layer was washed with aqueous NaHCO₃ and brine, dried (MgSO₄), filtered and concentrated to give title compound as a yellow oil (4.47 g, 111% yield). LCMS m/z=202.2 [M+H]$^+$.

Step B: Preparation of 3-hydroxy-N-methylbenzenesulfonamide

To a solution of 3-methoxy-N-methylbenzenesulfonamide (4.025 g, 20 mmol) in CH₂Cl₂ (20 mL) Boron Tribromide (20.00 mL, 20.00 mmol) was added slowly via syringe and the reaction was stirred for 1 hour. Additional Boron Tribromide (20.00 mL, 20.00 mmol) was added and the reaction was stirred overnight. The reaction was quenched with water and diluted with EtOAc. The organic layer was washed with water (2×) and brine, dried (MgSO₄), filtered and concentrated. The residue was purified via column chromatography (1:1 EtOAc/hexane) to give the title compound as a white solid (2.8 g, 75% yield). LCMS m/z=188.4 [M+H]$^+$.

Step C: Preparation of (S)—N-methyl-3-(oxiran-2-ylmethoxy)benzenesulfonamide

To a solution of 3-hydroxy-N-methylbenzenesulfonamide (1.263 g, 6.746 mmol) in acetone (20 mL) was added Potassium carbonate (3.729 g, 26.98 mmol). After stirring for 10 minutes (S)-oxiran-2-ylmethyl 3-nitrobenzenesulfonate (1.749 g, 6.746 mmol) was added. The reaction was sealed and heated to 70° C. for 2 hours, cooled to RT, filtered and concentrated. The residue was purified via column chromatography (1:3 EtOAc/hexane) to give 1.142 g (75% yield) of a clear oil as the title compound. LCMS m/z=244.2 [M+H]$^+$.

Example 1.7: Preparation of (S)-3-(oxiran-2-ylmethoxy)benzenesulfonamide

Step A: Preparation of disulfanediylbis(3,1-phenylene) diacetate

To a mixture of 3,3'-disulfanediyldiphenol (2.503 g, 10 mmol) and DIEA (5.225 mL, 30.00 mmol) in DCM (10 mL)

was added Acetyl chloride (2.355 g, 30.00 mmol). The reaction was stirred for 1 hour and diluted with EtOAc. The organic layer was washed with water (3×) and brine, dried (MgSO$_4$), filtered and concentrated. The residue was purified via column chromatography (1:3 EtOAc/hexane) to give the title compound as a clear oil (3.2 g, 96% yield). LCMS m/z=335.0 [M+H]$^+$.

Step B: Preparation of 3-hydroxybenzenesulfonyl chloride

To a solution of disulfanediylbis(3,1-phenylene) diacetate (3.208 g, 9.593 mmol) in AcOH (10 mL)/H$_2$O (3.333 mL) was added NCS (6.405 g, 47.97 mmol). The reaction was stirred for 1 hour, concentrated under vacuum and taken up in EtOAc. The organic layer was washed with water (3×) and brine, dried (MgSO$_4$), filtered and concentrated. The residue was purified via column chromatography (1:3 EtOAc/hexane) to give the title compound as a waxy white solid (1.94 g, 52% yield). LCMS m/z=193.0 [M+H]$^+$.

Step C: Preparation of 3-hydroxybenzenesulfonamide

To a solution of 3-hydroxybenzene-1-sulfonyl chloride (1.938 g, 10.06 mmol) in THF (30 mL) was added 7M aqueous ammonia (14.37 mL, 100.6 mmol). The reaction was stirred for 1 hour, concentrated under vacuum and taken up in EtOAc. The organic layer was washed with NaHCO$_3$ (3×) and brine, dried (MgSO$_4$), filtered and concentrated. The residue was purified via column chromatography (1:1 EtOAc/hexane) to give the title compound as a white solid (0.51 g, 29% yield). LCMS m/z=174.2 [M+H]$^+$.

Step D: Preparation of (S)-3-(oxiran-2-ylmethoxy)benzenesulfonamide

To a solution of 3-hydroxybenzenesulfonamide (0.511 g, 2.951 mmol) in acetone (20 mL) was added Potassium carbonate (1.631 g, 11.80 mmol). After stirring for 10 minutes, (S)-oxiran-2-ylmethyl 3-nitrobenzenesulfonate (0.765 g, 2.951 mmol) was added. The reaction was sealed and heated to 70° C. for 2 hours, filtered and concentrated. The residue was purified via column chromatography (1:1 EtOAc/hexane) to give the title compound as a clear oil (140 mg, 21% yield). LCMS m/z=459.0 [2M+H]$^+$.

Example 1.8: Preparation of 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide (Compound 505)

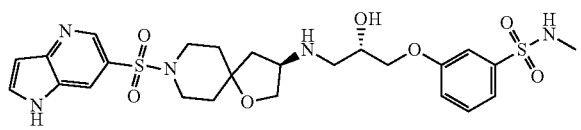 [SMILES: CNS(=O)(=O)c1cccc(OC[C@@H](O)CN[C@H]2COC3(CCN(S(=O)(=O)c4cnc5cc[nH]c5c4)CC3)C2)c1]

Step A: Preparation of benzyl (R)-3-(((S)-2-hydroxy-3-(3-(N-methylsulfamoyl)phenoxy)propyl)amino)-1-oxa-8-azaspiro[4.5]decane-8-carboxylate To a solution of (R)-benzyl 3-amino-1-oxa-8-azaspiro[4.5]decane-8-carboxylate (8.00 g, 27.55 mmol) in dioxane (30 mL) was added a solution of (S)—N-methyl-3-(oxiran-2-ylmethoxy)benzenesulfonamide (3.351 g, 13.78 mmol) in EtOH (8 mL). The reaction was stirred for 10 minutes, then sealed and heated to 90° C. for 2 hours. The mixture was concentrated and the residue was purified via column chromatography (1:9 MeOH/DCM) to give the title compound as a white solid (3.35 g, 45.6% yield). LC/MS m/z=534.4 [M+H]$^+$.

Step B: Preparation of benzyl (R)-3-((tert-butoxycarbonyl)((S)-2-hydroxy-3-(3-(N-methylsulfamoyl)phenoxy)propyl)amino)-1-oxa-8-azaspiro[4.5]decane-8-carboxylate To a solution of benzyl (R)-3-(((S)-2-hydroxy-3-(3-(N-methylsulfamoyl)phenoxy)propyl)amino)-1-oxa-8-azaspiro[4.5]decane-8-carboxylate (3.34 g, 6.259 mmol) in DCM (20 mL) was added (Boc)$_2$O (1.639 g, 7.511 mmol). The reaction was stirred for 18 hours and diluted with EtOAc. The organic layer was washed with water (3×) and brine, dried (MgSO$_4$), filtered and concentrated. The residue was purified via column chromatography (1:1 EtOAc/hexane) to give the title compound as a white solid (3.41 g, 86.1% yield). LC/MS m/z=634.8 [M+H]$^+$.

Step C: Preparation of tert-butyl ((S)-2-hydroxy-3-(3-(N-methylsulfamoyl)phenoxy)propyl)((R)-1-oxa-8-azaspiro[4.5]decan-3-yl)carbamate To a solution of benzyl (R)-3-((tert-butoxycarbonyl)((S)-2-hydroxy-3-(3-(N-methylsulfamoyl)phenoxy)propyl)amino)-1-oxa-8-azaspiro[4.5]decane-8-carboxylate (3.41 g, 5.381 mmol) in MeOH (20 mL) was added palladium/C (0.341 g, 0.320 mmol). A balloon of Hydrogen was added. The reaction was stirred for 2 hours, filtered and concentrated under vacuum to give the title compound as a white solid (2.69 g, 100% yield). LC/MS m/z=500.0 [M+H]$^+$.

Step D: Preparation of 6-(benzylthio)-1H-pyrrolo[3,2-b]pyridine

A mixture of 6-bromo-1H-pyrrolo[3,2-b]pyridine (1.970 g, 10 mmol), phenylmethanethiol (1.291 mL, 11.00 mmol), DIEA (3.484 mL, 20.00 mmol), Pd$_2$(dba)$_3$ (0.458 g, 0.500 mmol), and (9,9-dimethyl-9H-xanthene-4,5-diyl)bis(diphenylphosphine) (0.579 g, 1.000 mmol) in dioxane (10 mL) was heated to 150° C. for 2 hours under microwave conditions. The mixture was cooled to RT and taken up in EtOAc. The organic layer was washed with NaHCO$_3$ (3×) and brine, dried (MgSO$_4$), filtered and concentrated. The residue was purified via column chromatography (1:1 EtOAc/hexane) to give the title compound as an orange solid. LCMS m/z=241.0 [M+H]$^+$.

Step E: Preparation of tert-Butyl 6-(benzylthio)-1H-pyrrolo[3,2-b]pyridine-1-carboxylate To a solution of 6-(benzylthio)-1H-pyrrolo[3,2-b]pyridine (2.122 g, 8.830 mmol) and pyridine (1.428 mL, 17.66 mmol) in THF (20 mL) was added (Boc)$_2$O (2.312 g, 10.60 mmol). The reaction was stirred for 18 hours and diluted with EtOAc. The organic layer was washed with water (3×) and brine, dried (MgSO$_4$), filtered and concentrated. The residue was purified via column chromatography (1:1 EtOAc/hexane) to give the title compound as a yellow solid (2.782 g, 93% yield). LCMS m/z=341.4 [M+H]$^+$.

Step F: Preparation of tert-butyl 6-(chlorosulfonyl)-1H-pyrrolo[3,2-b]pyridine-1-carboxylate and 1H-pyrrolo[3,2-b]pyridine-6-sulfonyl chloride To a solution of tert-butyl 6-(benzylthio)-1H-pyrrolo[3,2-b]pyridine-1-carboxylate (2.782 g, 8.172 mmol) in AcOH (10 mL)/H₂O (3.333 mL) was added NCS (3.274 g, 24.52 mmol). The reaction was stirred for 5 hours, concentrated under vacuum and partitioned between DCM/aq. NaHCO₃. The layers were separated. The aqueous layer was extracted with DCM (2×). The combined organic layers were dried over MgSO₄, filtered and concentrated. The residue was purified via column chromatography (1:1 EtOAc/hexane) to give tert-butyl 6-(chlorosulfonyl)-1H-pyrrolo[3,2-b]pyridine-1-carboxylate (0.67 g, 26% yield), LCMS m/z=317.0 [M+H]⁺; and 1H-pyrrolo[3,2-b]pyridine-6-sulfonyl chloride sulfonyl chlorides (0.46 g, 26% yield), LCMS m/z=217.0 [M+H]⁺ as a white solid.

Step G: Preparation of tert-butyl ((R)-8-((1H-pyrrolo[3,2-b]pyridin-6-yl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (1.056 g, 2.114 mmol) in THF (10 mL) was added DIEA (0.736 mL, 4.228 mmol), followed by addition of 1H-pyrrolo[3,2-b]pyridine-6-sulfonyl chloride (0.458 g, 2.114 mmol). The reaction was stirred for 2 hours and diluted with EtOAc. The organic layer was washed with water (3×) and brine and concentrated. The residue was purified via column chromatography (1:1 EtOAc/hexane→1:9 MeOH/EtOAc) to give the title compound as a white solid (1.06 g 73.8% yield). LC/MS m/z=680.4 [M+H]⁺.

Step H: Preparation of tert-butyl 6-(((R)-3-((tert-butoxycarbonyl)((S)-2-hydroxy-3-(3-(N-methylsulfamoyl)phenoxy)propyl)amino)-1-oxa-8-azaspiro[4.5]decan-8-yl)sulfonyl)-1H-pyrrolo[3,2-b]pyridine-1-carboxylate To a solution of tert-butyl ((S)-2-hydroxy-3-(3-(N-methylsulfamoyl)phenoxy)propyl)((R)-1-oxa-8-azaspiro[4.5]decan-3-yl)carbamate (1.057 g, 2.115 mmol) in THF (10 mL) was added DIEA (0.737 mL, 4.230 mmol), followed by addition of tert-butyl 6-(chlorosulfonyl)-1H-pyrrolo[3,2b]pyridine-1-carboxylate (0.67 g, 2.115 mmol). The reaction was stirred for 2 hours and diluted with EtOAc. The organic layer was washed with water (3×) and brine and concentrated. The residue was purified via column chromatography (1:1 EtOAc/hexane→1:9 MeOH/EtOAc) to give the title compound as a white solid (1.31 g, 79.6% yield). LC/MS m/z=780.6 [M+H]⁺.

Step I: Preparation of 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide (Compound 505) as the Dihydrochloride To a solution of tert-butyl ((R)-8-((1H-pyrrolo[3,2-b]pyridin-6-yl)sulfonyl)-1-oxa-8-azaspiro[4.5]decan-3-yl)((S)-2-hydroxy-3-(3-(N-methylsulfamoyl)phenoxy)propyl)carbamate (1.06 g, 1.559 mmol, from Step G) and tert-butyl 6-(((R)-3-((tertbutoxycarbonyl)((S)-2hydroxy-3-(3-(N-methylsulfamoyl)phenoxy)propyl)amino)-1-oxa-8-azaspiro[4.5]decan-8yl)sulfonyl)-1Hpyrrolo[3,2-b]pyridine-1carboxylate (1.31 g, 1.68 mmol, from Step H) in EtOAc (20 mL) was added a few drops of water, followed by addition of 4N HCl in dioxane (11.69 mL, 46.78 mmol). The reaction was stirred for 18 hours and concentrated under vacuum to give the title compound as a yellow solid (2.117 g, 98.3% yield). LC/MS m/z=580.6 [M+H]⁺.

Step K: Preparation of 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide (Compound 505)

1M Sodium bicarbonate (6.488 mL, 6.488 mmol) was added to 3-((S)-3-(((R)-8-((1H-pyrrolo[3,2-b]pyridin-6-yl)sulfonyl)-1-oxa-8-azaspiro[4.5]decan3-yl)amino)-2-hydroxypropoxy)-N-methylbenzenesulfonamide dihydrochloride (2.117 g, 3.244 mmol). The reaction was mixed manually with a spatula until a gum formed. The aqueous layer was decanted off. The gum was washed with DCM (3×), taken up in enough MeOH to make a homogenous solution and concentrated under vacuum to give the title compound as a tan solid (1.9 g, 99.4% yield). LC/MS m/z=580.8 [M+H]⁺; ¹H NMR (400 MHz, CD₃OD) δ ppm 1.61-1.87 (m, 5H), 2.23 (dd, J=13.6, 8.0 Hz, 1H), 2.51 (s, 3H), 2.77-2.83 (m, 2H), 3.03-3.05 (m, 1H), 3.11-3.12 (m, 1H), 3.41-3.51 (m, 2H), 3.76-4.06 (m, 6H), 6.768 (d, J=0.8 Hz, 1H), 7.19 (ddd, J=8.4, 2.80, 1.2 Hz, 1H), 7.37 (t, J=2.4 Hz, 1H), 7.41-7.43 (m, 1H), 7.48 (t, J=7.6 Hz, 1H), 7.90 (d, J=3.2 Hz, 1H), 8.21 (dd, J=2.0, 0.8 Hz, 1H), 8.65 (d, J=2.0 Hz, 1H).

Example 1.9: Preparation of 3-((S)-2-hydroxy-3-((R)-8-(4-hydroxyquinolin-3-ylsulfonyl)-1-oxa-8-azaspiro[4.5]decan-3-ylamino)propoxy)-N-methyl-benzenesulfonamide (Compound 541) as the Dihydrochloride Salt

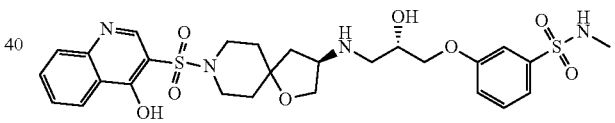

Step A: Preparation tert-butyl ((S)-2-hydroxy-3-(3-(N-methylsulfamoyl)phenoxy)propyl)((R)-8-((4-hydroxyquinolin-3-yl)sulfonyl)-1-oxa-8-azaspiro[4.5]decan-3-yl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (50 mg, 0.100 mmol) in THF (4 mL) was added DIEA (34.86 μl, 0.200 mmol), followed by addition of 4-hydroxyquinoline-3-sulfonyl chloride (24.39 mg, 0.100 mmol). The reaction was stirred for 2 hours, quenched with water and concentrated under vacuum. The residue was purified via column chromatography (1:1 EtOAc to 1:9 EtOAc/MeOH) to give the title compound as a white solid (26.4 mg, 37.3% yield). LC/MS m/z=707.4 [M+H]⁺.

Step B: Preparation of 3-((S)-2-hydroxy-3-(((R)-8-((4-hydroxyquinolin-3-yl)sulfonyl)-1-oxa-8-azaspiro[4.5]decan-3-yl)amino)propoxy)-N-methylbenzenesulfonamide To a solution of tert-butyl ((S)-2-hydroxy-3-(3-(N-methylsulfamoyl)phenoxy)propyl)((R)-8-((4-hydroxyquinolin-3- yl)sulfonyl)-1-oxa-8azaspiro[4.5]decan-3-yl)carbamate (10 mg, 14.15 µmol) in EtOAc (10 mL) was added a few drops of water followed by addition of 4N HCl in dioxane (70.74 µl, 0.283 mmol). The reaction was stirred for 1 hour and reduced under vacuum to give the title compound as a tan solid. LC/MS m/z=607.8 [M+H]$^+$; $^1$H NMR (400 MHz, CD$_3$OD) δ ppm 1.64-1.68 (m, 1H), 1.77-1.93 (m, 4H), 2.37 (dd, J=13.6, 8.4 Hz, 1H), 2.51 (s, 3H), 3.19-3.28 (m, 3H), 3.50-3.94 (m, 3H), 3.98-4.30 (m, 6H), 7.23 (m, 1H), 7.38-7.52 (m, 4H), 7.63 (d, J=8.0 Hz, 1H), 7.79 (m, 1H), 8.29 (dd, J=8.0, 1.2 Hz, 1H), 8.50 (s, 1H).

Example 1.10: Preparation 3-((S)-2-hydroxy-3-((R)-8-(4-hydroxyquinolin-3-ylsulfonyl)-1-oxa-8-azaspiro[4.5]decan-3-ylamino)propoxy)benzenesulfonamide (Compound 548) as the Hydrochloride Salt

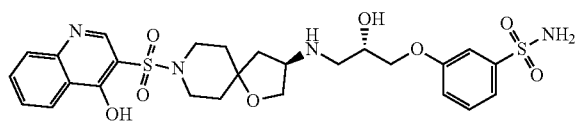 [SMILES: NS(=O)(=O)c1cccc(OC[C@@H](O)CN[C@H]2COC3(CCN(S(=O)(=O)c4cnc5ccccc5c4O)CC3)C2)c1]

Step A: Preparation of benzyl (R)-3-(((S)-2-hydroxy-3-(3-sulfamoylphenoxy)propyl)amino)-1-oxa-8-azaspiro[4.5]decane-8-carboxylate To a solution of (R)-benzyl 3-amino-1-oxa-8-azaspiro[4.5]decane-8-carboxylate (2.44 g, 8.403 mmol) in dioxane (10 mL)/EtOH (30 mL) was added (S)-3-(oxiran-2-ylmethoxy)benzenesulfonamide (0.963 g, 4.202 mmol). The reaction was sealed and heated to 90° C. for 18 hours. The mixture was concentrated and the residue was purified via column chromatography (1:9 MeOH/DCM) to give the title compound a white solid (1.96 g, 50.2% yield). LC/MS m/z=520.4 [M+H]$^+$.

Step B: Preparation of benzyl (R)-3-((tert-butoxycarbonyl)((S)-2-hydroxy-3-(3-sulfamoylphenoxy)propyl)amino)-1-oxa-8-azaspiro[4.5]decane-8-carboxylate To a mixture of (R)-benzyl 3-(((S)-2-hydroxy-3-(3-sulfamoylphenoxy)propyl)amino)-1-oxa-8-azaspiro[4.5]decane-8-carboxylate (1.096 g, 2.109 mmol) in THF (50 mL) was added DIEA (1.837 mL, 10.55 mmol) and (Boc)$_2$O (0.552 g, 2.531 mmol). The reaction was stirred for 18 hours. The mixture was diluted with EtOAc, washed with water (3×) and brine, dried (MgSO$_4$), filtered and concentrated. The residue was purified via column chromatography (1:1 EtOAc/hexane) to give the title compound as a white solid (1.22 g, 92.3% yield). LC/MS m/z=620.4 [M+H]$^+$.

Step C: Preparation of tert-butyl ((S)-2-hydroxy-3-(3-sulfamoylphenoxy)propyl)((R)-1-oxa-8-azaspiro[4.5]decan-3-yl)carbamate To a solution of (R)-benzyl 3-((tert-butoxycarbonyl)((S)-2-hydroxy-3-(3-sulfamoylphenoxy)propyl)amino)-1-oxa-8-azaspiro[4.5]decane-8carboxylate (1.218 g, 1.965 mmol) in MeOH (50 mL) was added palladium/C (0.122 g, 0.115 mmol) followed by the addition of a balloon of hydrogen. The reaction was stirred overnight, filtered to remove Pd, and concentrated under vacuum to give the title compound as a white solid (0.95 g, 99.8% yield). LC/MS m/z=486.4 [M+H]$^+$.

Step D: Preparation of tert-butyl ((S)-2-hydroxy-3-(3-sulfamoylphenoxy)propyl)((R)-8-((4-hydroxyquinolin-3-yl)sulfonyl)-1-oxa-8-azaspiro[4.5]decan-3-yl)carbamate To a solution of tert-butyl ((S)-2-hydroxy-3-(3-sulfamoylphenoxy)propyl)((R)-1-oxa-8-azaspiro[4.5]decan-3-yl)carbamate (0.200 g, 0.412 mmol) in THF (10 mL) was added DIEA (0.143 mL, 0.824 mmol), followed by addition of 4-hydroxyquinoline-3-sulfonyl chloride (0.130 g, 0.535 mmol). The reaction was stirred for 2 hours, quenched with water, and concentrated under vacuum. The residue was purified via column chromatography (1:1 EtOAc→9:1 EtOAc/MeOH) to give the title compound as a white solid (0.102 g, 35.7% yield). LC/MS m/z=693.2 [M+H]$^+$.

Step E: Preparation of 3-((S)-2-hydroxy-3-(((R)-8-((4-hydroxyquinolin-3-yl)sulfonyl)-1-oxa-8-azaspiro[4.5]decan-3-yl)amino)propoxy)benzenesulfonamide hydrochloride 4N HCl in dioxane (0.722 mL, 2.887 mmol) was added to a solution of tert-butyl ((S)-2-hydroxy-3-(3-sulfamoylphenoxy)propyl)((R)-8-((4hydroxyquinolin-3-yl)sulfonyl)-1-oxa-8-azaspiro[4.5]decan-3-yl)carbamate (0.100 g, 0.144 mmol) and a few drops of water in THF (5 mL). The reaction was stirred for 1 hour, concentrated under vacuum to give the title compound as a white solid (93.3 mg, 100% yield). LC/MS m/z=593.2 [M+H]$^+$; $^1$H NMR (400 MHz, CD$_3$OD) δ ppm 1.62-1.68 (m, 1H), 1.77-1.93 (m, 4H), 2.37 (dd, J=13.6, 8.4 Hz, 1H), 3.19-3.34 (m, 2H), 3.50-3.73 (m, 4H), 3.98-4.10 (m, 6H), 7.18 (m, 1H), 7.42-7.52 (m, 4H), 7.63 (d, J=8.0 Hz, 1H), 7.79 (m, 1H), 8.29 (dd, J=8.0, 1.2 Hz, 1H), 8.50 (s, 1H).

Example 1.11: Preparation of 3-((S)-3-((R)-8-(1H-pyrrolo[3,2-b]pyridin-6-ylsulfonyl)-1-oxa-8-azaspiro[4.5]decan-3-ylamino)-2-hydroxypropoxy)benzenesulfonamide (Compound 532) as the Dihydrochloride Salt

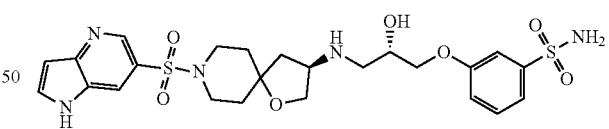

Step A: Preparation of tert-butyl 6-(((R)-3-((tert-butoxycarbonyl)((S)-2-hydroxy-3-(3-(N-methylsulfamoyl)phenoxy)propyl)amino)-1-oxa-8-azaspiro[4.5]decan-8-yl)sulfonyl)-1H-pyrrolo[3,2-b]pyridine-1-carboxylate To a solution of tert-butyl ((S)-2-hydroxy-3-(3-sulfamoylphenoxy)propyl)((R)-1-oxa-8-azaspiro[4.5]decan-3-yl)carbamate (20 mg, 41.19 µmol) in THF (5 mL) was added DIEA (14.35 µl, 82.37 µmol), followed by addition of tert-butyl 6-(chlorosulfonyl)-1H-pyrrolo[3,2-b]pyridine-1-carboxylate (16.96 mg, 53.54 µmol). The reaction was stirred for 2 hours, quenched with water and concentrated under vacuum. The residue was purified via column chromatography (1:1 EtOAc>1:9 EtOAc/MeOH) to give the title compound as a white solid (25 mg, 79.3% yield). LC/MS m/z=766.6 [M+H]+.

Step B: Preparation of 3-((S)-3-(((R)-8-((1H-pyrrolo[3,2-b]pyridin-6-yl)sulfonyl)-1-oxa-8-azaspiro[4.5]decan-3-yl)amino)-2-hydroxypropoxy)benzenesulfonamide dihydrochloride 4N HCl in dioxane (0.163 mL, 0.653 mmol) was added to a solution of tert-butyl 6-(((R)-3-((tert-butoxycarbonyl)((S)-2-hydroxy-3-(3sulfamoylphenoxy)propyl)amino)-1-oxa-8-azaspiro[4.5]decan-8-yl)sulfonyl)-1H-pyrrolo[3,2-b]pyridine-1-carboxylate (25 mg, 32.64 µmol) and a few drops of water in dioxane (5 mL). The reaction was stirred for 1 hour, concentrated under vacuum to give the title compound as an off white solid (19.9 mg, 99.2% yield). LC/MS m/z=566.4 [M+H]+; 1H NMR (400 MHz, CD3OD) δ ppm 1.68-1.98 (m, 5H), 2.37 (dd, J=14.0, 8.4 Hz, 1H), 2.77-2.89 (m, 2H), 3.25-3.35 (m, 2H), 3.60-3.75 (m, 2H), 3.86-4.36 (m, 6H), 7.0 (d, J=3.2 Hz, 1H), 7.15-7.18 (m, 1H), 7.44-7.50 (m, 3H), 8.36 (d, J=3.2 Hz, 1H), 8.78 (d, J=0.8 Hz, 1H), 9.0 (s, 1H).

Example 1.12: Preparation of 3-((S)-3-((R)-8-(1-ethyl-4-oxo-1,4-dihydroquinolin-3-ylsulfonyl)-1-oxa-8-azaspiro[4.5]decan-3-ylamino)-2-hydroxypropoxy)benzenesulfonamide (Compound 550) as the Hydrochloride Salt

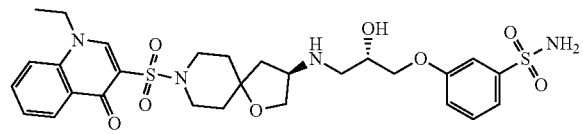 [SMILES: CCn1cc(S(=O)(=O)N2CCC3(CC2)C[C@@H](NC[C@H](O)COc2cccc(S(N)(=O)=O)c2)CO3)c(=O)c2ccccc21]

Step A: Preparation of 1-ethylquinolin-4(1H)-one

To a solution of quinolin-4-ol (25 g, 172.2 mmol) in DMF (100 mL) was added potassium carbonate (47.61 g, 344.5 mmol). The reaction was stirred at room temperature for 30 min. Bromoethane (17.87 mL, 241.1 mmol) was added. The reaction mixture was heated to 80° C. for overnight. After the reaction was completed and cooled down to room temperature, the mixture was filtered through a pad of Celite® under vacuum then washed with DCM. The resulting filtrate was concentrated then the residue was purified by silica gel column chromatography to give the title compound (13.65 g, 46%) as a yellow solid. LC/MS m/z=174.2 [M+H]+; 1H NMR (400 MHz, DMSO-d6) δ ppm 1.34 (t, J=7.07 Hz, 3H), 4.28 (q, J=7.16 Hz, 2H), 6.05 (d, J=7.58 Hz, 1H), 7.37 (ddd, J=7.96, 4.93, 3.03 Hz, 1H), 7.69-7.76 (m, 2H), 7.99 (d, J=7.58 Hz, 1H), 8.19 (d, J=7.83 Hz, 1H).

Step B: Preparation of 1-ethyl-4-oxo-1,4-dihydroquinoline-3-sulfonyl chloride

Freshly distilled sulfurochloridic acid (9.21 mL, 138.6 mmol) was added drop wise under N2 into a 3 necks round bottom flask containing 1-ethylquinolin-4(1H)-one (4 g, 23.09 mmol) until the bubbles slowed down. (Note: A lot of smoke formed and gas evolved.) The resulting clear brown solution was stirred at room temperature for 30 min and then heated at 100° C. under N2 overnight. The reaction was cooled down to room temperature. The mixture was slowly poured into crushed ice in a 500 mL beaker with vigorously stirring. The precipitate was filtered and washed with cold water to give the title compound (3.86 g, 54%) as a beige solid. LC/MS m/z=271.8 [M]+; 1H NMR (400 MHz, DMSO-d6) δ ppm 1.46 (t, J=7.07 Hz, 3H), 4.76 (q, J=7.07 Hz, 2H), 7.79 (t, J=7.58 Hz, 1H), 8.08 (dd, J=15.66, 1.52 Hz, 1H), 8.22 (d, J=8.84 Hz, 1H), 8.43 (dd, J=8.34, 1.52 Hz, 1H), 9.26 (s, 1H).

Step C: Preparation of tert-butyl ((R)-8-((1-ethyl-4-oxo-1,4-dihydroquinolin-3-yl)sulfonyl)-1-oxa-8-azaspiro[4.5]decan-3-yl)((S)-2-hydroxy-3-(3-sulfamoylphenoxy)propyl)carbamate To a solution of tert-butyl ((S)-2-hydroxy-3-(3-sulfamoylphenoxy)propyl)((R)-1-oxa-8-azaspiro[4.5]decan-3-yl)carbamate (20 mg, 41.19 µmol) in THF (10 mL) was added DIEA (14.35 µl, 82.37 µmol), followed by addition of 1-ethyl-4-oxo-1,4-dihydroquinoline-3-sulfonyl chloride (14.55 mg, 53.54 µmol). The reaction was stirred for 2 hours, quenched with water, and concentrated under vacuum. The residue was purified via column chromatography (1:1 EtOAc→1:9 EtOAc/MeOH) to give the title compound as a white solid (4.8 mg, 16.2% yield). LC/MS m/z=721.0 [M+H]+.

Step D: Preparation of 3-((S)-3-(((R)-8-((1-ethyl-4-oxo-1,4-dihydroquinolin-3-yl)sulfonyl)-1-oxa-8-azaspiro[4.5]decan-3-yl)amino)-2-hydroxypropoxy)benzenesulfonamide hydrochloride 4N HCl in dioxane (33.29 µl, 0.133 mmol) was added to a solution of tert-butyl ((R)-8-((1-ethyl-4-oxo-1,4-dihydroquinolin-3-yl)sulfonyl)-1-oxa-8azaspiro[4.5]decan-3-yl)((S)-2-hydroxy-3-(3-sulfamoylphenoxy)propyl)carbamate (4.8 mg, 6.7 µmol) in dioxane (5 mL). The reaction was stirred for 1 hour and concentrated under vacuum to give the title compound as a white solid (4.5 mg, 97.5% yield). LC/MS m/z=621.4 [M+H]+; 1H NMR (400 MHz, CD3OD) δ ppm 1.53 (t, J=7.2 Hz, 3H), 1.62-1.68 (m, 1H), 1.78-1.84 (m, 5H), 2.31-2.35 (m, 1H), 2.69 (s, 1H), 3.25-3.32 (m, 2H), 3.63-6.78 (m, 2H), 4.01-4.08 (m, 1H), 3.94-4.15 (m, 4H), 4.25-4.29 (m, 1H), 4.45-4.50 (m, 2H), 7.18 (m, 1H), 7.44-7.56 (m, 4H), 7.87-7.86 (m, 2H), 8.39 (d, J=8.0 Hz, 1H), 8.71 (s, 1H).

Example 1.13: Preparation of 3-((S)-3-((R)-8-(3-cyano-1H-pyrrolo[2,3-b]pyridin-5-ylsulfonyl)-1-oxa-8-azaspiro[4.5]decan-3-ylamino)-2-hydroxypropoxy)-N-methylbenzenesulfonamide (Compound 493) as the Dihydrochloride Salt

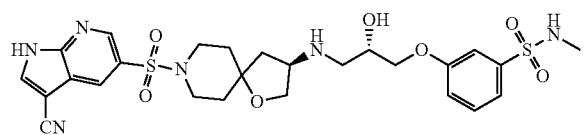 [SMILES: CNS(=O)(=O)c1cccc(OC[C@@H](O)CN[C@H]2COC3(CCN(S(=O)(=O)c4cnc5[nH]cc(C#N)c5c4)CC3)C2)c1]

Step A: Preparation of 5-(benzylthio)-1H-pyrrolo[2,3-b]pyridine-3-carbonitrile

A mixture of 5-bromo-1H-pyrrolo[2,3-b]pyridine-3-carbonitrile (0.110 g, 0.495 mmol), phenylmethanethiol (63.97

µl, 0.545 mmol), DIEA (0.173 mL, 0.991 mmol), Pd₂(dba)₃ (22.68 mg, 24.77 µmol), and (9,9-dimethyl-9H-xanthene-4,5-diyl)bis(diphenylphosphine) (28.66 mg, 49.54 µmol) in Toluene (10 mL) was heated to 90° C. for 18 hours, cooled to RT and taken up in EtOAc. The organic layer was washed with NaHCO₃ (3×) and brine, dried (MgSO₄), filtered and concentrated. The residue was purified via column chromatography (1:1 EtOAc/hexane) to give the title compound as a yellow solid (0.11 g, 84% yield). LC/MS m/z=266.0 [M+H]⁺.

Step B: Preparation of 3-cyano-1H-pyrrolo[2,3-b]pyridine-5-sulfonyl chloride

To a solution of 5-(benzylthio)-1H-pyrrolo[2,3-b]pyridine-3-carbonitrile (35 mg, 0.132 mmol) in AcOH (2 mL)/H₂O (0.667 mL) was added NCS (52.84 mg, 0.396 mmol). The reaction was stirred overnight and concentrated under vacuum. The mixture was partitioned between DCM/aq. NaHCO₃. The aqueous layer was extracted with DCM (2×). The combined organic layers were dried (MgSO₄), filtered and concentrated under vacuum to give a white solid (15.1 mg, 47.4% yield).

Step C: Preparation of tert-butyl ((R)-8-((3-cyano-1H-pyrrolo[2,3-b]pyridin-5-yl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (20 mg, 40.03 µmol) in THF (4 mL) was added DIEA (13.95 µl, 80.06 µmol), followed by addition of 3-cyano-1H-pyrrolo[2,3-b]pyridine-5-sulfonyl chloride (9.674 mg, 40.03 µmol). The reaction was stirred for 2 hours and diluted with EtOAc. The organic layer was washed with water (3×) and brine and concentrated. The residue was purified via column chromatography (1:1 EtOAc/hexane→1:9 MeOH/EtOAc) to give the title compound as a yellow solid (18 mg, 63.8% yield). LC/MS m/z=705.4 [M+H]⁺.

Step D: Preparation 3-((S)-3-(((R)-8-((3-cyano-1H-pyrrolo[2,3-b]pyridin-5-yl)sulfonyl)-1-oxa-8-azaspiro[4.5]decan-3-yl)amino)-2-hydroxypropoxy)-N-methylbenzenesulfonamide dihydrochloride To a solution of tert-butyl ((R)-8-((3-cyano-1H-pyrrolo[2,3-b]pyridin-5-yl)sulfonyl)-1-oxa-8-azaspiro[4.5]decan-3-yl)((S)-2-hydroxy-3-(3-(N-methylsulfamoyl)phenoxy)propyl) (17 mg, 20.76 µmol) in EtOAc (4 mL) was added a few drops of water, followed by addition of 4N HCl in dioxane (51.90 µl, 0.208 mmol). The reaction was stirred for 18 hours and concentrated under vacuum to give the title compound as a yellow solid (14.1 mg, 98.3% yield). LC/MS m/z=605.4 [M+H]⁺; ¹H NMR (400 MHz, CD₃OD) δ ppm 1.68-1.72 (m, 1H), 1.78-1.95 (m, 4H), 2.32 (dd, J=13.6, 8.0 Hz, 1H), 2.51 (s, 3H), 2.77-2.83 (m, 2H), 3.13-3.15 (m, 1H), 3.21-3.32 (m, 1H), 3.41-3.51 (m, 2H), 3.76-4.06 (m, 6H), 7.21 (m, 1H), 7.37 (t, J=2.4 Hz, 1H), 7.42-7.44 (m, 1H), 7.50 (t, J=7.6 Hz, 1H), 8.36 (s, 1H), 8.46 (d, J=2.0 Hz, 1H), 8.76 (d, J=2.0 Hz, 1H).

Example 1.14: Preparation of 3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide (Compound 419) as the Dihydrochloride Salt

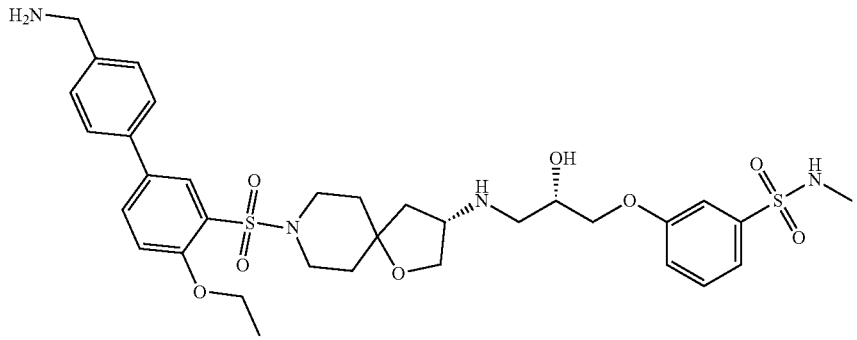 [SMILES: CCOc1ccc(-c2ccc(CN)cc2)cc1S(=O)(=O)N1CCC2(CC1)C[C@H](NC[C@H](O)COc1cccc(S(=O)(=O)NC)c1)CO2]

Step A: Preparation of tert-butyl ((S)-8-((4-bromo-2-ethoxyphenyl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-2-hydroxy-3-(3-(N-methylsulfamoyl)phenoxy)propyl)((S)-1-oxa-8-azaspiro[4.5]decan-3-yl)carbamate (75 mg, 0.150 mmol) in THF (2 mL) was added DIEA (52.29 µl, 0.300 mmol), followed by addition of 4-bromo-2-ethoxybenzene-1-sulfonyl chloride (67.45 mg, 0.225 mmol). The reaction was stirred for 18 hours and diluted with EtOAc. The organic layer was washed with water (3×) and brine, dried (MgSO₄), filtered and concentrated. The residue was purified via column chromatography (1:1 EtOAc/hexane) to give the title compound as a white solid (64 mg, 66% yield). LC/MS m/z=762.6[M+H]⁺.

Step B: Preparation of tert-butyl ((S)-8-((4'-(((tert-butoxycarbonyl)amino)methyl)-3-ethoxy-[1,1'-biphenyl]-4-yl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-8-((5-bromo-2-ethoxyphenyl)sulfonyl)-1-oxa-8-azaspiro[4.5]decan-3-yl)((S)-2-hydroxy-3-(3-(N-methylsulfamoyl)phenoxy)propyl)carbamate (64 mg, 83.91 µmol) in dioxane (1 mL) was added Pd(dppf)₂. DCM (6.903 mg, 8.4 µmol), The reaction was stirred for 10 minutes. Sodium carbonate (92.30 µl, 0.185 mmol) and (4-(((tert-butoxycarbonyl)amino)methyl)phenyl) boronic acid (25.28 mg, 0.101 mmol) were added. The reaction was heated to 90° C. for 18 hours and then quenched with water.

The aqueous layer was extracted with DCM (3×). The combined organic extracts were concentrated under vacuum. The residue was purified via column chromatography (1:1 EtOAc/hexane) to give the title compound as a white solid (65 mg, 87.1% yield). LC/MS m/z=889.6 [M+H]$^+$.

Step C: Preparation of 3-((S)-3-(((S)-8-((4'-(aminomethyl)-3-ethoxy-[1,1'-biphenyl]-4-yl)sulfonyl)-1-oxa-8-azaspiro[4.5]decan-3-yl)amino)-2-hydroxypropoxy)-N-methylbenzenesulfonamide dihydrochloride To a solution of tert-butyl ((S)-8-((4'-(((tert-butoxycarbonyl)amino)methyl)-4-ethoxy-[1,1'-biphenyl]-3-yl)sulfonyl)-1-oxa-8-azaspiro[4.5]decan-3yl)((S)-2-hydroxy-3-(3-(N-methylsulfamoyl)phenoxy)propyl)carbamate (65 mg, 73.11 μmol) in EtOAc (3 mL) was added a few drops of water followed by addition of 4N HCl in dioxane (0.366 mL, 1.462 mmol). The reaction was stirred at RT for 1 hour and concentrated under vacuum to give the title compound as a beige solid (58 mg, 101% yield). LC/MS m/z=689.8 [M+H]$^+$.

Example 1.15: Preparation of 3-((S)-2-hydroxy-3-((R)-8-(quinolin-3-ylsulfonyl)-1-oxa-8-azaspiro[4.5]decan-3-ylamino)propoxy)-N-methylbenzenesulfonamide (Compound 336) as the Dihydrochloride Salt

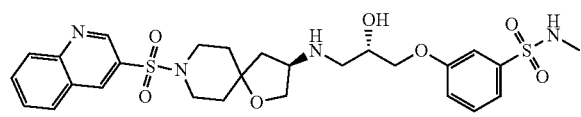 [SMILES: CNS(=O)(=O)c1cccc(OC[C@@H](O)CN[C@H]2COC3(CCN(S(=O)(=O)c4cnc5ccccc5c4)CC3)C2)c1]

Step A: Preparation of tert-butyl ((S)-2-hydroxy-3-(3-(N-methylsulfamoyl)phenoxy)propyl)((R)-8-(quinolin-3-ylsulfonyl)-1-oxa-8-azaspiro[4.5]decan-3-yl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (50 mg, 0.100 mmol) in THF (2 mL) was added DIEA (34.86 μl, 0.200 mmol), followed by addition of quinoline-3-sulfonyl chloride (34.18 mg, 0.150 mmol). The reaction was stirred overnight and then diluted with EtOAc. The organic layer was washed with water (3×) and brine and concentrated. The residue was purified via column chromatography (1:1 EtOAc/hexane) to give the title compound as a white solid (61 mg, 88% yield). LC/MS m/z=691.4 [M+H]$^+$.

Step B: Preparation of 3-((S)-2-hydroxy-3-(((R)-8-(quinolin-3-ylsulfonyl)-1-oxa-8-azaspiro[4.5]decan-3-yl)amino)propoxy)-N-methylbenzenesulfonamide dihydrochloride Tert-butyl ((S)-2-hydroxy-3-(3-(N-methylsulfamoyl)phenoxy)propyl)((R)-8-(quinolin-3-ylsulfonyl)-1-oxa-8-azaspiro[4.5]decan-3-yl)carbamate (60 mg, 86.85 μmol) was dissolved in EtOAc (5 mL), a few drops of water were added followed by the addition of 4N HCl in dioxane (0.434 mL, 1.737 mmol). The reaction was stirred for 1 hour and concentrated under vacuum to give the title compound as a white solid (57 mg, 98% yield). LC/MS m/z=591.4 [M+H]$^+$.

Example 1.16: Preparation of 3-((S)-2-hydroxy-3-((R)-8-(4-methyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide (Compound 300) as the Dihydrochloride Salt

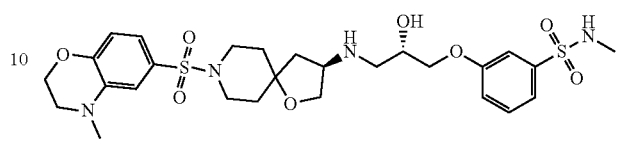

Step A: Preparation of tert-butyl ((S)-2-hydroxy-3-(3-(N-methylsulfamoyl)phenoxy)propyl)((R)-8-((4-methyl-3,4-dihydro-2H-benzo[b][1,4]oxazin-6-yl)sulfonyl)-1-oxa-8-azaspiro[4.5]decan-3-yl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (75 mg, 0.150 mmol) in THF (1 mL) was added triethylamine (41.85 μl, 0.300 mmol), followed by addition of 4-methyl-3,4-dihydro-2Hbenzo[b][1,4]oxazine-6-sulfonyl chloride (55.77 mg, 0.225 mmol), The reaction was stirred at RT overnight and then diluted with EtOAc. The organic layer was washed with water (3×) and brine and concentrated. The residue was purified via column chromatography (1:1 EtOAc/hexane) to give the title compound as a white solid (67 mg, 62% yield). LC/MS m/z=711.4 [M+H]$^+$.

Step B: Preparation of 3-((S)-2-hydroxy-3-(((R)-8-((4-methyl-3,4-dihydro-2H-benzo[b][1,4]oxazin-6-yl)sulfonyl)-1-oxa-8-azaspiro[4.5]decan-3-yl)amino) propoxy)-N-methylbenzenesulfonamide dihydrochloride To a solution of tert-butyl ((S)-2-hydroxy-3-(3-(N-methylsulfamoyl)phenoxy)propyl)((R)-8-((4-methyl-3,4-dihydro-2H-benzo[b][1,4]oxazin-6yl)sulfonyl)-1-oxa-8-azaspiro[4.5]decan-3-yl)carbamate (67 mg, 94.25 μmol) in EtOAc (10 mL) was added a few drops of water followed by addition of 4N HCl in dioxane (0.471 mL, 1.885 mmol). The reaction was stirred at RT for 18 hours and concentrated under vacuum to give the title compound as an off white solid (68.2 mg, 97% yield). LC/MS m/z=611.4 [M+H]$^+$.

Example 1.17: Preparation of 3-((S)-2-hydroxy-3-((R)-8-(quinolin-6-ylsulfonyl)-1-oxa-8-azaspiro[4.5]decan-3-ylamino)propoxy)-N-methylbenzenesulfonamide (Compound 344) as the Dihydrochloride Salt

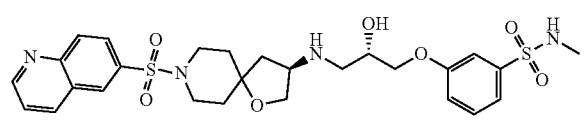 [SMILES: CNS(=O)(=O)c1cccc(OC[C@@H](O)CN[C@H]2COC3(CCN(S(=O)(=O)c4ccc5ncccc5c4)CC3)C2)c1]

Step A: Preparation of methyl 3-(quinolin-6-ylsulfonyl)propanoate

To a 5-mL microwave vial were added 6-bromoquinoline (200 mg, 0.96 mmol), sodium 3-methoxy-3-oxopropane-1- sulfinate (0.84 g, 4.81 mmol), and Copper (I) iodide (0.92 g, 4.81 mmol) followed by DMSO (2 mL). The reaction was degassed (2×) with nitrogen then heated at 110° C. overnight. After the reaction was cooled down room temperature, it was diluted with EtOAc. The resulting mixture was filtered through a pad of silica gel, washed with EtOAc, and then concentrated. The residue was purified by silica gel column chromatography to give the title compound (95 mg, 33%) as a yellow oil. LC/MS m/z=280.2 [M+H]$^+$; $^1$H NMR (400 MHz, CD$_3$D) δ ppm 2.77 (t, J=7.20 Hz, 2H), 3.55 (s, 3H), 3.65 (t, J=7.20 Hz, 2H), 7.72 (dd, J=8.46, 4.42 Hz, 1H), 8.17-8.22 (m, 1H), 8.24-8.29 (m, 1H), 8.61 (dd, J=8.46, 1.14 Hz, 1H), 8.64 (d, J=2.02 Hz, 1H), 9.07 (dd, J=4.29, 1.77 Hz, 1H).

Step B: Preparation of quinoline-6-sulfonyl chloride

To a solution of methyl 3-(quinolin-6-ylsulfonyl)propanoate (425 mg, 1.52 mmol) in THF (15 mL) at room temperature was added sodium methoxide (0.35 μL, 1.52 mmol). The reaction mixture was stirred for 30 min then concentrated to give methyl quinoline-6-sulfonate as a yellow solid. LC/MS m/z=266.0 [M+H]$^+$.

Methyl quinoline-6-sulfonate in the previous step was dissolved in CH$_2$Cl$_2$ (15.00 mL) at 0° C. then NCS (0.20 g, 1.52 mmol) was added. The reaction was stirred for 2 h. The reaction was quenched with brine then allowed to warm up to room temperature. The organic layer was separated and aqueous layer was washed with DCM. The combined organic layers were washed with water and brine, dried over Na$_2$SO$_4$, filtered and concentrated. The residue was purified by silica gel column chromatography to give the title compound (199 mg, 57%) as a beige solid. LC/MS m/z=228.2 [M+H]$^+$; $^1$H NMR (400 MHz, CD$_3$OD) δ ppm 7.78 (dd, J=8.59, 4.29 Hz, 1H), 8.35 (d, J=1.52 Hz, 2H), 8.69 (dd, J=8.59, 1.52 Hz, 1H), 8.86 (s, 1H), 9.14 (dd, J=4.29, 1.77 Hz, 1H).

Step C: Preparation of tert-butyl ((S)-2-hydroxy-3-(3-(N-methylsulfamoyl)phenoxy)propyl)((R)-8-(quinolin-6-ylsulfonyl)-1-oxa-8-azaspiro[4.5]decan-3-yl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (26 mg, 52.04 μmol) in THF (2 mL) was added DIEA (18.13 μl, 0.104 mmol), followed by addition of quinoline-6-sulfonyl chloride (17.77 mg, 78.06 μmol). The reaction was stirred overnight and diluted with EtOAc. The organic layer was washed with water (3×) and brine and concentrated. The residue was purified via column chromatography (1:1 EtOAc/hexane) to give the title compound as a white solid (37 mg, 99% yield). LC/MS m/z=691.4 [M+H]$^+$.

Step D: Preparation of 3-((S)-2-hydroxy-3-(((R)-8-(quinolin-6-ylsulfonyl)-1-oxa-8-azaspiro[4.5]decan-3-yl)amino)propoxy)-N-methylbenzenesulfonamide dihydrochloride To a solution of tert-butyl ((S)-2-hydroxy-3-(3-(N-methylsulfamoyl)phenoxy)propyl)((R)-8-(quinolin-6-ylsulfonyl)-1-oxa-8-azaspiro[4.5]decan-3yl)carbamate (37 mg, 53.56 μmol) in EtOAc (5 mL) was added a few drops of water followed by addition of 4N HCl in dioxane (0.268 mL, 1.071 mmol). The reaction was stirred for 1 hour and concentrated under vacuum to give the title compound as a white solid (30.6 mg, 82% yield). LC/MS m/z=591.4 [M+H]$^+$.

Example 1.18: Preparation 3-((S)-3-((R)-8-(7-fluoro-4-hydroxyquinolin-3-ylsulfonyl)-1-oxa-8-azaspiro[4.5]decan-3-ylamino)-2-hydroxypropoxy)-N-methylbenzenesulfonamide (Compound 539) as the Dihydrochloride Salt

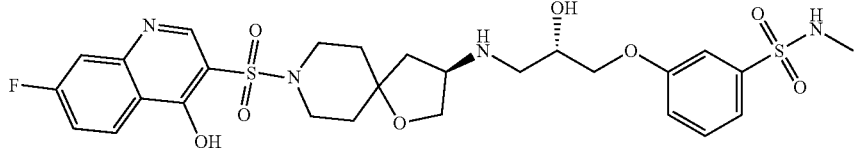 [SMILES: CNS(=O)(=O)c1cccc(OC[C@@H](O)CN[C@H]2COC3(CCN(S(=O)(=O)c4cnc5cc(F)ccc5c4O)CC3)C2)c1]

Step A: Preparation of 7-fluoro-4-hydroxyquinoline-3-sulfonyl chloride

To sulfurochloridic acid (10.71 g, 91.9 mmol, 30 eq.) at 0° C. was added 7-fluoroquinolin-4-ol (12-1) (500 mg, 3.06 mmol, 1.0 eq.) under N$_2$ atmosphere. The resulting solution was stirred at 90° C. for 16 h. After cooling to room temperature, the reaction mixture was added onto ice drop wise. The resulting precipitate was filtered and the filter cake was washed with CH$_3$CN/H$_2$O (2:1) to remove the less soluble sulfonic acid, the filtrate was lyophilized to give the title compound (550 mg, 65%) as a white solid. LC/MS: m/z=261.9 [M+H]$^+$; $^1$H NMR (400 MHz, DMSO-d): δ ppm 6.90 (br.s, 1H), 7.59 (td, J=8.9, 2.4 Hz, 1H), 7.78 (dd, J=9.8, 2.5 Hz, 1H), 8.41 (dd, J=9.3, 6.0 Hz, 1H), 8.99 (s, 1H).

Step B: Preparation of tert-butyl ((R)-8-((7-fluoro-4-hydroxyquinolin-3-yl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (50 mg, 0.100 mmol) in THF (4 mL) was added DIEA (34.86 μl, 0.200 mmol), followed by addition of 7-fluoro-4-hydroxyquinoline-3-sulfonyl chloride (26.19 mg, 0.100 mmol). The reaction was stirred for 2 hours, quenched with water and concentrated under vacuum. The residue was purified via column chromatography (1:1EtOAc/hexane→1:9 MeOH/EtOAc) to give the title compound as a white solid (40 mg, 55% yield). LC/MS m/z=725.4 [M+H]$^+$.

Step C: Preparation of 3-((S)-3-(((R)-8-((7-fluoro-4-hydroxyquinolin-3-yl)sulfonyl)-1-oxa-8-azaspiro[4.5]decan-3-yl)amino)-2-hydroxypropoxy)-N-methylbenzenesulfonamide dihydrochloride To a solution of tert-butyl ((R)-8-((7-fluoro-4-hydroxyquinolin-3-yl)sulfonyl)-1-oxa-8-azaspiro[4.5]decan-3-yl)

((S)-2-hydroxy-3-(3-(N-methylsulfamoyl)phenoxy)propyl)carbamate (36 mg, 49.67 μmol) in EtOAc (10 mL) was added a few drops of water followed by addition of 4N HCl in dioxane (0.248 mL, 0.993 mmol). The reaction was stirred for 1 hour and concentrated under vacuum to give the title compound as a yellow solid (34 mg, 96% yield). LC/MS m/z=625.4 [M+H]$^+$.

Example 1.19: Preparation of 3-((S)-3-((R)-8-((R)-1,3-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide (Compound 468) as the Dihydrochloride Salt purity, 1.0 eq.) in THF (40 mL) was added BH$_3$.THF (15.6 mL, 1 M solution in THF, 15.6 mmol, 11.4 eq.) dropwise at 0° C. under N$_2$ atmosphere. The mixture was then stirred at 25° C. for 15 hours. The reaction mixture was quenched by adding MeOH (4 mL) at 0° C., and then 1 M HCl was added to adjust pH<7. The mixture was then heated to reflux for 1 hour. After cooling, 1 M NaOH aqueous solution was added to adjust pH>7. The reaction mixture was diluted with H$_2$O (20 mL) and extracted with ethyl acetate (3×20 mL). The combined organic phase was washed with brine (30 mL), dried over anhydrous Na$_2$SO$_4$, filtered and concentrated in vacuo. The residue was purified by silica gel chromatography (SiO$_2$, Petroleum ether/Ethyl acetate=4:1 to 2:1 as

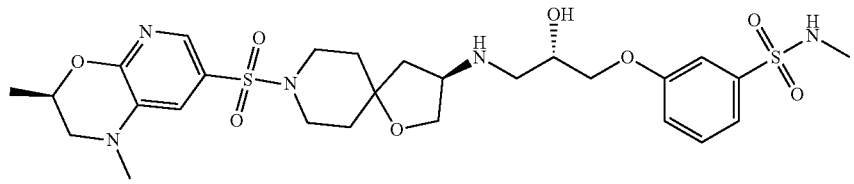

Step A: Preparation of (R)-methyl 2-((5-bromo-3-nitropyridin-2-yl)oxy)propanoate To a solution of 5-bromo-2-chloro-3-nitropyridine (4-1) (8.00 g, 33.7 mmol, 1.0 eq.), methyl (2R)-2-hydroxypropanoate (10.52 g, 101 mmol, 3.0 eq.) in MeCN (250 mL) was added K$_2$CO$_3$ (18.63 g, 135 mmol, 4.0 eq.). The reaction was stirred at 75° C. for 15 hours. After cooling, the mixture was filtered and the filtrate was concentrated in vacuo. The residue was purified by silica gel chromatography to give the title compound (4.84 g, 15.9 mmol, 47% yield) as a yellow oil.

Step B: Preparation of (R)-7-bromo-3-methyl-1H-pyrido[2,3-b][1,4]oxazin-2(3H)-one To a solution of (R)-methyl 2-((5-bromo-3-nitropyridin-2-yl)oxy)propanoate (4.80 g, 15.7 mmol, 1.0 eq.) in AcOH (250 mL) was added Fe powder (4.39 g, 78.7 mmol, 5.0 eq.), and then the mixture was heated to 80° C. for 1 hour. After cooling to room temperature, the mixture was filtered and the filtrate was concentrated in vacuo to give the title compound (10 g) without further purification.

Step C: Preparation of (R)-7-bromo-1,3-dimethyl-1H-pyrido[2,3-b][1,4]oxazin-2(3H)-one To a solution of (R)-7-bromo-3-methyl-1H-pyrido[2,3-b][1,4]oxazin-2(3H)-one (4-3) (4.81 g crude, 19.8 mmol, 1.0 eq.) in acetone (80 mL) was added MeI (3.98 g, 28.0 mmol, 1.4 eq.) and K$_2$CO$_3$ (2.74 g, 19.8 mmol, 1.0 eq.). The mixture was stirred at 50-70° C. for 15 hours. After cooling, the reaction mixture was filtered, and the filtrate was concentrated in vacuo. The residue was purified by silica gel chromatography to give the title compound (1.24 g, 4.82 mmol, 24% yield, 88% purity) as a white solid. LC/MS: m/z=256.9 [M+H]$^+$.

Step D: Preparation of (R)-7-bromo-1,3-dimethyl-2,3-dihydro-1H-pyrido[2,3-b][1,4]oxazine To a solution of (R)-7-bromo-1,3-dimethyl-1H-pyrido[2,3-b][1,4]oxazin-2(3H)-one (400 mg, 1.37 mmol, 88% eluent) to give the title compound (269 mg, 3.70 mmol, 71% yield) as a yellow solid. LCMS (ESI): m/z=242.9 [M+H]$^+$.

Step E: Preparation of (R)-7-(benzylthio)-1,3-dimethyl-2,3-dihydro-1H-pyrido[2,3-b][1,4]oxazine From (R)-7-bromo-1,3-dimethyl-2,3-dihydro-1H-pyrido[2,3-b][1,4]oxazine, the title compound was prepared using a similar method to the one described in Example 7, Step A. LCMS m/z=287.1 [M+H]$^+$; $^1$H NMR (CDCl$_3$, 400 MHz): δ ppm 1.42 (d, J=6.4 Hz, 3H), 2.73 (s, 3H), 2.98 (dd, J=11.5, 8.4 Hz, 1H), 3.16 (dd, J=11.6, 2.6 Hz, 1H), 3.97 (s, 2H), 4.48 (dqd, J=8.5, 6.3, 2.6 Hz, 1H), 6.66 (d, J=2.0 Hz, 1H), 7.18-7.32 (m, 5H), 7.57 (d, J=2.0 Hz, 1H).

Step F: Preparation of (R)-1,3-dimethyl-2,3-dihydro-1H-pyrido[2,3-b][1,4]oxazine-7-sulfonyl chloride To a solution of (R)-7-(benzylthio)-1,3-dimethyl-2,3-dihydro-1H-pyrido[2,3-b][1,4]oxazine (0.150 g, 0.524 mmol) in AcOH (5 mL)/H$_2$O (1.667 mL) was added NCS (0.210 g, 1.571 mmol). The reaction was stirred overnight, concentrated under vacuum, and taken up in EtOAc. The organic layer was washed with NaHCO$_3$ (2×) and brine, dried (MgSO$_4$), filtered and concentrated. The residue was purified via column chromatography (1:3 EtOAc/hexane) to give a yellow solid (90 mg, 66% yield). LCMS m/z=263.0 [M+H]$^+$.

Step G: Preparation of tert-butyl ((R)-8-(((R)-1,3-dimethyl-2,3-dihydro-1H-pyrido[2,3-b][1,4]oxazin-7-yl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (32 mg, 64.05 μmol) in THF (4 mL) was added DIEA (22.31 μl, 0.128 mmol), followed by addition of (R)-1,3-dimethyl-2,3-dihydro-1H-pyrido[2,3b][1,4]

oxazine-7-sulfonyl chloride (20.19 mg, 76.86 μmol). The reaction was stirred for 2 hours and diluted with EtOAc. The organic layer was washed with water (3×) and brine and concentrated. The residue was purified via column chromatography (1:1 EtOAc/hexane) to give the title compound as a white solid (38 mg, 82% yield). LCMS m/z=726.6 [M+H]⁺.

Step H: Preparation of 3-((S)-3-(((R)-8-(((R)-1,3-dimethyl-2,3-dihydro-1H-pyrido[2,3-b][1,4]oxazin-7-yl)sulfonyl)-1-oxa-8-azaspiro[4.5]decan-3-yl)amino)-2-hydroxypropoxy)-N-methylbenzenesulfonamide dihydrochloride To a solution of tert-butyl ((R)-8-(((R)-1,3-dimethyl-2,3-dihydro-1H-pyrido[2,3-b][1,4]oxazin-7-yl)sulfonyl)-1-oxa-8-azaspiro[4.5]decan-3-yl)((S)₂-hydroxy-3-(3-(N-methylsulfamoyl)phenoxy)propyl)carbamate (32 mg, 44.08 μmol) in EtOAc (10 mL) was added 4N HCl in dioxane (0.220 mL, 0.441 mmol). The reaction was stirred for 18 hours and concentrated under vacuum to give the tittle compound as a white solid (31 mg, 98% yield). LCMS m/z=626.6 [M+H]⁺.

Example 1.20: Preparation of 3-((S)-2-hydroxy-3-((R)-8-(3-(trifluoromethyl)-1H-pyrrolo[2,3-b]pyridin-5-ylsulfonyl)-1-oxa-8-azaspiro[4.5]decan-3-ylamino)propoxy)-N-methylbenzenesulfonamide (Compound 509) as the Dihydrochloride Salt

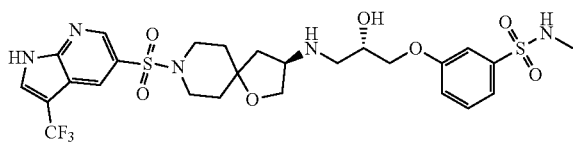 [SMILES: CNS(=O)(=O)c1cccc(OC[C@@H](O)CN[C@H]2COC3(CCN(S(=O)(=O)c4cnc5[nH]cc(C(F)(F)F)c5c4)CC3)C2)c1]

Step A: Preparation of 5-(benzylthio)-3-(trifluoromethyl)-1H-pyrrolo[2,3-b]pyridine A mixture of 5-bromo-3-(trifluoromethyl)-1H-pyrrolo[2,3-b]pyridine (0.250 g, 0.943 mmol), phenylmethanethiol (0.122 mL, 1.038 mmol), DIEA (0.329 mL, 1.887 mmol), Pd₂(dba)₃ (43.19 mg, 47.16 μmol), and (9,9-dimethyl-9H-xanthene-4,5-diyl)bis(diphenylphosphine) (54.58 mg, 94.33 μmol) in dioxane (10 mL) was stirred for 1 hour and heated to 150° C. for 2 hours under microwave conditions. The mixture was cooled to RT and taken up in EtOAc. The organic layer was washed with NaHCO₃ (3×) and brine, dried (MgSO₄), filtered and concentrated. The residue was purified via column chromatography (1:1 EtOAc/hexane) to give the title compound as a yellow solid (0.78 g, 95% yield). LCMS m/z=309.4 [M+H]⁺.

Step B: Preparation of 3-(trifluoromethyl)-1H-pyrrolo[2,3-b]pyridine-5-sulfonyl chloride To a solution of 5-(benzylthio)-3-(trifluoromethyl)-1H-pyrrolo[2,3-b]pyridine (0.276 g, 0.895 mmol) in AcOH (2 mL)/H₂O (0.667 mL) was added NCS (0.359 g, 2.686 mmol). The reaction was stirred overnight and concentrated under vacuum. The residue was partitioned between EtOAc/aq. NaHCO₃. The organic layer was washed with NaHCO₃ (2×) and brine, dried (MgSO₄), filtered and concentrated to give the title compound as a white solid (0.122 g, 48% yield). LCMS m/z=285.2 [M+H]⁺.

Step C: Preparation of tert-butyl ((S)-2-hydroxy-3-(3-(N-methylsulfamoyl)phenoxy)propyl)((R)-8-((3-(trifluoromethyl)-1H-pyrrolo[2,3-b]pyridin-5-yl)sulfonyl)-1-oxa-8-azaspiro[4.5]decan-3-yl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (30 mg, 60.05 μmol) in THF (4 mL) was added DIEA (20.92 μl, 0.120 mmol), followed by addition of 3-(trifluoromethyl)-1H-pyrrolo[2,3-b]pyridine-5sulfonyl chloride (17.09 mg, 60.05 μmol), The reaction was stirred for 2 hours and diluted with EtOAc. The organic layer was washed with water (3×) and brine and concentrated. The residue was purified via column chromatography (1:1 EtOAc/hexane→1:9 MeOH/EtOAc) to give the title compound as a white solid (32 mg, 71% yield). LCMS m/z=748.4 [M+H]⁺.

Step D: Preparation of 3-((S)-2-hydroxy-3-(((R)-8-((3-(trifluoromethyl)-1H-pyrrolo[2,3-b]pyridin-5-yl)sulfonyl)-1-oxa-8-azaspiro[4.5]decan-3-yl)amino)propoxy)-N-methylbenzenesulfonamide dihydrochloride To a solution of tert-butyl ((S)-2-hydroxy-3-(3-(N-methylsulfamoyl)phenoxy)propyl)((R)-8-((3-(trifluoromethyl)-1H-pyrrolo[2,3-b]pyridin-5yl)sulfonyl)-1-oxa-8-azaspiro[4.5]decan-3-yl)carbamate (30 mg, 40.12 μmol) in EtOAc (4 mL) was added a few drops of water, followed by addition of 4N HCl in dioxane (0.100 mL, 0.401 mmol), The reaction was stirred for 18 hours and concentrated under vacuum to give the title compound as a white solid (30 mg, 97% yield). LCMS m/z=648.4 [M+H]⁺.

Example 1.21: Preparation of 3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methylbenzenesulfonamide (Compound 61) as the 2,2,2-trifluoroacetate Salt

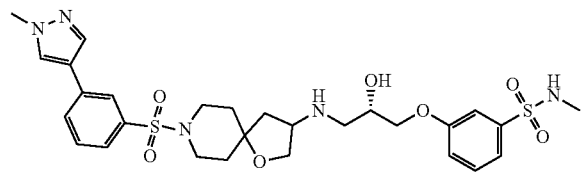

Step A: Preparation of benzyl 3-(((S)-2-hydroxy-3-(3-(N-methylsulfamoyl)phenoxy)propyl)amino)-1-oxa-8-azaspiro[4.5]decane-8-carboxylate To a solution of (S)—N-methyl-3-(oxiran-2-ylmethoxy)benzenesulfonamide (0.614 g, 2.524 mmol) in EtOH (20 mL) was added benzyl 3-amino-1oxa-8-azaspiro[4.5]decane-8-carboxylate (1.466 g, 5.048 mmol). The reaction was sealed and heated to 90° C. for 18 hours and concentrated. The residue was purified via column chromatography (1:9 MeOH/DCM) to give the title compound as a white solid (0.93 g, 69% yield). LCMS m/z 534.2 [M+H]⁺.

Step B: Preparation of benzyl 3-((tert-butoxycarbonyl)((S)-2-hydroxy-3-(3-(N-methylsulfamoyl)phenoxy)propyl)amino)-1-oxa-8-azaspiro[4.5]decane-8-carboxylate To a solution of benzyl 3-(((S)-2-hydroxy-3-(3-(N-methylsulfamoyl)phenoxy)propyl)amino)-1-oxa-8-azaspiro[4.5]decane-8-carboxylate (0.925 g, 1.733 mmol) in CH₂Cl₂ (5 mL) was added (Boc)₂O (0.378 g, 1.733 mmol), The reaction was stirred for 18 hours and diluted with EtOAc. The organic layer was washed with water (3×) and brine, dried (MgSO₄), filtered and concentrated. The residue was purified via column chromatography (1:1 EtOAc/hexane) to give the title compound as a white solid (0.97 g, 88% yield). LCMS m/z 634.4 [M+H]⁺.

Step C: Preparation of tert-butyl ((S)-2-hydroxy-3-(3-(N-methylsulfamoyl)phenoxy)propyl)(1-oxa-8-azaspiro[4.5]decan-3-yl)carbamate To a solution of benzyl 3-((tert-butoxycarbonyl)((S)-2-hydroxy-3-(3-(N-methylsulfamoyl)phenoxy)propyl)amino)-1-oxa-8-azaspiro[4.5]decane-8carboxylate (0.967 g, 1.526 mmol) in MeOH (20 mL) was added palladium/C (200 mg, 0.188 mmol). A balloon of Hydrogen was added. The reaction was stirred for 2 hours, filtered and concentrated under vacuum to give the title compound as a white solid (0.74 g, 97% yield). LCMS m/z 500.4 [M+H]⁺.

Step D: Preparation of tert-butyl (8-((3-bromophenyl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl ((S)-2-hydroxy-3-(3-(N-methylsulfamoyl)phenoxy)propyl)(1-oxa-8-azaspiro[4.5]decan-3-yl)carbamate (0.530 g, 1.061 mmol) in THF (20 mL) was added DIEA (0.370 mL, 2.122 mmol), followed by addition of 3-bromobenzene-1-sulfonyl chloride (0.325 g, 1.273 mmol). The reaction was stirred overnight and diluted with EtOAc. The organic layer was washed with water (3×) and brine and concentrated. The residue was purified via column chromatography (1:1 EtOAc/hexane) to give the title compound as a solid (0.64 g, 97% yield). LCMS m/z 720.4 [M+H]⁺.

Step E: Preparation 3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methyl-benzenesulfonamide 2,2,2trifluoroacetate A solution of tert-butyl (8-((3-bromophenyl)sulfonyl)-1-oxa-8-azaspiro[4.5]decan-3-yl)((S)-2-hydroxy-3-(3-(N-methylsulfamoyl)phenoxy)propyl)carbamate (10 mg, 13.91 μmol) and Pd(dppf)₂.DCM (2.289 mg, 2.8 μmol) in dioxane (0.3 mL) was added to a solution of 1-methyl-4-(4,4,5,5tetramethyl-1,3,2dioxaborolan-2-yl)-1Hpyrazole (14.48 mg, 69.57 μmol) and sodium carbonate (69.57 μl, 0.139 mmol) in dioxane (0.2 mL). The reaction was heated to 90° C. for 18 hours and quenched with water and concentrated. The residue was purified via prep LCMS. Appropriate fractions were pooled and lyophilized. The powder was taken up in DCM a few drops of water were added followed by addition of TFA (0.3 mL, 3.918 mmol), The reaction was stirred for 18 hours and concentrated under vacuum. The residue was purified via prep LCMS. Appropriate fractions were pooled and lyophilized to give the title compound as a brown solid (6.2 mg, 60% yield). LCMS m/z 620.4 [M+H]⁺.

Example 1.22: Preparation of 3-((2S)-2-hydroxy-3-(8-(4'-((isopropylamino)methyl)biphenyl-3-ylsulfonyl)-1-oxa-8-azaspiro[4.5]decan-3-ylamino) propoxy)-N-methylbenzenesulfonamide (Compound 303) as the bis-(2,2,2-trifluoroacetate) Salt

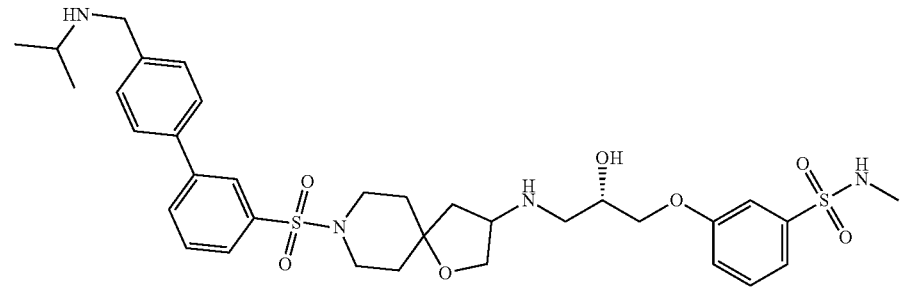 [SMILES: CNS(=O)(=O)c1cccc(OC[C@@H](O)CNC2COC3(CCN(S(=O)(=O)c4cccc(-c5ccc(CNC(C)C)cc5)c4)CC3)C2)c1]

Step A: Preparation tert-butyl ((S)-2-hydroxy-3-(3-(N-methylsulfamoyl)phenoxy)propyl)(8-((4'-(hydroxymethyl)-[1,1'-biphenyl]-3-yl)sulfonyl)-1-oxa-8-azaspiro[4.5]decan-3-yl)carbamate To a solution of tert-butyl (8-((3-bromophenyl)sulfonyl)-1-oxa-8-azaspiro[4.5]decan-3-yl)((S)-2-hydroxy-3-(3-(N-methylsulfamoyl)phenoxy)propyl)carbamate (0.369 g, 0.513 mmol) in dioxane (20 mL) was added Pd(dppf)₂.DCM (42.24 mg, 51.34 μmol). The reaction was stirred for 10 minutes. Sodium carbonate (0.565 mL, 1.130 mmol) and (4-(hydroxymethyl)phenyl)boronic acid (93.62 mg, 0.616 mmol) were added. The reaction was heated to 90° C. for 18 hours, cooled to RT, and taken up in EtOAc. The organic layer was washed with water, NH₄Cl (3×) and brine, dried (MgSO₄), filtered and concentrated. The residue was purified via column chromatography (1:1 EtOAc/Hexane→1:0 EtOAc/hexanes→1:9 MeOH/EtOAc) to give the title compound as a white solid (0.33 g, 85% yield). LCMS m/z 746.4 [M+H]⁺.

Step B: Preparation of 3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide bis(2,2,2trifluoroacetate)

To a solution of tert-butyl ((S)-2-hydroxy-3-(3-(N-methylsulfamoyl)phenoxy)propyl)(8-((4'-(hydroxymethyl)-[1,1'- biphenyl]-3-yl)sulfonyl)-1-oxa-8azaspiro[4.5]decan-3-yl) carbamate (10 mg, 13.41 μmol) in dioxane (1 mL) was added DIEA (14.01 μl, 80.44 μmol) and Methanesulfonyl chloride (3.113 μl, 40.22 μmol). The reaction was stirred for 30 minutes. Propan-2-amine (1.189 mg, 20.11 μmol) was added. The reaction was stirred overnight, quenched with water and concentrated. The residue was purified via prep LCMS. Appropriate fractions were pooled and lyophilized. The powder was taken up in DCM, a few drops of water were added followed by addition of TFA (20.53 μl, 0.268 mmol). The reaction was stirred for 1 hour and concentrated under vacuum to give the title compound as a brown oil (6.7 mg, 54.4% yield). LCMS m/z 687.8 [M+H]+.

Example 1.23: Preparation of N1-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide (Compound 354) as the 2,2,2-trifluoroacetate Salt Step B: Preparation of N1-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide 2,2,2trifluoroacetate A solution of tert-butyl (8-((4'-(aminomethyl)-[1,1'-biphenyl]-3-yl)sulfonyl)-1-oxa-8-azaspiro[4.5]decan-3-yl) ((S)-2-hydroxy-3-(3-(N-methylsulfamoyl)phenoxy)propyl) carbamate (8 mg, 10.74 μmol) and DIEA (18.71 μl, 0.107 mmol) was added to 2-amino-2-oxoacetic acid (1.913 mg, 21.48 μmol), followed by addition of T3P (Propylphosphonic anhydride solution) 50% weight in EtOAC (9.763 μl, 16.11 μmol). The reaction was stirred overnight and concentrated. The residue was purified via prep LCMS. Appropriate fractions were pooled and lyophilized. The powder was taken up in DCM and treated with 300 uL of TFA. The reaction was stirred overnight and concentrated under vacuum to give the title compound as a white solid (7.3 mg, 92% yield). LCMS m/z 716.4 [M+H]+.

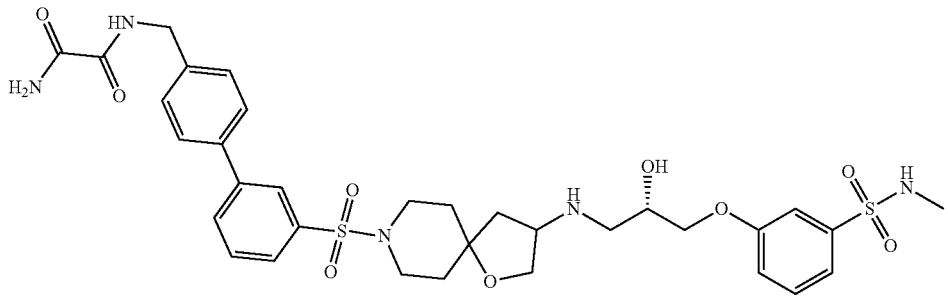 [SMILES: CNS(=O)(=O)c1cccc(OC[C@@H](O)CNC2COC3(CCN(S(=O)(=O)c4cccc(-c5ccc(CNC(=O)C(N)=O)cc5)c4)CC3)C2)c1]

Step A: Preparation of tert-butyl (8-((4'-(aminomethyl)-[1,1'-biphenyl]-3-yl)sulfonyl)-1-oxa-8-azaspiro[4.5]decan-3-yl)((S)-2-hydroxy-3-(3-(N-methylsulfamoyl)phenoxy)propyl)carbamate To a solution of tert-butyl (8-((3-bromophenyl)sulfonyl)-1-oxa-8-azaspiro[4.5]decan-3-yl)((S)-2-hydroxy-3-(3-(N-methylsulfamoyl)phenoxy)propyl)carbamate (0.100 g, 0.139 mmol) in dioxane (2 mL) was added Pd(dppf)2.DCM (11.45 mg, 13.91 μmol). The reaction was stirred for 10 minutes. Sodium carbonate (0.292 mL, 0.584 mmol) and (4-(aminomethyl)phenyl)boronic acid hydrochloride (31.30 mg, 0.167 mmol) were added. The reaction was heated to 90° C. for 18 hours and taken up in EtOAc. The organic layer was washed with water, NH4Cl (3×) and brine, dried (MgSO4), filtered and concentrated. The residue was purified via column chromatography (1:1EtOAc/hexane) to give the title compound as a white solid (25 mg, 24% yield). LCMS m/z 745.6 [M+H]+.

Example 1.24: Preparation of 3-((2S)-3-(8-(benzylsulfonyl)-1-oxa-8-azaspiro[4.5]decan-3-ylamino)-2-hydroxypropoxy)-N-methylbenzenesulfonamide (Compound 172) as the 2,2,2-trifluoroacetate Salt

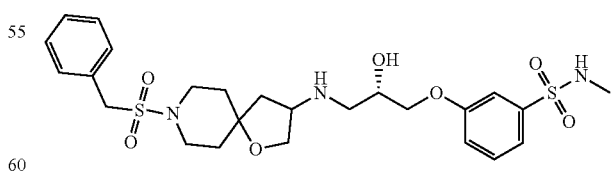

A solution of tert-butyl ((S)-2-hydroxy-3-(3-(N-methylsulfamoyl)phenoxy)propyl)(1-oxa-8-azaspiro[4.5]decan-3-yl)carbamate (10 mg, 20.02 μmol) and DIEA (6.973 μl, 40.03 μmol) in THF (0.3 mL) was added to a solution of phenylmethanesulfonyl chloride (4.6 mg, 24.02 μmol) in THF (0.2 mL). The reaction was stirred for 18 hours, quenched with water and concentrated. The residue was purified via prep LCMS. Appropriate fractions were pooled and lyophilized. The powder was taken up in DCM, a few drops of water were added followed by addition of TFA (0.3 mL, 3.918 mmol). The reaction was stirred for 18 hours and concentrated under vacuum to give the title compound as a white solid (7.1 mg, 52% yield). LCMS m/z 554.6 [M+H]+.

Example 1.25: Preparation of 3-((R)-3-((S)-2-hydroxy-3-(3-(N-methylsulfamoyl)phenoxy)propyl amino)-1-oxa-8-azaspiro[4.5]decan-8-ylsulfonyl)pyridine 1-oxide (Compound 496) as the Hydrochloride Salt

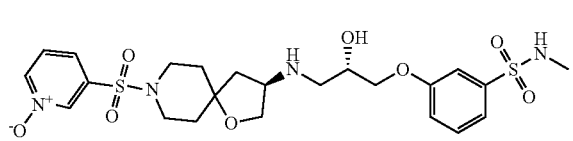

Step A: Preparation of tert-butyl ((S)-2-hydroxy-3-(3-(N-methylsulfamoyl)phenoxy)propyl)((R)-8-(pyridin-3-ylsulfonyl)-1-oxa-8-azaspiro[4.5]decan-3-yl)carbamate To a solution of tert-butyl ((S)-2-hydroxy-3-(3-(N-methylsulfamoyl)phenoxy)propyl)((R)-1-oxa-8-azaspiro[4.5]decan-3-yl)carbamate (45 mg, 90.07 µmol) in THF (4 mL) was added DIEA (31.38 µl, 0.180 mmol), followed by addition of pyridine-3-sulfonyl chloride (16.00 mg, 90.07 µmol). The reaction was stirred for 2 hours and diluted with EtOAc. The organic layer was washed with water (3×) and brine and concentrated. The residue was purified via column chromatography (1:1 EtOAc/hexane→1:9 MeOH/EtOAc) to give the title compound as a white solid (47 mg, 82% yield). LCMS m/z 641.2 [M+H]+.

Step B: Preparation of 3-(((R)-3-((tert-butoxycarbonyl)((S)-2-hydroxy-3-(3-(N-methylsulfamoyl)phenoxy)propyl)amino)-1-oxa-8-azaspiro[4.5]decan-8-yl)sulfonyl)pyridine 1-oxide To a solution of tert-butyl ((S)-2-hydroxy-3-(3-(N-methylsulfamoyl)phenoxy)propyl)((R)-8-(pyridin-3-ylsulfonyl)-1-oxa-8-azaspiro[4.5]decan-3yl)carbamate (47.3 mg, 73.82 µmol) in DCM (5 mL) was added 3-chloroperbenzoic acid (mCPBA) (66.17 mg, 0.295 mmol). The reaction was stirred for 1 hour. Not complete by LCMS, additional 3-Chloroperbenzoic acid (MCPBA) (66.17 mg, 0.295 mmol) was added. The reaction was stirred overnight and then diluted with EtOAc. The organic layer was washed with NaHCO3 (3×) and brine, dried (MgSO4), filtered and concentrated. The residue was purified via column chromatography (1:1EtOAc/hexane→1:9 MeOH/EtOAc to give the title compound as a white solid (40 mg, 82% yield). LCMS m/z 657.2 [M+H]+.

Step C: Preparation of 3-(((R)-3-(((S)-2hydroxy-3-(3-(N-methylsulfamoyl)phenoxy)propyl)amino)-1-oxa-8azaspiro[4.5]decan8yl)sulfonyl)pyridine 1-oxide hydrochloride To a solution of 3-(((R)-3-((tert-butoxycarbonyl)((S)-2-hydroxy-3-(3-(N-methylsulfamoyl)phenoxy)propyl)amino)-1-oxa-8-azaspiro[4.5]decan-8yl)sulfonyl)pyridine 1-oxide (39 mg, 59.38 µmol) in EtOAc (4 mL) was added a few drops of water, followed by addition of 4N HCl in dioxane (0.148 mL, 0.594 mmol). The reaction was stirred for 18 hours and concentrated under vacuum to give the title compound as a white solid (36 mg, 99% yield). LCMS m/z 557.4 [M+H]+.

Example 1.26: Preparation of 3-((S)-2-hydroxy-3-((R)-8-(4-methoxypyrimidin-2-yl)-1-oxa-8-azaspiro[4.5]decan-3-ylamino)propoxy)-N-methylbenzenesulfonamide (Compound 568) as the Dihydrochloride Salt

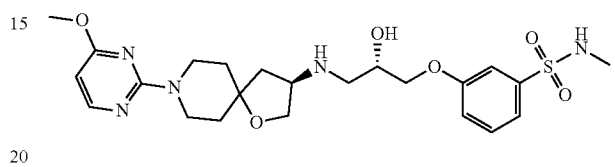

Step A: Preparation of 3-((S)-2-hydroxy-3-((R)-8-(4-methoxypyrimidin-2-yl)-1-oxa-8-azaspiro[4.5]decan-3-ylamino)propoxy)-N-methylbenzenesulfonamide dihydrochloride To a solution of tert-butyl ((S)-2-hydroxy-3-(3-(N-methylsulfamoyl)phenoxy)propyl)((R)-1-oxa-8-azaspiro[4.5]decan-3-yl)carbamate (10 mg, 20.02 µmol) and DIEA (10.46 µl, 60.05 µmol) in EtOH (2 mL) was added 2-chloro-4methoxypyrimidine (5.8 mg, 40.03 µmol). The reaction was sealed and heated to 90° C. for 18 hours and then concentrated. The residue was purified via prep LCMS. Appropriate fractions were pooled and lyophilized. The powder was taken up in THF (2.000 mL), a few drops of water was added and following by the addition of 4N HCl in dioxane (0.100 mL, 0.400 mmol). The reaction was stirred for 1 hour and concentrated under vacuum to give the title compound as a bis HCl salt (8.5 mg, 70% yield). LCMS m/z 508.4 [M+H]+.

Example 1.27: Preparation of 3-((S)-3-((R)-8-(4-benzylpyrimidin-2-yl)-1-oxa-8-azaspiro[4.5]decan-3-ylamino)-2-hydroxypropoxy)-N-methylbenzenesulfonamide (Compound 573) as the bis-(2,2,2-trifluoroacetate) Salt

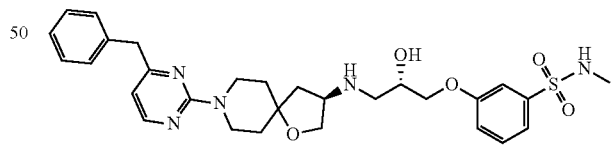

Step A: Preparation 3-((S)-3-((R)-8-(4-benzylpyrimidin-2-yl)-1-oxa-8-azaspiro[4.5]decan-3-ylamino)-2-hydroxypropoxy)-N-methylbenzenesulfonamide bis(2,2,2-trifluoroacetate)

To a solution of tert-butyl ((S)-2-hydroxy-3-(3-(N-methylsulfamoyl)phenoxy)propyl)((R)-1-oxa-8-azaspiro[4.5]decan-3-yl)carbamate (10 mg, 20.02 µmol) and DIEA (10.46 µl, 60.05 µmol) in EtOH (2 mL) was added 4-benzyl-2chloropyrimidine (8.2 mg, 40.03 µmol). The reaction was sealed and heated to 90° C. for 18 hours and concentrated.

The residue was purified via prep LCMS. Appropriate fractions were pooled and lyophilized. The powder was taken up in THF (2.000 mL). A few drops of water were added and the reaction was treated with 4N HCl in dioxane (0.100 mL, 0.400 mmol). The reaction was stirred for 1 hour and concentrated under vacuum to give the title compound bis HCl salt as a yellow product (6.4 mg, 40% yield). LCMS m/z 568.2 [M+H]$^+$.

Example 1.28: Preparation of 3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1R,2S)-2-hydroxycyclopentyl)benzenesulfonamide (Compound 437)

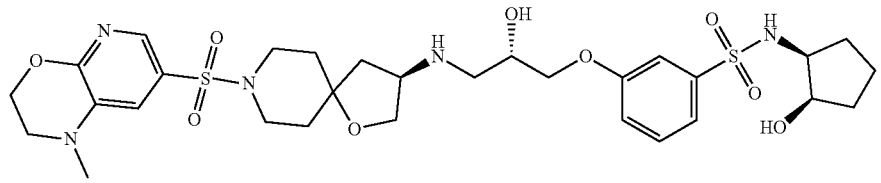 [SMILES: CN1CCOc2ncc(S(=O)(=O)N3CCC4(CC3)C[C@@H](NC[C@H](O)COc3cccc(S(=O)(=O)N[C@H]5CCC[C@H]5O)c3)CO4)cc21]

Step A: Preparation of 7-bromo-1-methyl-2,3-dihydro-1H-pyrido[2,3-b][1,4]oxazine To a solution of 7-bromo-2,3-dihydro-1H-pyrido[2,3-b][1,4]oxazine (1.40 g, 6.510 mmol) in DMF was added Sodium Hydride (60% weight, 0.391 g, 9.765 mmol). The reaction was stirred for 20 minutes. Iodomethane (0.924 g, 6.510 mmol) was added. The reaction was heated to 60° C. for 2 hours, concentrated under vacuum and taken up in EtOAc. The organic layer was washed with water (3×) and brine, dried (MgSO$_4$), filtered and concentrated. The residue was purified via column chromatography (1:1 EtOAc/hexane) to give the title compound as a white solid (1.22 g, 82% yield). LC/MS m/z=229.2 [M+H]$^+$.

Step B: Preparation of 7-(benzylthio)-1-methyl-2,3-dihydro-1H-pyrido[2,3-b][1,4]oxazine A mixture of 7-bromo-1-methyl-2,3-dihydro-1H-pyrido[2,3-b][1,4]oxazine (0.687 g, 3 mmol), phenylmethanethiol (0.387 mL, 3.300 mmol), DIEA (1.045 mL, 6.000 mmol), Pd$_2$(dba)$_3$ (0.137 g, 0.150 mmol), and (9,9-dimethyl-9H-xanthene-4,5-diyl)bis(diphenylphosphine) (0.174 g, 0.300 mmol) in Toluene (10 mL) was heated to 110° C. for 3 hours and cooled to RT. The mixture was taken up in EtOAc. The organic layer was washed with NaHCO$_3$ (3×) and brine, dried (MgSO$_4$), filtered and concentrated. The residue was purified via column chromatography (1:3 EtOAc/hexane) to give the title compound as an orange oil (0.77 g, 95% yield). LC/MS m/z=273.2 [M+H]$^+$.

Step C: Preparation of 1-methyl-2,3-dihydro-1H-pyrido[2,3-b][1,4]oxazine-7-sulfonyl chloride To a solution of 7-(benzylthio)-1-methyl-2,3-dihydro-1H-pyrido[2,3-b][1,4]oxazine (0.573 g, 2.104 mmol) in AcOH (5 mL)/H$_2$O (1.667 mL) was added NCS (0.843 g, 6.311 mmol). The reaction was stirred for 18 hours and concentrated under vacuum. The residue was taken up in EtOAc. The organic layer was washed with NaHCO$_3$ (3×) and brine, dried (MgSO$_4$) and concentrated. The residue was purified via column chromatography (1:3 EtOAc/hexane) to give the title compound as a yellow oil that slowly solidified (0.35 g, 68% yield). LC/MS m/z=249.2 [M+H]$^+$.

Step D: Preparation of tert-butyl (R)-(1-oxa-8-azaspiro[4.5]decan-3-yl)carbamate To a solution of (R)-benzyl 3-((tert-butoxycarbonyl)amino)-1-oxa-8-azaspiro[4.5]decane-8-carboxylate (1.171 g, 3 mmol) in MeOH (20 mL) was added palladium/C (0.117 g, 0.110 mmol). A balloon of Hydrogen was added. The reaction was stirred for 2 hours, filtered, and concentrated under vacuum to give the title compound as a white solid (0.8 g, 100% yield). LC/MS m/z=257.6 [M+H]$^+$.

Step E: Preparation of tert-butyl (R)-(8-((1-methyl-2,3-dihydro-1H-pyrido[2,3-b][1,4]oxazin-7-yl)sulfonyl)-1-oxa-8-azaspiro[4.5]decan-3-yl)carbamate To a solution of (R)-tert-butyl 1-oxa-8-azaspiro[4.5]decan-3-ylcarbamate (0.769 g, 3 mmol) and DIEA (1.829 mL, 10.50 mmol) in THF (30 mL) was added 1-methyl-2,3-dihydro-1H-pyrido[2,3-b][1,4]oxazine-7-sulfonyl chloride (0.746 g, 3.000 mmol). The reaction was stirred overnight. The resulting precipitate was filtered off and washed with EtOAc to give 0.333 g of a white solid. Mother liquor was concentrated under vacuum. The residue was taken up in EtOAc and washed with water (3×) and brine, dried (MgSO$_4$), filtered and concentrated. The residue was purified via column chromatography (1:3 EtOAc/hexane) to give the title compound as a white solid. The products of from both the workups were combined to give the title compound as a white solid (0.54 g, 80% yield). LC/MS m/z=469.6 [M+H]$^+$.

Step F: Preparation of (R)-8-((1-methyl-2,3-dihydro-1H-pyrido[2,3-b][1,4]oxazin-7-yl)sulfonyl)-1-oxa-8-azaspiro[4.5]decan-3-amine To a solution of (R)-tert-butyl (8-((1-methyl-2,3-dihydro-1H-pyrido[2,3-b][1,4]oxazin-7-yl)sulfonyl)-1-oxa-8-azaspiro[4.5]decan-3-yl)carbamate (0.536 g, 1.144 mmol) in EtOAc (20 mL) was added a few drops of water followed by addition of 4N HCl in dioxane (5.720 mL, 22.88 mmol). The reaction was stirred for 1 hour and concentrated under vacuum. The residue was partitioned between NaHCO$_3$ and EtOAc. The aqueous layer was extracted with EtOAc (2×). Combined extracts were washed with brine, dried (MgSO$_4$), filtered and concentrated to give a 48 mg of a white solid. The solid was triturated in EtOH and filtered. Filtrate was concentrated under vacuum to give the title compound as of a white solid (0.438 g, 100% yield). LC/MS m/z=369.2 [M+H]$^+$.

Step G: Preparation of 3-hydroxy-N-((1R,2S)-2-hydroxycyclopentyl)benzenesulfonamide To a solution of 3-(chlorosulfonyl)phenyl acetate (0.208 g, 0.886 mmol) in CH$_2$Cl$_2$ (10 mL) was added (1R,2S)-2- aminocyclopentanol hydrochloride (0.122 g, 0.886 mmol) and DIEA (0.340 mL, 1.950 mmol). The reaction was stirred for an hour. Ammonia (1.899 mL, 13.30 mmol) was added. The reaction was stirred for another hour, concentrated under vacuum and taken up in EtOAc. The organic layer was washed with NaHCO₃ (3×) and brine, dried (MgSO₄), filtered and concentrated. The residue was purified via column chromatography (1:1 EtOAc/hexane) to give the title compound as a waxy white solid (0.11 g, 50% yield). LC/MS m/z=258.2 [M+H]⁺.

Step H: Preparation of N-((1R,2S)-2-hydroxycyclopentyl)-3-(((S)-oxiran-2-yl)methoxy)benzenesulfonamide To a solution of 3-hydroxy-N-((1R,2S)-2hydroxycyclopentyl)benzenesulfonamide (0.113 g, 0.439 mmol) in acetone (10 mL) was added Potassium carbonate (0.243 g, 1.757 mmol). The reaction was stirred for 5 minutes. (S)—Oxiran-2-ylmethyl 3-nitrobenzenesulfonate (0.114 g, 0.439 mmol) was added. The reaction was heated to 70° C. for 1 hour, filtered and concentrated under vacuum. The residue was purified via column chromatography (1:1 EtOAc/hexane) to give the title compound as a waxy white solid (98 mg, 71% yield). LC/MS m/z=314.2 [M+H]⁺.

Step I: 3-((S)-2-hydroxy-3-(((R)-8-((1-methyl-2,3-dihydro-1H-pyrido[2,3-b][1,4]oxazin-7-yl)sulfonyl)-1-oxa-8-azaspiro[4.5]decan-3-yl)amino)propoxy)-N-((1R,2S)-2-hydroxycyclopentyl)benzenesulfonamide To a solution of N-((1R,2S)-2-hydroxycyclopentyl)-3-((S)-oxiran-2-ylmethoxy)benzenesulfonamide (60.04 mg, 65.14 μmol) in EtOH (5 mL) was added (R)-8-((1-methyl-2,3-dihydro-1H-pyrido[2,3-b][1,4]oxazin-7-yl)sulfonyl)-1-oxa-8-azaspiro[4.5]decan-3-amine (48 mg, 0.130 mmol), The reaction was sealed and heated to 90° C. for 18 hours and concentrated. The residue was purified via column chromatography (1:9 MeOH/DCM) to give a white solid. Not pure enough by LCMS. The residue was repurified via prep LCMS. Appropriate fractions were pooled and lyophilized. The powder was taken up in MeOH and bound to an SCX column. Eluting the SCX column with 2M NH₃/MeOH to give the title compound as a white solid (9.7 mg, 22% yield). LC/MS m/z=682.4 [M+H]⁺.

Example 1.29: Preparation of 3-((2S)-2-hydroxy-3-(8-(4'-((isopentylamino)methyl)biphenyl-3-ylsulfonyl)-1-oxa-8-azaspiro[4.5]decan-3-ylamino)propoxy)-N-methylbenzenesulfonamide (Compound 320) as the bis-(2,2,2-trifluoroacetate) Salt To a solution of tert-butyl ((S)-2-hydroxy-3-(3-(N-methylsulfamoyl)phenoxy)propyl)(8-((4'-(hydroxymethyl)-[1,1'-biphenyl]-3-yl)sulfonyl)-1-oxa-8azaspiro[4.5]decan-3-yl)carbamate (10 mg, 13.41 mol) in dioxane (1 mL) was added DIEA (14.01 μl, 80.44 μmol) and methanesulfonyl chloride (3.113 μl, 40.22 μmol). The reaction was stirred for 30 minutes. 3-Methylbutan-1-amine (1.75 mg, 20.11 mol) was added. The reaction was stirred overnight and quenched with water. The residue was purified via prep LCMS. Appropriate fractions were pooled and lyophilized. The powder was taken up in DCM, and a few drops of water were added followed by addition of TFA (20.53 μl, 0.268 mmol). The reaction was stirred for 1 hour and concentrated under vacuum to give the title compound as a yellow solid (8.5 mg, 67% yield). LC/MS m/z=715.4[M+H]⁺.

Example 1.30: Other Intermediates of the Present Invention

The following intermediates were prepared using similar methods to the ones described in the above examples using commercially available compounds or synthesized according to literature preparation.

| Chemical Name | MS Observed [M + 1] |
|---|---|
| 1H-benzo[d]imidazole-5-sulfonyl chloride | 217.0 |
| 1,8-dimethyl-2,3-dihydro-1H-pyrido[2,3-b][1,4]oxazine-7-sulfonyl chloride | 263.2 |
| 1,6-dimethyl-2,3-dihydro-1H-pyrido[2,3-b][1,4]oxazine-7-sulfonyl chloride | 263.0 |
| 1-ethyl-2,3-dihydro-1H-pyrido[2,3-b][1,4]oxazine-7-sulfonyl chloride | 263.2 |
| 5-oxo-6,7-dihydro-5H-pyrrolo[3,4-b]pyridine-3-sulfonyl chloride | 233.2 |
| 2-oxo-2,3-dihydro-1H-imidazo[4,5-b]pyridine-6-sulfonyl chloride | 234.0 |
| 5,6,7,8-tetrahydroquinoline-3-sulfonyl chloride | 232.2 |
| 3,4-dihydro-2H-pyrano[2,3-b]pyridine-6-sulfonyl chloride | 234.0 |
| 2,3-dihydro-[1,4]dioxino[2,3-b]pyridine-7-sulfonyl chloride | 236.0 |
| 4-methyl-3,4-dihydro-2H-pyrido[3,2-b][1,4]oxazine-7-sulfonyl chloride | 249.2 |
| 1,3,3-trimethyl-2,3-dihydro-1H-pyrido[2,3-b][1,4]oxazine-7-sulfonyl chloride | 277.2 |
| tert-butyl 7-(chlorosulfonyl)-2,3-dihydro-1H-pyrido[2,3-b][1,4]oxazine-1-carboxylate | 335.4 |
| (S)-1,3-dimethyl-2,3-dihydro-1H-pyrido[2,3-b][1,4]oxazine-7-sulfonyl chloride | 263.2 |
| 2-oxo-2,3-dihydro-1H-pyrrolo[2,3-b]pyridine-5-sulfonyl chloride | 233.2 |
| 1H-pyrazolo[4,3-b]pyridine-6-sulfonyl chloride | 218.0 |
| 8-fluoro-4-hydroxyquinoline-3-sulfonyl chloride | 261.9 |

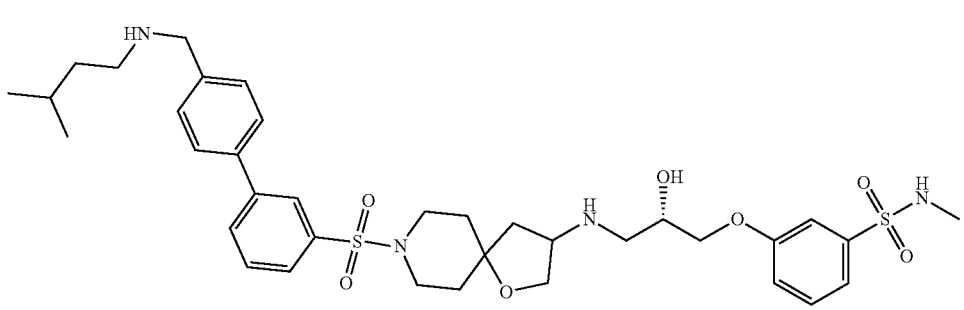 [SMILES: CNS(=O)(=O)c1cccc(OC[C@@H](O)CNC2COC3(CCN(S(=O)(=O)c4cccc(-c5ccc(CNCCC(C)C)cc5)c4)CC3)C2)c1]

| Chemical Name | MS Observed [M + 1] |
|---|---|
| 4-hydroxy-8-methylquinoline-3-sulfonyl chloride | 258.0 |
| 4-hydroxyquinoline-3-sulfonyl chloride | 244.2 |
| 1'-methyl-1',2'-dihydrospiro[cyclopropane-1,3'-pyrido[2,3-b][1,4]oxazine]-7'-sulfonyl chloride | 275.2 |
| 4-hydroxy-6-methylquinoline-3-sulfonyl chloride | 258.1 |
| 6-fluoro-4-hydroxyquinoline-3-sulfonyl chloride | 262.0 |
| 1-methyl-4-oxo-1,4-dihydroquinoline-3-sulfonyl chloride | 258.2 |

Example 1.31: Preparation of Additional Compounds of the Present Invention

The following compounds were prepared using similar methods to the ones described in the above examples from proper intermediate(s). The intermediates were obtained through commercial sources or synthesized as describe above or according to literature preparation. The specific LCMS [M+H]$^+$ for compounds of the present invention are provided below:

| Cmpd No. | Exact Mass | MS Observed |
|---|---|---|
| 1 | 589.2 | 590.2 |
| 2 | 617.2 | 618.2 |
| 3 | 645.3 | 646.4 |
| 4 | 603.2 | 604.6 |
| 5 | 657.2 | 658.6 |
| 6 | 617.2 | 618.4 |
| 7 | 645.3 | 646.2 |
| 8 | 629.2 | 630.2 |
| 9 | 639.2 | 640.2 |
| 10 | 631.2 | 632.4 |
| 12 | 619.2 | 620.6 |
| 13 | 633.2 | 634.6 |
| 14 | 539.2 | 540.2 |
| 15 | 573.1 | 574.4 |
| 16 | 593.2 | 594.6 |
| 17 | 573.1 | 574.4 |
| 18 | 569.2 | 570.2 |
| 19 | 567.2 | 568.6 |
| 20 | 617.1 | 618.2 |
| 21 | 553.2 | 554.8 |
| 22 | 595.2 | 596.4 |
| 23 | 567.2 | 568.4 |
| 24 | 610.2 | 611.2 |
| 25 | 581.2 | 582.4 |
| 26 | 557.2 | 558.4 |
| 27 | 569.2 | 570.6 |
| 28 | 557.2 | 558.2 |
| 29 | 589.2 | 590.4 |
| 30 | 589.2 | 590.4 |
| 31 | 615.2 | 616.4 |
| 32 | 564.2 | 565.2 |
| 33 | 607.2 | 608.6 |
| 34 | 557.2 | 558.4 |
| 35 | 573.1 | 574.4 |
| 36 | 595.2 | 596.6 |
| 37 | 617.2 | 618.2 |
| 38 | 607.2 | 608.6 |
| 39 | 564.2 | 565.4 |
| 40 | 583.2 | 584.4 |
| 41 | 595.2 | 596.4 |
| 42 | 596.2 | 597.4 |
| 43 | 617.2 | 618.4 |
| 44 | 564.2 | 565.4 |
| 45 | 607.2 | 608 |
| 46 | 633.2 | 634.4 |
| 47 | 647.2 | 648.6 |
| 48 | 633.2 | 634.4 |
| 49 | 647.2 | 648.6 |
| 50 | 659.2 | 660.4 |
| 51 | 633.2 | 634.6 |
| 52 | 617.1 | 620.4 |
| 53 | 553.2 | 554.6 |
| 54 | 617.1 | 620.4 |
| 55 | 589.2 | 590.4 |
| 56 | 583.2 | 584.6 |
| 57 | 623.2 | 624.2 |
| 58 | 612.1 | 613.2 |
| 59 | 634.2 | 635.8 |
| 60 | 647.2 | 648.4 |
| 61 | 619.2 | 620.4 |
| 62 | 687.2 | 688.8 |
| 63 | 604.2 | 605.2 |
| 64 | 605.2 | 606.8 |
| 65 | 659.2 | 660.6 |
| 66 | 621.2 | 622.4 |
| 67 | 644.2 | 645.4 |
| 68 | 633.2 | 634.4 |
| 69 | 633.2 | 634.6 |
| 70 | 649.2 | 650.6 |
| 71 | 693.2 | 694 |
| 72 | 640.2 | 641.4 |
| 73 | 650.2 | 651.4 |
| 74 | 615.2 | 616.4 |
| 75 | 647.2 | 648.6 |
| 76 | 618.2 | 619 |
| 77 | 695.2 | 696.4 |
| 78 | 605.2 | 606.4 |
| 79 | 644.2 | 645.2 |
| 80 | 647.2 | 648.4 |
| 81 | 661.3 | 662.4 |
| 82 | 659.2 | 660.6 |
| 83 | 658.2 | 659.6 |
| 84 | 605.2 | 606.4 |
| 85 | 694.2 | 695.4 |
| 86 | 708.2 | 709.4 |
| 87 | 673.2 | 674.4 |
| 88 | 616.2 | 617.4 |
| 89 | 665.2 | 666.4 |
| 90 | 629.2 | 630.4 |
| 91 | 618.2 | 619.2 |
| 92 | 690.2 | 691.4 |
| 93 | 643.2 | 644.4 |
| 94 | 631.2 | 632.4 |
| 95 | 649.2 | 650.4 |
| 96 | 633.2 | 634.6 |
| 97 | 659.3 | 660.8 |
| 98 | 645.3 | 646.4 |
| 99 | 645.2 | 646.4 |
| 100 | 659.3 | 660.8 |
| 101 | 603.2 | 604.6 |
| 102 | 616.2 | 617.44 |
| 103 | 631.2 | 632.6 |
| 104 | 617.2 | 618 |
| 105 | 672.3 | 673.4 |
| 106 | 616.2 | 617.4 |
| 107 | 630.2 | 631.6 |
| 108 | 647.2 | 648.4 |
| 109 | 635.2 | 636.6 |
| 110 | 630.2 | 631.6 |
| 111 | 630.2 | 631.6 |
| 112 | 659.2 | 660.4 |
| 113 | 677.2 | 678.4 |
| 114 | 670.2 | 671.4 |
| 115 | 722.2 | 723.4 |
| 116 | 635.2 | 636.4 |
| 117 | 654.2 | 655.4 |
| 118 | 645.2 | 646.2 |
| 119 | 557.2 | 558.4 |
| 120 | 609.3 | 610.6 |
| 121 | 683.2 | 684.6 |
| 122 | 633.2 | 634.6 |
| 123 | 615.2 | 616.4 |
| 124 | 631.2 | 632.6 |

| Cmpd No. | Exact Mass | MS Observed |
|---|---|---|
| 125 | 545.2 | 546.4 |
| 126 | 610.2 | 611.6 |
| 127 | 623.2 | 624.6 |
| 128 | 597.1 | 598.4 |
| 129 | 619.1 | 620 |
| 130 | 632.2 | 633.6 |
| 131 | 529.2 | 530.4 |
| 132 | 619.2 | 620.4 |
| 133 | 641.1 | 642.4 |
| 134 | 575.2 | 576.4 |
| 135 | 583.2 | 584.6 |
| 136 | 583.2 | 584.4 |
| 137 | 597.2 | 598.4 |
| 138 | 607.1 | 608.6 |
| 139 | 591.1 | 592.4 |
| 140 | 607.1 | 608.6 |
| 141 | 575.2 | 576.2 |
| 142 | 607.1 | 608.4 |
| 143 | 587.2 | 588.4 |
| 144 | 591.1 | 592.4 |
| 145 | 598.1 | 599.2 |
| 146 | 579.2 | 580.6 |
| 147 | 583.2 | 584.4 |
| 148 | 603.1 | 604.4 |
| 149 | 571.2 | 572.4 |
| 150 | 571.2 | 572.4 |
| 151 | 587.2 | 588.4 |
| 152 | 611.2 | 612.4 |
| 153 | 599.2 | 600.4 |
| 154 | 567.2 | 568.2 |
| 155 | 651 | 654.4 |
| 156 | 575.2 | 576.6 |
| 157 | 598.1 | 599.2 |
| 158 | 607.1 | 608.6 |
| 159 | 631.1 | 634.6 |
| 160 | 571.2 | 572.4 |
| 161 | 699.2 | 700.4 |
| 162 | 611.2 | 612.2 |
| 163 | 591.2 | 592.2 |
| 169 | 619.2 | 620.4 |
| 170 | 699.2 | 700.4 |
| 171 | 623.2 | 624.4 |
| 172 | 553.2 | 554.6 |
| 173 | 611.2 | 612.4 |
| 174 | 615.2 | 616.2 |
| 175 | 595.2 | 596.6 |
| 176 | 583.2 | 584.2 |
| 177 | 597.1 | 598 |
| 178 | 613.1 | 616.2 |
| 179 | 571.2 | 572.2 |
| 180 | 578.2 | 579.6 |
| 181 | 579.1 | 580.4 |
| 182 | 594.2 | 595.4 |
| 183 | 595.2 | 596.6 |
| 184 | 595.2 | 596.6 |
| 185 | 615.1 | 616.2 |
| 186 | 636.2 | 637.2 |
| 187 | 621.2 | 622.2 |
| 188 | 558.2 | 559.2 |
| 189 | 610.2 | 611.4 |
| 190 | 685.1 | 686.4 |
| 191 | 693.2 | 694.2 |
| 192 | 529.2 | 530.4 |
| 193 | 543.2 | 544.4 |
| 194 | 543.2 | 544.4 |
| 195 | 587.2 | 588.4 |
| 196 | 545.1 | 546.4 |
| 197 | 631.1 | 632.2 |
| 198 | 578.2 | 579.6 |
| 199 | 591.1 | 592.4 |
| 200 | 591.1 | 592.2 |
| 201 | 575.2 | 576.4 |
| 202 | 591.1 | 592.4 |
| 203 | 651.1 | 652.4 |
| 204 | 571.2 | 572.6 |
| 205 | 575.2 | 576.4 |

| Cmpd No. | Exact Mass | MS Observed |
|---|---|---|
| 206 | 603.1 | 604.6 |
| 207 | 603.1 | 604.6 |
| 208 | 680.1 | 681.4 |
| 209 | 647.2 | 648.6 |
| 210 | 658.2 | 659.2 |
| 211 | 708.2 | 709.4 |
| 212 | 645.2 | 646 |
| 213 | 684.2 | 685.6 |
| 214 | 668.2 | 669.6 |
| 215 | 619.2 | 620.4 |
| 216 | 619.2 | 620.6 |
| 217 | 578.2 | 579.8 |
| 218 | 631.1 | 634.4 |
| 219 | 631.1 | 634.6 |
| 220 | 647.1 | 648.4 |
| 221 | 592.2 | 593.4 |
| 222 | 623.2 | 624.6 |
| 223 | 623.2 | 624.6 |
| 224 | 587.2 | 588.4 |
| 225 | 597.2 | 598.2 |
| 226 | 585.2 | 586.4 |
| 227 | 645.1 | 648.6 |
| 228 | 624.2 | 625.2 |
| 229 | 611.2 | 612.4 |
| 230 | 633.2 | 634.8 |
| 231 | 607.2 | 608.8 |
| 232 | 572.2 | 573.6 |
| 233 | 635.2 | 636.6 |
| 234 | 624.2 | 625.6 |
| 235 | 629.1 | 630.4 |
| 236 | 583.2 | 584.4 |
| 237 | 631.1 | 634.6 |
| 238 | 587.2 | 588.4 |
| 239 | 598.1 | 599.4 |
| 240 | 587.2 | 588.4 |
| 241 | 587.2 | 588.4 |
| 242 | 597.2 | 598.4 |
| 243 | 605.2 | 606.6 |
| 244 | 597.1 | 598.2 |
| 245 | 597.1 | 598.4 |
| 246 | 587.2 | 588 |
| 247 | 597.2 | 598.4 |
| 248 | 585.2 | 586.4 |
| 249 | 645.1 | 648.4 |
| 250 | 624.2 | 625.6 |
| 251 | 611.2 | 612.4 |
| 252 | 633.2 | 634.6 |
| 253 | 607.2 | 608.8 |
| 254 | 572.2 | 573.4 |
| 255 | 635.2 | 636.6 |
| 256 | 624.2 | 625.6 |
| 257 | 629.1 | 630.2 |
| 258 | 619.2 | 620.6 |
| 259 | 651 | 654.4 |
| 260 | 659.1 | 662.6 |
| 261 | 633.2 | 634.6 |
| 262 | 615.1 | 616.4 |
| 263 | 594.2 | 595.2 |
| 264 | 623.2 | 624.4 |
| 265 | 567.2 | 568.6 |
| 266 | 583.2 | 584.2 |
| 267 | 583.2 | 584.6 |
| 268 | 571.2 | 572.6 |
| 269 | 571.2 | 572.2 |
| 270 | 631.1 | 634.4 |
| 271 | 631.1 | 634.4 |
| 272 | 647.2 | 648.6 |
| 273 | 658.2 | 659.8 |
| 274 | 708.2 | 709.4 |
| 275 | 645.2 | 646.4 |
| 276 | 684.2 | 685.6 |
| 277 | 668.2 | 669.4 |
| 278 | 610.2 | 611.4 |
| 279 | 610.2 | 611.4 |
| 280 | 619.2 | 620.4 |
| 281 | 619.2 | 620.4 |

| Cmpd No. | Exact Mass | MS Observed |
|---|---|---|
| 282 | 633.2 | 634.8 |
| 283 | 633.2 | 634.6 |
| 284 | 616.2 | 617.4 |
| 285 | 616.2 | 617.4 |
| 286 | 631.2 | 632.6 |
| 287 | 631.2 | 632.4 |
| 288 | 644.2 | 645 |
| 289 | 644.2 | 645.2 |
| 290 | 582.2 | 583.6 |
| 291 | 694.2 | 695.4 |
| 292 | 694.2 | 695.4 |
| 293 | 654.2 | 655.4 |
| 294 | 654.2 | 655.4 |
| 295 | 605.2 | 606.2 |
| 296 | 605.2 | 606.2 |
| 297 | 670.2 | 671.6 |
| 298 | 670.2 | 671.4 |
| 299 | 610.2 | 611.4 |
| 300 | 610.2 | 611.4 |
| 301 | 658.2 | 659.6 |
| 302 | 672.3 | 673.2 |
| 303 | 686.3 | 687.4 |
| 304 | 688.3 | 689.6 |
| 305 | 715.3 | 716.8 |
| 306 | 575.2 | 576.2 |
| 307 | 644.2 | 645.2 |
| 308 | 654.3 | 655.4 |
| 309 | 642.3 | 643.4 |
| 310 | 702.2 | 705.2 |
| 311 | 681.2 | 682.4 |
| 312 | 668.2 | 669.4 |
| 313 | 690.3 | 691.6 |
| 314 | 664.3 | 665.6 |
| 315 | 692.2 | 693.4 |
| 316 | 681.3 | 682.6 |
| 317 | 660.3 | 661.6 |
| 318 | 617.2 | 618.2 |
| 319 | 700.3 | 701.4 |
| 320 | 714.3 | 715.4 |
| 321 | 726.2 | 727.4 |
| 322 | 540.2 | 541.2 |
| 323 | 590.2 | 591.4 |
| 324 | 540.2 | 541.4 |
| 325 | 579.2 | 580.6 |
| 326 | 579.2 | 580.6 |
| 327 | 580.2 | 581.4 |
| 328 | 579.2 | 580.6 |
| 329 | 571.2 | 572.2 |
| 330 | 581.2 | 582.6 |
| 331 | 579.2 | 580.2 |
| 332 | 597.2 | 598.4 |
| 333 | 624.2 | 625.2 |
| 334 | 638.2 | 639.6 |
| 335 | 590.2 | 591.4 |
| 336 | 590.2 | 591.2 |
| 337 | 618.1 | 619 |
| 338 | 683.2 | 684 |
| 339 | 708.2 | 709.4 |
| 340 | 702.3 | 703.6 |
| 341 | 645.2 | 646.2 |
| 342 | 620.2 | 621.4 |
| 343 | 590.2 | 591.4 |
| 344 | 590.2 | 591.4 |
| 345 | 731.3 | 732.6 |
| 346 | 716.2 | 717.6 |
| 347 | 690.3 | 691.6 |
| 348 | 729.3 | 730.4 |
| 349 | 652.3 | 653.6 |
| 350 | 624.2 | 625.6 |
| 351 | 624.2 | 625.4 |
| 352 | 730.2 | 731.6 |
| 353 | 701.3 | 702.6 |
| 354 | 715.2 | 716.4 |
| 355 | 596.2 | 597.6 |
| 356 | 621.2 | 622.4 |
| 357 | 674.2 | 675.6 |
| 358 | 686.2 | 687.8 |
| 359 | 686.3 | 687.9 |
| 360 | 700.3 | 701.5 |
| 361 | 714.3 | 715.8 |
| 362 | 686.3 | 687.7 |
| 363 | 700.3 | 701.6 |
| 364 | 714.3 | 715.7 |
| 365 | 658.2 | 659.8 |
| 366 | 674.2 | 675.6 |
| 367 | 712.2 | 713.8 |
| 368 | 658.2 | 659.4 |
| 369 | 650.2 | 651.5 |
| 370 | 641.2 | 642.6 |
| 371 | 744.3 | 745.4 |
| 372 | 717.3 | 718.4 |
| 373 | 658.2 | 659.8 |
| 374 | 645.2 | 646.6 |
| 375 | 645.2 | 646.4 |
| 376 | 658.2 | 659.6 |
| 377 | 678.2 | 679.2 |
| 378 | 568.2 | 569.4 |
| 379 | 673.2 | 674.4 |
| 380 | 697.2 | 698.2 |
| 381 | 644.2 | 645.4 |
| 382 | 644.2 | 645.4 |
| 383 | 657.2 | 658.4 |
| 384 | 674.2 | 675.4 |
| 385 | 674.2 | 675.6 |
| 386 | 570.2 | 571.4 |
| 387 | 645.2 | 646.4 |
| 388 | 646.2 | 647.6 |
| 389 | 568.2 | 569.6 |
| 390 | 569.2 | 570.6 |
| 391 | 568.2 | 569.4 |
| 392 | 569.2 | 570.6 |
| 393 | 622.2 | 623.6 |
| 394 | 622.2 | 623.6 |
| 395 | 556.2 | 557 |
| 396 | 570.2 | 571.2 |
| 397 | 584.2 | 585.2 |
| 398 | 569.2 | 570.4 |
| 399 | 611.2 | 612.2 |
| 400 | 645.2 | 646.2 |
| 401 | 655.2 | 656.4 |
| 402 | 616.2 | 617.4 |
| 403 | 728.2 | 729.6 |
| 404 | 688.3 | 689.4 |
| 405 | 672.3 | 673.6 |
| 406 | 625.2 | 626.6 |
| 407 | 616.2 | 617.6 |
| 408 | 616.2 | 617.6 |
| 409 | 607.2 | 608.8 |
| 410 | 607.2 | 608.6 |
| 411 | 728.2 | 729.6 |
| 412 | 730.2 | 733.2 |
| 413 | 611.2 | 612.4 |
| 414 | 611.2 | 612.2 |
| 415 | 728.2 | 730 |
| 416 | 728.2 | 729.8 |
| 417 | 641.2 | 642.8 |
| 418 | 655.2 | 656.6 |
| 419 | 688.3 | 689.8 |
| 420 | 688.3 | 689.8 |
| 421 | 623.2 | 624.6 |
| 422 | 583.2 | 584.4 |
| 423 | 625.2 | 626.6 |
| 424 | 688.3 | 689.8 |
| 425 | 557.2 | 558.4 |
| 426 | 613.2 | 614.4 |
| 427 | 681.2 | 682.6 |
| 428 | 599.2 | 600.6 |
| 429 | 598.2 | 599.5 |
| 430 | 624.2 | 625.7 |
| 431 | 695.3 | 696.6 |
| 432 | 655.2 | 656.4 |
| 433 | 510.2 | 511.2 |

| Cmpd No. | Exact Mass | MS Observed |
|---|---|---|
| 434 | 655.2 | 656.6 |
| 435 | 695.3 | 696.6 |
| 436 | 655.2 | 656.4 |
| 437 | 681.2 | 682.4 |
| 439 | 730.3 | 731.6 |
| 440 | 672.3 | 673.2 |
| 441 | 583.2 | 584.6 |
| 442 | 625.2 | 626.6 |
| 443 | 611.2 | 612.2 |
| 444 | 597.2 | 598 |
| 445 | 584.2 | 585.4 |
| 446 | 670.2 | 671.5 |
| 447 | 658.2 | 659.8 |
| 448 | 674.2 | 675.2 |
| 449 | 674.2 | 675.4 |
| 450 | 655.2 | 656.4 |
| 451 | 627.2 | 628.6 |
| 452 | 640.2 | 641.6 |
| 453 | 654.2 | 655.6 |
| 454 | 627.2 | 628.4 |
| 455 | 626.2 | 627.6 |
| 456 | 625.2 | 626.4 |
| 457 | 643.2 | 644.4 |
| 458 | 597.2 | 598.6 |
| 459 | 655.2 | 656.4 |
| 460 | 636.2 | 637 |
| 461 | 661.2 | 662.2 |
| 462 | 731.3 | 732.6 |
| 463 | 700.3 | 701.4 |
| 464 | 700.3 | 701.4 |
| 465 | 641.2 | 642.4 |
| 466 | 625.2 | 626.6 |
| 467 | 625.2 | 626.2 |
| 468 | 625.2 | 626.6 |
| 469 | 639.2 | 640.4 |
| 470 | 639.2 | 640.2 |
| 471 | 655.2 | 656.2 |
| 472 | 625.2 | 626.2 |
| 473 | 639.2 | 640.4 |
| 474 | 637.2 | 638.6 |
| 475 | 594.2 | 595.6 |
| 476 | 641.2 | 642.4 |
| 477 | 596.2 | 597.4 |
| 478 | 595.2 | 596.4 |
| 479 | 594.2 | 595.6 |
| 480 | 598.2 | 599.4 |
| 481 | 611.2 | 612.4 |
| 482 | 581.2 | 582.6 |
| 483 | 596.2 | 597.6 |
| 484 | 595.2 | 596.6 |
| 485 | 591.2 | 592.4 |
| 486 | 594.2 | 595.6 |
| 487 | 625.2 | 626.6 |
| 488 | 596.2 | 597.4 |
| 489 | 606.2 | 607.6 |
| 490 | 580.2 | 581.6 |
| 491 | 580.2 | 581.6 |
| 492 | 634.2 | 635.6 |
| 493 | 604.2 | 605.4 |
| 494 | 620.2 | 621.6 |
| 495 | 580.2 | 581.6 |
| 496 | 556.2 | 557.4 |
| 497 | 594.2 | 595.4 |
| 498 | 608.2 | 609.5 |
| 499 | 595.2 | 596.6 |
| 500 | 597.2 | 598.2 |
| 501 | 593.2 | 594.2 |
| 502 | 580.2 | 581.6 |
| 503 | 579.2 | 580.6 |
| 505 | 579.2 | 580.6 |
| 506 | 579.2 | 580.6 |
| 507 | 579.2 | 580.6 |
| 508 | 609.2 | 610.6 |
| 509 | 647.2 | 648.4 |
| 510 | 613.1 | 614.4 |
| 511 | 608.2 | 609.6 |
| 512 | 593.2 | 594.6 |
| 513 | 627.2 | 628.4 |
| 514 | 595.2 | 596.6 |
| 515 | 608.2 | 609.6 |
| 516 | 594.2 | 595.4 |
| 517 | 627.2 | 628.4 |
| 518 | 610.2 | 611.6 |
| 519 | 594.2 | 595.4 |
| 520 | 593.2 | 594.4 |
| 521 | 609.2 | 610.4 |
| 522 | 610.2 | 611.6 |
| 523 | 594.2 | 595.6 |
| 524 | 648.2 | 649.6 |
| 525 | 652.2 | 653.2 |
| 526 | 593.2 | 594.4 |
| 527 | 627.2 | 628.4 |
| 528 | 620.2 | 621.6 |
| 529 | 579.2 | 580.6 |
| 530 | 623.2 | 624.6 |
| 531 | 648.2 | 649.2 |
| 532 | 565.2 | 566.4 |
| 533 | 620.2 | 621.6 |
| 534 | 624.2 | 625.4 |
| 535 | 648.2 | 649.6 |
| 536 | 652.2 | 653.6 |
| 537 | 579.2 | 580.8 |
| 538 | 620.2 | 621.6 |
| 539 | 624.2 | 625.4 |
| 540 | 624.2 | 625.2 |
| 541 | 606.2 | 607.8 |
| 542 | 606.2 | 607.2 |
| 543 | 638.2 | 639.2 |
| 544 | 664.2 | 665.4 |
| 545 | 648.2 | 649.6 |
| 546 | 652.2 | 653.6 |
| 547 | 620.2 | 621.2 |
| 548 | 592.2 | 593.2 |
| 549 | 606.2 | 607.6 |
| 550 | 620.2 | 621.4 |
| 551 | 634.2 | 635.8 |
| 552 | 610.2 | 611.6 |
| 553 | 606.2 | 607.2 |
| 554 | 610.2 | 611.2 |
| 555 | 610.2 | 611.2 |
| 556 | 579.2 | 580.2 |
| 557 | 634.2 | 635.4 |
| 558 | 579.2 | 580.2 |
| 559 | 580.2 | 581.2 |
| 560 | 575.2 | 576.4 |
| 561 | 476.2 | 477 |
| 562 | 576.2 | 577.2 |
| 563 | 565.2 | 566.2 |
| 564 | 580.2 | 581.4 |
| 565 | 581.2 | 582.2 |
| 566 | 576.2 | 577.6 |
| 567 | 674.2 | 675.4 |
| 568 | 507.2 | 508.4 |
| 569 | 492.2 | 493.2 |
| 570 | 567.3 | 568.4 |
| 571 | 505.2 | 506 |
| 572 | 553.2 | 554.2 |
| 573 | 567.3 | 568.2 |
| 574 | 545.2 | 546.2 |
| 575 | 491.2 | 492 |
| 576 | 477.2 | 478.2 |
| 577 | 505.2 | 506.4 |
| 578 | 575.3 | 576.6 |
| 579 | 519.3 | 520.4 |
| 580 | 553.2 | 554.4 |
| 581 | 535.2 | 536.2 |
| 582 | 521.2 | 522.4 |
| 583 | 545.2 | 546.2 |
| 584 | 537.2 | 538.2 |
| 585 | 545.2 | 546.2 |
| 586 | 477.2 | 478.4 |
| 587 | 570.2 | 571.2 |

| Cmpd No. | Exact Mass | MS Observed |
|---|---|---|
| 588 | 584.2 | 585.2 |
| 589 | 477.2 | 478.4 |
| 590 | 617.1 | 620 |
| 591 | 559.1 | 560.2 |
| 592 | 573.1 | 574.4 |
| 593 | 583.2 | 584.4 |
| 594 | 567.3 | 568.4 |

Example 2: $IC_{50}$ Determinations in Homogeneous Time-Resolved Fluorescence (HTRF®) cAMP Antagonist Assays HTRF cAMP assays were performed according to manufacturer's instructions (Cisbio, cAMP Dynamic 2 Assay Kit; #62AM4PEJ). CHO-K1 cells stably expressing recombinant receptor were harvested and suspended in warm PBS to make a 300,000 cells/mL stock. This cell suspension was dispensed into 384 well assay plates (PerkinElmer Proxi-Plate #6008280) at 5 μL per well (1500 cells/well) along with a cAMP standard curve.

Compounds were dissolved and serially diluted (5-fold) in DMSO to generate a 10-point dose response stock. The stock was then diluted 100-fold in assay buffer (PBS containing 1 mM IBMX) before a volume of 2.5 μL was added to the cells (the final, top concentration of compound in the dose-response is typically 10 or 100 μM). After a brief incubation, 2.5 μL of isoproterenol stock, prepared at a concentration 4 times its $EC_{90}$ at the receptor of interest, was added to the wells. The $EC_{90}$ for isoproterenol, a beta-adrenergic agonist, was determined in separate experiments using standard methods to measure agonist potencies.

Following a 1-hour incubation at room temperature, 5 μL of cAMP-D2 Reagent diluted in Lysis Buffer was added to each well followed by 5 μL of Cryptate Reagent. Plates were further incubated at room temperature for 1 hour prior to reading. Time resolved fluorescence measurements were collected on a suitable, HTRF-capable plate reader.

Counts from the plate reader were fit to the cAMP standard curve on the assay plate in order to determine cAMP concentrations in each well, and these values were used to construct dose-response curves to obtain $IC_{50}$ values.

Specific $IC_{50}$ values for certain compounds are provided below in TABLE B.

TABLE B

Beta-3 Adrenergic Receptor $IC_{50}$ Values

| Cmpd No. | $IC_{50}$ | Cmpd No. | $IC_{50}$ | Cmpd No. | $IC_{50}$ | Cmpd No. | $IC_{50}$ |
|---|---|---|---|---|---|---|---|
| 1 | 5.4 nM | 149 | 20.6 nM | 297 | 15.9 nM | 445 | 30.4 nM |
| 2 | 21.1 nM | 150 | 13.5 nM | 298 | 26 nM | 446 | 11.9 nM |
| 3 | 133 nM | 151 | 5.38 nM | 299 | 11.8 nM | 447 | 19.9 nM |
| 4 | 11.2 nM | 152 | 90.7 nM | 300 | 10.9 nM | 448 | 32 nM |
| 5 | 220 nM | 153 | 43.6 nM | 301 | 31.6 nM | 449 | 12.2 nM |
| 6 | 24.3 nM | 154 | 34.4 nM | 302 | 458 nM | 450 | 28.2 nM |
| 7 | 285 nM | 155 | 4.36 nM | 303 | 32.6 nM | 451 | 2.13 μM |
| 8 | 38.7 nM | 156 | 25.4 nM | 304 | 43 nM | 452 | 25.7 nM |
| 9 | 107 nM | 157 | 26.4 nM | 305 | 63.5 nM | 453 | 115 nM |
| 10 | 49.2 nM | 158 | 25.6 nM | 306 | 65.4 nM | 454 | 453 nM |
| 11 | 15.1 nM | 159 | 4.78 nM | 307 | 3.37 μM | 455 | 25.1 nM |
| 12 | 31.7 nM | 160 | 14.6 nM | 308 | 1.82 μM | 456 | 16.4 nM |
| 13 | 28.7 nM | 161 | 83.7 nM | 309 | 3 μM | 457 | 29.6 nM |
| 14 | 30.1 nM | 162 | 42.6 nM | 310 | 877 nM | 458 | 45.7 nM |
| 15 | 12.4 nM | 163 | 64.1 nM | 311 | 2 μM | 459 | 160 nM |
| 16 | 7.47 nM | 164 | 84.9 nM | 312 | 3.17 μM | 460 | 3.02 μM |
| 17 | 15.3 nM | 165 | 311 nM | 313 | 4.01 μM | 461 | 31.9 nM |
| 18 | 20.8 nM | 166 | 143 nM | 314 | 716 nM | 462 | 107 nM |
| 19 | 10 nM | 167 | 2.15 μM | 315 | 1.07 μM | 463 | 24.3 nM |
| 20 | 13.2 nM | 168 | 1.47 μM | 316 | 1.94 μM | 464 | 13.9 nM |
| 21 | 13.4 nM | 169 | 11.6 nM | 317 | 1.01 μM | 465 | 26.3 nM |
| 22 | 15 nM | 170 | 50.6 nM | 318 | 2.18 μM | 466 | 101 nM |
| 23 | 13.8 nM | 171 | 30.7 nM | 319 | 34.3 nM | 467 | 33.4 nM |
| 24 | 106 nM | 172 | 78.9 nM | 320 | 26.3 nM | 468 | 31.1 nM |
| 25 | 26 nM | 173 | 29 nM | 321 | 70.5 nM | 469 | 31.3 nM |
| 26 | 34.1 nM | 174 | 125 nM | 322 | 73.5 nM | 470 | 35.8 nM |
| 27 | 13.8 nM | 175 | 23.8 nM | 323 | 24.8 nM | 471 | 69 nM |
| 28 | 16.2 nM | 176 | 23.3 nM | 324 | 78 nM | 472 | 35.4 nM |
| 29 | 4.53 nM | 177 | 11.9 nM | 325 | 42.7 nM | 473 | 59.2 nM |
| 30 | 4.41 nM | 178 | 20.8 nM | 326 | 11.7 nM | 474 | 44.2 nM |
| 31 | 21 nM | 179 | 8.15 nM | 327 | 92.1 nM | 475 | 33.2 nM |
| 32 | 16.6 nM | 180 | 29.8 nM | 328 | 37 nM | 476 | 38.9 nM |
| 33 | 17.6 nM | 181 | 24.3 nM | 329 | 156 nM | 477 | 52.3 nM |
| 34 | 24.2 nM | 182 | 105 nM | 330 | 36.7 nM | 478 | 204 nM |
| 35 | 18.9 nM | 183 | 16.4 nM | 331 | 19.6 nM | 479 | 32.1 nM |
| 36 | 13.2 nM | 184 | 11.9 nM | 332 | 17.9 nM | 480 | 75.3 nM |
| 37 | 49.3 nM | 185 | 7.25 nM | 333 | 9.02 nM | 481 | 31.1 nM |
| 38 | 18.7 nM | 186 | 15.7 nM | 334 | 27.3 nM | 482 | 1.51 μM |
| 39 | 30.7 nM | 187 | 7.72 nM | 335 | 12.1 nM | 483 | 41.8 nM |
| 40 | 577 nM | 188 | 18.1 nM | 336 | 15.3 nM | 484 | 278 nM |
| 41 | 6.82 nM | 189 | 8.51 nM | 337 | 18.6 nM | 485 | 35.8 nM |
| 42 | 31.9 nM | 190 | 18 nM | 338 | 47.1 nM | 486 | 41.5 nM |
| 43 | 74 nM | 191 | 80.9 nM | 339 | 42.4 nM | 487 | 25.2 nM |
| 44 | 34.1 nM | 192 | 28.3 nM | 340 | 30.9 nM | 488 | 38.1 nM |
| 45 | 19.4 nM | 193 | 54.8 nM | 341 | 28.5 nM | 489 | 33.9 nM |
| 46 | 54.1 nM | 194 | 97.6 nM | 342 | 42.6 nM | 490 | 37.3 nM |
| 47 | 155 nM | 195 | 23.4 nM | 343 | 27.7 nM | 491 | 24.4 nM |
| 48 | 133 nM | 196 | 39.7 nM | 344 | 42.7 nM | 492 | 33 nM |
| 49 | 107 nM | 197 | 12.8 nM | 345 | 107 nM | 493 | 10.6 nM |
| 50 | 87.2 nM | 198 | 8.65 nM | 346 | 126 nM | 494 | 62.4 nM |
| 51 | 58.5 nM | 199 | 15 nM | 347 | 33.5 nM | 495 | 50.6 nM |
| 52 | 14.1 nM | 200 | 22.2 nM | 348 | 36.7 nM | 496 | 541 nM |
| 53 | 21.8 nM | 201 | 17.1 nM | 349 | 67.9 nM | 497 | 16.4 nM |
| 54 | 17.4 nM | 202 | 10.8 nM | 350 | 21.8 nM | 498 | 117 nM |
| 55 | 18 nM | 203 | 14.9 nM | 351 | 38.6 nM | 499 | 73 nM |
| 56 | 387 nM | 204 | 12.1 nM | 352 | 167 nM | 500 | 28.8 nM |
| 57 | 31.7 nM | 205 | 14 nM | 353 | 58 nM | 501 | 22.9 nM |
| 58 | 43 nM | 206 | 9.62 nM | 354 | 35.2 nM | 502 | 18.9 nM |
| 59 | 14.5 nM | 207 | 8.79 nM | 355 | 17.2 nM | 503 | 28.9 nM |
| 60 | 58.8 nM | 208 | 64.6 nM | 356 | 16.9 nM | 504 | 217 nM |
| 61 | 13.5 nM | 209 | 41 nM | 357 | 15.7 nM | 505 | 8.46 nM |
| 62 | 44.9 nM | 210 | 20.4 nM | 358 | 16.1 nM | 506 | 11.9 nM |
| 63 | 19.3 nM | 211 | 16.5 nM | 359 | 17.9 nM | 507 | 58.8 nM |
| 64 | 11.1 nM | 212 | 13.6 nM | 360 | 20.5 nM | 508 | 211 nM |
| 65 | 85.6 nM | 213 | 49.1 nM | 361 | 22.1 nM | 509 | 6.95 nM |
| 66 | 22.7 nM | 214 | 31.4 nM | 362 | 27.5 nM | 510 | 4.89 nM |
| 67 | 23.1 nM | 215 | 7.41 nM | 363 | 123 nM | 511 | 20.4 nM |
| 68 | 36.9 nM | 216 | 57.7 nM | 364 | 144 nM | 512 | 6.62 nM |
| 69 | 21.1 nM | 217 | 35.1 nM | 365 | 20.7 nM | 513 | 6.36 nM |
| 70 | 25.7 nM | 218 | 39.3 nM | 366 | 27.5 nM | 514 | 176 nM |
| 71 | 31.2 nM | 219 | 25.3 nM | 367 | 31.2 nM | 515 | 74.9 nM |
| 72 | 28.7 nM | 220 | 19.1 nM | 368 | 35.2 nM | 516 | 166 nM |
| 73 | 22.1 nM | 221 | 9.58 nM | 369 | 14.6 nM | 517 | 7.74 nM |
| 74 | 236 nM | 222 | 109 nM | 370 | 47.8 nM | 518 | 133 nM |
| 75 | 39.8 nM | 223 | 13.6 nM | 371 | 42 nM | 519 | 68.4 nM |
| 76 | 26.5 nM | 224 | 33.1 nM | 372 | 41.8 nM | 520 | 14.6 nM |
| 77 | 17.5 nM | 225 | 186 nM | 373 | 24.4 nM | 521 | 98.3 nM |
| 78 | 20.7 nM | 226 | 155 nM | 374 | 15.7 nM | 522 | 22.2 nM |
| 79 | 7.15 nM | 227 | 31.3 nM | 375 | 25.4 nM | 523 | 273 nM |
| 80 | 14.3 nM | 228 | 24.2 nM | 376 | 499 nM | 524 | 87.2 nM |
| 81 | 16.6 nM | 229 | 272 nM | 377 | 18.9 nM | 525 | 21.6 nM |
| 82 | 15.9 nM | 230 | 85.4 nM | 378 | 131 nM | 526 | 6.97 nM |
| 83 | 99.9 nM | 231 | 72.6 nM | 379 | 11.1 nM | 527 | 9.03 nM |
| 84 | 9.09 nM | 232 | 188 nM | 380 | 102 nM | 528 | 10.2 nM |
| 85 | 9.73 nM | 233 | 156 nM | 381 | 357 nM | 529 | 124 nM |
| 86 | 9.36 nM | 234 | 52.6 nM | 382 | 21 nM | 530 | 214 nM |
| 87 | 66.1 nM | 235 | 108 nM | 383 | 21.8 nM | 531 | 50.5 nM |
| 88 | 9.82 nM | 236 | 54.9 nM | 384 | 11 nM | 532 | 12.7 nM |
| 89 | 429 nM | 237 | 42.8 nM | 385 | 11 nM | 533 | 24.4 nM |

TABLE B-continued

Beta-3 Adrenergic Receptor IC$_{50}$ Values

| Cmpd No. | IC$_{50}$ | Cmpd No. | IC$_{50}$ | Cmpd No. | IC$_{50}$ | Cmpd No. | IC$_{50}$ |
|---|---|---|---|---|---|---|---|
| 90 | 49.2 nM | 238 | 38.4 nM | 386 | 57.9 nM | 534 | 20.8 nM |
| 91 | 1.12 µM | 239 | 22.3 nM | 387 | 30.8 nM | 535 | 43.9 nM |
| 92 | 1.99 µM | 240 | 28.4 nM | 388 | 79.4 nM | 536 | 166 nM |
| 93 | 112 nM | 241 | 27.8 nM | 389 | 475 nM | 537 | 101 nM |
| 94 | 59.8 nM | 242 | 420 nM | 390 | 153 nM | 538 | 54.2 nM |
| 95 | 159 nM | 243 | 26.2 nM | 391 | 446 nM | 539 | 26 nM |
| 96 | 42.1 nM | 244 | 76.1 nM | 392 | 168 nM | 540 | 32.7 nM |
| 97 | 127 nM | 245 | 15.5 nM | 393 | 141 nM | 541 | 13.4 nM |
| 98 | 71.1 nM | 246 | 38.6 nM | 394 | 46.9 nM | 542 | 15.6 nM |
| 99 | 121 nM | 247 | 27.2 nM | 395 | 206 nM | 543 | 66.7 nM |
| 100 | 256 nM | 248 | 40.5 nM | 396 | 30.3 nM | 544 | 32.7 nM |
| 101 | 9.62 nM | 249 | 29.5 nM | 397 | 115 nM | 545 | 121 nM |
| 102 | 26 nM | 250 | 24.2 nM | 398 | 51.3 nM | 546 | 53 nM |
| 103 | 10.5 nM | 251 | 32.9 nM | 399 | 20.2 nM | 547 | 179 nM |
| 104 | 17.3 nM | 252 | 29.3 nM | 400 | 33.1 nM | 548 | 14.3 nM |
| 105 | 31.2 nM | 253 | 22.6 nM | 401 | 25.3 nM | 549 | 140 nM |
| 106 | 13.3 nM | 254 | 97.3 nM | 402 | 20.4 nM | 550 | 40.3 nM |
| 107 | 10.9 nM | 255 | 55.1 nM | 403 | 80.6 nM | 551 | 74.7 nM |
| 108 | 13.4 nM | 256 | 21.1 nM | 404 | 13 nM | 552 | 17.8 nM |
| 109 | 13.7 nM | 257 | 37 nM | 405 | 51.8 nM | 553 | 23.6 nM |
| 110 | 19 nM | 258 | 67.9 nM | 406 | 31.1 nM | 554 | 34.6 nM |
| 111 | 26.3 nM | 259 | 23.1 nM | 407 | 23 nM | 555 | 21.3 nM |
| 112 | 239 nM | 260 | 20.3 nM | 408 | 39.1 nM | 556 | 48.5 nM |
| 113 | 213 nM | 261 | 47.5 nM | 409 | 180 nM | 557 | 83.9 nM |
| 114 | 10.3 nM | 262 | 54.3 nM | 410 | 389 nM | 558 | 13.6 nM |
| 115 | 33.5 nM | 263 | 30.8 nM | 411 | 9.84 nM | 559 | 34.7 nM |
| 116 | 23.5 nM | 264 | 39 nM | 412 | 49.6 nM | 560 | 19.2 nM |
| 117 | 14.5 nM | 265 | 28.8 nM | 413 | 14 nM | 561 | 429 nM |
| 118 | 24.1 nM | 266 | 24.7 nM | 414 | 16.8 nM | 562 | 16.3 nM |
| 119 | 203 nM | 267 | 9.43 nM | 415 | 19.5 nM | 563 | 26.4 nM |
| 120 | 36.4 nM | 268 | 12.3 nM | 416 | 262 nM | 564 | 27 nM |
| 121 | 67 nM | 269 | 24.7 nM | 417 | 112 nM | 565 | 51.2 nM |
| 122 | 34.1 nM | 270 | 16.7 nM | 418 | 172 nM | 566 | 78.6 nM |
| 123 | 40.5 nM | 271 | 7.53 nM | 419 | 9.69 nM | 567 | 17.9 nM |
| 124 | 36.2 nM | 272 | 107 nM | 420 | 10.2 nM | 568 | 411 nM |
| 125 | 78.1 nM | 273 | 15.5 nM | 421 | 16.9 nM | 569 | 427 nM |
| 126 | 13 nM | 274 | 21.1 nM | 422 | 16.7 nM | 570 | 143 nM |
| 127 | 14.9 nM | 275 | 21.3 nM | 423 | 12.6 nM | 571 | 237 nM |
| 128 | 11.4 nM | 276 | 200 nM | 424 | 51.3 nM | 572 | 65.6 nM |
| 129 | 24.9 nM | 277 | 46.7 nM | 425 | 216 nM | 573 | 115 nM |
| 130 | 8.32 nM | 278 | 12.8 nM | 426 | 98.6 nM | 574 | 609 nM |
| 131 | 84.7 nM | 279 | 31.6 nM | 427 | 184 nM | 575 | 216 nM |
| 132 | 10.8 nM | 280 | 98 nM | 428 | 61.5 nM | 576 | 528 nM |
| 133 | 65.4 nM | 281 | 10.7 nM | 429 | 149 nM | 577 | 102 nM |
| 134 | 37.9 nM | 282 | 15.5 nM | 430 | 93.4 nM | 578 | 424 nM |
| 135 | 33.3 nM | 283 | 84.6 nM | 431 | 1.16 µM | 579 | 340 nM |
| 136 | 23.5 nM | 284 | 11.6 nM | 432 | 196 nM | 580 | 262 nM |
| 137 | 23.8 nM | 285 | 25 nM | 433 | 352 nM | 581 | 788 nM |
| 138 | 14.2 nM | 286 | 20.5 nM | 434 | 578 nM | 582 | 100 µM |
| 139 | 10.2 nM | 287 | 21.9 nM | 435 | 191 nM | 583 | 1.84 µM |
| 140 | 11.3 nM | 288 | 13.4 nM | 436 | 367 nM | 584 | 266 nM |
| 141 | 35.1 nM | 289 | 16.5 nM | 437 | 472 nM | 585 | 202 nM |
| 142 | 16.8 nM | 290 | 175 nM | 438 | 20.5 nM | 586 | 762 nM |
| 143 | 17.1 nM | 291 | 8.84 nM | 439 | 27.2 nM | 587 | 2.39 µM |
| 144 | 12.2 nM | 292 | 30.1 nM | 440 | 112 nM | 588 | 1.96 µM |
| 145 | 21.5 nM | 293 | 16.2 nM | 441 | 81.1 nM | 589 | 1.45 µM |
| 146 | 36.2 nM | 294 | 56.2 nM | 442 | 367 nM | 590 | 17.4 nM |
| 147 | 13 nM | 295 | 7.22 nM | 443 | 36.9 nM | 591 | 149 nM |
| 148 | 11 nM | 296 | 17.5 nM | 444 | 31.8 nM | 592 | 21 nM |

Example 3: Ki Determination by Radioligand Binding

Radioligand binding assays are performed using the commercially available adrenergic receptor agonist [$^{125}$I]Cyanopindolol as the radioligand and non-specific binding is determined in the presence of unlabeled L-748,337 at a saturating concentration of 10 µM. For the beta-3 adrenergic receptor, the radioligand is used in the assay at a final concentration of 0.4 nM. Membrane pellets prepared from CHO-K1 cells stably expressing recombinant beta-3 adrenergic receptors are prepared using standard methods and stored at −80° C. Membranes are thawed on ice and resuspended in Assay Buffer (20 mM HEPES, pH 7.4, 10 mM MgCl$_2$) by dounce homogenization. Competition experiments consist of addition of 145 µL of membranes, 50 µL of radioligand stock, and 5 µL of test compound diluted in DMSO to 96-well microtiter plates. Plates are incubated for one hour at room temperature and the assay terminated by rapid filtration through Perkin Elmer GF/C filtration, plates pretreated with 0.5% PEI, under vacuum pressure using a 96-well Packard filtration apparatus. Plates are rapidly washed several times with ice-cold Assay Buffer and then dried overnight at 45° C. Finally, 25 µL of BetaScint scintillation cocktail is added to each well and plates counted in a Packard TopCount scintillation counter. In each competition study, test compounds are dosed at eight to ten concentrations with triplicate determinations at each test concentration. A reference compound, typically isoproterenol, is included in every experiment for quality control purposes.

Raw counts from scintillation counters are fit to a non-linear least squares curve fitting program to obtain IC$_{50}$ values. Ki values are determined from IC$_{50}$ values using the Cheng-Prusoff equation and the radioligand Kd. Mean Ki values and 95% confidence intervals are calculated from the mean log(Ki) value.

Example 4: Beta-3 Adrenergic Receptor Antagonists in Chronic Heart Failure Models Beta-3 adrenergic receptor antagonists can be evaluated for effects on cardiac contractility in chronic heart failure (CHF) rats. Beta-3 adrenergic receptor expression is weak in the normal rat heart and higher in the rat heart with CHF. Because beta-3 adrenergic receptor expression is higher in the rat heart with CHF, a compound of the present invention was evaluated for the ability to attenuate the negative contractile effects of the beta-3 adrenergic receptor agonist BRL 37344 (BRL) compared to baseline in this CHF rat model.

Myocardial infarction was induced in male Sprague-Dawley rats by performing left coronary descending artery ligation. The rats were anesthetized using an isoflurane vaporizer (Summit Medical; 5% induction and 2-3% during the surgery), intubated, and placed on a ventilator (Cat. #55-0000, Harvard Apparatus, Holliston, Mass.) supplying 2-3% isoflurane in oxygen at a tidal volume of 2.5 m/stroke at a rate of 70 strokes per minute. A 2-cm incision was made to open the chest with a hemostat. The left coronary descending artery was ligated with a 7-0 Prolene suture 3 mm from origin of the left coronary descending artery. The chest was then closed using 4-0 silk suture (Cat #1677G, Ethicon, Somerville, N.J.), and the rats were taken off the ventilator and placed in a home cage following spontaneous breathing.

Heart failure was evaluated weekly following surgery by testing impaired left ventricular function by echocardiography. Left ventricle end-diastolic volume (LVEDV) and left ventricle end-systolic volume (LVESV) were measured for at least three consecutive cardiac cycles in long-axis view images. Ejection Fraction (EF %) was calculated using the following formula: EF %=(LVEDV−LVESV)/LVEDV. An ejection fraction<30% was used at the cutoff for heart failure.

A direct determination of left ventricular function was used for all rats to evaluate the effects of compounds on left ventricular contractility. Right carotid artery catheterization was used for contractility measurements. The rats were anesthetized with an intraperitoneal injection of INACTIN® (Cat #T-133, Sigma, St. Louis, Mo.) (100 mg/kg body weight), and a Millar MIKRO-TIP® pressure catheter (Cat #SPR-320NR, Millar, Inc., Houston, Tex.) was passed through the carotid artery into left ventricle. Left ventricular pressure (LVP) was monitored by LabChart with POWERLAB® Data Acquisition System (ADInstruments, Sydney, Australia).

Jugular vein catheterization was used for compound administration. A silastic catheter (Cat #427411, BD, Franklin Lakes, N.J.) was introduced into the jugular vein, and a right venous catheter was connected to an automated drug delivery system (11 Plus Syringe Pump, Harvard Apparatus, Holliston, Mass.).

Development of CHF was monitored by echocardiography in rats after the surgically-induced myocardial infarction. When the EF % fell below 30% (typically 3-5 months following artery ligation), each animal was prepared for drug testing. Vehicle was administered for 10 minutes following stabilization. In separate animals, the test compound was then administered for 10 minutes at the following doses of 3 mg/kg/hr, 10 mg/kg/hr, and 30 mg/kg/hr, at the end of each infusion (vehicle and test compound) a bolus of BRL (3 µg/kg) was adminstered. A blood sample (800 microliters whole blood) was then taken from the left venous catheter immediately following each 10-minute drug infusion to monitor plasma concentrations of test compound.

Figure 20:
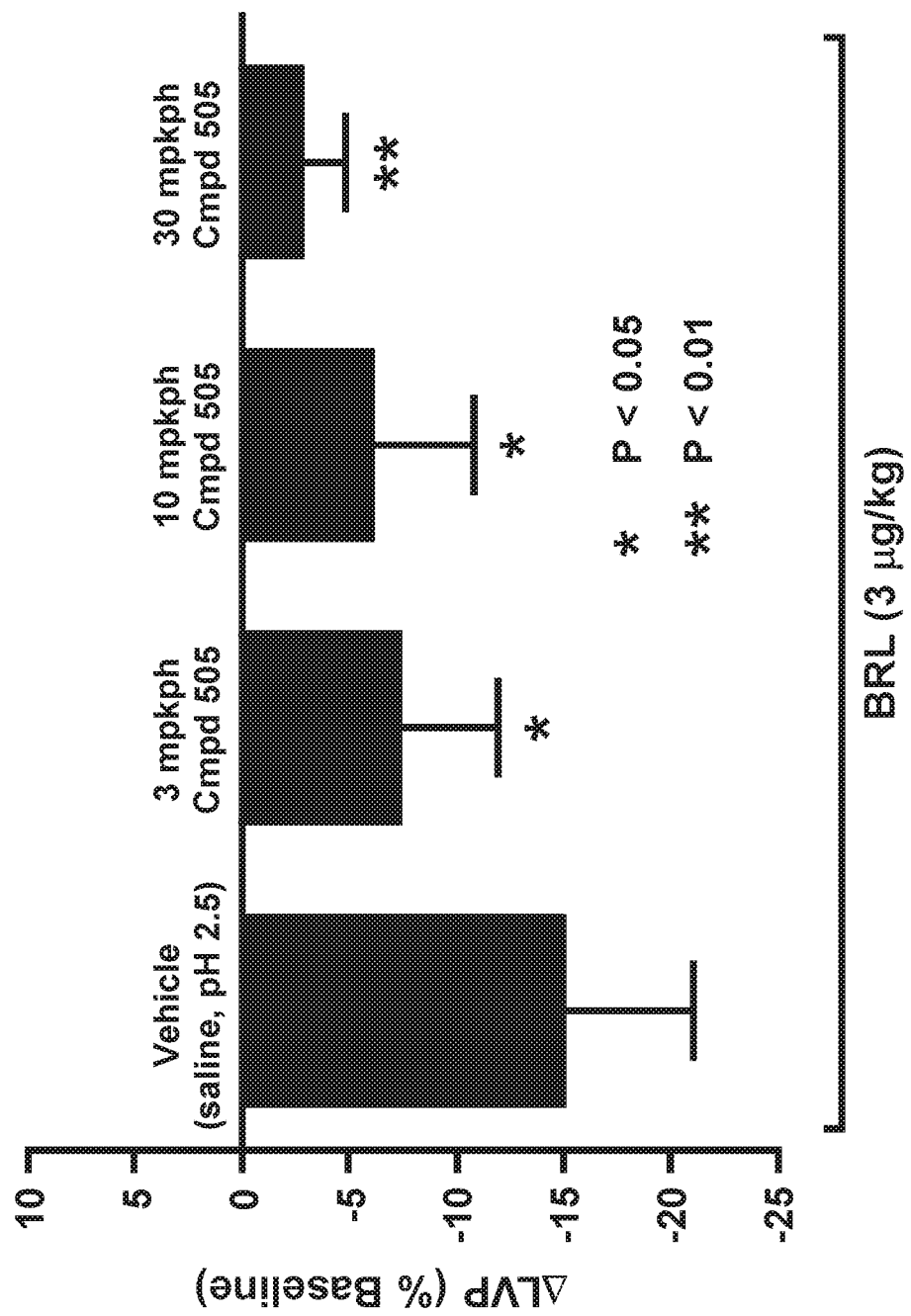
FIG. 20 shows the inhibition of negative effects of BRL on left ventricular pressure (LVP) in chronic heart failure (CHF) rats with Compound 505 in a dose dependent manner (Example 4), where "mpkph" refers to "mg/kg/hr" in FIG. 20.

Compound 505 showed a dose-dependent improvement in left ventricular pressure in the rat model of chronic heart failure (see FIG. 20).

Those skilled in the art will recognize that various modifications, additions, substitutions, and variations to the illustrative examples set forth herein can be made without departing from the spirit of the invention and are, therefore, considered within the scope of the invention.

The invention claimed is:

1. A compound selected from the group consisting of:
   3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methylbenzenesulfonamide, (Compound 61);
   3-((2S)-3-(8-(benzylsulfonyl)-1-oxa-8-azaspiro[4.5]decan-3-ylamino)-2-hydroxypropoxy)-N-methylbenzenesulfonamide, (Compound 172);
   3-((S)-2-hydroxy-3-((R)-8-(4-methyl-3,4-dihydro-2H-benzo[b][1,4]oxazin-6-ylsulfonyl)-1-oxa-8-azaspiro[4.5]decan-3-ylamino)propoxy)-N-methylbenzenesulfonamide, (Compound 300);
   3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide, (Compound 303);
   3-((2S)-2-hydroxy-3-(8-(4'-((isopentylamino)methyl)biphenyl-3-ylsulfonyl)-1-oxa-8-azaspiro[4.5]decan-3-ylamino)propoxy)-N-methylbenzenesulfonamide, (Compound 320);
   3-((S)-2-hydroxy-3-((R)-8-(quinolin-3-ylsulfonyl)-1-oxa-8-azaspiro[4.5]decan-3-ylamino)propoxy)-N-methylbenzenesulfonamide, (Compound 336);
   3-((2S)-3-(8-(4'-((2,2-difluoroethylamino)methyl)biphenyl-3-ylsulfonyl)-1-oxa-8-azaspiro[4.5]decan-3-ylamino)-2-hydroxypropoxy)-N-methylbenzenesulfonamide, (Compound 339);
   3-((S)-2-hydroxy-3-((R)-8-(quinolin-6-ylsulfonyl)-1-oxa-8-azaspiro[4.5]decan-3-ylamino)propoxy)-N-methylbenzenesulfonamide, (Compound 344);
   $N^1$-((3'-(3-((S)-2-hydroxy-3-(3-(N-methylsulfamoyl)phenoxy)propylamino)-1-oxa-8-azaspiro[4.5]decan-8-yl sulfonyl)biphenyl-4-yl)methyl)oxalamide, (Compound 354);
   3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide, (Compound 419);
   3-((S)-2-hydroxy-3-((R)-8-(1-methyl-2,3-dihydro-1H-pyrido[2,3-b][1,4]oxazin-7-ylsulfonyl)-1-oxa-8-azaspiro[4.5]decan-3-ylamino)propoxy)-N-((1R,2S)-2-hydroxycyclopentyl)benzenesulfonamide, (Compound 437);
   3-((S)-3-((R)-8-((R)-1,3-dimethyl-2,3-dihydro-1H-pyrido[2,3-b][1,4]oxazin-7-ylsulfonyl)-1-oxa-8-azaspiro[4.5]decan-3-ylamino)-2-hydroxypropoxy)-N-methylbenzenesulfonamide, (Compound 468);
   3-((S)-3-((R)-8-(3-cyano-1H-pyrrolo[2,3-b]pyridin-5-ylsulfonyl)-1-oxa-8-azaspiro[4.5]decan-3-ylamino)-2-hydroxypropoxy)-N-methylbenzenesulfonamide, (Compound 493);
   3-((R)-3-((S)-2-hydroxy-3-(3-(N-methylsulfamoyl)phenoxy)propylamino)-1-oxa-8-azaspiro[4.5]decan-8-ylsulfonyl)pyridine 1-oxide, (Compound 496);
   3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide, (Compound 505);
   3-((S)-2-hydroxy-3-((R)-8-(3-(trifluoromethyl)-1H-pyrrolo[2,3-b]pyridin-5-ylsulfonyl)-1-oxa-8-azaspiro[4.5]decan-3-ylamino)propoxy)-N-methylbenzenesulfonamide, (Compound 509);
   3-((S)-3-((R)-8-(1H-pyrrolo[3,2-b]pyridin-6-ylsulfonyl)-1-oxa-8-azaspiro[4.5]decan-3-ylamino)-2-hydroxypropoxy)benzenesulfonamide, (Compound 532);
   3-((S)-2-hydroxy-3-((R)-8-(4-hydroxyquinolin-3-ylsulfonyl)-1-oxa-8-azaspiro[4.5]decan-3-ylamino)propoxy)-N-methylbenzenesulfonamide, (Compound 541);
   3-((S)-2-hydroxy-3-((R)-8-(4-hydroxyquinolin-3-ylsulfonyl)-1-oxa-8-azaspiro[4.5]decan-3-ylamino)propoxy)benzenesulfonamide, (Compound 548);
   3-((S)-3-((R)-8-(1-ethyl-4-oxo-1,4-dihydroquinolin-3-ylsulfonyl)-1-oxa-8-azaspiro[4.5]decan-3-ylamino)-2-hydroxypropoxy)benzenesulfonamide, (Compound 550);
   3-((S)-2-hydroxy-3-((R)-8-(4-methoxypyrimidin-2-yl)-1-oxa-8-azaspiro[4.5]decan-3-ylamino)propoxy)-N-methylbenzenesulfonamide, (Compound 568); and
   3-((S)-3-((R)-8-(4-benzylpyrimidin-2-yl)-1-oxa-8-azaspiro[4.5]decan-3-ylamino)-2-hydroxypropoxy)-N-methylbenzenesulfonamide, (Compound 573); and
   pharmaceutically acceptable salts, solvates, and hydrates thereof.

2. The compound according to claim 1, wherein the compound is:
   3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methylbenzenesulfonamide, (Compound 61); and pharmaceutically acceptable salts, solvates, and hydrates thereof.

3. The compound according to claim 1, wherein the compound is:
   $N^1$-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide, (Compound 354); and pharmaceutically acceptable salts, solvates, and hydrates thereof.

4. The compound according to claim 1, wherein the compound is:
   3-((2S)-3-(8-(4'-((2,2-difluoroethylamino)methyl)biphenyl-3-ylsulfonyl)-1-oxa-8-azaspiro[4.5]decan-3-ylamino)-2-hydroxypropoxy)-N-methylbenzenesulfonamide, (Compound 339); and pharmaceutically acceptable salts, solvates, and hydrates thereof.

5. The compound according to claim 1, wherein the compound is:
   3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide, (Compound 303); and pharmaceutically acceptable salts, solvates, and hydrates thereof).

6. The compound according to claim 1, wherein the compound is:
   3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide, (Compound 419); and pharmaceutically acceptable salts, solvates, and hydrates thereof).

7. The compound according to claim 1, wherein the compound is:
   3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide, (Compound 505); and pharmaceutically acceptable salts, solvates, and hydrates thereof).

8. The compound according to claim 1, wherein the compound is:
   3-((S)-2-hydroxy-3-((R)-8-(4-hydroxyquinolin-3-ylsulfonyl)-1-oxa-8-azaspiro[4.5]decan-3-ylamino)propoxy)-N-methylbenzenesulfonamide, (Compound 541); and pharmaceutically acceptable salts, solvates, and hydrates thereof).

9. The compound according to claim 1, wherein the compound is:
   3-((S)-2-hydroxy-3-((R)-8-(4-methoxypyrimidin-2-yl)-1-oxa-8-azaspiro[4.5]decan-3-ylamino)propoxy)-N-methylbenzenesulfonamide, (Compound 568); and pharmaceutically acceptable salts, solvates, and hydrates thereof).

10. The compound according to claim 1, wherein the compound is:
    3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methylbenzenesulfonamide, (Compound 61).

11. The compound according to claim 1, wherein the compound is:
    $N^1$-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide, (Compound 354).

12. The compound according to claim 1, wherein the compound is:
    3-((2S)-3-(8-(4'-((2,2-difluoroethylamino)methyl)biphenyl-3-ylsulfonyl)-1-oxa-8-azaspiro[4.5]decan-3-ylamino)-2-hydroxypropoxy)-N-methylbenzenesulfonamide, (Compound 339).

13. The compound according to claim 1, wherein the compound is:
    3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide, (Compound 303).

14. The compound according to claim 1, wherein the compound is:
    3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide, (Compound 419).

15. The compound according to claim 1, wherein the compound is:
    3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide, (Compound 505).

16. The compound according to claim 1, wherein the compound is:
    —((S)-2-hydroxy-3-((R)-8-(4-hydroxyquinolin-3-ylsulfonyl)-1-oxa-8-azaspiro[4.5]decan-3-ylamino)propoxy)-N-methylbenzenesulfonamide, (Compound 541).

17. The compound according to claim 1, wherein the compound is:
    3-((S)-2-hydroxy-3-((R)-8-(4-methoxypyrimidin-2-yl)-1-oxa-8-azaspiro[4.5]decan-3-ylamino)propoxy)-N-methylbenzenesulfonamide, (Compound 568).

18. A method for treating heart failure in an individual, comprising administering to said individual in need thereof, a therapeutically effective amount of a compound according to claim 1.

19. The method according to claim 18, wherein the compound is:
    3-((2S)-2-hydroxy-3-(8-(3-(1-methyl-1H-pyrazol-4-yl)phenylsulfonyl)-1-oxa-8-azaspiro[4.5]decan-3-ylamino)propoxy)-N-methylbenzenesulfonamide, (Compound 61).

20. The method according to claim 18, wherein the compound is:
    $N^1$-((3'-(3-((S)-2-hydroxy-3-(3-(N-methylsulfamoyl)phenoxy)propylamino)-1-oxa-8-azaspiro[4.5]decan-8-ylsulfonyl)biphenyl-4-yl)methyl)oxalamide, (Compound 354).

21. The method according to claim 18, wherein the compound is:
    3-((2S)-3-(8-(4'-(2,2-difluoroethylamino)methyl)biphenyl-3-ylsulfonyl)-1-oxa-8-azaspiro[4.5]decan-3-ylamino)-2-hydroxypropoxy)-N-methylbenzenesulfonamide, (Compound 339).

22. The method according to claim 18, wherein the compound is:
    3-((2S)-2-hydroxy-3-(8-(4'-((isopropylamino)methyl)biphenyl-3-ylsulfonyl)-1-oxa-8-azaspiro[4.5]decan-3-ylamino)propoxy)-N-methylbenzenesulfonamide, (Compound 303).

23. The method according to claim 18, wherein the compound is:
    3-((S)-3-((S)-8-(4'-(aminomethyl)-4-ethoxybiphenyl-3-ylsulfonyl)-1-oxa-8-azaspiro[4.5]decan-3-ylamino)-2-hydroxypropoxy)-N-methylbenzenesulfonamide, (Compound 419).

24. The method according to claim 18, wherein the compound is:
    3-((S)-3-((R)-8-(1H-pyrrolo[3,2-b]pyridin-6-ylsulfonyl)-1-oxa-8-azaspiro[4.5]decan-3-ylamino)-2-hydroxypropoxy)-N-methylbenzenesulfonamide, (Compound 505).

25. The method according to claim 18, wherein the compound is:
- —((S)-2-hydroxy-3-((R)-8-(4-hydroxyquinolin-3-ylsulfonyl)-1-oxa-8-azaspiro[4.5]decan-3-ylamino)propoxy)-N-methylbenzenesulfonamide, (Compound 541).

26. The method according to claim 18, wherein the compound is:
- 3-((S)-2-hydroxy-3-((R)-8-(4-methoxypyrimidin-2-yl)-1-oxa-8-azaspiro[4.5]decan-3-ylamino)propoxy)-N-methylbenzenesulfonamide, (Compound 568).

* * * * *

UNITED STATES PATENT AND TRADEMARK OFFICE
CERTIFICATE OF CORRECTION

PATENT NO. : 11,339,172 B2  
APPLICATION NO. : 16/769507  
DATED : May 24, 2022  
INVENTOR(S) : Thuy-Anh Tran et al.

Page 1 of 1

It is certified that error appears in the above-identified patent and that said Letters Patent is hereby corrected as shown below:

On the Title Page

Item (56), Column 2, (Other Publications), Line 6, delete "Intropes," and insert -- Inotropes, --;

Item (56), Column 2, (Other Publications), Line 12, delete "innercation" and insert -- innervation --;

Item (56), Column 2, (Other Publications), Line 17, delete "Radiopharm," and insert
-- Radiopharm. --;

In the Claims

Column 151, Line 14, Claim 5, delete "thereof)." and insert -- thereof. --;

Column 151, Line 21, Claim 6, delete "thereof)." and insert -- thereof. --;

Column 151, Line 29, Claim 7, delete "thereof)." and insert -- thereof. --;

Column 151, Line 36, Claim 8, delete "thereof)." and insert -- thereof. --;

Column 151, Line 43, Claim 9, delete "thereof)." and insert -- thereof. --;

Column 152, Line 45, Claim 21, delete "(4'-(2,2" and insert -- (4'-((2,2 --.

Signed and Sealed this  
Twenty-third Day of August, 2022

*Katherine Kelly Vidal*

Katherine Kelly Vidal  
*Director of the United States Patent and Trademark Office*